(12) United States Patent
Bae et al.

(10) Patent No.: US 9,028,977 B2
(45) Date of Patent: May 12, 2015

(54) COMPOUND, METHOD FOR PREPARING SAME AND ORGANIC ELECTRONIC DEVICE USING SAME

(75) Inventors: Jae-Soon Bae, Daejeon Metropolitan City (KR); Ji-Eun Kim, Daejeon Metropolitan City (KR); Jeung-Gon Kim, Daejeon Metropolitan City (KR); Jun-Gi Jang, Daejeon Metropolitan City (KR)

(73) Assignee: LG Chem, Ltd., Seoul (KR)

( * ) Notice: Subject to any disclaimer, the term of this patent is extended or adjusted under 35 U.S.C. 154(b) by 242 days.

(21) Appl. No.: 13/120,380

(22) PCT Filed: Sep. 23, 2009

(86) PCT No.: PCT/KR2009/005431
§ 371 (c)(1),
(2), (4) Date: Mar. 22, 2011

(87) PCT Pub. No.: WO2010/036027
PCT Pub. Date: Apr. 1, 2010

(65) Prior Publication Data
US 2011/0168992 A1      Jul. 14, 2011

(30) Foreign Application Priority Data
Sep. 23, 2008   (KR) .................. 10-2008-0093440

(51) Int. Cl.
| | | |
|---|---|---|
| H01L 51/54 | (2006.01) | |
| C07D 333/50 | (2006.01) | |
| C07D 409/10 | (2006.01) | |
| C07D 307/92 | (2006.01) | |
| C07D 333/74 | (2006.01) | |
| C07D 209/86 | (2006.01) | |
| C07D 263/57 | (2006.01) | |
| C07D 333/36 | (2006.01) | |
| C07D 403/04 | (2006.01) | |
| C07D 405/10 | (2006.01) | |
| H01L 51/00 | (2006.01) | |
| H01L 51/50 | (2006.01) | |

(52) U.S. Cl.
CPC ............ *C07D 333/74* (2013.01); *C07D 209/86* (2013.01); *C07D 263/57* (2013.01); *C07D 307/92* (2013.01); *C07D 333/36* (2013.01); *C07D 403/04* (2013.01); *C07D 405/10* (2013.01); *C07D 409/10* (2013.01); *H01L 51/0061* (2013.01); *H01L 51/0073* (2013.01); *H01L 51/0074* (2013.01); *H01L 51/008* (2013.01); *H01L 51/5012* (2013.01); *H01L 51/5048* (2013.01); *H01L 2251/308* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 5,077,142 A | 12/1991 | Sakon et al. | |
| 5,543,631 A | 8/1996 | Weinberger | |
| 2004/0076853 A1 | 4/2004 | Jarikov | |
| 2006/0235060 A1 | 10/2006 | Yoshida et al. | |
| 2007/0063190 A1 | 3/2007 | Kobayashi et al. | |
| 2008/0166594 A1* | 7/2008 | Ito et al. ...................... | 428/704 |
| 2009/0261717 A1 | 10/2009 | Buesing et al. | |

FOREIGN PATENT DOCUMENTS

| | | |
|---|---|---|
| CN | 101223156 A | 7/2008 |
| EP | 1593675 A1 | 11/2005 |
| EP | 1962354 A1 | 12/2006 |
| JP | 05-034904 A | 2/1993 |
| JP | 5-197140 A | 8/1993 |
| JP | 2001-210472 A | 8/1997 |
| JP | 9-297414 A | 11/1997 |
| JP | 10-26836 A | 1/1998 |
| JP | 2004-206893 A | 7/2004 |
| JP | 2005-132838 A | 5/2005 |
| JP | 2007-145833 A | 6/2007 |
| JP | 2009-049090 A | 3/2009 |

(Continued)

OTHER PUBLICATIONS

Yao, T. et al., "Synthesis of Polycyclic Aromatics and Heteroaromatics via Electrophilic Cyclization", Journal of Organic Chemistry, 2005, vol. 70, No. 9, pp. 3511-3517.

(Continued)

*Primary Examiner* — J. L. Yang
(74) *Attorney, Agent, or Firm* — McKenna Long & Aldridge LLP

(57) ABSTRACT

The present invention relates to a novel compound of Formula 1,

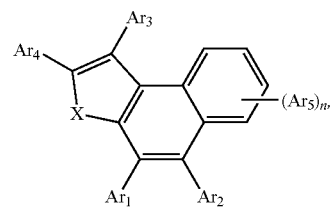

a method for manufacturing the same, and an organic electronic device using the same, and the novel compound according to the present invention may act as a hole injection, hole transport, electron injection and transport, or light emitting material in an organic light emitting device and an organic electronic device, and the device according to the present invention shows excellent properties in terms of efficiency, a driving voltage, and stability.

20 Claims, 6 Drawing Sheets

(56) References Cited

FOREIGN PATENT DOCUMENTS

| WO | WO 2004-072053 A1 | 8/2004 |
| WO | WO 2006-128800 A1 | 12/2006 |
| WO | WO 2007-069569 | 6/2007 |
| WO | WO 2008-006449 A1 | 1/2008 |

OTHER PUBLICATIONS

Fischer, E. et al., "Synthesis of New Sulfur Heteroaromatics Isoelectronic with Dibenzo [g,p] chrysene by Photocyclization of Thienyl- and Phenyl-Substituted Ethenes", Journal of Organic Chemistry, 1966, vol. 61, No. 20, pp. 6997-7005.

Shi, Z. et al., "A Palladium-Catalyzed Oxidative Cycloaromatization of Biaryls with Alkynes Using Molecular Oxygen as the Oxidant", Angewandte Chemie, Sep. 8, 2009, vol. 48, pp. 7895-7898.

Erik Fischer, et al., "Synthesis of New Sulfur Heteroaromatics Isoelectronic with Dibenzo[g,p]chrysene by Photocyclization of Thienyl- and Phenyl-Substituted Ethenes", 1996 American Chemical Society, Department of Chemistry, University of Copenhagen, J. Org. Chem. 1996, 61, pp. 6997-7005.

Tuanli tao et al., "Synthesis of Polycyclic Aromatics and Heteroaromatics via Electrophilic Cyclization", JOC Article, Department of Chemistry, Iowa State University, J. Org. Chem. 2005, 70, pp. 3511-3517.

"Synthesis of New Sulfur Heteroaromatics Isoelectronic with Dibenzo [g, p]chrysene by Photocyclization of Thienyl-and Phenyl-Substituted Ethenes", Erik Fischer et al., J. Org. Chem., vol. 61, No. 20, pp. 6997-7005.

"Synthesis of Polycyclic Aromatics and Heteroaromatics via Electrophilic Crclization", Tuanli Yao et al., J. Org. Chem., vol. 70, No. 9, pp. 3511-3517.

\* cited by examiner

Figure 1
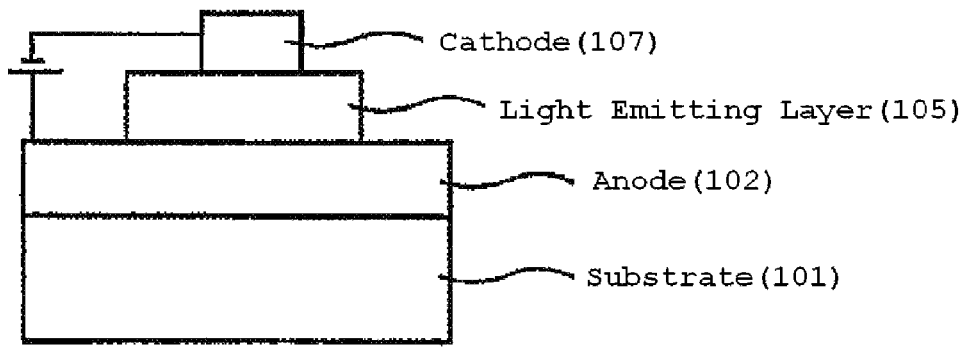
[Figure 2
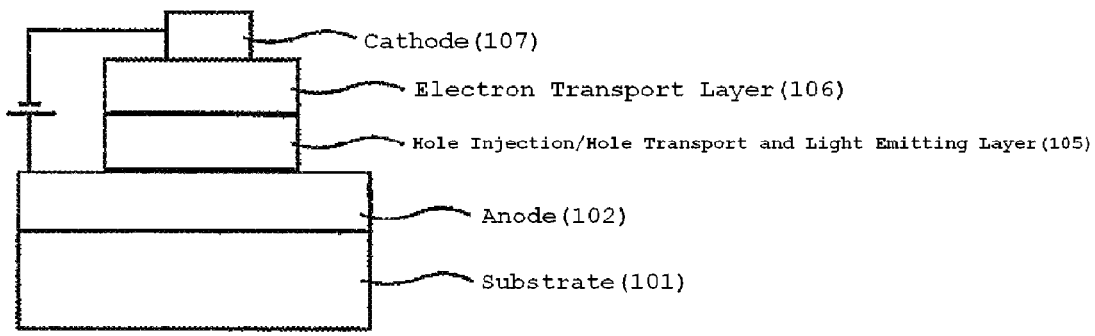
Figure 3
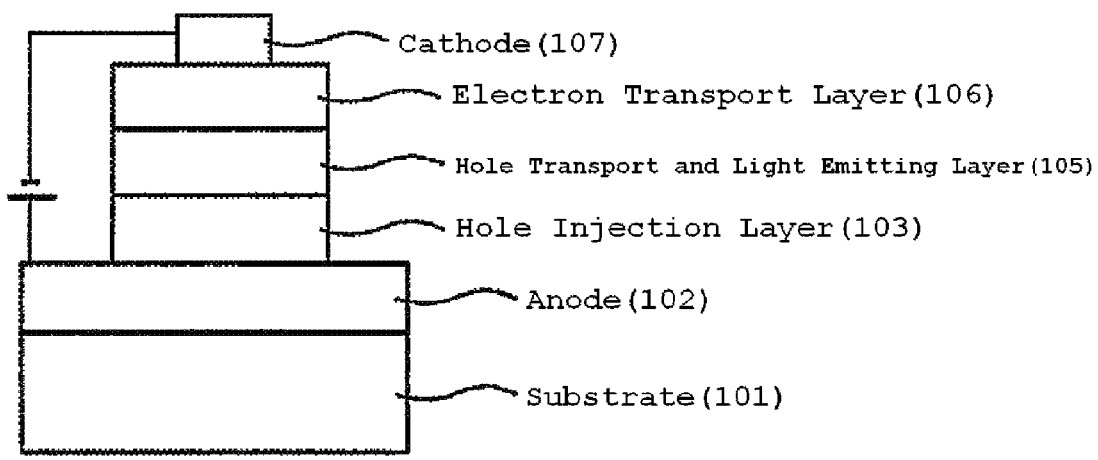

COMPOUND, METHOD FOR PREPARING SAME AND ORGANIC ELECTRONIC DEVICE USING SAME

TECHNICAL FIELD

This application claims the priority to PCT/KR2009/005431 filed on Sep. 23, 2009 and Korean Patent Application No. 10-2008-0093440 filed on Sep. 23, 2008, all of which are hereby incorporated by reference in their entirety. The present invention relates to a novel compound, a method for manufacturing the same, and an organic electronic device using the same.

BACKGROUND ART

An organic electronic device means a device that requires exchanging of electric charges between electrodes using holes and/or electrons and organic materials. The organic electronic device may be largely divided into the following categories according to an operation principle. First, there is an electronic device in which an exiton is formed in an organic material layer by a photon that flows from an external light source to the device, the exiton is separated into electrons and holes, and the electrons and the holes are transferred to the other electrodes and used as a current source (voltage source). Second, there is an electronic device in which holes and/or electrons are injected into an organic material semiconductor forming an interface in respects to the electrode by applying a voltage or a current to two or more electrodes, and the device is operated by the injected electrons and holes.

As examples of the organic electronic device, there are an organic light emitting device, an organic solar cell, an organic photoconductor (OPC), an organic transistor and the like, and all of them require a hole injection or transport material, an electron injection or transport material or a light emitting material in order to drive the device. Hereinafter, an organic light emitting device will be mainly described in detail. However, in the organic electronic devices, all of the hole injection or transport material, an electron injection or transport material or a light emitting material are operated on the basis of the similar principle.

In general, an organic light emitting phenomenon means a phenomenon that converts electric energy into light energy by using an organic material. The organic light emitting device using the organic light emitting phenomenon has a structure which generally includes an anode, a cathode, and an organic layer that is disposed between them. Herein, most organic layers have a multilayered structure that includes different materials in order to increase efficiency and stability of the organic light emitting device, and for example, it may include a hole injection layer, a hole transport layer, a light emitting layer, an electron transport layer, an electron injection layer and the like. In the organic light emitting device structure, if a voltage is applied between two electrodes, holes are injected from an anode and electrons are injected from a cathode to the organic material layer, and when the injected holes and the electrons meet each other, an exciton is formed, and light is emitted when the exciton falls to a bottom state. It is known that this organic light emitting device has properties such as magnetic light emission, high brightness, high efficiency, low driving voltage, a wide viewing angle, high contrast, high speed response and the like.

In the organic light emitting device, the material that is used in the organic material layer may be classified into a light emitting material and an electric charge material, for example, a hole injection material, a hole transport material, an electron transport material, an electron injection material according to a function thereof. In addition, the light emitting material may be classified into blue, green, and red light emitting materials and yellow and orange light emitting materials in order to realize better natural colors according to the emission color. Meanwhile, in the case of when only one material is used as a light emitting material, by interaction between molecules, there are problems in that the maximum light emitting wavelength moves to the long wavelength, the color purity is lowered, or efficiency of the device is lowered because of reduced effect of light emission. Therefore, in order to increase color purity and increase emission efficiency through transferring of energy, a host/dopant system may be used as the light emitting material.

In order to sufficiently show excellent properties of the above organic light emitting device, a material constituting the organic material layer in the device, for example, the hole injection material, the hole transport material, the light emitting material, the electron transport material, the electron injection material and the like should be supported by stable and efficient materials. However, the development of a stable and efficient organic material layer material for organic light emitting devices has not yet been made. Therefore, there is a demand for developing a novel material, and the demand for developing the novel material is similarly applied to the other organic electronic device.

DISCLOSURE

Technical Problem

Therefore, the present inventors have synthesized a novel compound, and found the fact that when the compound acts as a hole injection, hole transport, electron injection and transport, or light emitting material in an organic electronic device, an interfacial property and electric charge transport ability are excellent, thereby accomplishing the present invention.

It is an object of the present invention to provide a novel compound that is capable of being used in an organic electronic device, a method for manufacturing the same, and an organic electronic device using the same.

Technical Solution

In order to accomplish the above object, a first aspect of the present invention provides the following novel compound.

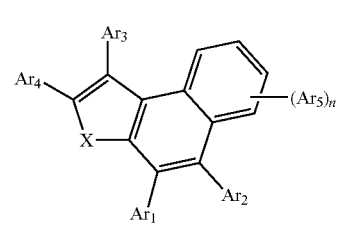

[Formula 1]

wherein the substituent group will be described in detail below.

In order to accomplish the above object, a second aspect of the present invention provides an organic electronic device using the above novel compound.

Advantageous Effects

A novel compound according to the present invention may act as a hole injection, hole transport, electron injection and transport, or light emitting material in an organic light emitting device and an organic electronic device, and the device according to the present invention shows excellent properties in terms of efficiency, a driving voltage, and stability.

DESCRIPTION OF DRAWINGS

FIGS. 1 to 4 are views that illustrate a structure of an organic light emitting device that is capable of being applied to the present invention;

BEST MODE

Figure 4:
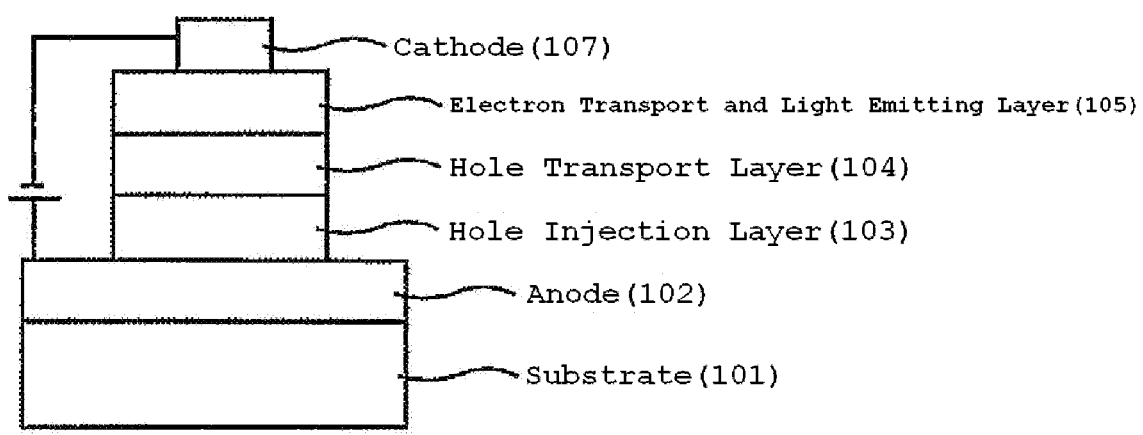
Figure 5:
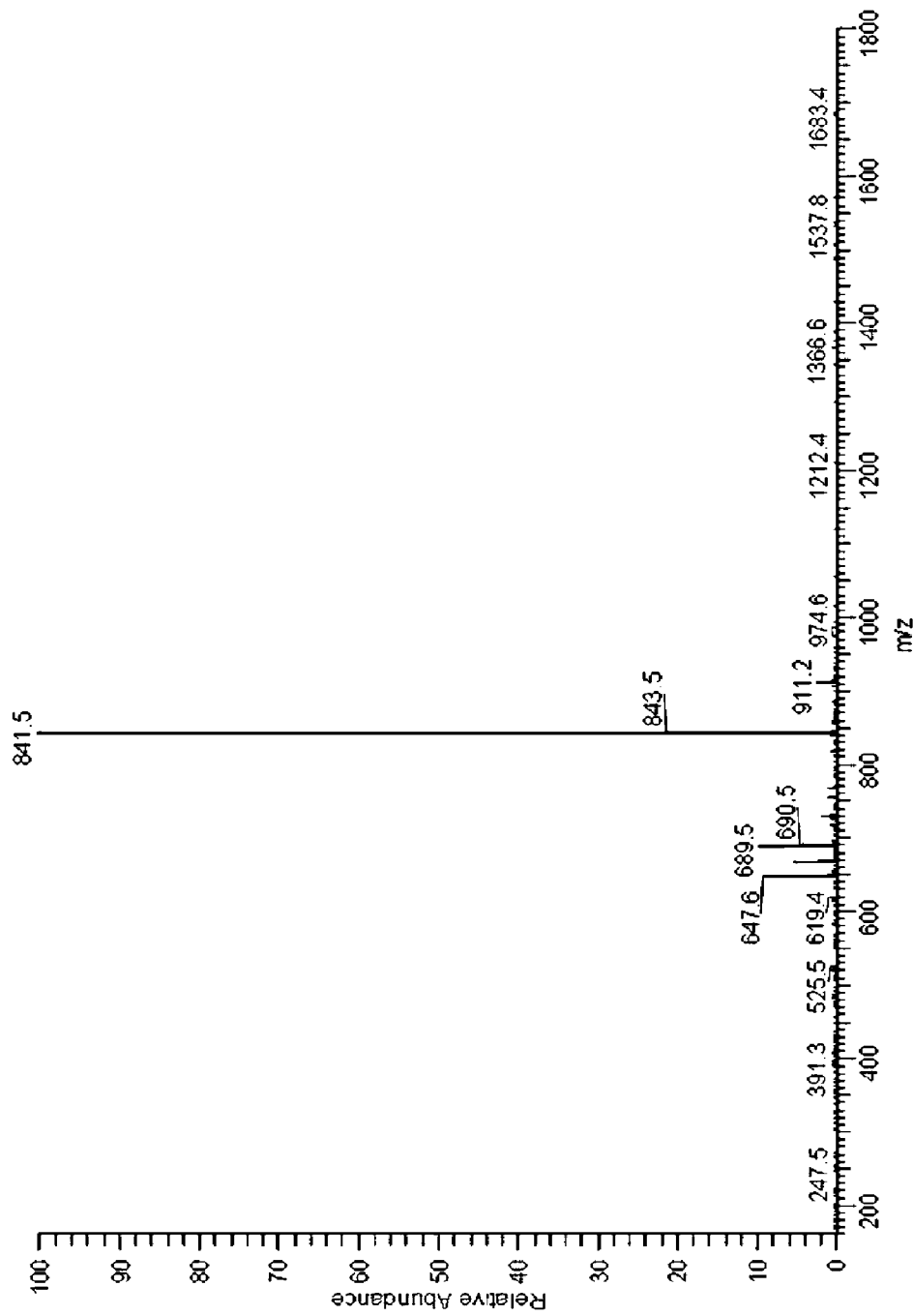
FIG. 5 is a mass spectrum of the compound 1-2-9.
Figure 6:
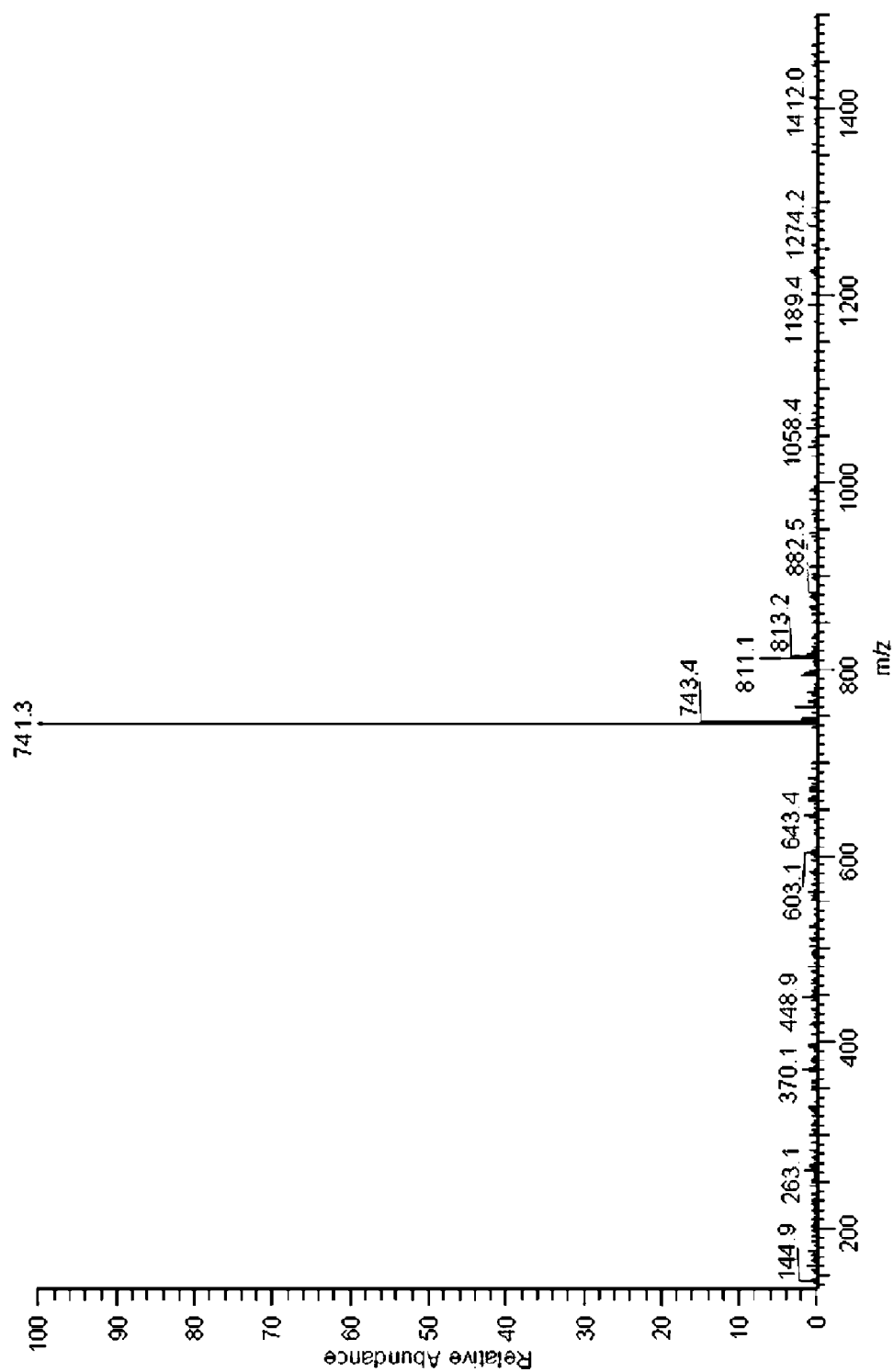
FIG. 6 is a mass spectrum of the compound 1-3-1.
Figure 7:
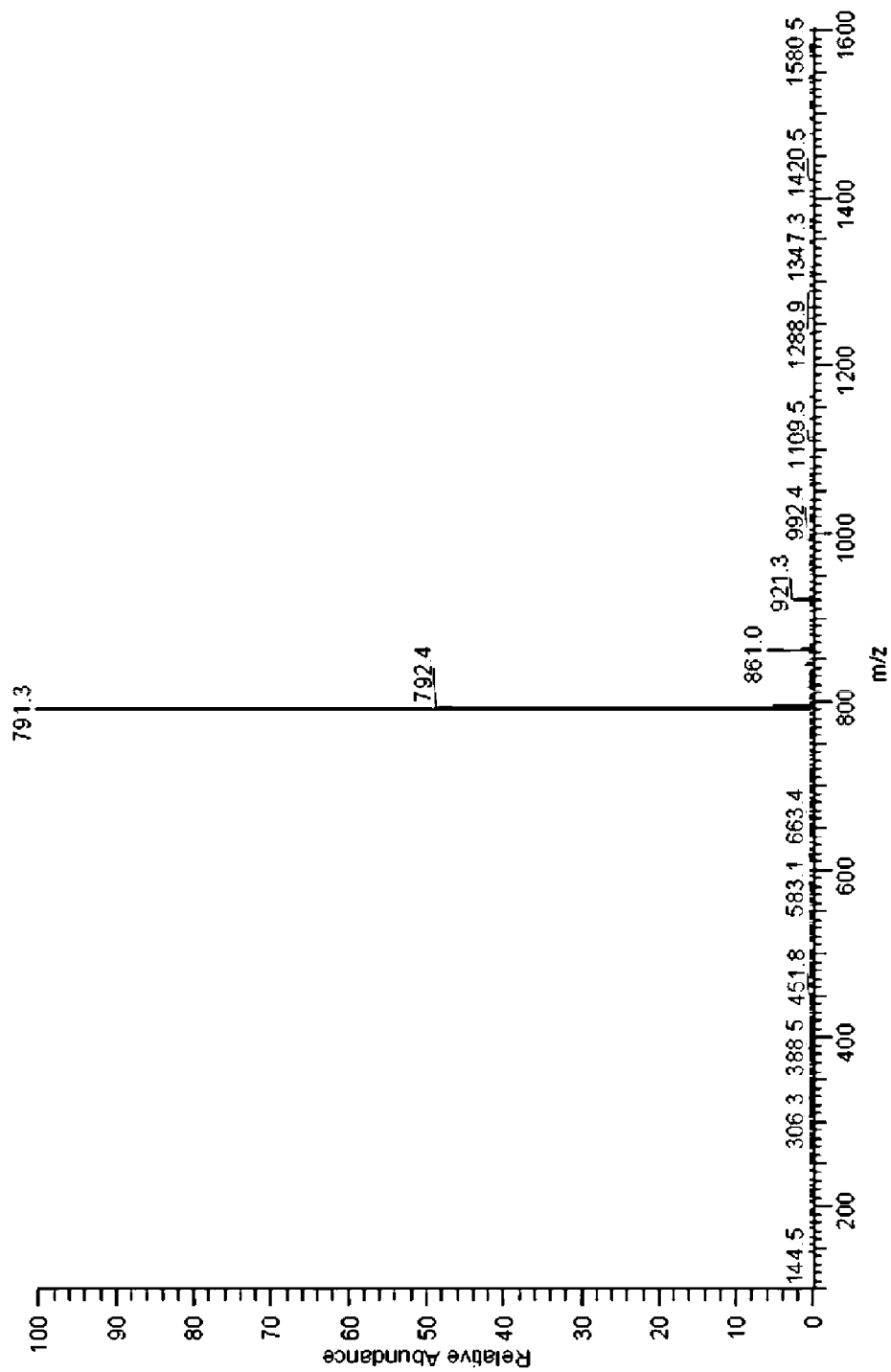
FIG. 7 is a mass spectrum of the compound 1-1-7.
Figure 8:
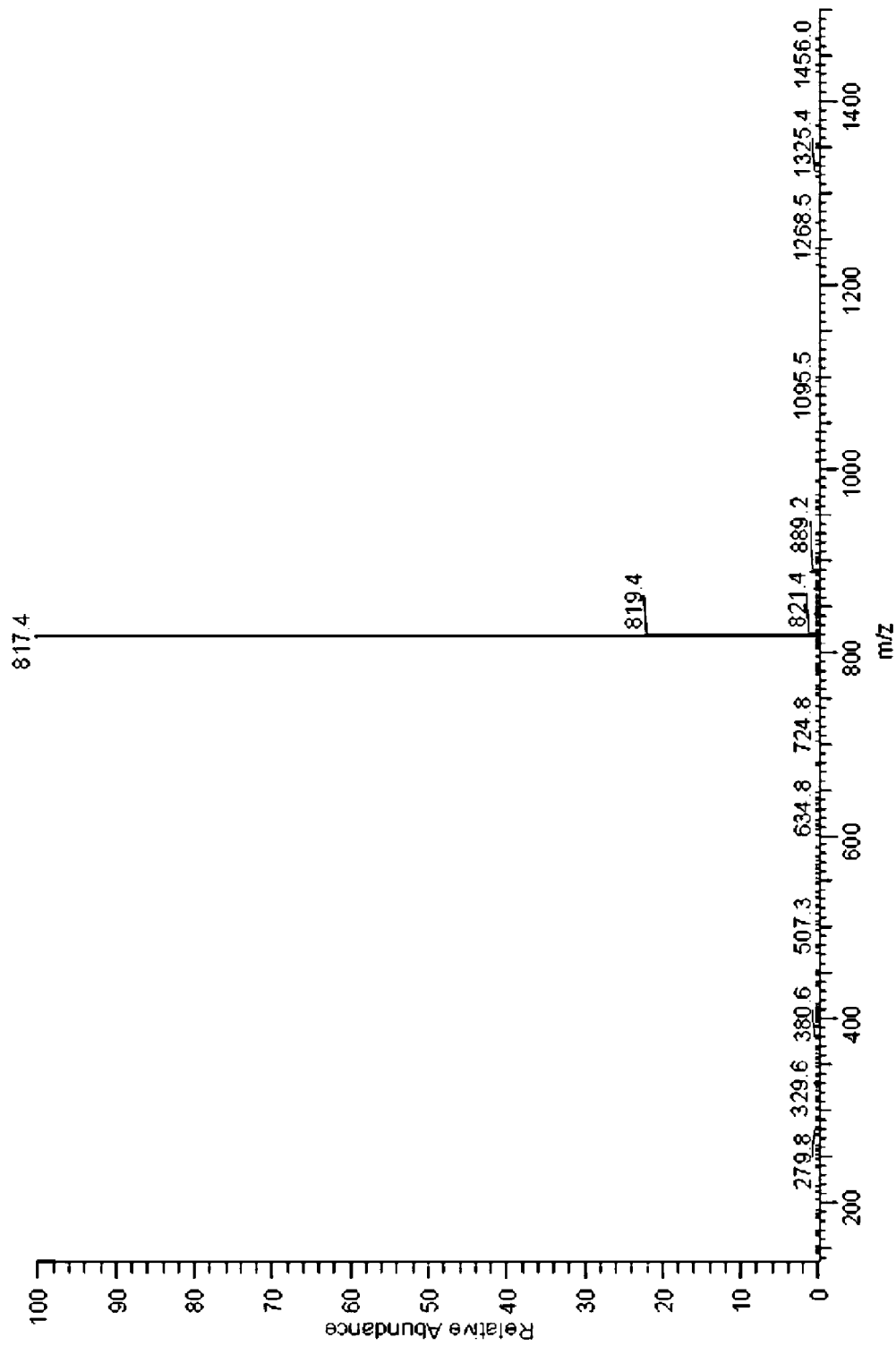
FIG. 8 is a mass spectrum of the compound 1-2-10.

The novel compound according to the present invention is characterized in that it is represented by the following Formula 1:

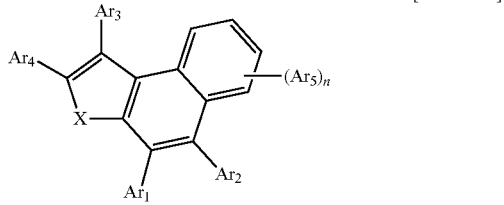

[Formula 1]

wherein X is S or O, n is an integer in the range of 0 to 4, $Ar_1$, $Ar_2$, $Ar_3$, $Ar_4$, and $Ar_5$ may be the same as or different from each other, and each independently selected from the group consisting of hydrogen atom; heavy hydrogen atom; halogen group; amino group; nitrile group; nitro group; amide group; $C_1$~$C_{30}$ alkoxy group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; $C_6$~$C_{30}$ aryloxy group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; $C_1$~$C_{30}$ alkylthioxy group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; $C_6$~$C_{30}$ arylthioxy group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; $C_1$~$C_{30}$ alkylaminyl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; $C_6$~$C_{60}$ aralkylaminyl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; $C_6$~$C_{60}$ arylaminyl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; $C_6$~$C_{60}$ aryl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_6$~$C_{30}$ aryloxy group, $C_1$~$C_{30}$ alkylthioxy group, $C_6$~$C_{30}$ arylthioxy group, $C_3$~$C_{30}$ cycloalkyl group, $C_2$~$C_{30}$ heterocycloalkyl group, substituted or unsubstituted $C_1$~$C_{30}$ alkylaminyl group, substituted or unsubstituted $C_1$~$C_{30}$ aralkylaminyl group, substituted or unsubstituted $C_6$~$C_{60}$ arylaminyl group, $C_6$~$C_{60}$ aryl group and $C_3$~$C_{60}$ heteroaryl group; $C_3$~$C_{60}$ heteroaryl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_6$~$C_{30}$ aryloxy group, $C_1$~$C_{30}$ alkylthioxy group, $C_6$~$C_{30}$ arylthioxy group, $C_3$~$C_{30}$ cycloalkyl group, $C_2$~$C_{30}$ heterocycloalkyl group, substituted or unsubstituted $C_1$~$C_{30}$ alkylaminyl group, substituted or unsubstituted $C_1$~$C_{30}$ aralkylaminyl group, substituted or unsubstituted $C_6$~$C_{60}$ arylaminyl group, $C_6$~$C_{60}$ aryl group and $C_3$~$C_{60}$ heteroaryl group; boron group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; silyl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; and ester group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group, or may form an aliphatic, aromatic, aliphatic hetero or aromatic hetero condensated ring or a spiro bond in conjunction with an adjacent group.

In addition, it is preferable that the compound that is represented by Formula 1 according to the present invention is represented by the following Formula 2 or 3:

[Formula 2]

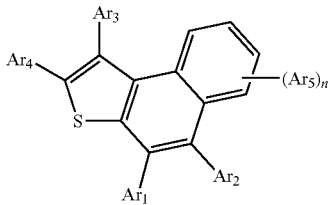

[Formula 3]

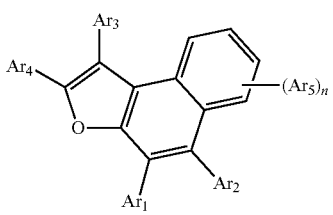

wherein, $Ar_1$ to $Ar_5$ and n are the same as those defined in Formula 1.

In addition, it is preferable that the compound that is represented by Formula 1 according to the present invention is represented by the following Formula 4:

[Formula 4]

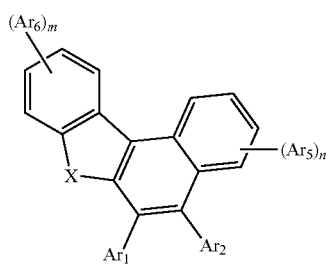

wherein X is S or O, m and n are each independently 0 to 4, $Ar_1$, $Ar_2$, $Ar_5$ and $Ar_6$ and n are the same as definition of $Ar_1$ to $Ar_5$ of Formula 1.

In the compound that is represented by Formula 1, it is preferable that $Ar_1$ is $C_6$~$C_{60}$ aryl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_6$~$C_{30}$ aryloxy group, $C_1$~$C_{30}$ alkylthioxy group, $C_6$~$C_{30}$ arylthioxy group, $C_3$~$C_{30}$ cycloalkyl group, $C_2$~$C_{30}$ heterocycloalkyl group, substituted or unsubstituted $C_1$~$C_{30}$ alkylaminyl group, substituted or unsubstituted $C_1$~$C_{30}$ aralkylaminyl group, substituted or unsubstituted $C_6$~$C_{60}$ arylaminyl group, substituted or unsubstituted $C_6$~$C_{60}$ aryl group and substituted or unsubstituted $C_3$~$C_{60}$ heteroaryl group.

In addition, in the compound that is represented by Formula 1, it is preferable that $Ar_1$ is $C_6$~$C_{60}$ heteroaryl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_6$~$C_{30}$ aryloxy group, $C_1$~$C_{30}$ alkylthioxy group, $C_6$~$C_{30}$ arylthioxy group, $C_3$~$C_{30}$ cycloalkyl group, $C_2$~$C_{30}$ heterocycloalkyl group, substituted or unsubstituted $C_1$~$C_{30}$ alkylaminyl group, substituted or unsubstituted $C_1$~$C_{30}$ aralkylaminyl group, substituted or unsubstituted $C_6$~$C_{60}$ arylaminyl group, substituted or unsubstituted $C_6$~$C_{60}$ aryl group and substituted or unsubstituted $C_3$~$C_{60}$ heteroaryl group.

In addition, in the compound that is represented by Formula 1, it is preferable that $Ar_2$ to $Ar_5$ may be the same as or different from each other, and each independently $C_6$~$C_{60}$ arylaminyl group that is substituted or unsubstituted by one or more groups that are selected from the group consisting of heavy hydrogen atom, halogen group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{30}$ heteroaryl group.

In addition, in the compound that is represented by Formula 1, it is preferable that $Ar_2$ to $Ar_5$ may be the same as or different from each other, and each independently $C_6$~$C_{60}$ aryl group that is substituted or unsubstituted by one or more groups that are selected from the group consisting of heavy hydrogen atom, halogen group, amino group, nitrile group, nitro group, $C_1$~$C_{30}$ alkyl group, $C_2$~$C_{30}$ alkenyl group, $C_1$~$C_{30}$ alkoxy group, $C_6$~$C_{30}$ aryloxy group, $C_1$~$C_{30}$ alkylthioxy group, $C_6$~$C_{30}$ arylthioxy group, $C_3$~$C_{30}$ cycloalkyl group, $C_2$~$C_{30}$ heterocycloalkyl group, substituted or unsubstituted $C_1$~$C_{30}$ alkylaminyl group, substituted or unsubstituted $C_1$~$C_{30}$ aralkylaminyl group, substituted or unsubstituted $C_6$~$C_{60}$ arylaminyl group, $C_6$~$C_{60}$ aryl group and $C_3$~$C_{60}$ heteroaryl group.

In addition, in the compound that is represented by Formula 1, it is preferable that $Ar_2$ to $Ar_5$ may be the same as or different from each other, and each independently $C_3$~$C_{60}$ heteroaryl group that is substituted or unsubstituted by one or more groups that are selected from the group consisting of heavy hydrogen atom, halogen group, amino group, nitrile group, nitro group, $C_1$~$C_{30}$ alkyl group, $C_2$~$C_{30}$ alkenyl group, $C_1$~$C_{30}$ alkoxy group, $C_6$~$C_{30}$ aryloxy group, $C_1$~$C_{30}$ alkylthioxy group, $C_6$~$C_{30}$ arylthioxy group, $C_3$~$C_{30}$ cycloalkyl group, $C_2$~$C_{30}$ heterocycloalkyl group, substituted or unsubstituted $C_1$~$C_{30}$ alkylaminyl group, substituted or unsubstituted $C_1$~$C_{30}$ aralkylaminyl group, substituted or unsubstituted $C_6$~$C_{60}$ arylaminyl group, $C_6$~$C_{60}$ aryl group and $C_3$~$C_{60}$ heteroaryl group.

In addition, in the compound that is represented by Formulas 2 to 4, it is preferable that $Ar_1$ to $Ar_6$ may be the same as or different from each other, and each independently selected from the group consisting of $C_6$~$C_{60}$ arylaminyl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group; $C_6$~$C_{60}$ aryl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_6$~$C_{30}$ aryloxy group, $C_1$~$C_{30}$ alkylthioxy group, $C_6$~$C_{30}$ arylthioxy group, $C_3$~$C_{30}$ cycloalkyl group, $C_2$~$C_{30}$ heterocycloalkyl group, substituted or unsubstituted $C_1$~$C_{30}$ alkylaminyl group, substituted or unsubstituted $C_1$~$C_{30}$ aralkylaminyl group, substituted or unsubstituted $C_6$~$C_{60}$ arylaminyl group, $C_6$~$C_{60}$ aryl group and $C_3$~$C_{60}$ heteroaryl group; and $C_3$~$C_{60}$ heteroaryl group that is substituted or unsubstituted by one or more groups that are selected from the group consisting of heavy hydrogen atom, halogen group, hydroxy group, formyl group, amino group, nitrile group, nitro group, $C_1$~$C_{30}$ alkyl group, $C_2$~$C_{30}$ alkenyl group, $C_1$~$C_{30}$ alkoxy group, $C_6$~$C_{30}$ aryloxy group, $C_1$~$C_{30}$ alkylthioxy group, $C_6$~$C_{30}$ arylthioxy group, $C_3$~$C_{30}$ cycloalkyl group, $C_2$~$C_{30}$ heterocycloalkyl group, substituted or unsubstituted $C_1$~$C_{30}$ alkylaminyl group, substituted or unsubstituted $C_1$~$C_{30}$ aralkylaminyl group, substituted or unsubstituted $C_6$~$C_{60}$ arylaminyl group, $C_6$~$C_{60}$ aryl group and $C_3$~$C_{60}$ heteroaryl group.

In Formula 1, the arylaminyl group is an amine group that is substituted by the above-mentioned aryl group, and is preferably the following groups but is not limited thereto.

1
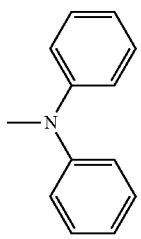

2
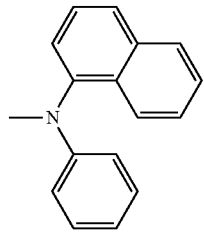

3
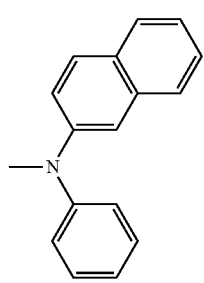

4
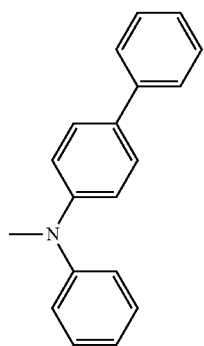

5
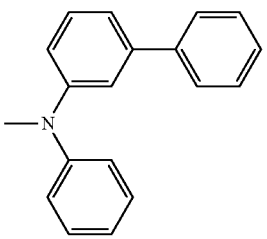

6
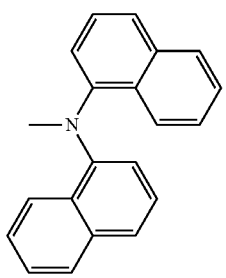

7
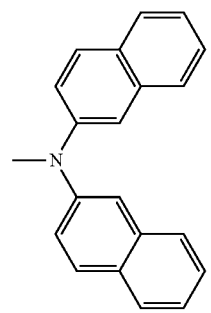

8
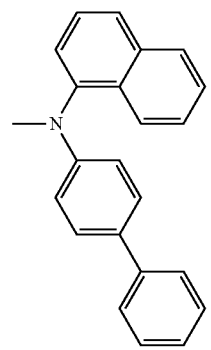

9
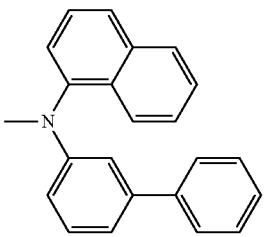

10
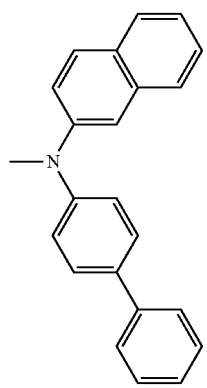
11
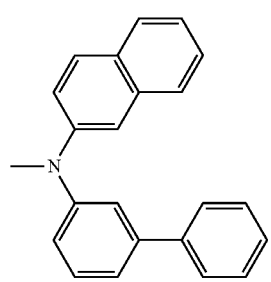
12
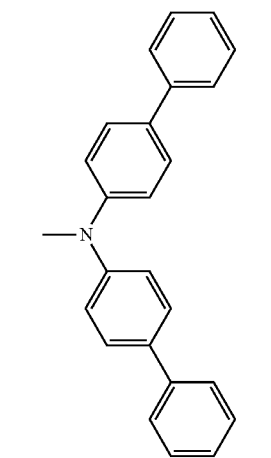
13
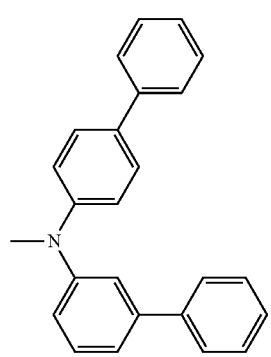
14
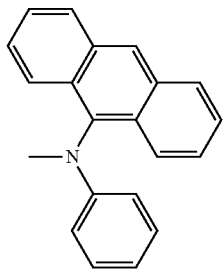
15
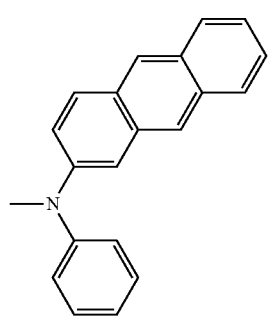
16
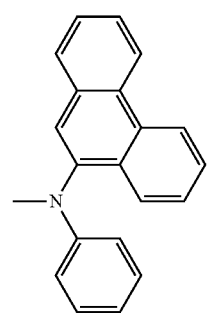
17
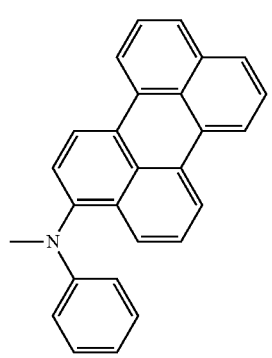
18
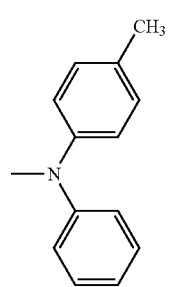

19
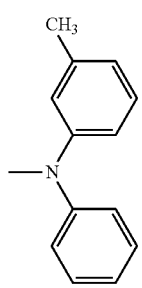
20
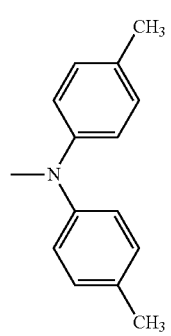
21
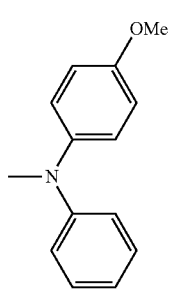
22
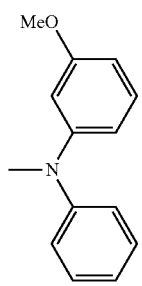
23
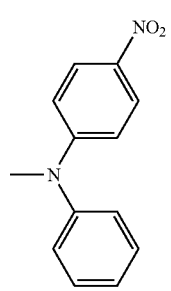
24
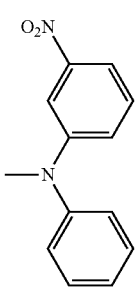
25
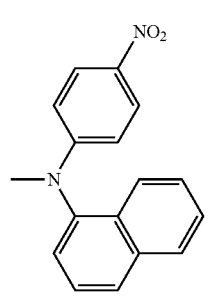
26
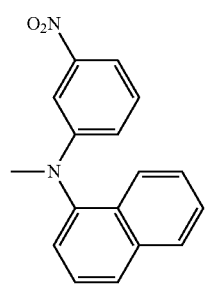
27
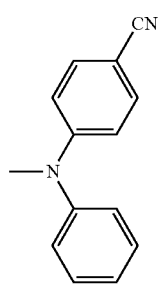
28
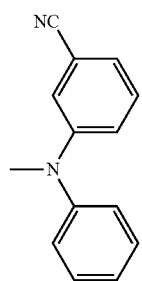

| 29 | 34 |
|---|---|
| 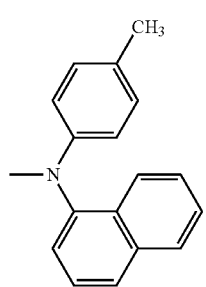 | 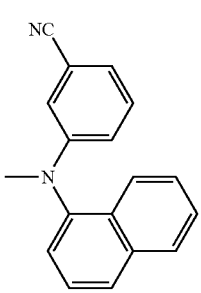 |
| 30 | 35 |
| 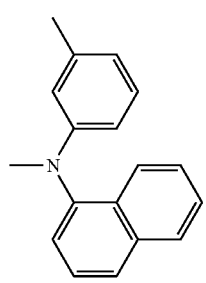 | 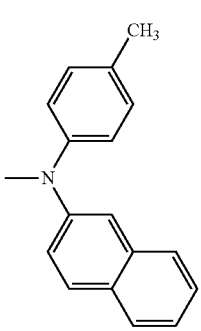 |
| 31 | 36 |
| 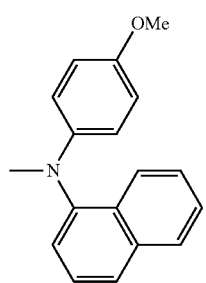 | 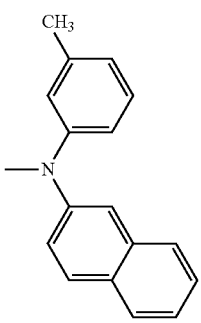 |
| 32 | 37 |
| 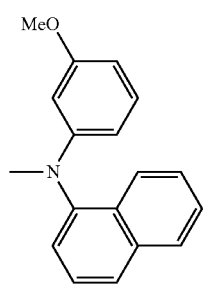 | 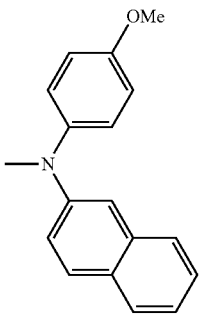 |
| 33 | 38 |
| 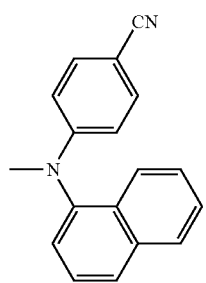 | 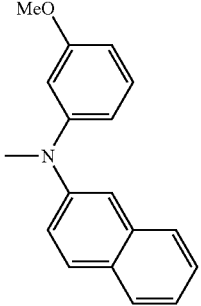 |

39
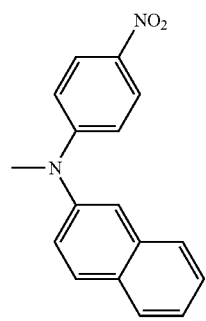
40
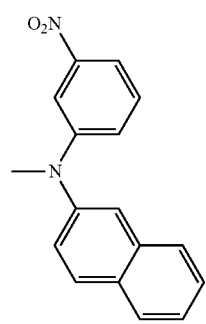
41
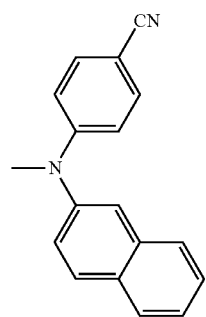
42
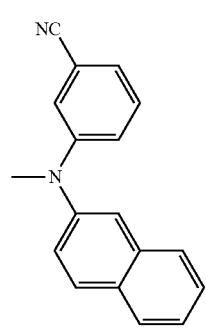
43
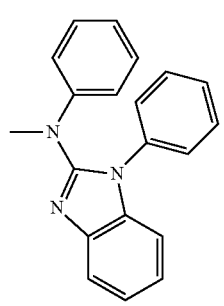
44
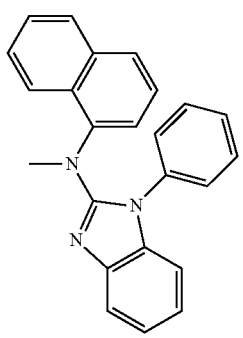
45
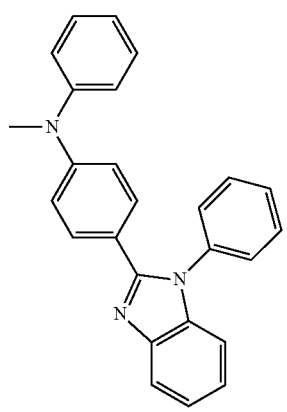
46
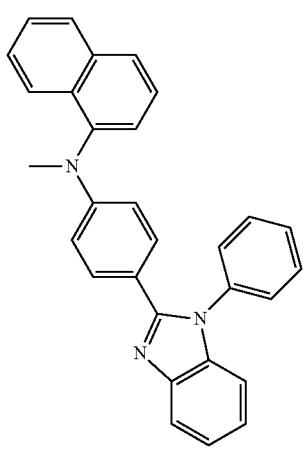
47
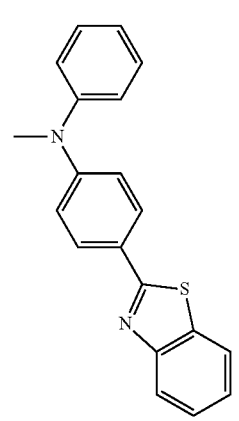

48
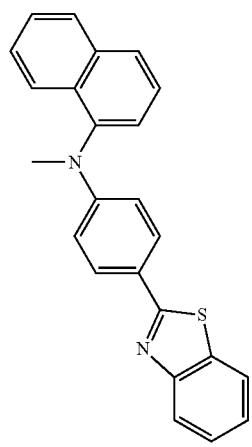
49
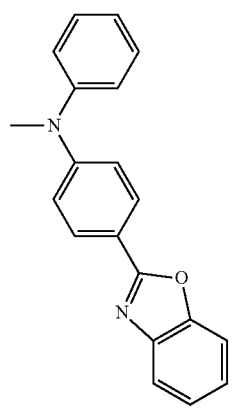
50
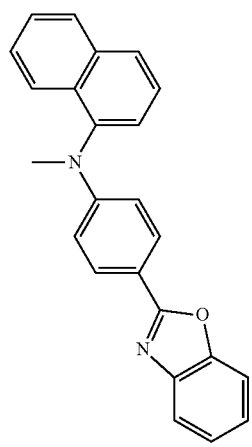
51
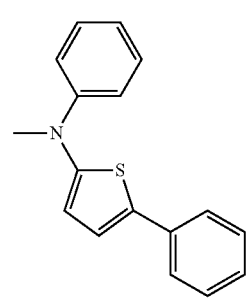
52
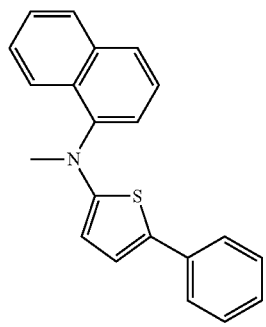
53
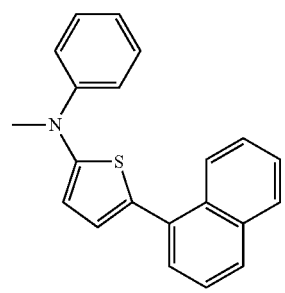
54
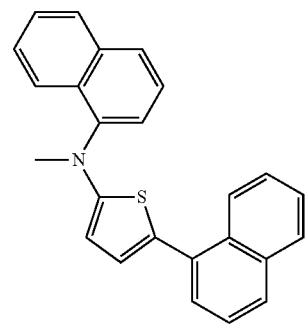
55
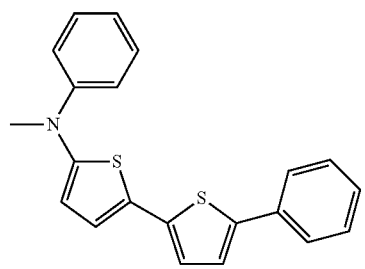
56
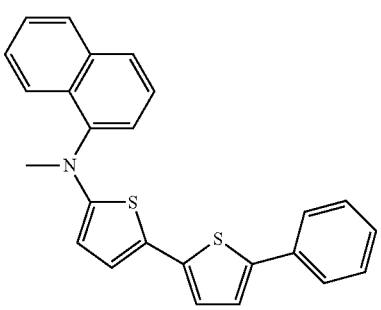

57
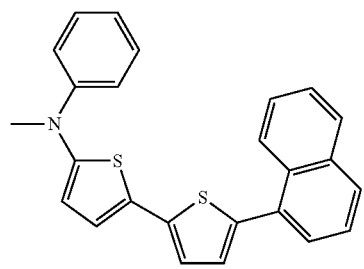
58
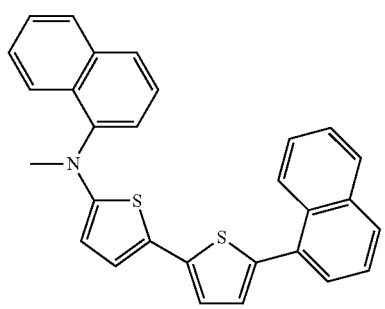
59
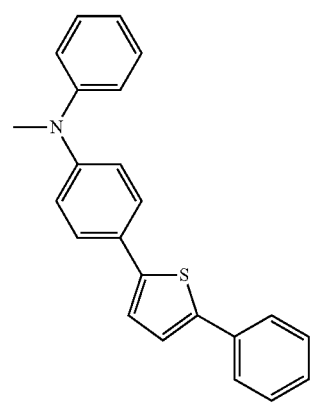
60
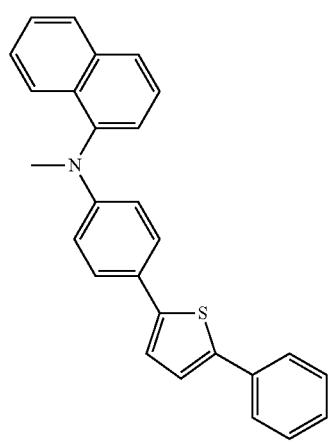
61
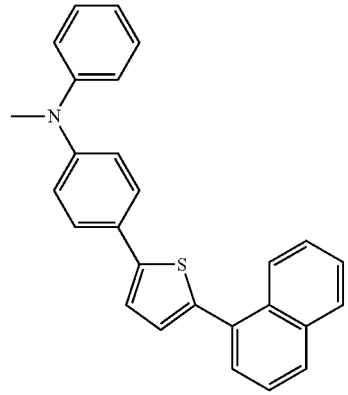
62
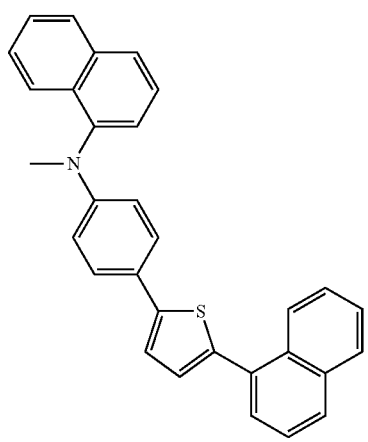
63
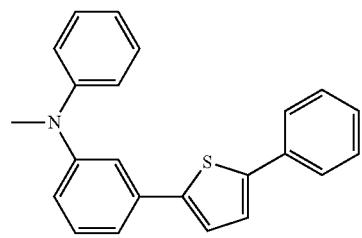
64
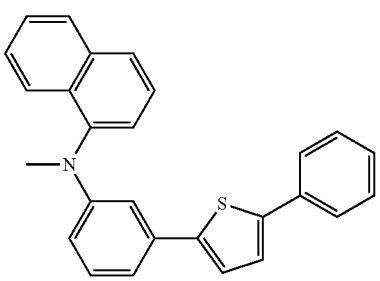
65
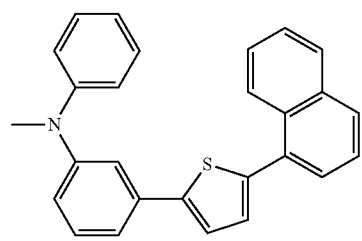

66
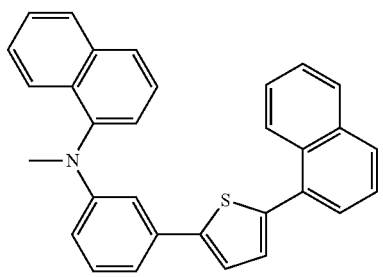
67
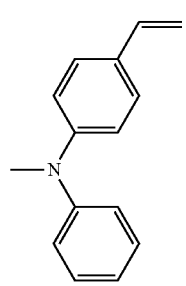
68
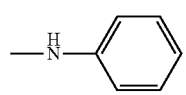
69
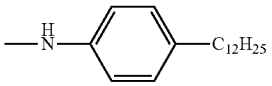
70
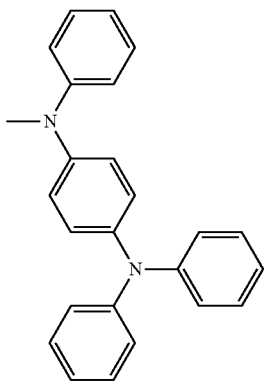
71
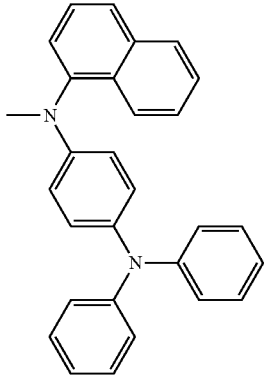
72
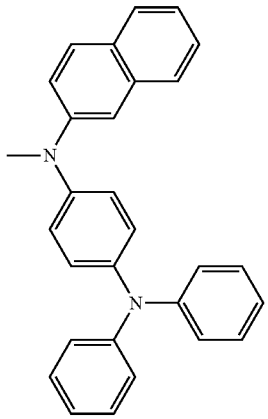
73
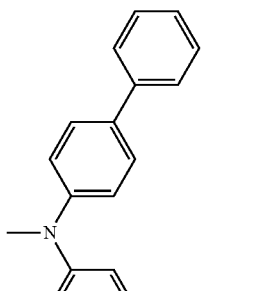
74
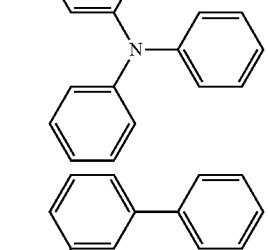
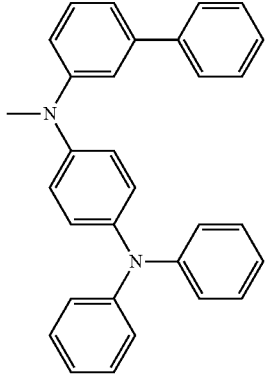
75
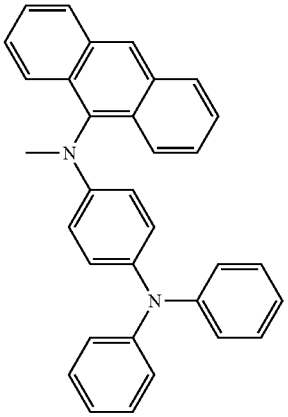

76
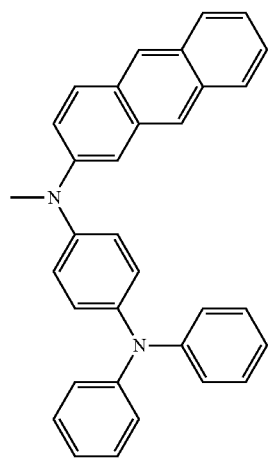
77
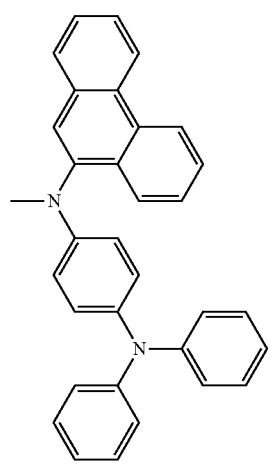
78
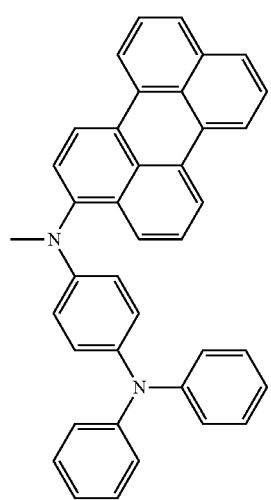
79
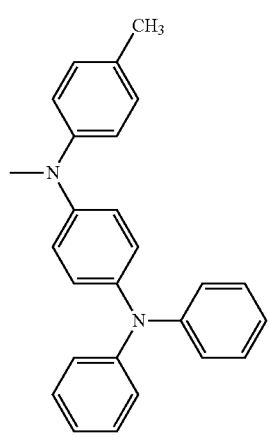
80
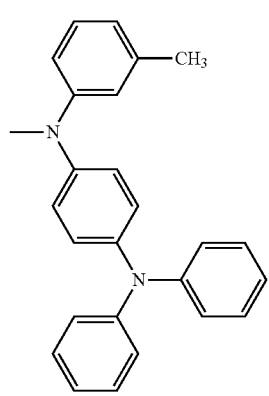
81
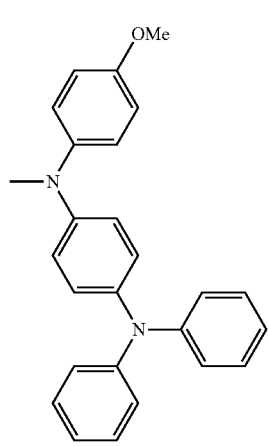
82
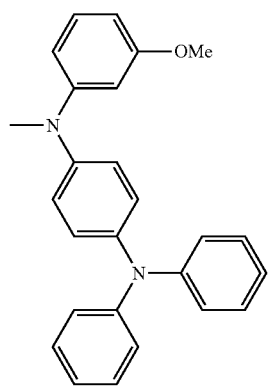

83
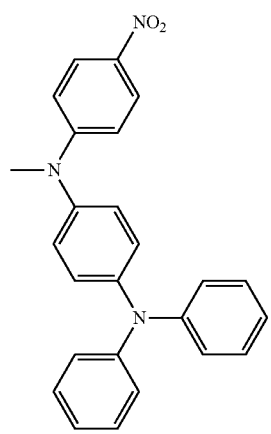
84
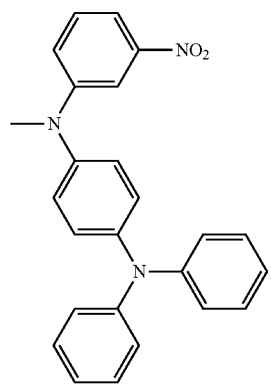
85
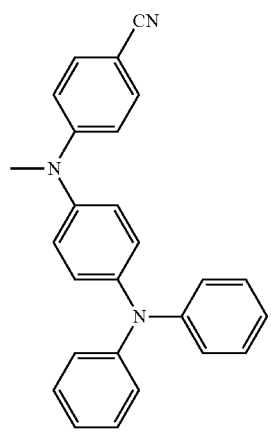
86
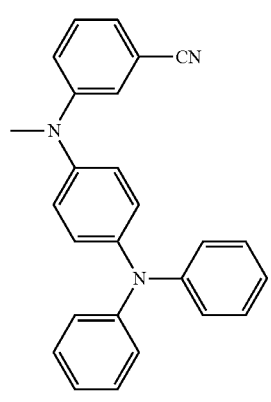
87
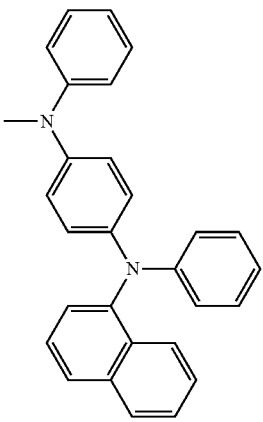
88
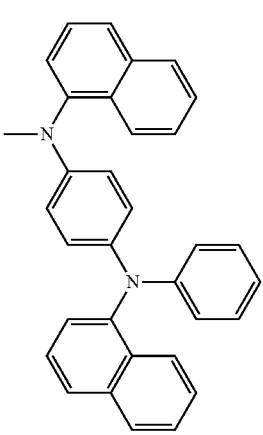
89
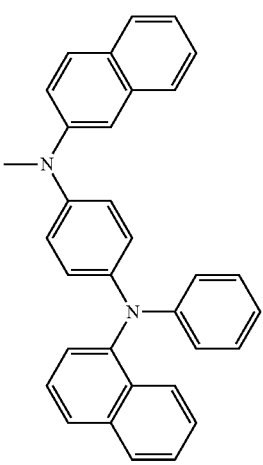

90
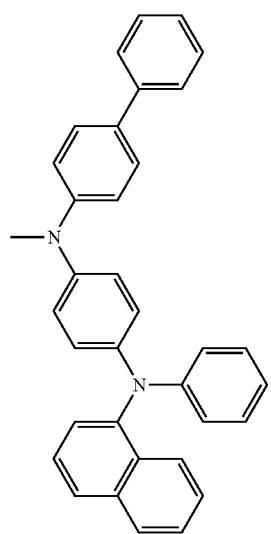
91
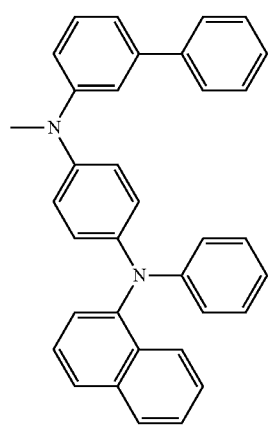
92
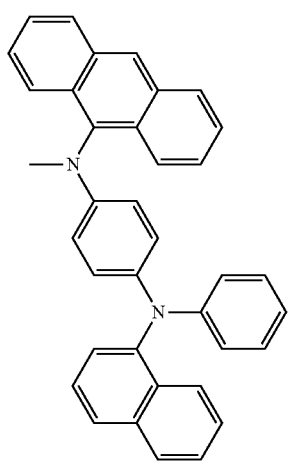
93
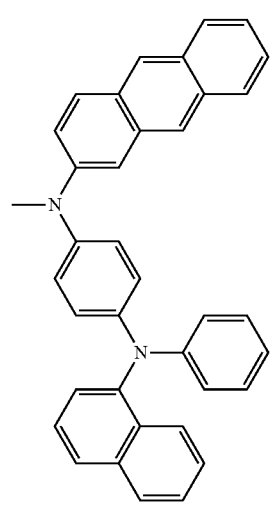
94
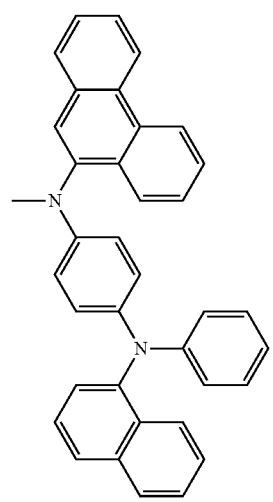
95
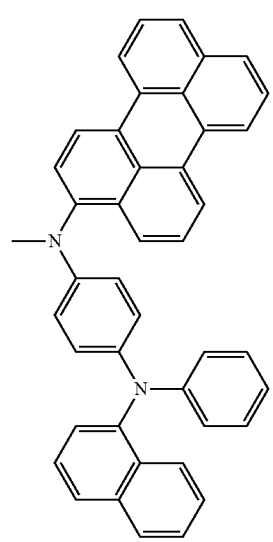

96
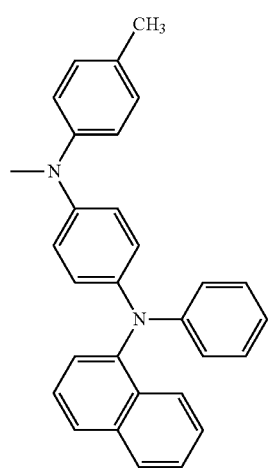
97
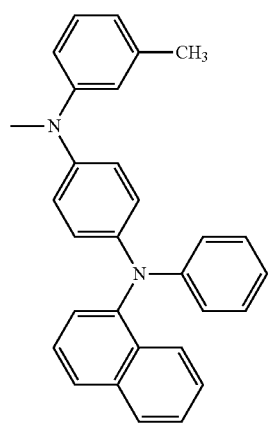
98
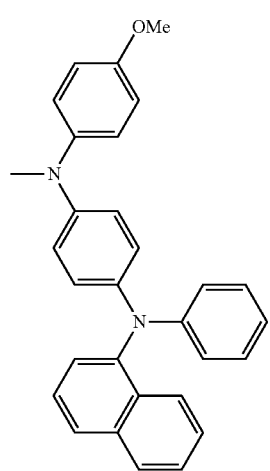
99
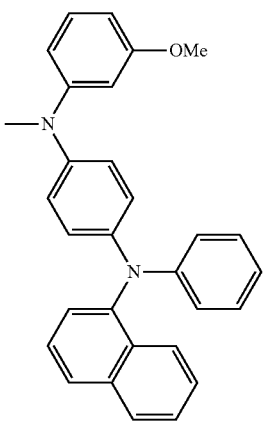
100
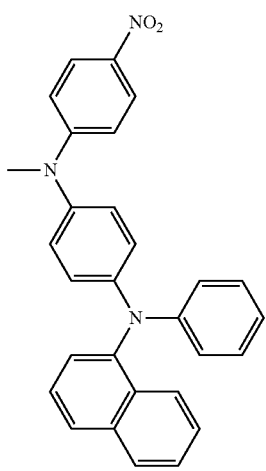
101
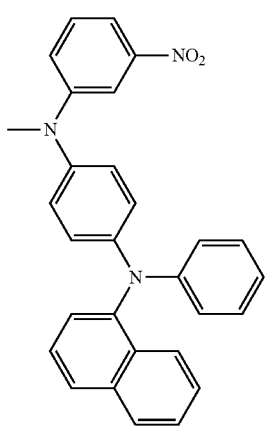

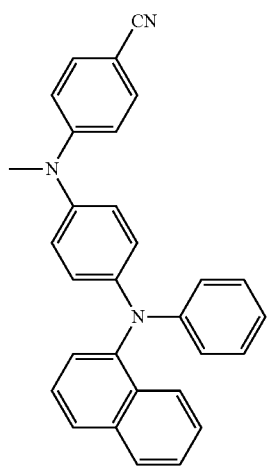 102
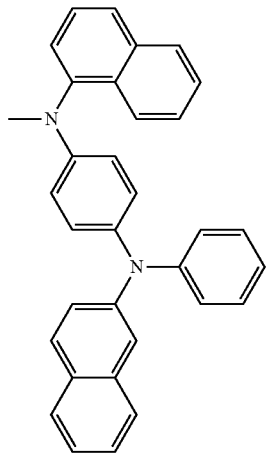 105
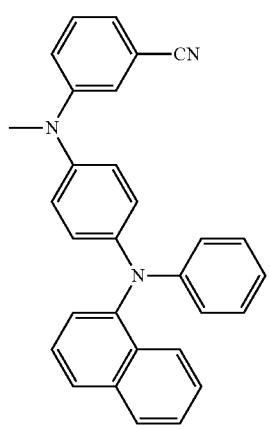 103
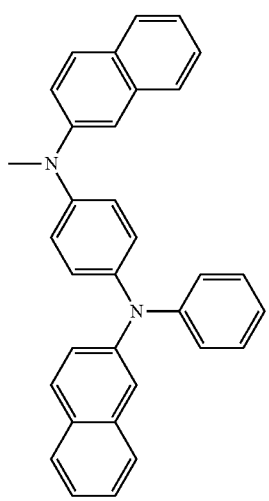 106
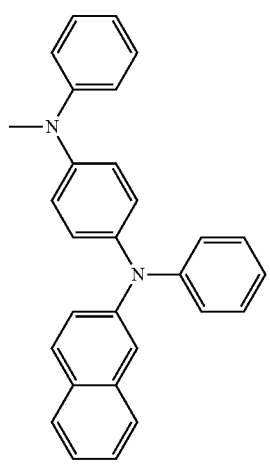 104
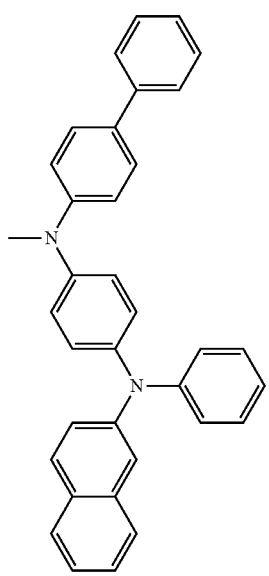 107

108
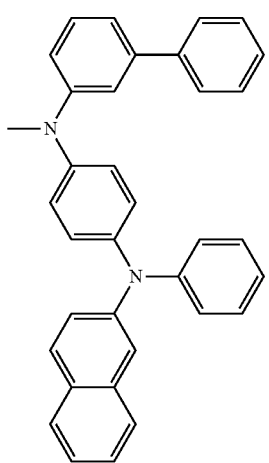
109
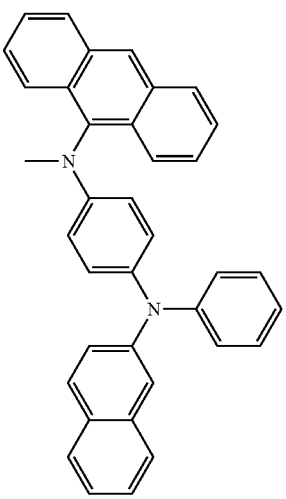
110
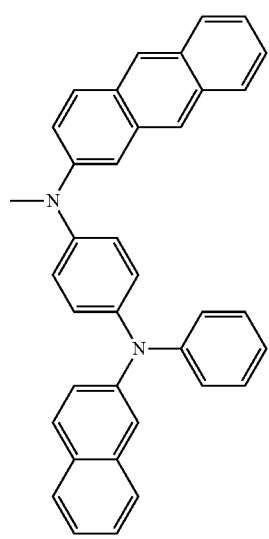
111
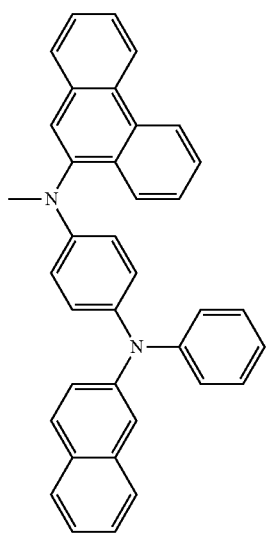
112
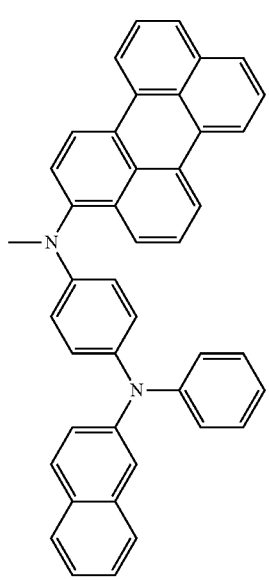
113
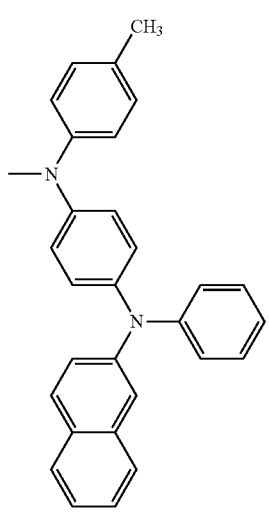

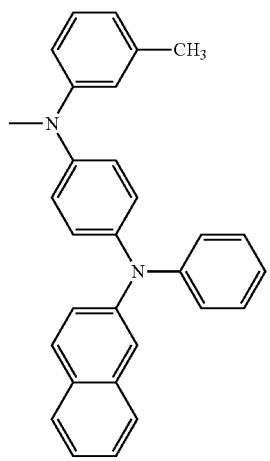
114
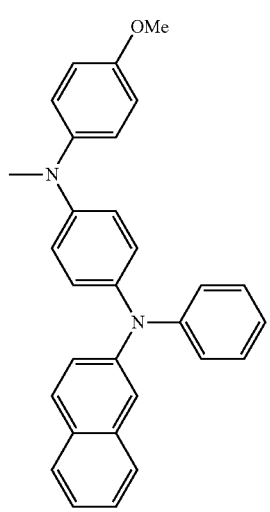
115
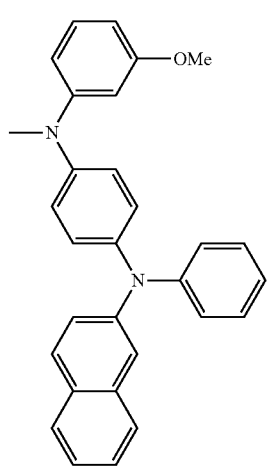
116
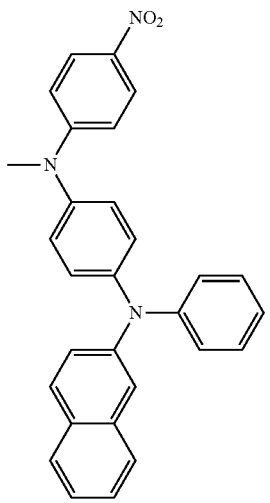
117
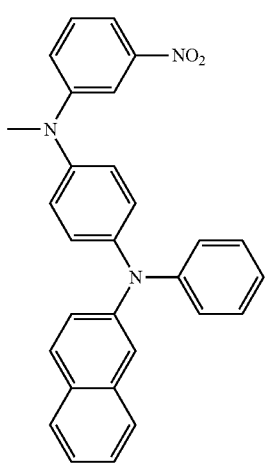
118
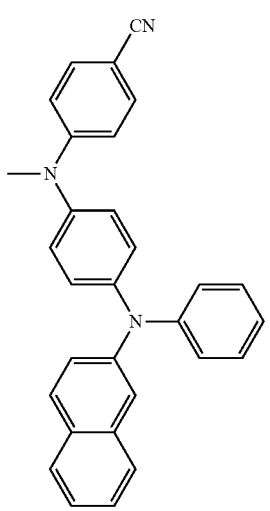
119

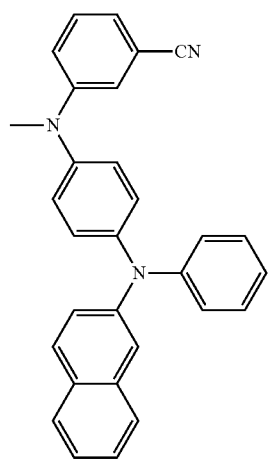
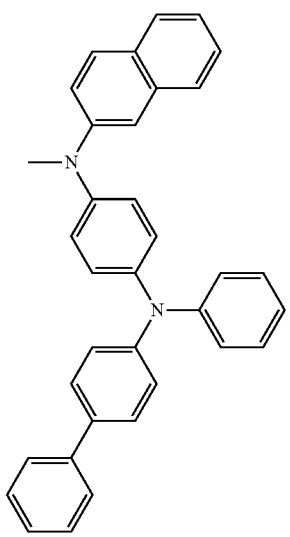

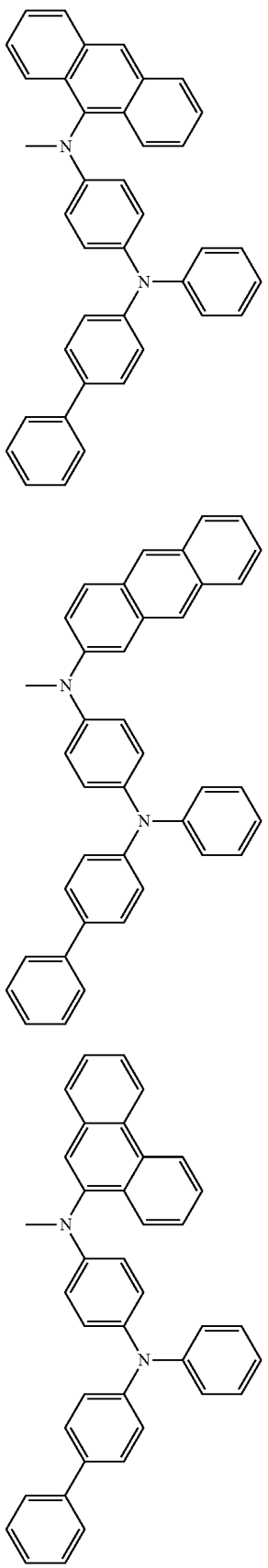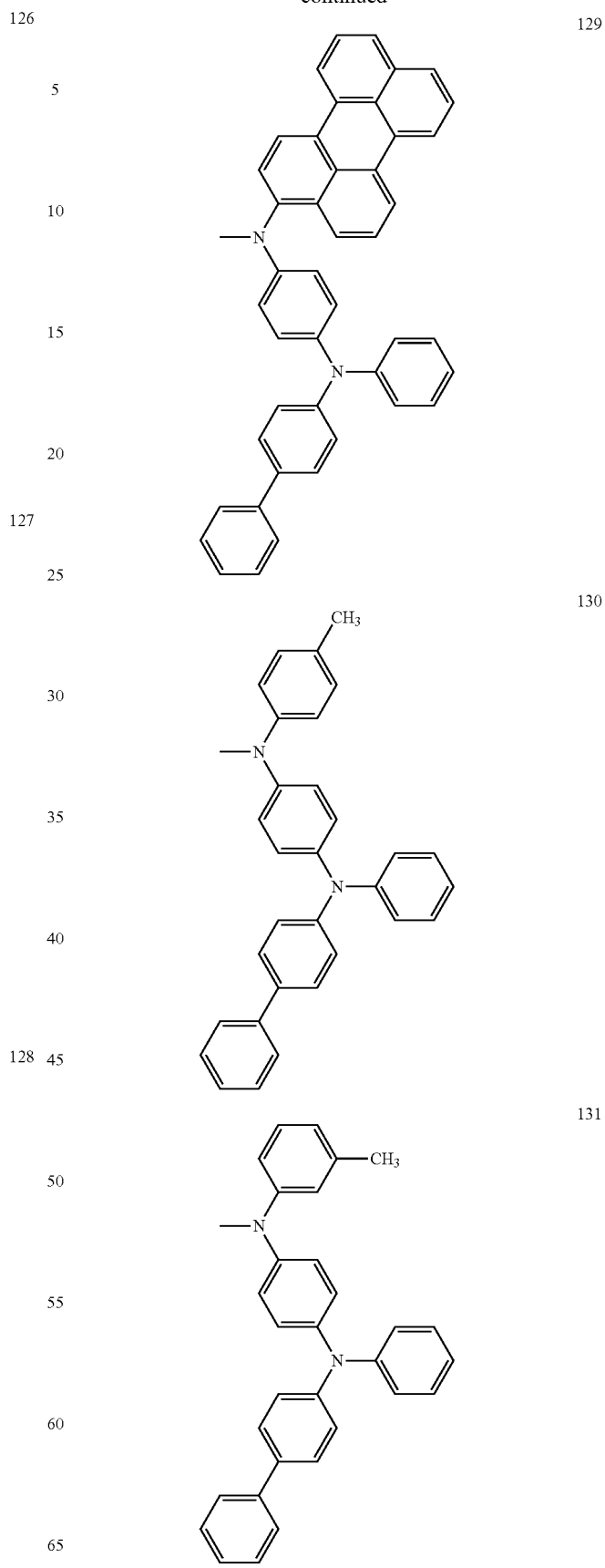

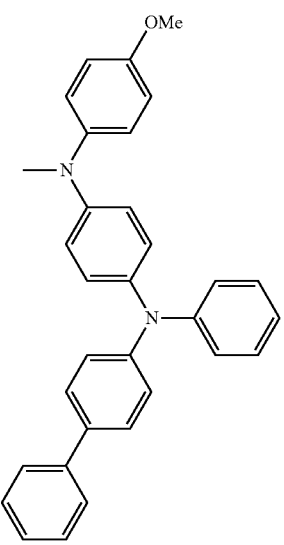
132
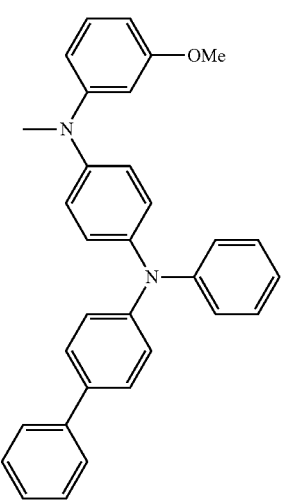
133
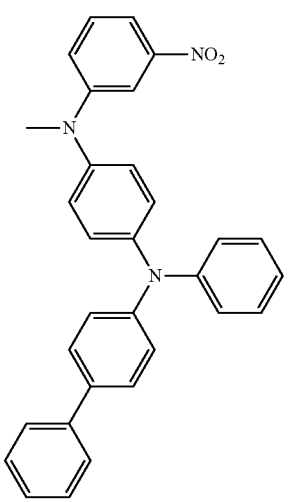
135
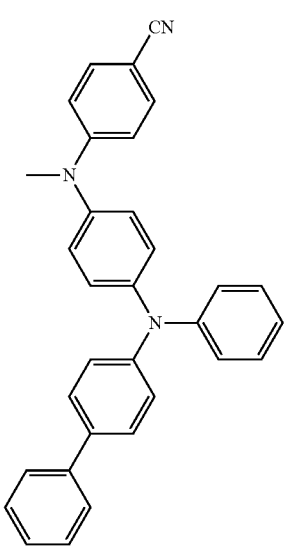
136
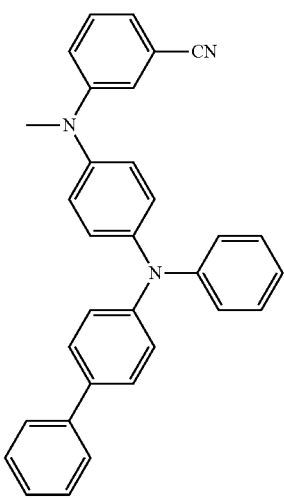
137

138

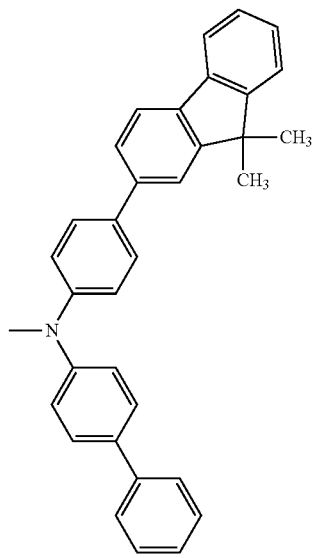

139

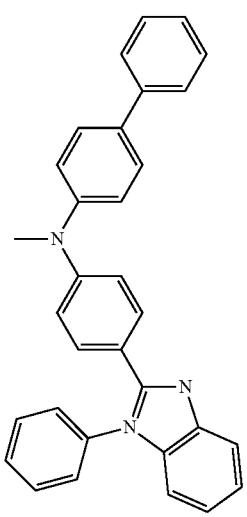

Preferable examples of the aryl group may be selected from the groups that are represented by the following Structural Formulas:

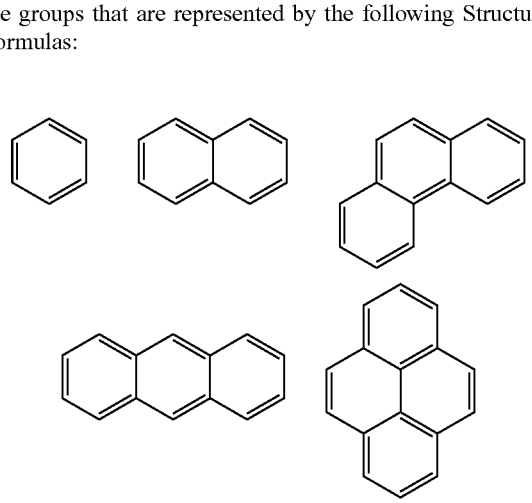

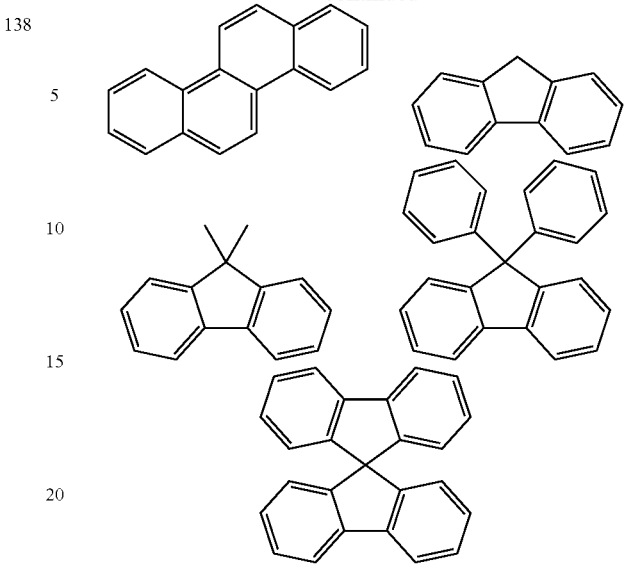

Preferable examples of the heteroaryl group may be selected from the groups that are represented by the following Structural Formulas:

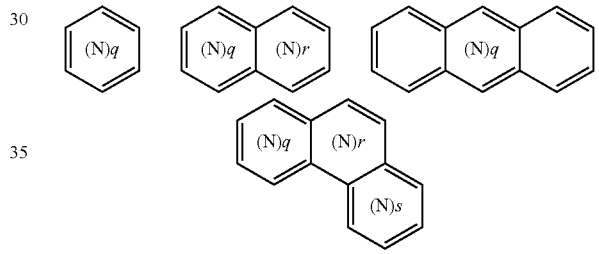

In the above Formulas, (N)q, (N)r and (N)s means that at least one nitrogen atoms exist instead of a carbon atom in a benzene ring. In (N)q, (N)r and (N)s, q, r and s are each an integer in the range of 1 to 3.

In addition, it may be selected from the compounds or condensated ring compounds thereof having the following structure including at least one of N, S, or O in the ring.

The substituent group that is used in the present invention may be defined by the following description.

The alkyl group, alkoxy group, and alkenyl group may be a straight chain or a branched chain, and the number of carbon atoms is not particularly limited but it is preferable that it is in the range of 1 to 30. In particular, in the case of when the substituent group of Formula 1 is the alkyl group, the number of carbon atoms of the alkyl group does not affect a conjugation length of the compound, but affects an application method to the organic light emitting device of the compound, for example, application of a vacuum deposition method or a solution coating method. Accordingly, the number of carbon atoms of the alkyl group is not particularly limited.

As examples of the alkyl group, there are methyl group, ethyl group, propyl group, isopropyl group, butyl group, t-butyl group, pentyl group, hexyl group and heptyl group, but it is not limited thereto.

As examples of the alkenyl group, there is the alkenyl group that is bonded with the aryl group, such as the stylbenyl group, the styrenyl group and the like.

The aryl group may be a monocycle or a polycycle, and the number of carbon atoms is not particularly limited, but it is preferable that it is in the range of 6 to 60. As examples of the monocyclic aryl group, there are the phenyl group, the biphenyl group, the terphenyl group, fluorene group, stilbene and the like, and as examples of the polycyclic aryl group, there are the naphthyl group, the anthracenyl group, the phenanthryl group, the pyrenyl group, the perylenyl group, the crycenyl group and the like, but the scope of the present invention is not limited thereto.

The heteroaryl group may be a monocycle or a polycycle, a heteroatom, and a ring group that includes O, N or S, and the number of carbon atoms is not particularly limited, but it is preferable that the number of carbon atoms is in the range of 3 to 60.

It is preferable that the number of carbon atoms of the cycloalkyl group is in the range of 3 to 30, which is the range that does not provide sterical hindrance, and as detailed examples thereof, cyclopentyl group or cyclohexyl group is more preferable.

As examples of the halogen group, there are fluorine, chlorine, bromine, or iodine.

The spiro bond means a ring structure that realizes bonding through one atom, and the ring structure may be a monocycle or a polycycle.

In the present specification, "substituted or unsubstituted" means that it is substituted or unsubstituted by one or more groups that are selected from the group consisting of heavy hydrogen atom, halogen group, amino group, nitrile group, nitro group, $C_1$~$C_{30}$ alkyl group, $C_2$~$C_{30}$ alkenyl group, $C_1$~$C_{30}$ alkoxy group, $C_3$~$C_{30}$ cycloalkyl group, $C_2$~$C_{30}$ heterocycloalkyl group, $C_6$~$C_{60}$ aryl group and $C_3$~$C_{60}$ heteroaryl group.

In Formula 1, it is preferable that $Ar_1$ is hydrogen, substituted or unsubstituted aryl group, or substituted or unsubstituted heteroaryl group, and in detail, it is preferable that it is hydrogen, substituted or unsubstituted phenyl group, substituted or unsubstituted naphthyl group, substituted or unsubstituted phenanthryl group, substituted or unsubstituted pyridyl group. At this time, as the substituent group, heavy hydrogen, halogen atoms such as fluorine, chlorine, and bromine, hydroxy group, nitrile group, nitro group, amino group, substituted amin group, alkoxy group such as methoxy group, alkyl group such as methyl group, ethyl group, tert-butyl group, and carbonyl group are preferable. It is more preferable that $Ar_1$ is hydrogen or phenyl group.

In Formula 1, it is preferable that $Ar_2$, $Ar_3$ and $Ar_4$ are in detail the substituent groups described in the following Table, and the following groups may be substituted by one or more groups of heavy hydrogen atom, halogen atoms such as fluorine, chlorine, iodine and the like, nitrile group, heteroaryl group, aryl group in which the heavy hydrogen atom is substituted, nitrile group substituted aryl group, arylaminyl group and arylaminyl group substituted aryl group.

However, the scope of the present invention is not limited to the following examples.

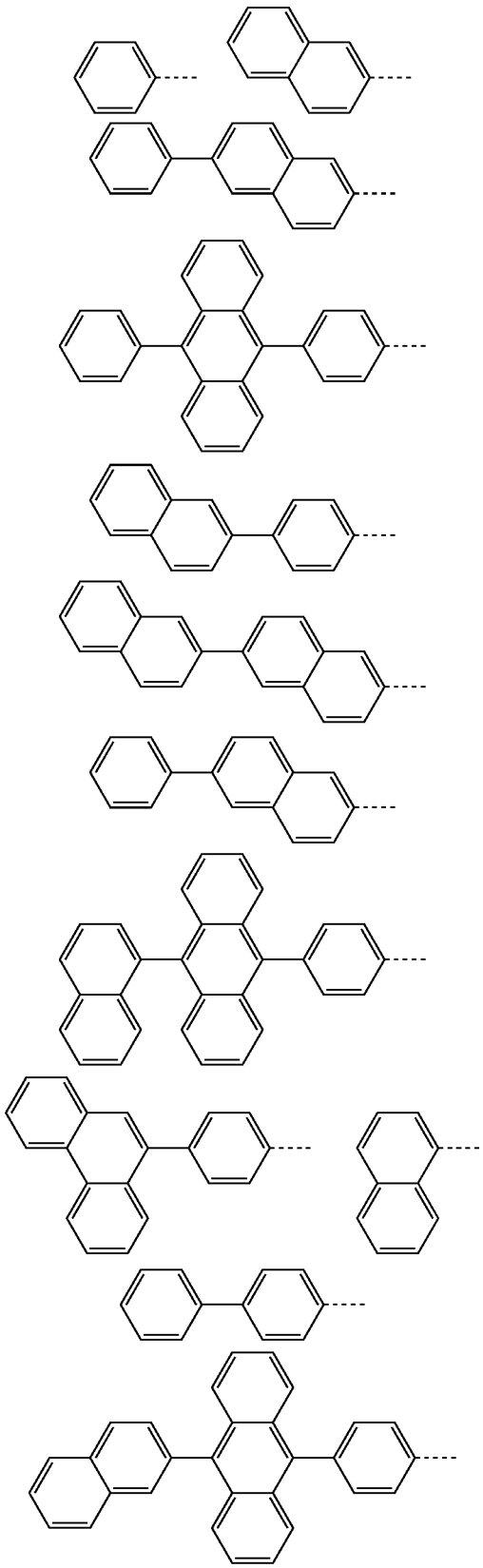

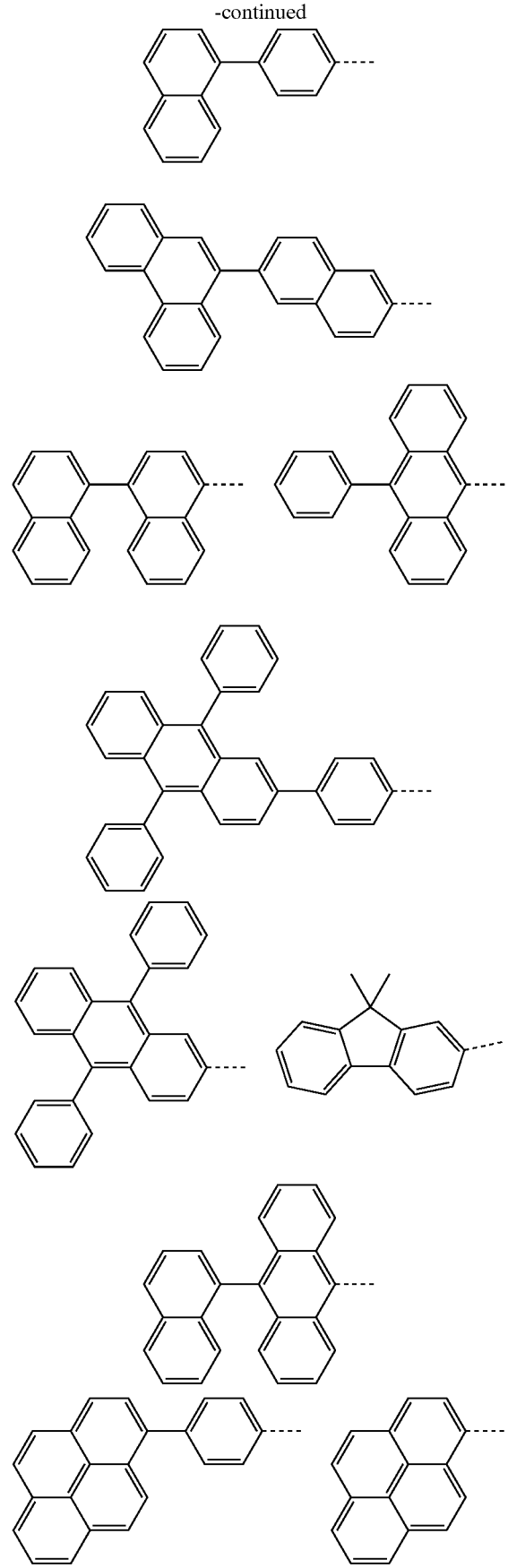
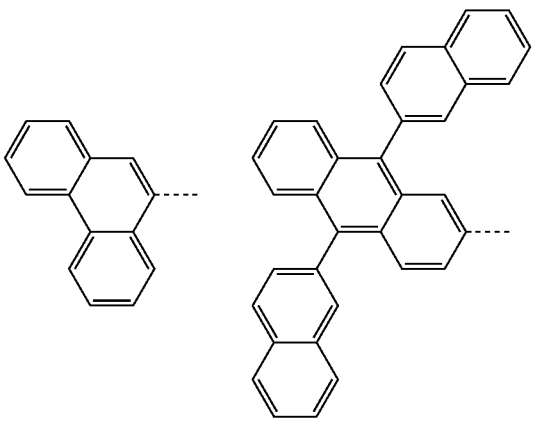
In addition, the present invention provides a method for manufacturing the derivative that is represented by Formula 1.
According to an embodiment of the present invention, in Formula 1, the manufacturing method of Formula 1 may be carried out in the same sequence as the following Reaction Equation 1, but is not limited thereto.
[Reaction Equation 1]
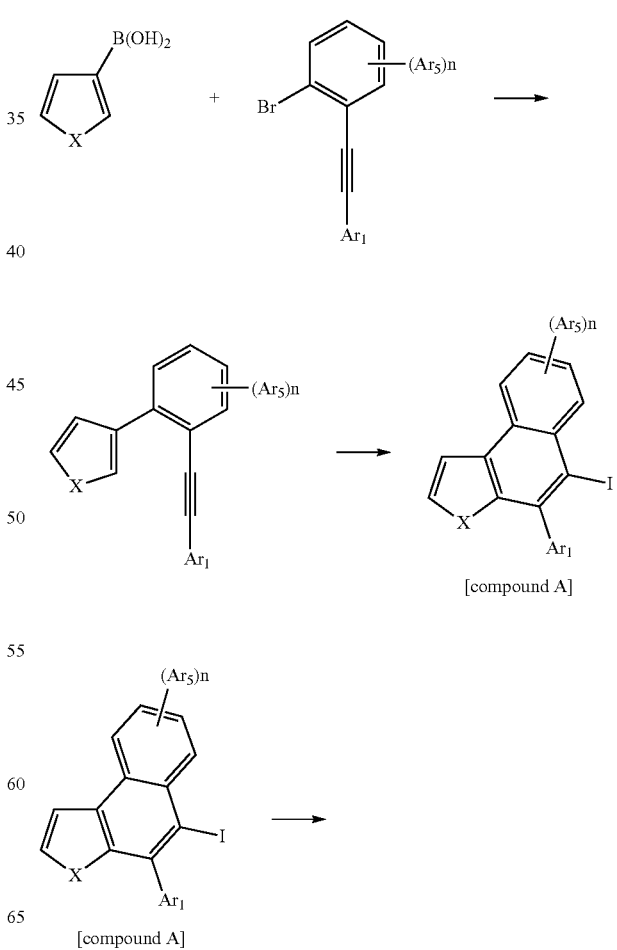

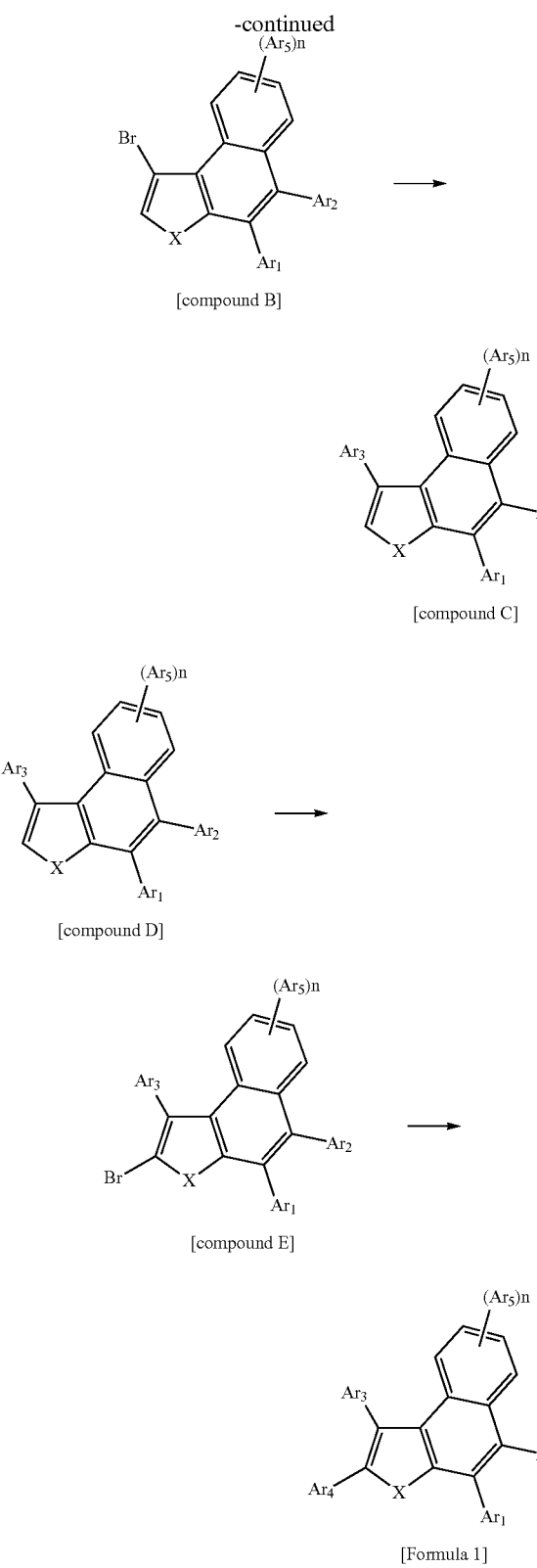

[compound B]

[compound C]

[compound D]

[compound E]

[Formula 1]

In Reaction Equation 1, $Ar_1$ to $Ar_5$ are the same as those defined in Formula 1.

According to Reaction Equation 1, pentagonal heteroaryl boronic acid is subjected to Suzuki coupling in conjunction with the alkyne compound to which the halogen group is introduced under the Pd catalyst. To the manufactured compound, the mixture in which ICl is dissolved in $CH_2Cl_2$ is dropped and agitated according to the manufacturing method that is described in the document [Journal of Organic Chemistry 2005, 70(9), 3511-3517], such that the compound A to which the iodo group is introduced is obtained in a solid form. By the manufacturing method that includes the method in which under the Pd catalyst, after the boronic acid or boron ester reactants are subjected to Suzuki Coupling and $Ar_2$ is introduced, the bromo group is introduced by NBS or $Br_2$, and while under the Pd catalyst, the Suzuki coupling and the bromination reaction are repeated, $Ar_3$, $Ar_4$ are sequentially introduced, the compound of Formula 1 according to the present invention may be manufactured.

According to another embodiment of the present invention, in Reaction Equation 1, by using pentagonal 5-heteroaryl boronic acid in which the benzene ring is condensated instead of the pentagonal heteroaryl boronic acid, the compound of Formula 4 may be manufactured.

As shown in Reaction Equations 1-1 to 1-4, $Ar_1$ may be introduced from the substituted or unsubstituted acetylene group. In detail, in the case of $Ar_1$, the phenyl group is intorduced from the substituted or unsubstituted phenylacetylene, and the naphthyl group may be introduced from the substituted or unsubstituted naphthylacetylene. In addition, from the substituted or unsubstituted phenanthrylacetylene, the phenanthryl group may be introduced, and from the substituted or unsubstituted pyridylacetylene, the pyridyl group may be introduced. $Ar_1$ may be substituted by $Ar_1'$, $Ar_1'$ may introduce the other substituent groups by a general known reaction. The possible acetylene compound is shown in Table 2.

[Reaction Eq. 1-1]

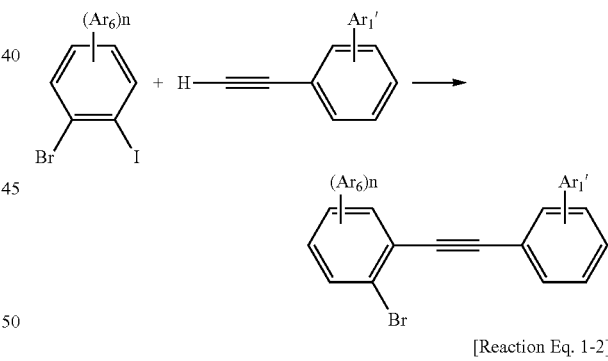

[Reaction Eq. 1-2]

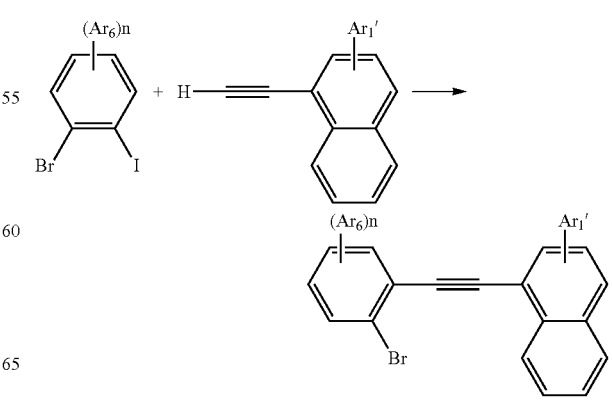

51
-continued
[Reaction Eq. 1-3]
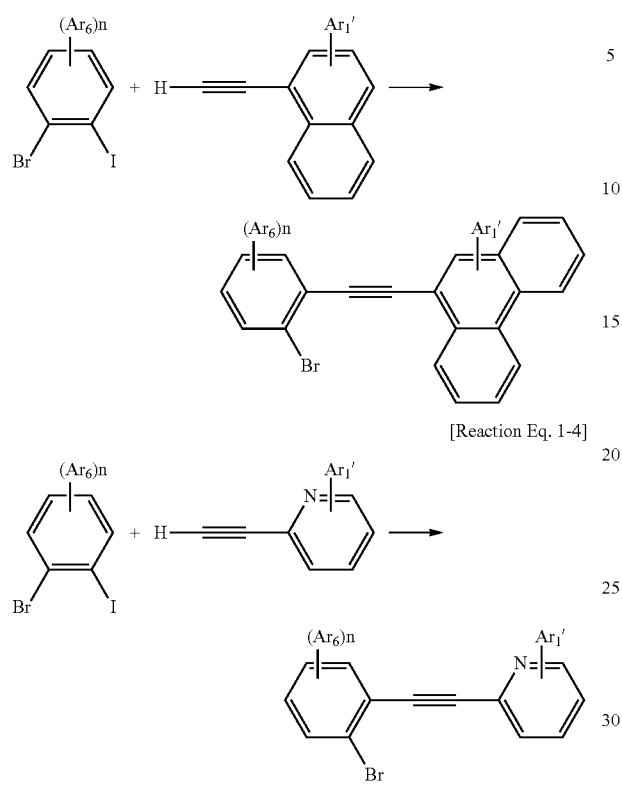
[Reaction Eq. 1-4]
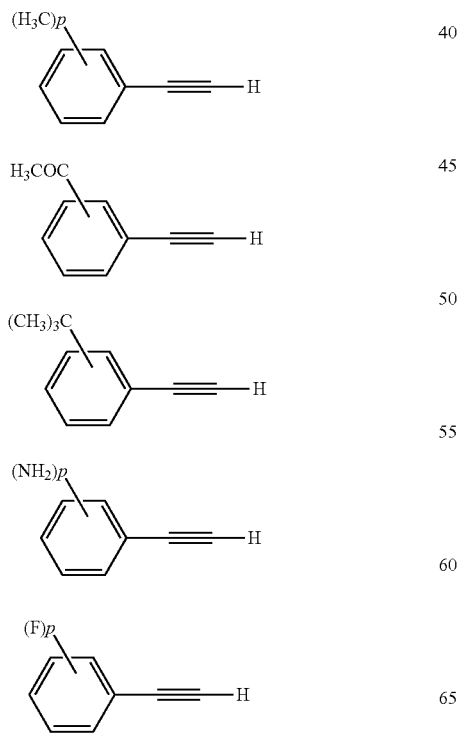
52
TABLE 2
| Reactant |
|---|
| 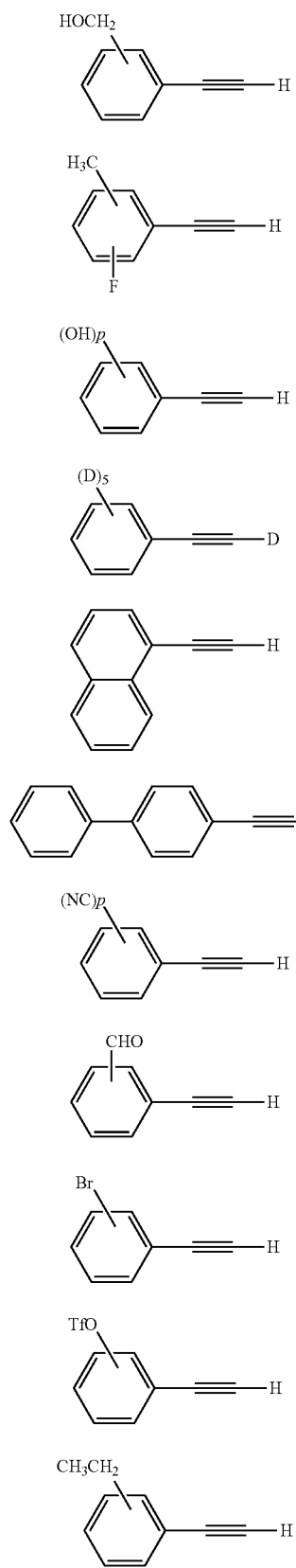 |

TABLE 2-continued

Reactant

[Structure: 4-nitrophenylacetylene — O₂N-C₆H₄-C≡C-H]

[Structure: 4-(R₁)(R₂)N-phenylacetylene — (R₁)(R₂)N-C₆H₄-C≡C-H]

[Structure: 4-acetylphenylacetylene — CH₃CO-C₆H₄-C≡C-H]

[Structure: 4-trifluoromethylphenylacetylene — F₃C-C₆H₄-C≡C-H]

[Structure: 2-ethynylpyridine]

[Structure: 6-methyl-2-ethynylpyridine, H₃C on pyridine]

[Structure: ethynylphenanthrene]

[Structure: 6-acetoxy-2-ethynylnaphthalene — CH₃CO-naphthyl-C≡C-H]

In Table 2, p is an integer in the range of 0 to 5.

In Reaction Equations 1-1 to 1-4 and Table 2, $Ar_1$ is preferably substituted or unsubstituted phenyl group, substituted or unsubstituted naphthyl group, substituted or unsubstituted phenanthryl group, substituted or unsubstituted pyridyl group, and more preferably phenyl group.

At this time, as the substituent group, as shown in Table 2, heavy hydrogen, halogen atoms such as fluorine, chlorine, and bromine, hydroxy group, nitrile group, nitro group, amino group, substituted amin group, alkoxy group such as methoxy group, alkyl group such as methyl group, ethyl group, tert-butyl group, and carbonyl group are preferable.

In addition, at this time, as the substituent group, when the substituent group $Ar_1'$ introduced to the acetylene group is Br—, TfO—, since the substituent group such as aryl group, heteroaryl group, arylamin group is easily introduced under the Pd catalyst, as defined in Formula 1, $Ar_1$ may be aryl group or heteroaryl group introduced as various substituent groups.

In addition, at this time, as the substituent group, when the substituent group $Ar_1'$ which is introduced to the acetylene group is —CHO (formyl group), by a known reaction, since the heteroaryl group such as imidazole group, oxazole group, thiazole group including N, O or S may be manufactured, as defined in Formula 1, $Ar_1$ may be the aryl group to which the heteroaryl group is introduced.

In Formulas 1 to 4, $Ar_2$ is preferably hydrogen, heavy hydrogen, iodo group, boronic acid, silyl group, and alkyl group. This is because $Ar_2$ introduced by the iodo may introduce hydrogen, heavy hydrogen, silyl group, alkyl group by lithiation.

In addition, $Ar_2$ may be substituted by substituted or unsubstituted aryl group, substituted or unsubstituted heteroaryl group, or substituted or unsubstituted arylamin group and the like. These substituents may be introduced under the Pd catalyst through Suzuki coupling or arylamin coupling.

The preferable aryl group is phenyl group, biphenyl group, terphenyl group, fluorene group, naphthyl group, phenanthryl, pyrenyl, anthracenyl group.

The preferable heteroaryl group is carbazole group, triazine group, quinoline group, imidazole group, quinazoline group, thiophenyl group, imidazole group, oxazole group, thiazole group and the like.

The preferable arylamino group is amino group that is substituted by aryl group, arylamino group that is substituted by aryl group, arylamino group that is substituted by heteroaryl group, and arylamino group that is substituted by alkylaryl group.

Since $Ar_3$ is introduced by using the same manufacturing method as $Ar_2$, it is preferably hydrogen, heavy hydrogen, bromo group, boronic acid, silyl group, alkyl group, aryl group, heteroaryl group, arylamin group and the like.

Since $Ar_4$ is introduced by using the same manufacturing method as $Ar_2$, it is preferably hydrogen, heavy hydrogen, bromo group, boronic acid, silyl group, alkyl group, aryl group, heteroaryl group, arylamin group and the like.

In addition, the present invention provides an organic electronic device which includes a first electrode, a second electrode, and one or more organic material layers that are disposed between the first electrode and the second electrode, wherein one or more layers of the organic material layers include the compound that is represented by Formula 1.

The organic electronic device according to the present invention may be manufactured by using a manufacturing method and a material of a general organic electronic device, except that one or more organic material layers are formed by using the above compounds.

It is preferable that the organic material layer includes a hole injection layer or a hole transport layer, and the hole injection layer or hole transport layer includes the compound of Formula 1.

In addition, the hole injection layer or hole transport layer may further include a dopant material.

It is preferable that the organic material layer includes a light emitting layer, and the light emitting layer includes the compound of Formula 1.

In addition, the light emitting layer may further include a fluorescent dopant material or phosphorescent dopant material.

In addition, it is preferable that the organic material layer includes an electron injection layer or an electron transport layer, and the electron injection layer or electron transport layer includes the compound of Formula 1.

In addition, the electron injection layer or electron transport layer may further include a dopant material.

It is preferable that the organic electronic device may be selected from the group consisting of an organic light emitting device, an organic solar cell, an organic photoconductor (OPC) drum and an organic transistor, and the organic light emitting device is the most preferable example.

Hereinafter, the organic light emitting device will be described.

The compound of Formula 1 may be used as an organic material layer in the organic light emitting device because of pecularity of the structure.

In an embodiment of the present invention, the organic light emitting device may have a structure that includes a first electrode, a second electrode, and an organic material layer that is disposed between them. The organic light emitting device may be manufactured by using a manufacturing method and a material of a general organic electronic device, except that the compound according to the present invention is used in one or more layers of the organic material layer of the organic light emitting device. The organic material layer of the organic light emitting device according to the present invention may have a single layer structure including one layer and a multilayered structure that includes two or more layers including a light emitting layer. In the case of when the organic material layer of the organic light emitting device according to the present invention has the multilayered structure, for example, this may be a structure in which hole injection layer, hole transport layer, light emitting layer, electron transport layer and the like are layered. However, the structure of the organic light emitting device is not limited to this, but may comprise a smaller number of organic material layers. In the organic material layer having a multilayered structure, the compound of Formula 1 may be included in a light emitting layer, a layer that performs simultaneously hole injection/hole transport and light emission, a layer that performs simultaneously hole transport and light emission, or a layer that performs simultaneously electron transport and light emission.

For example, the structure of the organic light emitting device may have a structure shown in FIGS. 1 to 4, but is not limited thereto.

FIG. 1 illustrates a structure of the organic light emitting device in which an anode 102, a light emitting layer 105 and a cathode 107 are sequentially layered on a substrate 101. In this structure, the compound of Formula 1 may be included in the light emitting layer 105.

FIG. 2 illustrates a structure of the organic light emitting device in which an anode 102, a hole injection/hole transport and light emitting layer 105, an electron transport layer 106 and a cathode 107 are sequentially layered on a substrate 101. In this structure, the compound of Formula 1 may be included in the hole injection/hole transport and light emitting layer 105.

FIG. 3 illustrates a structure of the organic light emitting device in which a substrate 101, an anode 102, a hole injection layer 103, a hole transport and light emitting layer 105, an electron transport layer 106 and a cathode 107 are sequentially layered. In this structure, the compound of Formula 1 may be included in the hole injection/hole transport and light emitting layer 105.

FIG. 4 illustrates a structure of the organic light emitting device in which a substrate 101, an anode 102, a hole injection layer 103, a hole transport layer 104, an electron transport and light emitting layer 105 and a cathode 107 are sequentially layered. In this structure, the compound of Formula 1 may be included in the electron transport and light emitting layer 105.

For example, the organic light emitting device according to the present invention may be manufactured by forming an anode by depositing metal or metal oxides having the conductivity or an alloy thereof on a substrate by using a PVD (physical vapor deposition) method such as sputtering or e-beam evaporation, forming the organic material layer that includes hole injection layer, hole transport layer, light emitting layer and electron transport layer thereon, and depositing the material that is capable of being used as a cathode thereon. In addition to this method, an organic light emitting device may be manufactured by sequentially depositing a cathode, an organic material layer, and an anode material on a substrate.

The organic material layer may have a multilayered structure that includes a hole injection layer, a hole transport layer, a light emitting layer, and an electron transport layer, but is not limited thereto and may have a single layer structure. The organic material layer may be manufactured in a smaller number of layer by using various polymer materials and by using not a deposition method but a solvent process, for example, spin coating, dip coating, doctor blading, screen printing, inkjet printing, heat transferring method and the like.

As the anode material, in general, it is preferable to use the material having the large work function so as to smoothly perform hole injection into the organic material layer. As examples of the anode material that is capable of being used in the present invention, there are metal or alloy thereof such as vanadium, chrome, copper, zinc, gold and the like; metal oxides such as zinc oxides, indium oxides, indium tin oxides (ITO), indium zinc oxides (IZO) and the like; a combination of metal and oxides such as $ZnO:Al$ or $SnO_2:Sb$; conductive polymers such as poly(3-methyl compound), poly[3,4-(ethylene-1,2-dioxy) compound](PEDT), polypyrole and polyaniline, but it is not limited thereto.

As the cathode material, in general, it is preferable to use the material having the small work function so as to smoothly perform electron injection into the organic material layer. As detailed examples of the cathode material, there are metal such as magnesium, calcium, sodium, potassium, titanium, indium, yttrium, lithium, gadolinium, aluminium, silver, tin, and lead or an alloy thereof; a multilayered structure material such as LiF/Al or $LiO_2$/Al, but it is not limited thereto.

The hole injection material is a material that is capable of well receiving holes from the anode at a low voltage, and it is preferable that the HOMO (highest occupied molecular orbital) of the hole injection material is a value between the work function of the anode material and the HOMO of the organic material layer around them. As detailed examples of the hole injection material, there are metal porphyrine, oligo compound, arylamine-based organic material, hexanitrile-hexaazatriphenylene-based organic material, quinacridone-based organic material, perylene-based organic material, anthraquinone and polyaniline and poly compound-based conductive polymers, but it is not limited thereto.

The hole transport material is a material that receives the holes from the anode or the hole injection layer and transfer them to the light emitting layer, and it is preferable to use the material having the large mobility to the holes. As detailed examples thereof, there are arylamine-based organic material, a conductive polymer, and a block copolymer in which a conjugate portion and a conjugate portion are simultaneously included, but it is not limited thereto.

The light emitting material is a material that receives the holes and the electrons from the hole transport layer and the electron transport layer, combines them, such that light at a range of visible rays is emitted, and it is preferable to use the material having excellent photon efficiency to fluorescence or phosphorescence. As detailed examples thereof, there are a 8-hydroxy-quinoline aluminium complex (Alq$_3$); a carbazole-based compound; a dimerized styryl compound; BAlq; 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, anthracene, pyrene and the like, but it is not limited thereto.

The electron transport material is a material that receives the electrons from the cathode and transfer them to the light emitting layer, and it is preferable to use the material having the large mobility to the electrons. As detailed examples thereof, there are a 8-hydroxyquinoline Al complex; a complex including Alq$_3$; an organic radical compound; a hydroxyflavone-metal complex; oxazole, thiazole and imidazole-based compound and condensated ring compound thereof; quinoline and quinoline condensated ring compound; phenanthroline and phenanthroline condensated rinig compound; quinazoline and quinazoline condensated ring compound and the like, but it is not limited thereto.

The organic light emitting device according to the present invention may be a front side light emitting type, a rear side light emitting type, or a both sides light emitting type according to the used material.

The compound according to the present invention may be operated in a principle that is similar to a principle applied to the organic light emitting device in organic solar cell, organic photoconductor, organic transistor, and organic electronic device.

MODE FOR INVENTION

Hereinafter, preferable Preparation Examples will be described in order to help understanding of the present invention. However, the following Preparation Examples are set forth to illustrate the present invention, but the scope of the present invention is not limited thereto.

The compound of Formula 1 according to the present invention can be manufactured with multistage chemical reactions. The above compounds may be manufactured by using the methods described in the following Preparation Examples. As described in the following Synthesis Examples, the compounds of Formula 1 may be manufactured from the following intermediate compounds. In the intermediate compounds, Br may be substituted by any other reactive atom or functional group.

Table 1 shows reactants that were used in the manufacturing of Formula 1, and the reactants were synthesized by using a general or known method, or used by purchasing commercial product.

TABLE 1

| No. | Reactant |
|---|---|
| S-1 | ![naphthalen-2-ylboronic acid] |
| S-2 | ![naphthalen-1-ylboronic acid] |
| S-3 | ![phenylboronic acid] |
| S-4 | ![deuterated phenylboronic acid] |
| S-5 | ![boronic acid with phenyl-anthracene-naphthalene substituent] |

TABLE 1-continued
| No. | Reactant |
|---|---|
| S-6 | 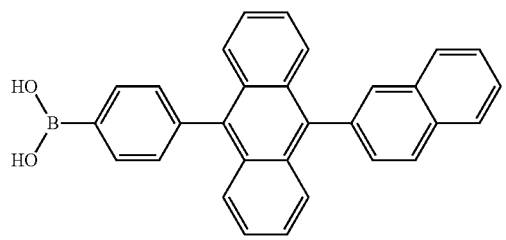 [SMILES: OB(O)c1ccc(-c2c3ccccc3c(-c3ccc4ccccc4c3)c3ccccc23)cc1] |
| S-7 | 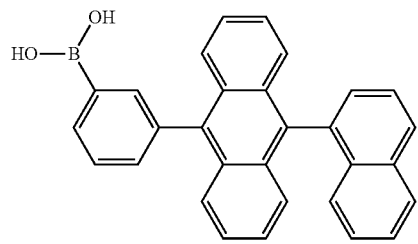 [SMILES: OB(O)c1cccc(-c2c3ccccc3c(-c3cccc4ccccc34)c3ccccc23)c1] |
| S-8 | 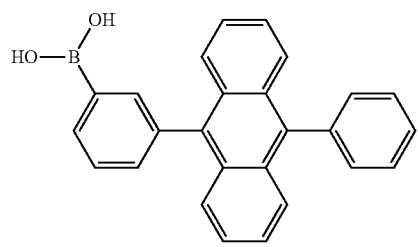 [SMILES: OB(O)c1cccc(-c2c3ccccc3c(-c3ccccc3)c3ccccc23)c1] |
| S-9 | 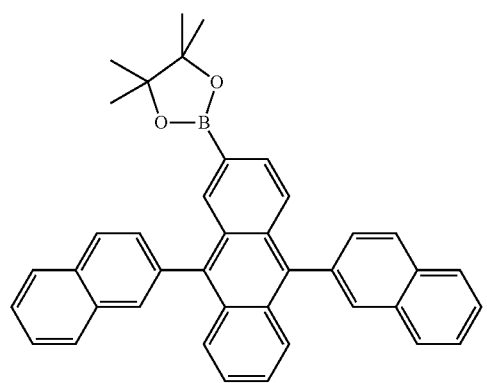 [SMILES: CC1(C)OB(c2ccc3c(-c4ccc5ccccc5c4)c4ccccc4c(-c4ccc5ccccc5c4)c3c2)OC1(C)C] |
| S-10 | 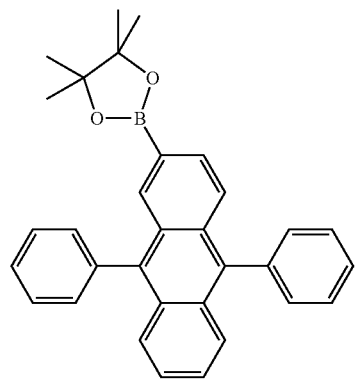 [SMILES: CC1(C)OB(c2ccc3c(-c4ccccc4)c4ccccc4c(-c4ccccc4)c3c2)OC1(C)C] |
| S-11 | 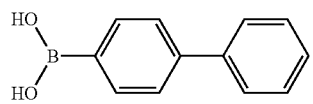 |

TABLE 1-continued

| No. | Reactant |
|---|---|
| S-12 | 4'-deuterated-biphenyl-4-boronic acid (phenyl ring with 5 D substituents) |
| S-13 | (4-chlorophenyl)boronic acid |
| S-14 | (4'-chloro-[1,1'-biphenyl]-4-yl)boronic acid |
| S-15 | 2-(4-(4,4,5,5-tetramethyl-1,3,2-dioxaborolan-2-yl)phenyl)-1-phenyl-1H-benzo[d]imidazole |
| S-16 | 2,4-diphenyl-6-(4-(4,4,5,5-tetramethyl-1,3,2-dioxaborolan-2-yl)phenyl)-1,3,5-triazine |
| S-17 | 1-(4-(4,4,5,5-tetramethyl-1,3,2-dioxaborolan-2-yl)phenyl)-2-phenyl-1H-benzo[d]imidazole |
| S-18 | (4-(9H-carbazol-9-yl)phenyl)boronic acid |
| S-19 | (9,9-dimethyl-9H-fluoren-2-yl)boronic acid |

TABLE 1-continued
| No. | Reactant |
|---|---|
| S-20 | 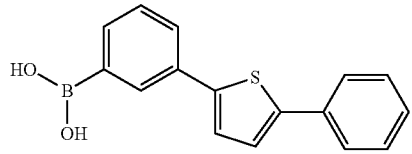 [SMILES: OB(O)c1cccc(-c2ccc(-c3ccccc3)s2)c1] |
| S-21 | 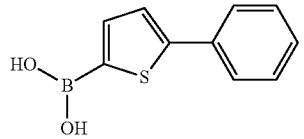 [SMILES: OB(O)c1ccc(-c2ccccc2)s1] |
| S-22 | 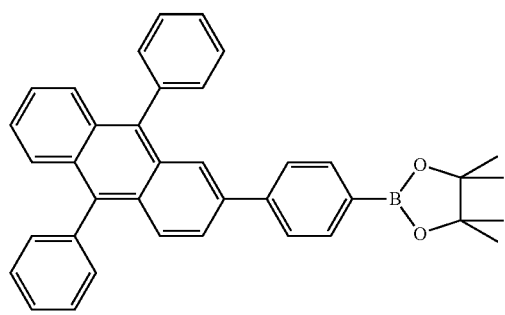 [SMILES: CC1(C)OB(c2ccc(-c3ccc4c(-c5ccccc5)c5ccccc5c(-c5ccccc5)c4c3)cc2)OC1(C)C] |
| S-23 | 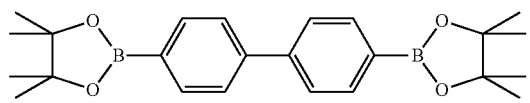 |
| S-24 | 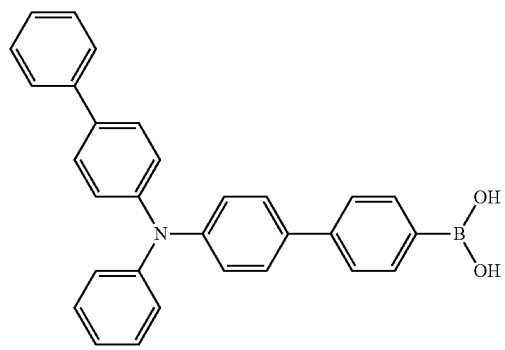 [SMILES: OB(O)c1ccc(-c2ccc(N(c3ccccc3)c3ccc(-c4ccccc4)cc3)cc2)cc1] |
| S-25 | 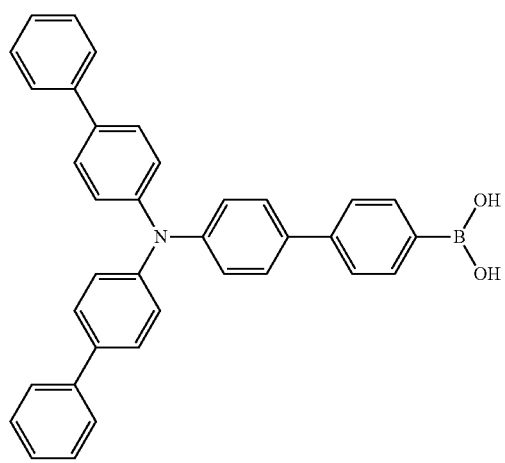 [SMILES: OB(O)c1ccc(-c2ccc(N(c3ccc(-c4ccccc4)cc3)c3ccc(-c4ccccc4)cc3)cc2)cc1] |

TABLE 1-continued
| No. | Reactant |
|---|---|
| S-26 | 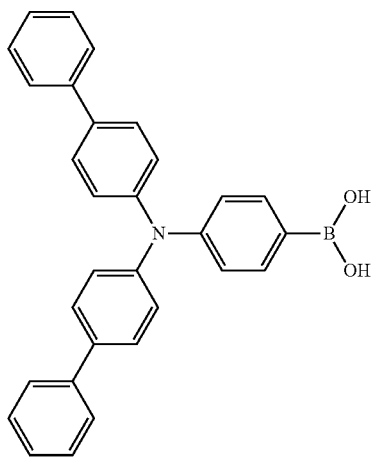 [SMILES: OB(O)c1ccc(N(c2ccc(-c3ccccc3)cc2)c2ccc(-c3ccccc3)cc2)cc1] |
| S-27 | 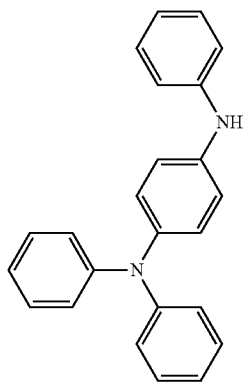 [SMILES: c1ccc(Nc2ccc(N(c3ccccc3)c3ccccc3)cc2)cc1] |
| S-28 | 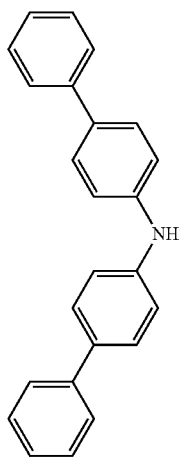 [SMILES: c1ccc(-c2ccc(Nc3ccc(-c4ccccc4)cc3)cc2)cc1] |
| S-29 | 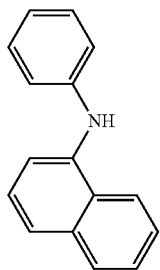 [SMILES: c1ccc(Nc2cccc3ccccc23)cc1] |

TABLE 1-continued

| No. | Reactant |
|---|---|
| S-30 | carbazole |
| S-31 | 2-naphthyl-6-naphthyl boronic acid pinacol ester |
| S-32 | 1,4-phenylenebis(boronic acid pinacol ester) |
| S-33 | 9-(4-(boronic acid pinacol ester)phenyl)-10-(2-naphthyl)anthracene |
| S-34 | 2-(4-(boronic acid pinacol ester)phenyl)-1,10-phenanthroline |
| S-35 | 1-(3-(boronic acid pinacol ester)phenyl)pyrene |
| S-36 | 3-(4-(boronic acid pinacol ester)phenyl)-9-(4,6-diphenyl-1,3,5-triazin-2-yl)carbazole |

TABLE 1-continued
| No. | Reactant |
|---|---|
| S-37 | 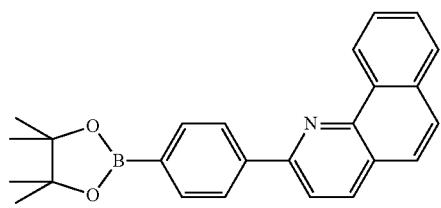 [SMILES: CC1(C)OB(c2ccc(-c3ccc4ccc5ccccc5c4n3)cc2)OC1(C)C] |
| S-38 | 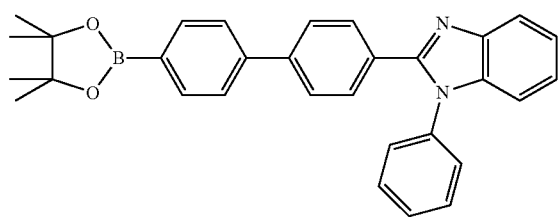 [SMILES: CC1(C)OB(c2ccc(-c3ccc(-c4nc5ccccc5n4-c4ccccc4)cc3)cc2)OC1(C)C] |
| S-39 | 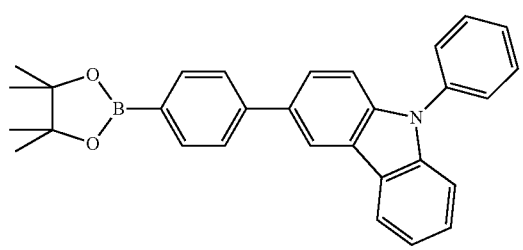 [SMILES: CC1(C)OB(c2ccc(-c3ccc4c(c3)c3ccccc3n4-c3ccccc3)cc2)OC1(C)C] |
| S-40 | 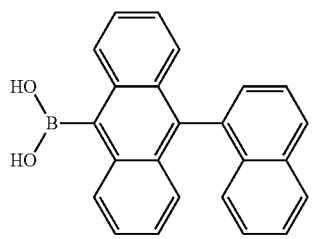 [SMILES: OB(O)c1c2ccccc2c(-c2cccc3ccccc23)c2ccccc12] |
| S-41 | 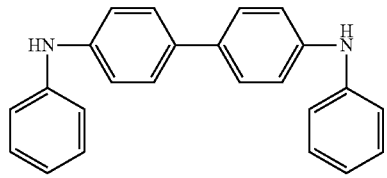 [SMILES: c1ccc(Nc2ccc(-c3ccc(Nc4ccccc4)cc3)cc2)cc1] |
| S-42 | 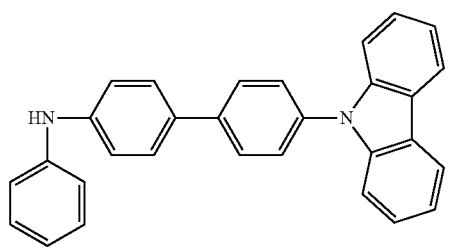 [SMILES: c1ccc(Nc2ccc(-c3ccc(-n4c5ccccc5c5ccccc54)cc3)cc2)cc1] |

TABLE 1-continued

| No. | Reactant |
|---|---|
| S-43 | 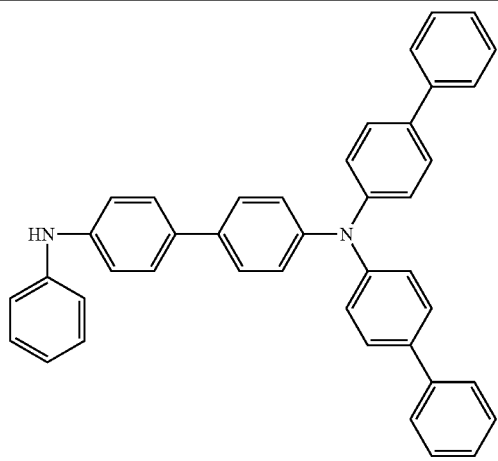 |
| S-44 | 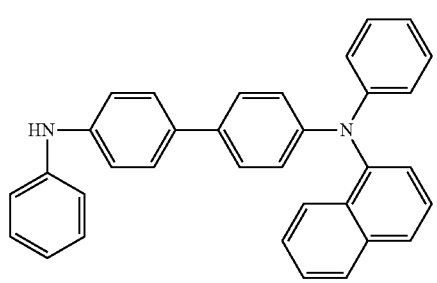 [SMILES: c1ccc(Nc2ccc(-c3ccc(N(c4ccccc4)c4cccc5ccccc45)cc3)cc2)cc1] |

SYNTHESIS EXAMPLE 1

Synthesis of the Compound A-1

1-1. Synthesis of the Compound A-1-1

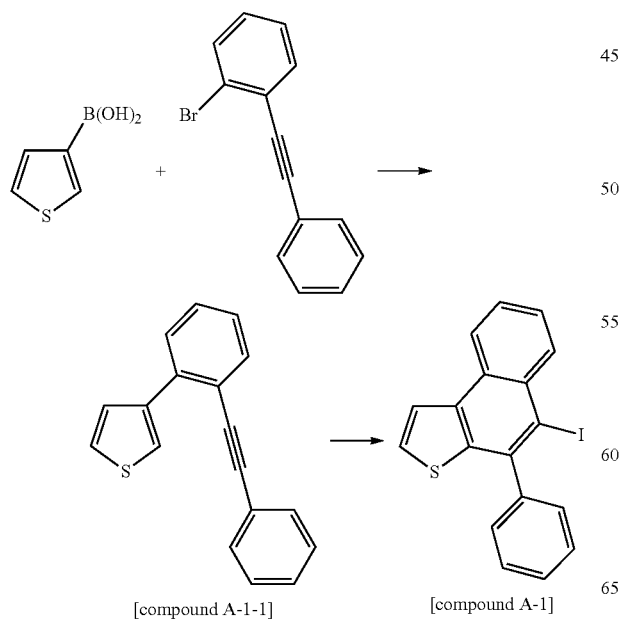

1-bromo-2-(2-phenylethynyl)-benzene (16.3 g, 63.5 mmol), thiophen-3-yl-3-boronic acid (9.75 g, 76.2 mmol), and sodium carbonate (21.1 g, 152.4 mmol) were suspended in the mixture of toluene (200 mL), ethanol (100 mL) and water (100 mL). To the suspension solution, tetrakis(triphenylphosphine)palladium (2.1 g, 1.83 mmol) was applied. The mixture was refluxed and agitated for about 24 hours, and the refluxed mixture was cooled to room temperature. The organic material layer was separated, wahsed with water, and the aqueous layer was extracted with chloroform. The organic extract was dried on magnesium sulfate and concentrated under the vacuum to synthesize the compound A-1-1 (16.7 g, yield 84%).

MS $[M+H]^+=261$ 1-2. Synthesis of the Compound A-1

After the compound A-1-1 (6.2 g, 23.8 mmol) was dissolved in $CHCl_3$ (100 mL), ICl (3.87 g, 23.8 mmol) was dissolved in $CHCl_3$ 10 mL, slowly dropped, and agitated for 12 hours. The formed yellow solid was filtered, washed with hexane, and dried to synthesize the compound A-1 (3 g, yield 32%).

MS $[M]^+=386$

SYNTHESIS EXAMPLE 2

Synthesis of the Compound A-2

2-1. Synthesis of the Compound A-2-1

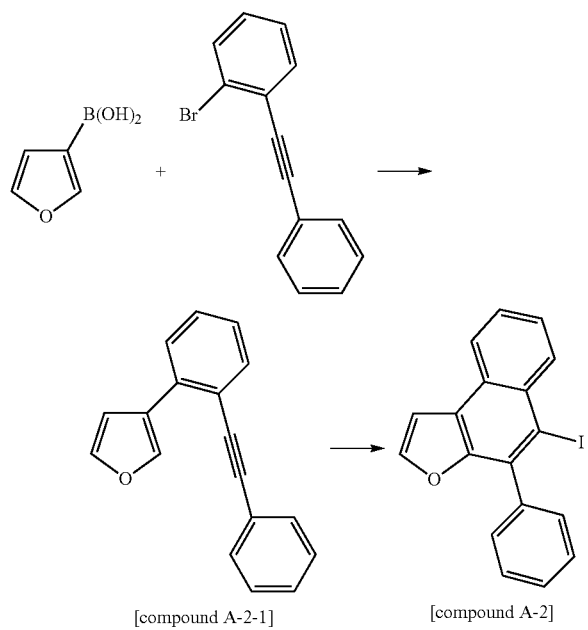

[compound A-2-1]    [compound A-2]

1-bromo-2-(2-phenylethynyl)-benzene (15.4 g, 60.0 mmol), furan-3-yl-3-boronic acid (4.8 g, 58.0 mmol), and sodium carbonate (17.6 g, 152.4 mmol) were suspended in the mixture of toluene (200 mL), ethanol (100 mL) and water (100 mL). To the suspension solution, tetrakis(triphenylphosphine)palladium (2.0 g, 2.00 mmol) was applied. The mixture was refluxed and agitated for about 24 hours, and the refluxed mixture was cooled to room temperature. The organic material layer was separated, washed with water, and the aqueous layer was extracted with chloroform. The organic extract was dried on magnesium sulfate and concentrated under the vacuum to synthesize the compound A-2-1 (14.4 g, yield 67%).

MS [M+H]$^+$=245

2-2. Synthesis of the Compound A-2

After the compound A-1-2 (14.4 g, 58.9 mmol) was dissolved in CHCl$_3$ (120 mL), ICl (9.58 g, 58.9 mmol) was dissolved in CHCl$_3$ 15 mL, slowly dropped, and agitated for 12 hours. The formed yellow solid was filtered, washed with hexane, and dried to synthesize the compound A-2 (10.5 g, yield 48%).

MS [M]$^+$=370

SYNTHESIS EXAMPLE 3

Synthesis of the Compound A-3

3-1. Synthesis of the Compound A-3-1

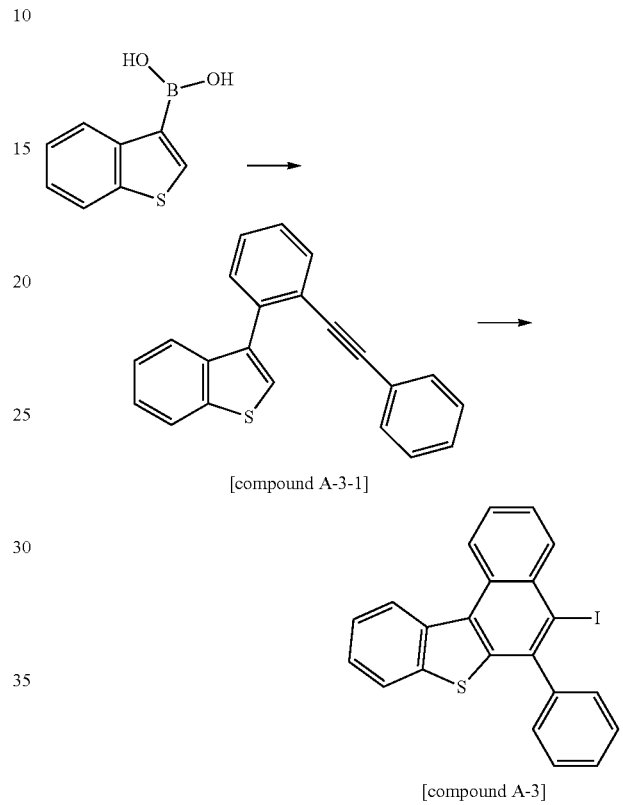

[compound A-3-1]

[compound A-3]

In the synthesis of the compound A-1-1, the compound A-3-1 (13.2 g, yield 56%) was synthesized by using the same method as the compound A-1-1, except that benzo[b]thiophen-3-yl-3-boronic acid (13.6 g, 76.2 mmol) was used instead of thiophene-3-boronic acid, and 1-bromo-2-(2-phenylethynyl)-benzene (19.6 g, 76.2 mmol), and sodium carbonate (21.1 g, 153 mmol) were used.

MS [M+H]$^+$=311

3-2. Synthesis of the Compound A-3

After the compound A-3-1 (11 g, 35.6 mmol) was dissolved in CHCl$_3$ (100 mL), ICl (5.79 g, 23.8 mmol) was dissolved in CHCl$_3$ 10 mL, slowly dropped, and agitated for 12 hours. The formed yellow solid was filtered, washed with hexane, and dried to synthesize the compound A-3 (11.2 g, yield 72%).

MS [M]$^+$=436

SYNTHESIS EXAMPLE 4

Synthesis of the Compound A-4

4-1. Synthesis of the Compound A-4-1

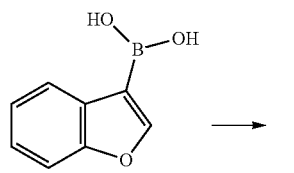

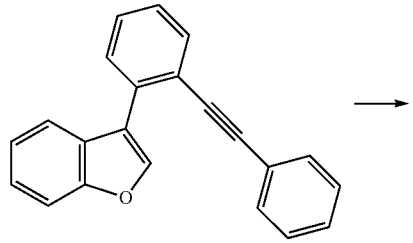

[compound A-4-1]

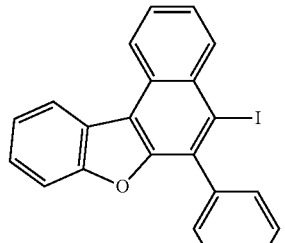

[compound A-4]

In the synthesis of the compound A-1-1, the compound A-4-1 (9.1 g, yield 62%) was synthesized by using the same method as the compound A-1-1, except that benzofuran-3-yl-3-boronic acid (8.1 g, 50.0 mmol) was used instead of thiophene-3-boronic acid, and 1-bromo-2-(2-phenylethynyl)-benzene (13.4 g, 52.0 mmol), and sodium carbonate (15.8 g, 153 mmol) were used.

MS [M+H]$^+$=295

4-2. Synthesis of the Compound A-4

After the compound A-4-1 (9.1 g, 30.9 mmol) was dissolved in CHCl$_3$ (80 mL), ICl (5.4 g, 33.0 mmol) was dissolved in CHCl$_3$ 20 mL, slowly dropped, and agitated for 12 hours. The formed yellow solid was filtered, washed with hexane, and dried to synthesize the compound A-4 (8.3 g, yield 64%).

MS [M]$^+$=420

SYNTHESIS EXAMPLE 1-1-NO

Synthesis of the Compound 1B-1-No

The compound A-1, and 1 to 1.5 equivalents of the substituted or unsubstituted arylboronic acid (or arylboron ester) or the substituted or unsubstituted heteroarylboronic acid (or arylboron ester) like the reactant S-No. described in Table 1-1 were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to synthesize the 1B-1-No compound, and the results thereof are described in Table 1-1-1.

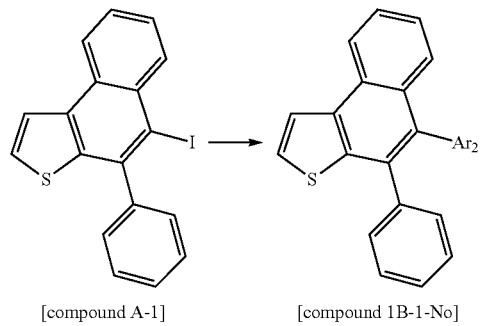

[compound A-1]      [compound 1B-1-No]

TABLE 1-1-1

| Syn. Ex. 1-1-No | Product 1B-1-No | Reactant | Ar2 | MS [M + H]$^+$ |
|---|---|---|---|---|
| 1-1-1 | compound 1B-1-1 | S-1 | naphthyl | 387 |
| 1-1-2 | compound 1B-1-2 | S-3 | phenyl | 337 |
| 1-1-3 | compound 1B-1-3 | S-5 | 9-phenyl-10-naphthyl-anthracenyl-phenyl | 639 |

TABLE 1-1-1-continued

| Syn. Ex. 1-1-No | Product 1B-1-No | Reactant Ar2 | MS [M + H]+ |
|---|---|---|---|
| 1-1-4 | compound 1B-1-4 | S-8 | 589 |
| 1-1-5 | compound 1B-1-5 | S-13 | 370 |
| 1-1-6 | compound 1B-1-6 | S-14 | 446 |
| 1-1-7 | compound 1B-1-7 | S-10 | 589 |
| 1-1-8 | compound 1B-1-8 | S-9 | 689 |

SYNTHESIS EXAMPLE 1-1-1

Synthesis of the Compound 1B-1-1

Naphthalen-2-yl-2-boronic acid (1.6 g, 9.3 mmol) that was the reactant S-1 of Table 1, the compound A-1 (3 g, 7.8 mmol), and sodium carbonate (2.4 g, 15.5 mmol) were suspended in the mixture of toluene (100 mL), ethanol (10 mL) and water (20 mL).

To the suspension solution, tetrakis(triphenylphosphine) palladium (0.2 g, 1.6 mmol) was applied. The mixture was refluxed and agitated for about 24 hours, and the refluxed mixture was cooled to room temperature. The organic material layer was separated, wahsed with water, and the aqueous layer was extracted with chloroform. The organic extract was dried on magnesium sulfate and concentrated under the vacuum to synthesize the compound 1B-1-1 (2.3 g, yield 77%).

MS [M+H]+=387

SYNTHESIS EXAMPLE 1-1-2

Synthesis of the Compound 1B-1-2

In Synthesis Example 1-1-1, it was synthesized by using the same method to synthesize the compound 1B-1-2, except that phenylboronic acid S-3 was used instead of naphthalene-2-yl-2-boronic acid.

MS: [M+H]+=337

SYNTHESIS EXAMPLE 1-1-3 to 1-1-8

Synthesis of the Compound 1B-1-3 to 1B-1-8

In Synthesis Example 1-1-1, it was synthesized by using the same method to synthesize the compounds 1B-1-3, 1B-1-4, 1B-1-5, 1B-1-6, 1B-1-7, and 1B-1-8, except that the reactants S-5, S-8, S-13, S-14, S-10, and S-9 were used instead of naphthalene-2-yl-2-boronic acid.

SYNTHESIS EXAMPLE 1-2-NO

Synthesis of the Compound 1C-1-No

The compound 1B-1-No was dissolved in chloroform, and 1 equivalent of N-bromo succinimide was added thereto, and agitated for 3 to 8 hours at normal temperature. Distilled water was put into the reaction solution, the termination of the reaction was carried out, and the organic material layer was extracted. The reaction solution was concentrated, and recrystalized with EtOH to synthesize the compound 1C-1-No, and the results are described in Table 1-2-1.

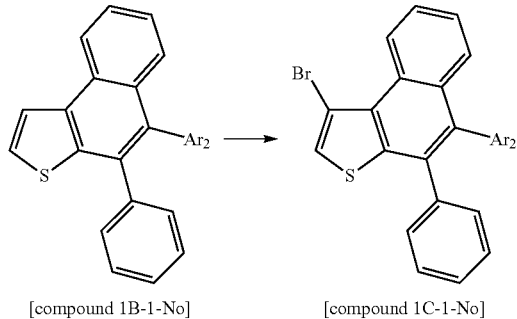

[compound 1B-1-No]   [compound 1C-1-No]

TABLE 1-2-1

| Syn. Ex. 1-2-No | Product 1C-1-No | Reactant 1B-1-No | Ar2 | MS [M]+ |
|---|---|---|---|---|
| 1-2-1 | compound 1C-1-1 | compound 1B-1-1 | naphthyl | 465 |
| 1-2-2 | compound 1C-1-2 | compound 1B-1-2 | phenyl | 415 |
| 1-2-3 | compound 1C-1-3 | compound 1B-1-3 | 9-phenyl-10-(naphthyl)anthracenyl-phenyl | 717 |
| 1-2-4 | compound 1C-1-4 | compound 1B-1-4 | 9,10-diphenylanthracenyl | 667 |
| 1-2-5 | compound 1C-1-5 | compound 1B-1-5 | 4-chlorophenyl | 449 |
| 1-2-6 | compound 1C-1-6 | compound 1B-1-6 | 4'-chlorobiphenyl | 525 |
| 1-2-7 | compound 1C-1-7 | compound 1B-1-7 | 9,10-diphenylanthracenyl | 667 |

TABLE 1-2-1-continued

| Syn. Ex. 1-2-No | Product 1C-1-No | Reactant 1B-1-No | Ar2 | MS [M]+ |
|---|---|---|---|---|
| 1-2-8 | compound 1C-1-8 | compound 1B-1-8 | 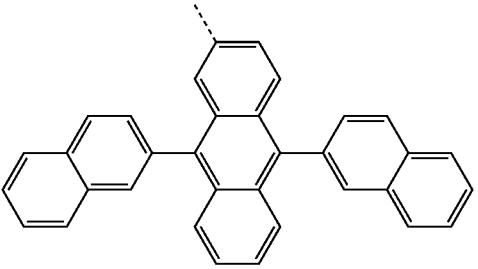 | 767 |

SYNTHESIS EXAMPLE 1-2-1

Synthesis of the Compound 1C-1-1

After the compound 1B-1-1 (2.3 g, 6.0 mmol) was dissolved in DMF 20 mL, NBS (1.1 g, 6.0 mmol) was applied thereto and agitated at normal temperature for 2 hours. After water 50 mL was applied thereto to precipitate the solid, it was filtered, washed with ethanol, and dried to synthesize the compound 1C-1-1 (2.1 g, yield 85%).

MS $[M]^+$=465

SYNTHESIS EXAMPLE 1-2-2

Synthesis of the Compound 1C-1-2

In Synthesis Example 1-2-1, it was synthesized by using the same method to synthesize the compound 1C-1-2, except that the compound 1B-1-2 was used instead of the compound 1B-1-1.

MS: $[M]^+$=415

Synthesis of Synthesis Example 1-2-3 to 1-2-8. Synthesis of the Compounds 1C-1-3 TO 1C-1-8

In Synthesis Example 1-2-1, it was synthesized by using the same method to synthesize the compounds 1C-1-3, 1C-1-4, 1C-1-5, 1C-1-6, 1C-1-7, 1C-1-8, except that the compounds 1B-1-3, 1B-1-4, 1B-1-5, 1B-1-6, 1B-1-7, and 1B-1-8 were used instead of the compound 1B-1-1.

GENERAL SYNTHESIS EXAMPLE 1-3-NO

Synthesis of the Compound 1D-1~5-No

The compound 1C-1-No, and 1 to 1.5 equivalents of the substituted or unsubstituted arylboronic acid (or arylboron ester) or the substituted or unsubstituted heteroarylboronic acid (or arylboron ester) like the reactant S-No. described in Table 1-1 were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to synthesize the 1D-1-5-No compound.

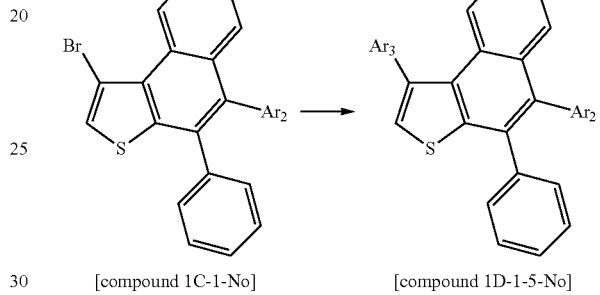

[compound 1C-1-No]     [compound 1D-1-5-No]

SYNTHESIS EXAMPLE 1-3-1

Synthesis of the Compound 1D-1-1

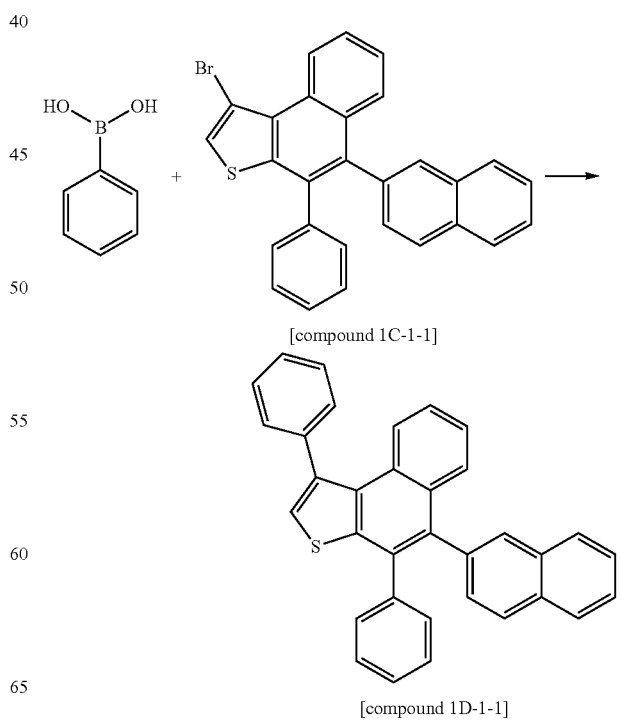

Phenyl boronic acid (1 g, 8.2 mmol), the compound 1C-1-1 (2.1 g, 5.1 mmol), and sodium carbonate (1.4 g, 10.2 mmol) were suspended in the mixture of toluene (50 mL), ethanol (10 mL) and water (20 mL). To the suspension solution, tetrakis(triphenylphosphine)palladium (0.12 g, 1.0 mmol) was applied. The mixture was refluxed and agitated for about 15 hours, and the refluxed mixture was cooled to room temperature. The organic material layer was separated, wahsed with water, and the aqueous layer was extracted with chloroform. The organic extract was dried on magnesium sulfate and concentrated under the vacuum to synthesize the compound 1D-1-1 (1.8 g, yield 77%).

SYNTHESIS EXAMPLE 1-3-2

Synthesis of the Compound 1D-1-2

In Synthesis Example 1-3-1, it was synthesized by using the same method to synthesize the compound 1D-1-2, except that the reactant S-1 was used instead of the phenyl boronic acid reactant S-3.

SYNTHESIS EXAMPLE 1-3-3

Synthesis of the Compound 1D-1-3

In Synthesis Example 1-3-1, it was synthesized by using the same method to synthesize the compound 1D-1-3, except that the reactant S-11 was used instead of the phenyl boronic acid reactant S-3.

SYNTHESIS EXAMPLE 1-3-4 TO 1-3-8

Synthesis of the Compounds 1D-1-4 to 1D-1-8

In Synthesis Example 1-3-1, it was synthesized by using the same method to synthesize the compounds 1D-1-4, 1D-1-5, 1D-1-6, 1D-1-7, and 1D-1-8, except that the reactants S-20, S-12, S-8, S-10, and S-4 were used instead of the phenyl boronic acid reactant S-3.

TABLE 1-3-1

| Syn. Ex. 1-3-No | Product 1D-1-No | Ar3 | Ar2 | MS [M + H]+ |
|---|---|---|---|---|
| 1-3-1 | compound 1D-1-1 | phenyl | naphthyl | 463 |
| 1-3-2 | compound 1D-1-2 | naphthyl | naphthyl | 513 |
| 1-3-3 | compound 1D-1-3 | biphenyl | naphthyl | 539 |
| 1-3-4 | compound 1D-1-4 | 2,5-diphenyl thiophene | naphthyl | 621 |
| 1-3-5 | compound 1D-1-5 | deuterated biphenyl | naphthyl | 544 |

TABLE 1-3-1-continued

| Syn. Ex. 1-3-No | Product 1D-1-No | Ar3 | Ar2 | MS [M + H]+ |
|---|---|---|---|---|
| 1-3-6 | compound 1D-1-6 | (9,10-diphenylanthracen-2-yl with m-phenyl linker) | (naphthalen-2-yl) | 715 |
| 1-3-7 | compound 1D-1-7 | (9,10-diphenylanthracen-2-yl) | (naphthalen-2-yl) | 715 |
| 1-3-8 | compound 1D-1-8 | (tetradeuterophenyl, D at 2,3,4,5-positions) | (naphthalen-2-yl) | 468 |

SYNTHESIS EXAMPLE 1-4-1

Synthesis of the Compounds 1D-2-1

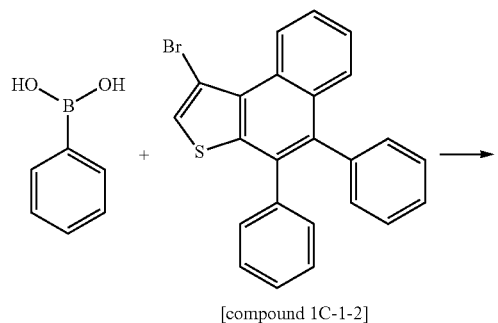

[compound 1C-1-2]

[compound 1D-2-1]

Phenyl boronic acid S-3 (2.2 g, 18.0 mmol), the compound 1C-1-2 (7.45 g, 16.0 mmol), and sodium carbonate (4.98 g, 36.0 mmol) were suspended in the mixture of toluene (150 mL), ethanol (20 mL) and water (40 mL). To the suspension solution, tetrakis(triphenylphosphine)palladium (0.24 g, 2.00 mmol) was applied. The mixture was refluxed and agitated for about 15 hours, and the refluxed mixture was cooled to room temperature. The organic material layer was separated, washed with water, and the aqueous layer was extracted with chloroform. The organic extract was dried on magnesium sulfate and concentrated under the vacuum to synthesize the compound 1D-2-1 (6.7 g, yield 90%).

SYNTHESIS EXAMPLE 1-4-2 TO 1-4-12

Synthesis of the Compounds 1D-2-2 to 1D-2-12

In Synthesis Example 1-4-1, it was synthesized by using the same method to synthesize the compounds 1D-2-2 to 1D-2-11, except that the reactants S-1, S-11, S-20, S-12, S-8, S-10, S-4, S-19, S-15, and S-17 were used instead of the phenyl boronic acid reactant S-3.

The results are described in Table 1-4-1.

TABLE 1-4-1
| Syn. Ex. 1-4-No | Product 1D-2-No | Ar3 | Ar2 | MS [M + H]+ |
|---|---|---|---|---|
| 1-4-1 | compound 1D-2-1 | 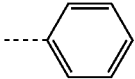 | 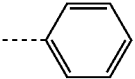 | 413 |
| 1-4-2 | compound 1D-2-2 | 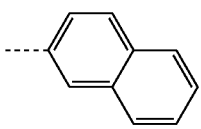 | 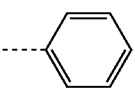 | 463 |
| 1-4-3 | compound 1D-2-3 | 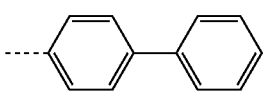 | 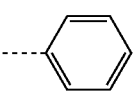 | 489 |
| 1-4-4 | compound 1D-2-4 | 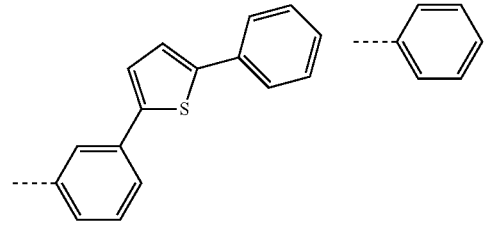 |  | 571 |
| 1-4-5 | compound 1D-2-5 | 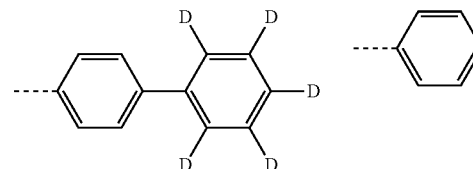 | 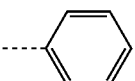 | 494 |
| 1-4-6 | compound 1D-2-6 | 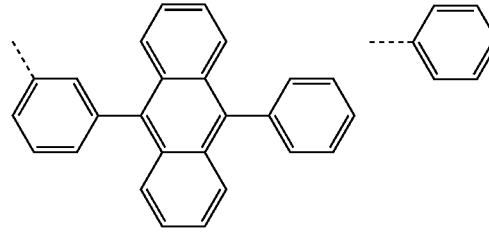 | 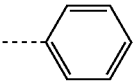 | 665 |
| 1-4-7 | compound 1D-2-7 | 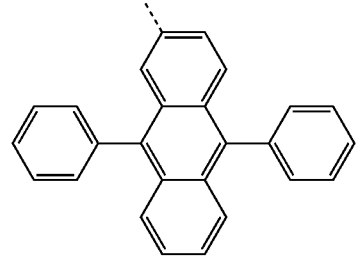 | 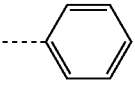 | 665 |
| 1-4-8 | compound 1D-2-8 | 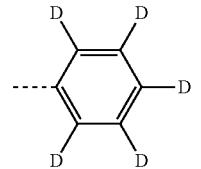 | 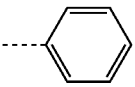 | 418 |

TABLE 1-4-1-continued

| Syn. Ex. 1-4-No | Product 1D-2-No | Ar3 | Ar2 | MS [M + H]+ |
|---|---|---|---|---|
| 1-4-9 | compound 1D-2-9 | (9,9-dimethylfluorenyl) | phenyl | 529 |
| 1-4-10 | compound 1D-2-10 | (1-phenyl-2-(4-phenyl)benzimidazolyl) | phenyl | 605 |
| 1-4-11 | compound 1D-2-11 | (1-(4-phenyl)-2,4,5-triphenylimidazolyl) | phenyl | 707 |

SYNTHESIS EXAMPLE 1-5-1

Synthesis of the Compound 1D-3-1

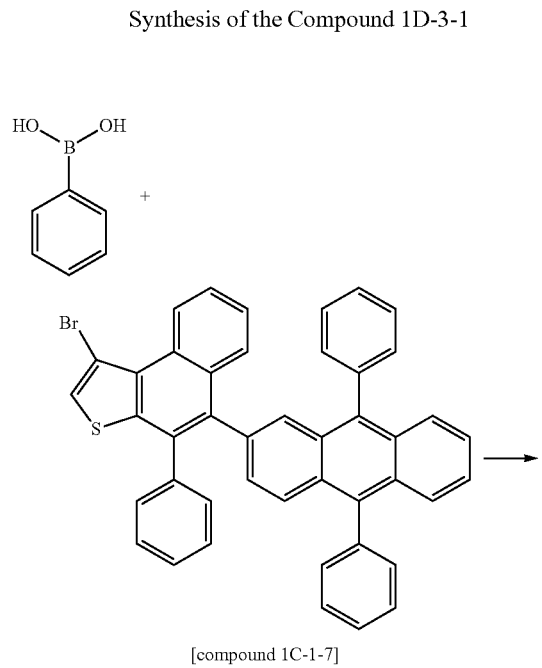

[compound 1C-1-7] → [compound 1D-3-1]

Phenyl boronic acid S-3 (2.2 g, 18.0 mmol), the compound 1C-1-7 (10.68 g, 16.0 mmol), and sodium carbonate (4.98 g, 36.0 mmol) were suspended in the mixture of toluene (150 mL), ethanol (20 mL) and water (40 mL). To the suspension solution, tetrakis(triphenylphosphine)palladium (0.24 g, 2.0 mmol) was applied. The mixture was refluxed and agitated for about 15 hours, and the refluxed mixture was cooled to room temperature. The formed solid was filtered and washed with water and ethanol. It was dried in the oven under the vacuum to synthesize the compound 1D-3-1 (9.26 g, yield 87%).

SYNTHESIS EXAMPLE 1-5-2

Synthesis of the Compound 1D-3-2

In Synthesis Example 1-5-1, it was synthesized by using the same method to synthesize the compound 1D-3-2, except that the reactant S-1 was used instead of the reactant S-3.

SYNTHESIS EXAMPLE 1-5-3 TO 1-5-5

Synthesis of the Compounds 1D-3-3 to 1D-3-5

In Synthesis Example 1-5-1, it was synthesized by using the same method to synthesize the compounds 1D-3-3 to 1D-3-13, except that the reactants S-11, S-12, and S-4 were used instead of the phenyl boronic acid reactant S-3.

TABLE 1-5-1

| Syn. Ex. 1-5-No | Product 1D-3-No | Ar3 | Ar2 | MS [M + H]+ |
|---|---|---|---|---|
| 1-5-1 | compound 1D-3-1 | 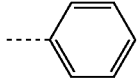 | 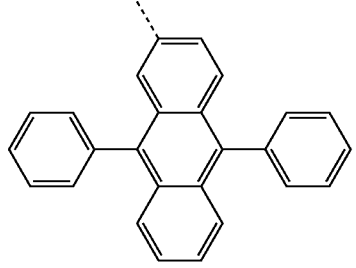 | 665 |
| 1-5-2 | compound 1D-3-2 | 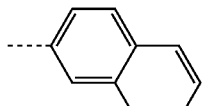 | 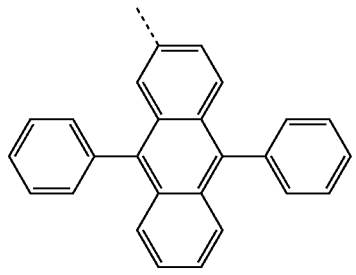 | 715 |
| 1-5-3 | compound 1D-3-3 | 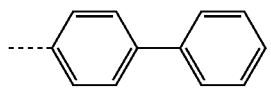 | 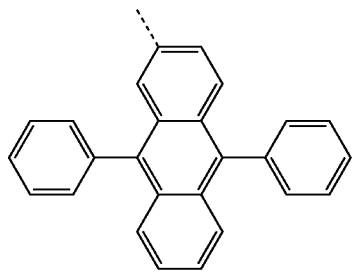 | 741 |
| 1-5-4 | compound 1D-3-4 | 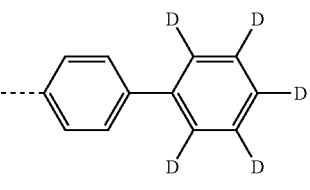 | 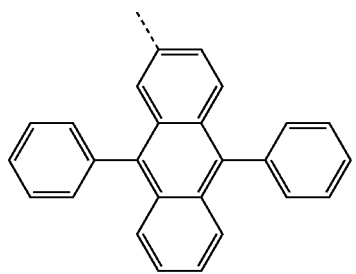 | 746 |

TABLE 1-5-1-continued
| Syn. Ex. 1-5-No | Product 1D-3-No | Ar3 | Ar2 | MS [M + H]+ |
|---|---|---|---|---|
| 1-5-5 | compound 1D-3-5 | | | 670 |
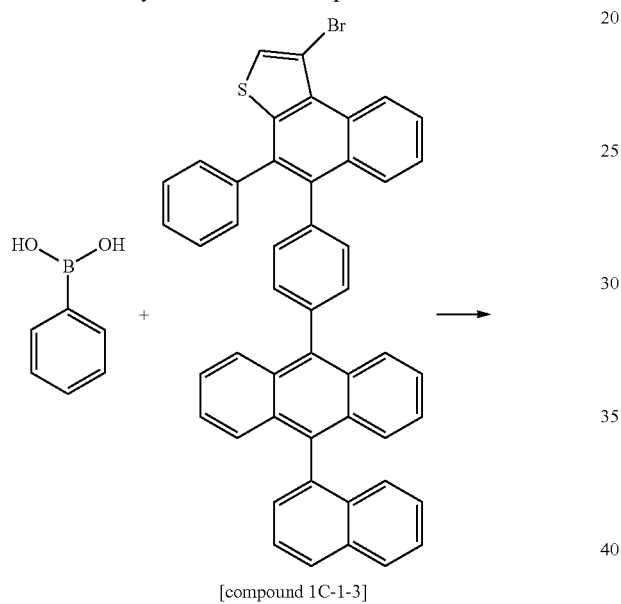
SYNTHESIS EXAMPLE 1-6-1
Synthesis of the Compound 1D-4-1
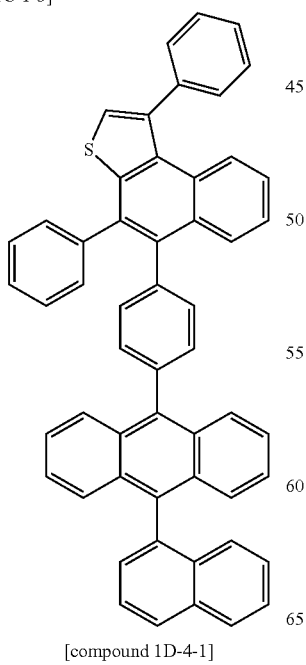
[compound 1C-1-3]
[compound 1D-4-1]

Phenyl boronic acid S-3 (2.2 g, 18.0 mmol), the compound 1C-1-3 (10.68 g, 16.0 mmol), and sodium carbonate (4.98 g, 36.0 mmol) were suspended in the mixture of toluene (150 mL), ethanol (20 mL) and water (40 mL). To the suspension solution, tetrakis(triphenylphosphine)palladium (0.24 g, 2.0 mmol) was applied. The mixture was refluxed and agitated for about 15 hours, and the refluxed mixture was cooled to room temperature. The formed solid was filtered and washed with water and ethanol. It was dried in the oven under the vacuum to synthesize the compound 1D-4-1 (9.26 g, yield 87%).

SYNTHESIS EXAMPLE 1-6-2

Synthesis of the Compound 1D-4-2

In Synthesis Example 1-6-1, it was synthesized by using the same method to synthesize the compound 1D-4-2, except that the reactant S-1 was used instead of the phenyl boronic acid reactant S-3.

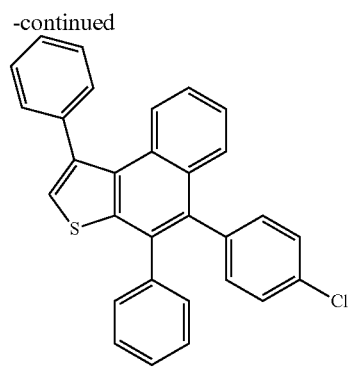

[compound 1D-5-1]

Phenyl boronic acid S-3 (2.44 g, 20.0 mmol), the compound 1C-1-5 (8.1 g, 18.0 mmol), and sodium carbonate (4.98 g, 36.0 mmol) were suspended in the mixture of toluene

TABLE 1-6-1

| Syn. Ex. 1-6-No | Product 1D-4-No | Ar3 | Ar2 | MS [M + H]+ |
|---|---|---|---|---|
| 1-6-1 | compound 1D-4-1 | (phenyl) | (structure) | 714 |
| 1-6-2 | compound 1D-4-2 | (naphthyl) | (structure) | 764 |

SYNTHESIS EXAMPLE 1-7-1

Synthesis of the Compound 1D-5-1

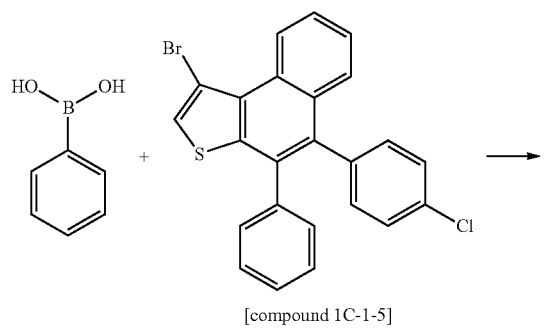

[compound 1C-1-5]

(150 mL), ethanol (20 mL) and water (40 mL). To the suspension solution, tetrakis(triphenylphosphine)palladium (0.24 g, 2.0 mmol) was applied. The mixture was refluxed and agitated for about 15 hours, and the refluxed mixture was cooled to room temperature. The formed solid was filtered and washed with water and ethanol. It was dried in the oven under the vacuum to synthesize the compound 1D-5-1 (7.08 g, yield 88%).

SYNTHESIS EXAMPLE 1-7-2 TO 1-7-3

Synthesis of the Compounds 1D-5-2 to 1D-5-3

In Synthesis Example 1-7-1, it was synthesized by using the same method to synthesize the compounds 1D-5-2 to 1D-5-3, except that the reactants S-1, and S-11 were used instead of the phenyl boronic acid reactant S-3.

SYNTHESIS EXAMPLE 1-7-4

Synthesis of the Compound 1D-5-4

In Synthesis Example 1-7-4, it was synthesized by using the same method to synthesize the compound 1D-5-4, except that the reactant S-11 was used instead of the phenyl boronic acid reactant S-3 and the compound 1C-1-6 was used instead of the compound 1C-1-5.

TABLE 1-7-1

| Syn. Ex. 1-7-No | Product 1D-5-No | Ar3 | Ar2 | MS [M + H]+ |
|---|---|---|---|---|
| 1-7-1 | compound 1D-5-1 | phenyl | 4-chlorophenyl | 447 |
| 1-7-2 | compound 1D-5-2 | 2-naphthyl | 4-chlorophenyl | 496 |
| 1-7-3 | compound 1D-5-3 | biphenyl | 4-chlorophenyl | 522 |
| 1-7-4 | compound 1D-5-4 | biphenyl | 4'-chloro-biphenyl | 599 |

GENERAL SYNTHESIS EXAMPLE 1-8~11-NO

Synthesis of the Compound 1E-1~4-No

The compounds 1D-1-No to 1D-5-No were dissolved in chloroform, and 1 equivalent of N-bromo succinimide was added thereto, and agitated for 3 to 6 hours at normal temperature. The solid was formed by applying distilled water to the reaction solution, filtered and dried, and recrystallized with CHCl₃/EtOH to synthesize the compounds 1E-1-No, 1E-2-No, 1E-3-No, and 1E-4-No

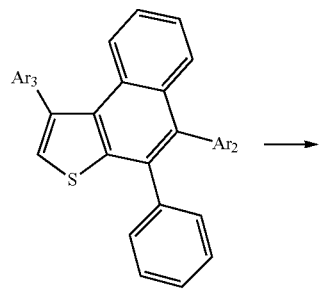

[compound 1D-1-No to 1D-5-No]

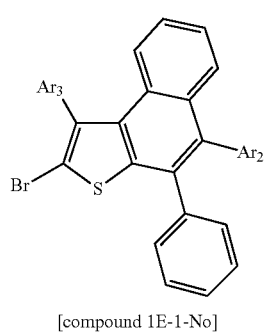

[compound 1E-1-No]

SYNTHESIS EXAMPLE 1-8-1

Synthesis of the Compound 1E-1-1

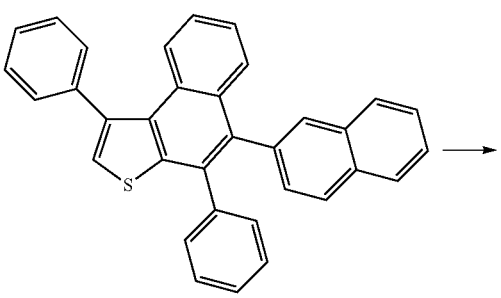

[compound 1D-1-1]

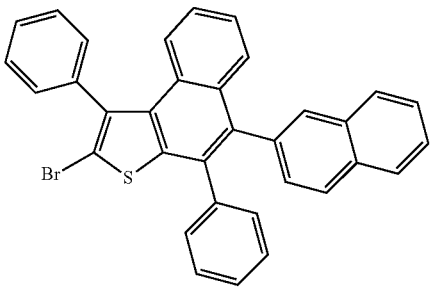

[compound 1E-11]

After the compound 1D-1-1 (4.6 g, 10.0 mmol) was dissolved in DMF 40 mL, NBS (1.8 g, 10.0 mmol) was applied thereto and agitated at normal temperature for 3 hours. After water 100 mL was applied thereto to precipitate the solid, it is filtered, washed with ethanol, and dried to synthesize the compound 1E-1-1 (4.98 g, yield 92%).

SYNTHESIS EXAMPLE 1-8-2 TO 1-11-5

Synthesis of the Compounds 1E-1-2 to 1E-4-5

The compound was manufactured by using the same method as Synthesis Example 1-8-1, except that the corresponding compounds 1D-1-No to 1D-5-No were used instead of the compound 1D-1-1. The results are described in the following Tables 1-8-1 to 1-11-1.

TABLE 1-8-1

| Syn. Ex. 1-8-No | Product 1E-1-No | Ar3 | Ar2 | MS [M]+ |
|---|---|---|---|---|
| 1-8-1 | compound 1E-1-1 | phenyl | naphthyl | 541 |
| 1-8-2 | compound 1E-1-2 | naphthyl | naphthyl | 591 |
| 1-8-3 | compound 1E-1-3 | biphenyl | naphthyl | 617 |
| 1-8-4 | compound 1E-1-4 | 2,5-diphenylthiophene (linked at meta-phenyl) | naphthyl | 699 |
| 1-8-5 | compound 1E-1-5 | biphenyl (one ring with 4 D) | naphthyl | 622 |
| 1-8-6 | compound 1E-1-6 | 9,10-diphenylanthracene (linked via meta-phenyl) | naphthyl | 793 |
| 1-8-7 | compound 1E-1-7 | 9,10-diphenylanthracene (linked at 2-position) | naphthyl | 793 |
| 1-8-8 | compound 1E-1-8 | phenyl-d4 | naphthyl | 546 |

TABLE 1-9-1
| Syn. Ex. 1-9-No | Product 1E-2-No | Ar3 | Ar2 | MS [M]+ |
|---|---|---|---|---|
| 1-9-1 | compound 1E-2-1 | 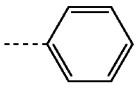 | 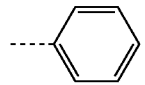 | 491 |
| 1-9-2 | compound 1E-2-2 | 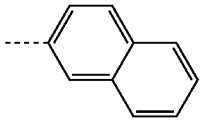 | 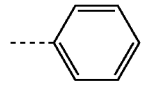 | 541 |
| 1-9-3 | compound 1E-2-3 | 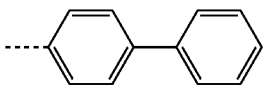 | 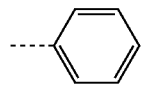 | 567 |
| 1-9-4 | compound 1E-2-4 | 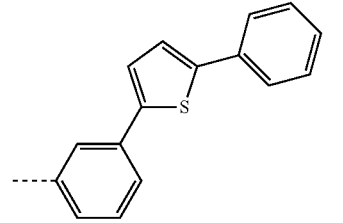 | 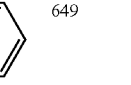 | 649 |
| 1-9-5 | compound 1E-2-5 | 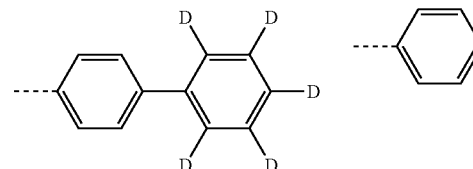 | 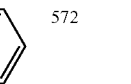 | 572 |
| 1-9-6 | compound 1E-2-6 | 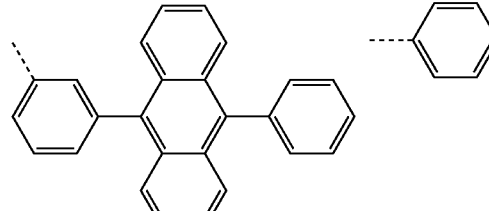 | 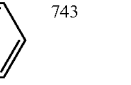 | 743 |
| 1-9-7 | compound 1E-2-7 | 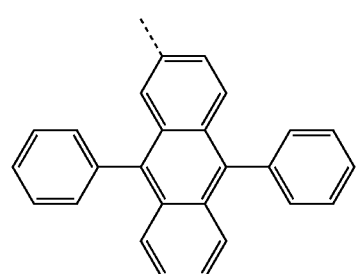 | 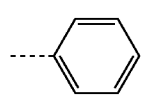 | 743 |
| 1-9-8 | compound 1E-2-8 | 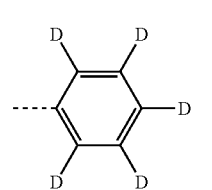 | 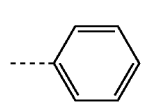 | 496 |

TABLE 1-9-1-continued

| Syn. Ex. 1-9-No | Product 1E-2-No | Ar3 | Ar2 | MS [M]+ |
|---|---|---|---|---|
| 1-9-9 | compound 1E-2-9 | 9,9-dimethylfluoren-2-yl | phenyl | 607 |
| 1-9-10 | compound 1E-2-10 | 4-(1-phenyl-1H-benzimidazol-2-yl)phenyl | phenyl | 683 |
| 1-9-11 | compound 1E-2-11 | 4-(2,4,5-triphenyl-1H-imidazol-1-yl)phenyl | phenyl | 785 |

TABLE 1-10-1

| Syn. Ex. 1-10-No | Product 1E-3-No | Ar3 | Ar2 | MS [M]+ |
|---|---|---|---|---|
| 1-10-1 | compound 1E-3-1 | phenyl | 4-(10-(naphthalen-1-yl)anthracen-9-yl)phenyl | 793 |
| 1-10-2 | compound 1E-3-2 | naphthalen-2-yl | 4-(10-(naphthalen-1-yl)anthracen-9-yl)phenyl | 843 |
| 1-10-3 | compound 1E-3-3 | phenyl | 3-(10-phenylanthracen-9-yl)phenyl | 743 |

TABLE 1-10-1-continued

| Syn. Ex. 1-10-No | Product 1E-3-No | Ar3 | Ar2 | MS [M]+ |
|---|---|---|---|---|
| 1-10-4 | compound 1E-3-4 | phenyl | 2-substituted 9,10-diphenylanthracene | 743 |
| 1-10-5 | compound 1E-3-5 | phenyl | 2-substituted 9,10-di(2-naphthyl)anthracene | 843 |
| 1-10-6 | compound 1E-3-6 | 4-biphenyl | 2-substituted 9,10-diphenylanthracene | 819 |
| 1-10-7 | compound E-3-7 | 2-naphthyl | 2-substituted 9,10-diphenylanthracene | 793 |
| 1-10-8 | compound E-3-8 | 4-(phenyl-d5)phenyl | 2-substituted 9,10-diphenylanthracene | 824 |

TABLE 1-10-1-continued

| Syn. Ex. 1-10-No | Product 1E-3-No | Ar3 | Ar2 | MS [M]+ |
|---|---|---|---|---|
| 1-10-9 | compound 1E-3-9 | 2-naphthyl | 3-(10-phenylanthracen-9-yl)phenyl | 793 |

TABLE 1-11-1

| Syn. Ex. 1-11-No | Product 1E-4-No | Ar3 | Ar2 | MS [M]+ |
|---|---|---|---|---|
| 1-11-1 | compound 1E-4-1 | phenyl | 4-chlorophenyl | 525 |
| 1-11-2 | compound 1E-4-2 | biphenyl-4-yl | 4-chlorophenyl | 601 |
| 1-11-3 | compound 1E-4-3 | phenyl | 4'-chlorobiphenyl-4-yl | 601 |
| 1-11-4 | compound 1E-4-4 | biphenyl-4-yl | 4'-chlorobiphenyl-4-yl | 677 |
| 1-11-5 | compound 1E-4-5 | 2-naphthyl | 4-chlorophenyl | 575 |

SYNTHESIS EXAMPLE 2-1-No

Synthesis of the Compound 2B-1-No

The compound A-2, and 1 to 1.5 equivalents of the substituted or unsubstituted arylboronic acid (or arylboron ester) or the substituted or unsubstituted heteroarylboronic acid (or arylboron ester) like the reactant S—No. described in Table 1 were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to synthesize the 2B-1-No compound, and the results thereof are described in Table 2-1-1.

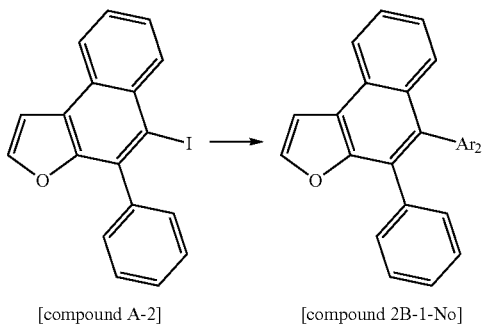

[compound A-2] → [compound 2B-1-No]

SYNTHESIS EXAMPLE 2-1-1

Synthesis of the Compound 2B-1-1

In Synthesis Example 1-1-1, the compound 2B-1-1 was synthesized by using the same method, except that naphthalen-2-yl-2-boronic acid that was the reactant S-1 of Table 1 and the compound A-2 were used.

SYNTHESIS EXAMPLE 2-1-2 TO 2-1-6

Synthesis of the Compounds 2B-1-2 to 2B-1-6

In Synthesis Example 2-1-1, it was synthesized by using the same method to synthesize the compounds 2B-1-2, 2B-1-3, 2B-1-4, 2B-1-5, and 2B-1-6, except that the reactants S-3, S-5, S-8, S-10, and S-9 were used instead of naphthalene-2-yl-2-boronic acid.

TABLE 2-1-1

| Syn. Ex. 2-1-No | Product 2B-1-No | reactant | Ar2 | MS [M + H]+ |
|---|---|---|---|---|
| 2-1-1 | compound 2B-1-1 | S-1 | 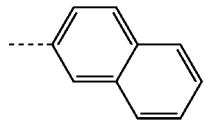 | 371 |
| 2-1-2 | compound 2B-1-2 | S-3 | 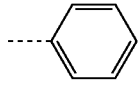 | 321 |
| 2-1-3 | compound 2B-1-3 | S-5 | 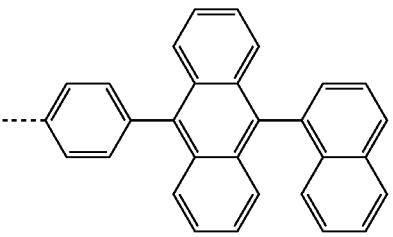 | 623 |
| 2-1-4 | compound 2B-1-4 | S-8 | 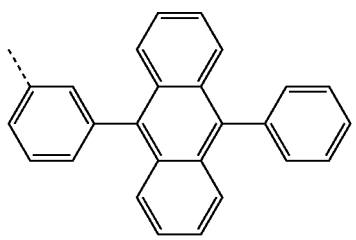 | 573 |
| 2-1-5 | compound 2B-1-5 | S-10 | 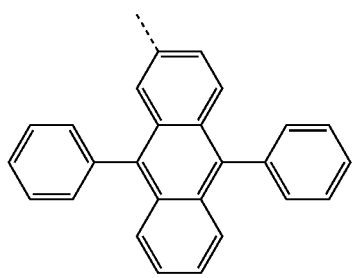 | 572 |
| 2-1-6 | compound 2B-1-6 | S-9 | 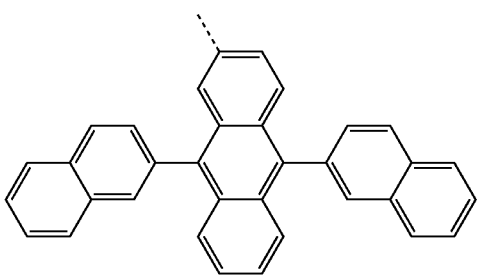 | 673 |

SYNTHESIS EXAMPLE 2-2-No

Synthesis of the Compound 2C-1-No

The compound 2B-1-No was dissolved in chloroform, and 1 equivalent of N-bromo succinimide was added thereto, and agitated for 3 to 8 hours at normal temperature. Distilled water was put into the reaction solution, the termination of the reaction was carried out, and the organic material layer was extracted. The reaction solution was concentrated, and recrystallized with EtOH to synthesize the compound 2C-1-No, and the results are described in Table 2-2-1.

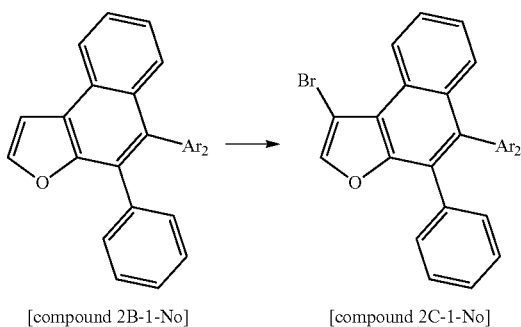

[compound 2B-1-No]    [compound 2C-1-No]

SYNTHESIS EXAMPLE 2-2-1

Synthesis of the Compound 2C-1-1

In Synthesis Example 1-2-1, it was synthesized by using the same method to synthesize the compound 2C-1-1, except that the compound 2B-1-1 was used instead of the compound 1B-1-1.

SYNTHESIS OF SYNTHESIS EXAMPLES 2-2-2 TO 2-2-6

Synthesis of the Compounds 2C-1-3 to 2C-1-6

In Synthesis Example 2-2-1, it was synthesized by using the same method to synthesize the compounds 2C-1-2, 2C-1-3, 2C-1-4, 2C-1-5, and 2C-1-6, except that the compounds 2B-1-2, 2B-1-3, 2B-1-4 2B-1-5, and 2B-1-6 were used instead of the compound 2B-1-1.

The results are described in Table 2-2-1.

TABLE 2-2-1

| Syn. Ex. 2-2-No | Product 2C-1-No | reactant 2B-1-No | Ar2 | MS [M]+ |
|---|---|---|---|---|
| 2-2-1 | compound 2C-1-1 | compound 2B-1-1 | naphthalene | 449 |
| 2-2-2 | compound 2C-1-2 | compound 2B-1-2 | phenyl | 399 |
| 2-2-3 | compound 2C-1-3 | compound 2B-1-3 | 9-(naphthalen-1-yl)-10-phenylanthracene linker | 701 |
| 2-2-4 | compound 2C-1-4 | compound 2B-1-4 | 9,10-diphenylanthracene linker (meta) | 651 |

TABLE 2-2-1-continued

| Syn. Ex. 2-2-No | Product 2C-1-No | reactant 2B-1-No | Ar2 | MS [M]+ |
|---|---|---|---|---|
| 2-2-5 | compound 2C-1-5 | compound 2B-1-5 | | 651 |
| 2-2-6 | compound 2C-1-6 | compound 2B-1-6 | | 751 |

GENERAL SYNTHESIS EXAMPLE 2-3-NO

Synthesis of the Compound 2D-1-No

The compound 2C-1-No, and 1 to 1.5 equivalents of the substituted or unsubstituted arylboronic acid (or arylboron ester) or the substituted or unsubstituted heteroarylboronic acid (or arylboron ester) like the reactant S—No. described in Table 1 were put, dissolved in THF, 0.02 equivalents of Pd(PPh$_3$) and 2 equivalents or more of 2M K$_2$CO$_3$/H$_2$O aqueous solution were added, and heated and agitated for 3 to 16 hours. The reaction mixture was cooled to normal temperature, filtered or extracted with the organic solvent, separated, purified, and dried to synthesize the 2D-1-No compound.

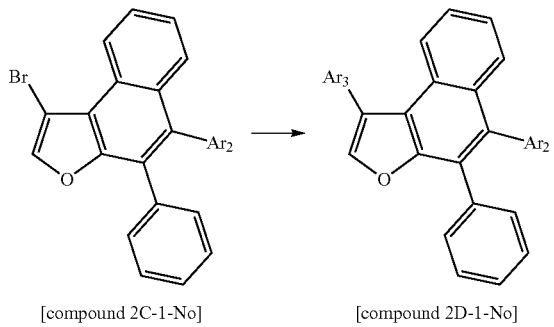

[compound 2C-1-No]    [compound 2D-1-No]

SYNTHESIS EXAMPLE 2-3-1

Synthesis of the Compound 2D-1-1

In Synthesis Example 1-3-1, it was synthesized by using the same method to synthesize the compound 2D-1-1, except that the phenyl boronic acid reactant S-3 and the compound 2C-1-1 were used instead of the compound 1C-1-1.

SYNTHESIS EXAMPLE 2-3-2

Synthesis of the Compound 2D-1-2

In Synthesis Example 2-3-1, it was synthesized by using the same method to synthesize the compound 2D-1-2, except that the reactant S-1 was used instead of the phenyl boronic acid reactant S-3.

SYNTHESIS EXAMPLE 2-3-3

Synthesis of the Compound 2D-1-3

In Synthesis Example 2-3-1, it was synthesized by using the same method to synthesize the compound 2D-1-3, except that the reactant S-1 was used instead of the phenyl boronic acid reactant S-3 and the compound 2C-1-2 was used instead of the compound 2C-1-1.

SYNTHESIS EXAMPLE 2-3-4

Synthesis of the Compound 2D-1-4

In Synthesis Example 2-3-1, it was synthesized by using the same method to synthesize the compound 2D-1-4, except that the compound 2C-1-3 was used instead of the compound 2C-1-1.

SYNTHESIS EXAMPLE 2-3-5

Synthesis of the Compound 2D-1-5

In Synthesis Example 2-3-1, it was synthesized by using the same method to synthesize the compound 2D-1-5, except that the reactant S-11 was used instead of the phenyl boronic acid reactant S-3 and the compound 2C-1-4 was used instead of the compound 2C-1-1.

SYNTHESIS EXAMPLE 2-3-6

Synthesis of the Compound 2D-1-6

In Synthesis Example 2-3-1, it was synthesized by using the same method to synthesize the compound 2D-1-6, except that the reactant S-4 was used instead of the phenyl boronic acid reactant S-3 and the compound 2C-1-5 was used instead of the compound 2C-1-1.

SYNTHESIS EXAMPLE 2-3-7

Synthesis of the Compound 2D-1-7

In Synthesis Example 2-3-1, it was synthesized by using the same method to synthesize the compound 2D-1-7, except that the compound 2C-1-6 was used instead of the compound 2C-1-1.

The results are described in Table 2-3-1.

TABLE 2-3-1

| Syn. Ex. 2-3-No | Product 2D-1-No | Ar3 | Ar2 | MS [M + H]+ |
|---|---|---|---|---|
| 2-3-1 | compound 2D-1-1 | phenyl | naphthyl | 447 |
| 2-3-2 | compound 2D-1-2 | naphthyl | naphthyl | 497 |
| 2-3-3 | compound 2D-1-3 | naphthyl | phenyl | 447 |
| 2-3-4 | compound 2D-1-4 | phenyl | 10-(naphthyl)anthracen-9-yl-phenyl | 699 |
| 2-3-5 | compound 2D-1-5 | biphenyl | 10-phenylanthracen-9-yl-phenyl | 725 |
| 2-3-6 | compound 2D-1-6 | d4-phenyl | 9,10-diphenylanthracen-2-yl | 654 |

TABLE 2-3-1-continued

| Syn. Ex. 2-3-No | Product 2D-1-No | Ar3 | Ar2 | MS [M + H]+ |
|---|---|---|---|---|
| 2-3-7 | compound 2D-1-7 | phenyl | 9,10-di(2-naphthyl)anthracen-2-yl | 749 |

SYNTHESIS EXAMPLE 2-4-1 TO 2-4-7

Synthesis of the Compounds 2E-1-1 to 2E-1-7

In Synthesis Example 1-4-1, it was synthesized by using the same method to synthesize the compounds 2E-1-1 to 2E-1-7, except that the compounds 2D-1-1 to 2D-1-7 were used instead of the compound 1-4-1.

TABLE 2-4-1

| Syn. Ex. 2-4-No | Product 2E-1-No | Ar3 | Ar2 | MS [M]+ |
|---|---|---|---|---|
| 2-4-1 | compound 2E-1-1 | phenyl | 2-naphthyl | 525 |
| 2-4-2 | compound 2E-1-2 | 2-naphthyl | 2-naphthyl | 575 |
| 2-4-3 | compound 2E-1-3 | 2-naphthyl | phenyl | 525 |
| 2-4-4 | compound 2E-1-4 | phenyl | 9-phenyl-10-(1-naphthyl)anthracen-2-yl | 696 |
| 2-4-5 | compound 2E-1-5 | 4-biphenyl | 9,10-diphenylanthracen-2-yl | 724 |

TABLE 2-4-1-continued
| Syn. Ex. 2-4-No | Product 2E-1-No | Ar3 | Ar2 | MS [M]+ |
|---|---|---|---|---|
| 2-4-6 | compound 2E-1-6 | | | 653 |
| 2-4-7 | compound 2E-1-7 | | | 748 |
SYNTHESIS EXAMPLE 3-1-1
Synthesis of the Compound 1F-1-1
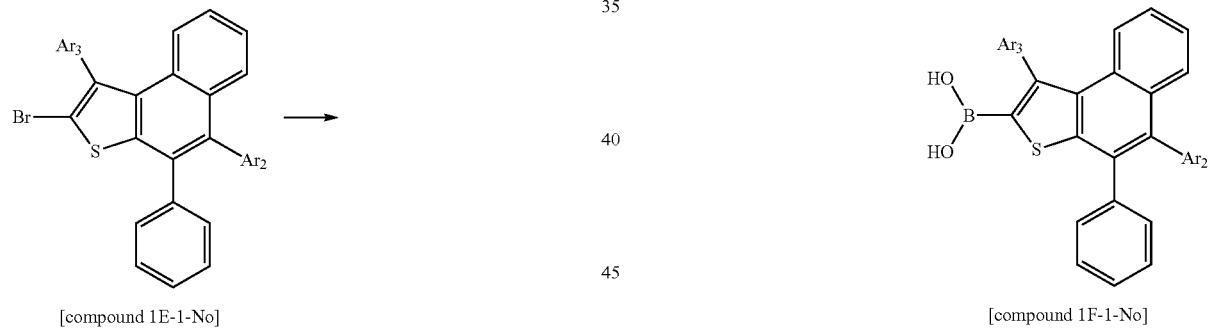
[compound 1E-1-No] → [compound 1F-1-No]
TABLE 3-1-1
| Syn. Ex. 3-1-No | Product 1F-1-No | MS [M + H]+ |
|---|---|---|
| 3-1-1 | compound 1F-1-1 | 457 |

TABLE 3-1-1-continued

| Syn. Ex. 3-1-No | Product 1F-1-No | MS [M + H]+ |
|---|---|---|
| 3-1-2 | compound 1F-1-2 | 507 |
| 3-1-3 | compound 1F-1-3 | 491 |

To the compound 1E-2-1 (20.3 g, 41.3 mmol) solution that was manufactured in Synthesis Example 1-9-1 in anhydrous THF (50 mL), n-BuLi (61.9 mmol, 24.8 mL in 2.5 M hexane solution) was dropped under the nitrogen atmosphere at −78° C. After the mixture was agitated for about 1 hour, trimethyl borate (14 mL, 123.9 mmol) was dropped at −78° C. After about 30 min, the cooling vessel was removed, and the mixture was agitated at room temperature for about 3 hours. 1N HCl (200 mL) was added to the above mixture, and extracted with ethyl acetate. The organic material layer was dried on magnesium sulfate and concentrated under the vacuum. The crude product was agitated with petroleum ether and precipitated, filtered, and dried to synthesize the compound 1F-1-1 (11.9 g, yield 63%).

SYNTHESIS EXAMPLE 3-1-2

Synthesis of the Compound 1F-1-2

In Synthesis Example 3-1-1, it was synthesized by using the same method to synthesize the compound 1F-1-2, except that the compound 1E-1-1 was used instead of the compound 1E-2-1.

SYNTHESIS EXAMPLE 3-1-3

Synthesis of the Compound 1F-1-3

In Synthesis Example 3-1-1, it was synthesized by using the same method to synthesize the compound 1F-1-3, except that the compound 2E-1-1 was used instead of the compound 1E-2-1.

PREPARATION EXAMPLE 1-1-NO

Preparation of the Compound 1-1-No

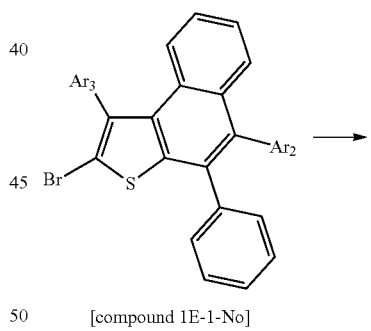

[compound 1E-1-No]

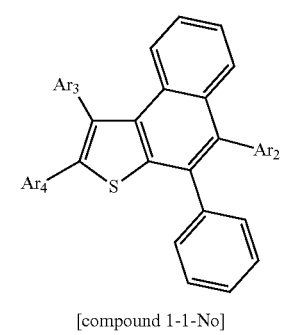

[compound 1-1-No]

The compound 1E-1-No, and 1 to 1.5 equivalents of the substituted or unsubstituted arylboronic acid (or arylboron ester) or the substituted or unsubstituted heteroarylboronic acid (or arylboron ester) were put, dissolved in THF, 0.02 equivalents of Pd(PPh₃) and 2 equivalents or more of 2M K₂CO₃/H₂O aqueous solution were added, and heated and agitated for 3 to 16 hours. The reaction mixture was cooled to normal temperature, filtered or extracted with the organic solvent, separated, purified, and dried to prepare the following 1-1-No compound, and the results thereof are described in Table 1-1.

PREPARATION EXAMPLE 1-1-7

Preparation of the Compound 1-1-7

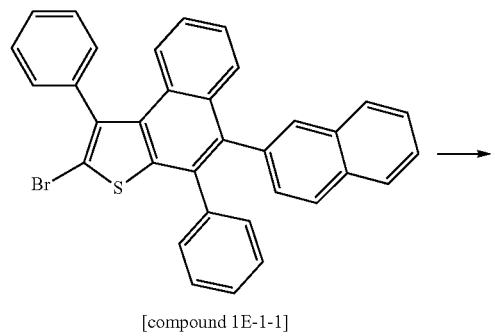

[compound 1E-1-1]

→

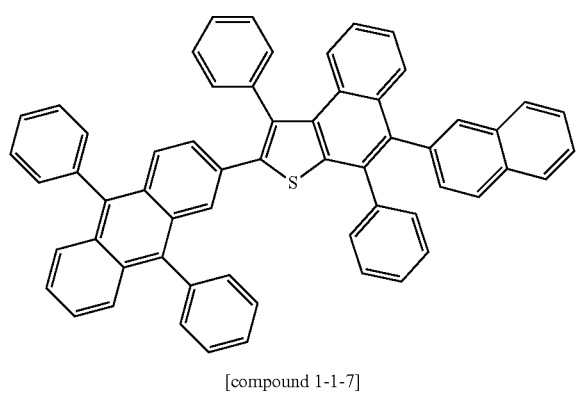

[compound 1-1-7]

2-[9,10-diphenyl-2-anthracenyl]-4,4,5,5-tetramethyl-1,3,2-dioxaborolane (2.2 g, 4.9 mmol) that was the reactant S-10, the compound 1E-1-1 (2.2 g, 4.1 mmol) that was prepared in Synthesis Example 1-8-1, and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 1-1-7 (2.5 g, yield 76%).

PREPARATION EXAMPLE 1-1-1 TO 1-1-6

Preparation of the Compounds 1-1-1 to 1-1-6

In Synthesis Example 1-1-7, it was synthesized by using the same method to prepare the compounds 1-1-1, 1-1-2, 1-1-3, 1-1-4, 1-1-5, and 1-1-6, except that the reactants S-1, S-11, S-20, S-12, S-8, S-10 were used instead of the reactant S-3.

PREPARATION EXAMPLE 1-1-8 TO
PREPARATION EXAMPLE 1-1-14

Preparation of the Compounds 1-1-8 to 1-1-14

In Synthesis Example 1-1-7, it was synthesized by using the same method to prepare the compounds 1-1-8, 1-1-9, 1-1-10, 1-1-11, 1-1-12, 1-1-13, and 1-1-14, except that the reactants S-4, S-19, S-15, S-17, S-21, S-18, and S-16 were used instead of the reactant S-3.

In Preparation Examples 1-1-1 to 1-1-6 and Preparation Examples 1-1-8 to 1-1-14, they were prepared by using the same method as Preparation Example 1-1-7 by using the compound 1E-1-1 and boronic acid or boron ester compounds in the reactants of Table 1.

TABLE 1-1

| Prep. Ex. 1-1-No | Product 1-1-No | structure | MS [M + H]+ |
|---|---|---|---|
| 1-1-1 | compound 1-1-1 | 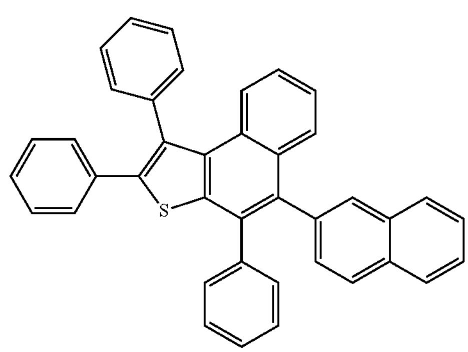 [SMILES: c1ccc(-c2sc3c(-c4ccccc4)c(-c4ccc5ccccc5c4)c4ccccc4c3c2-c2ccccc2)cc1] | 539 |

TABLE 1-1-continued

| Prep. Ex. 1-1-No | Product 1-1-No | structure | MS [M + H]+ |
|---|---|---|---|
| 1-1-2 | compound 1-1-2 | 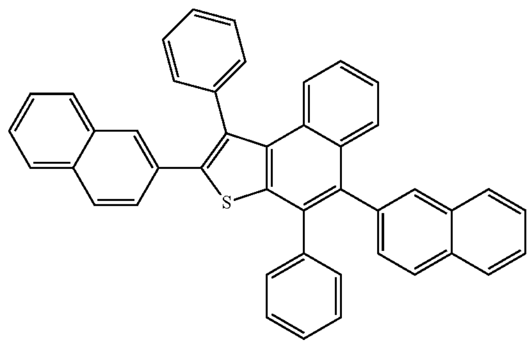 [SMILES: c1ccc(-c2c(-c3ccc4ccccc4c3)c3ccccc3c3c(-c4ccccc4)c(-c4ccc5ccccc5c4)sc23)cc1] | 589 |
| 1-1-3 | compound 1-1-3 | 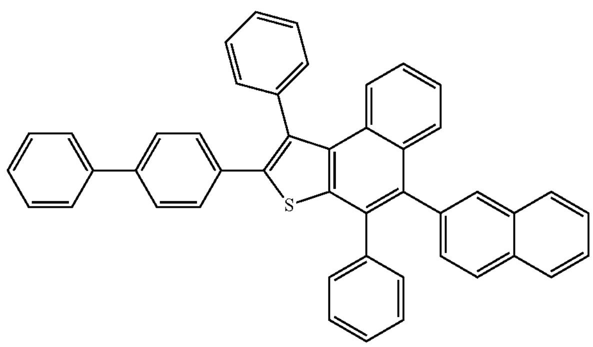 [SMILES: c1ccc(-c2ccc(-c3sc4c(-c5ccccc5)c(-c5ccc6ccccc6c5)c5ccccc5c4c3-c3ccccc3)cc2)cc1] | 615 |
| 1-1-4 | compound 1-1-4 | 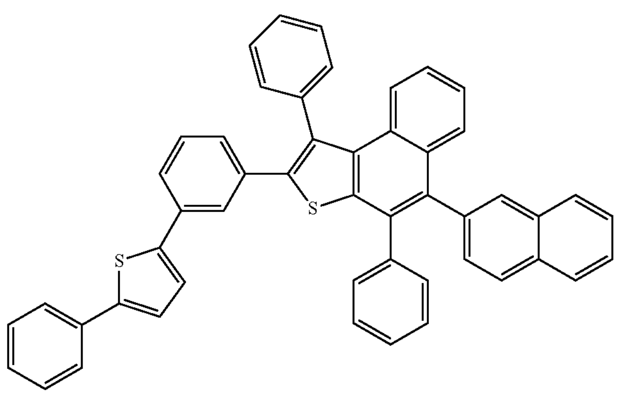 [SMILES: c1ccc(-c2ccc(-c3cccc(-c4sc5c(-c6ccccc6)c(-c6ccc7ccccc7c6)c6ccccc6c5c4-c4ccccc4)c3)s2)cc1] | 697 |
| 1-1-5 | compound 1-1-5 | 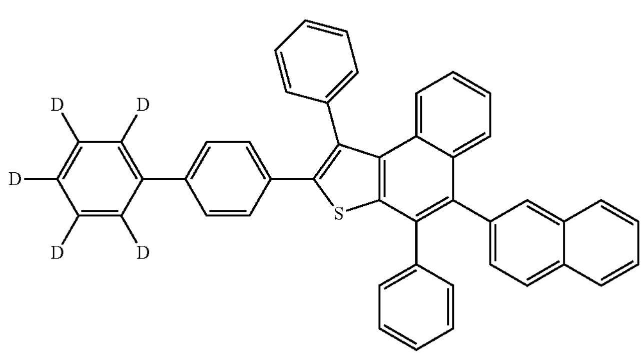 [SMILES: [2H]c1c([2H])c([2H])c(-c2ccc(-c3sc4c(-c5ccccc5)c(-c5ccc6ccccc6c5)c5ccccc5c4c3-c3ccccc3)cc2)c([2H])c1[2H]] | 620 |

TABLE 1-1-continued

| Prep. Ex. 1-1-No | Product 1-1-No | structure | MS [M + H]+ |
|---|---|---|---|
| 1-1-6 | compound 1-1-6 | 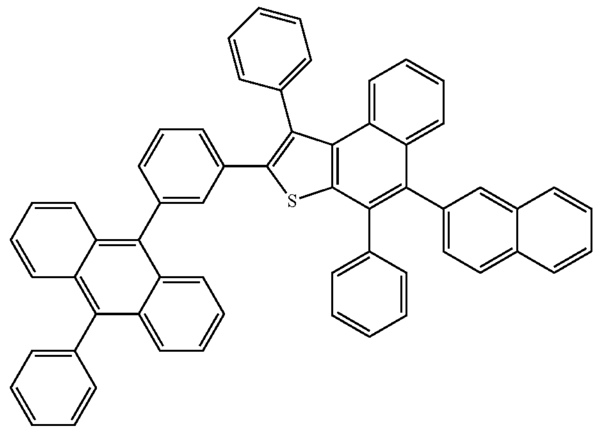 [SMILES: c1ccc(-c2c3ccccc3c(-c3cccc(-c4sc5c(-c6ccccc6)c(-c6ccc7ccccc7c6)c6ccccc6c5c4-c4ccccc4)c3)c3ccccc23)cc1] | 791 |
| 1-1-7 | compound 1-1-7 | 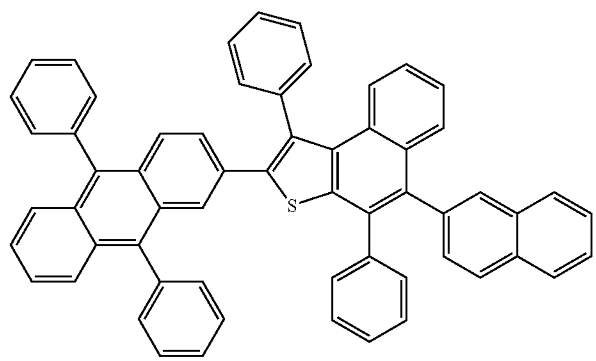 | 791 |
| 1-1-8 | compound 1-1-8 | 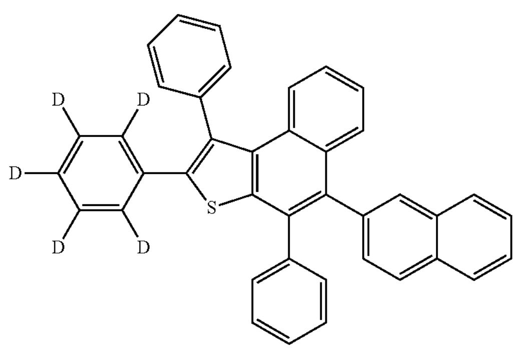 [SMILES: [2H]c1c([2H])c([2H])c(-c2sc3c(-c4ccccc4)c(-c4ccc5ccccc5c4)c4ccccc4c3c2-c2ccccc2)c([2H])c1[2H]] | 544 |
| 1-1-9 | compound 1-1-9 | 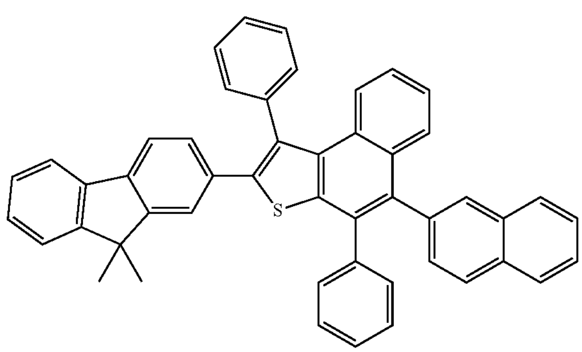 [SMILES: CC1(C)c2ccccc2-c2ccc(-c3sc4c(-c5ccccc5)c(-c5ccc6ccccc6c5)c5ccccc5c4c3-c3ccccc3)cc21] | 655 |

TABLE 1-1-continued

| Prep. Ex. 1-1-No | Product 1-1-No | structure | MS [M + H]+ |
|---|---|---|---|
| 1-1-10 | compound 1-1-10 | 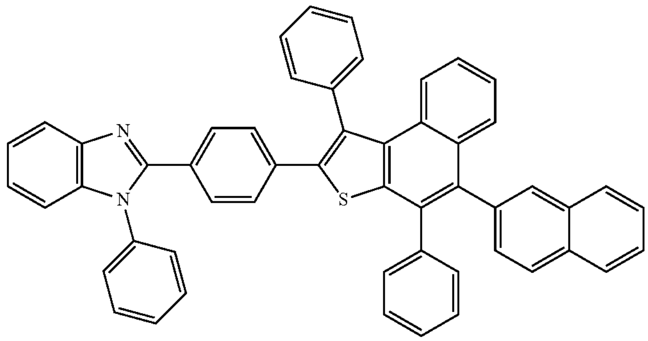 [SMILES: c1ccc(-c2c(-c3ccc4ccccc4c3)c3ccccc3c3c(-c4ccccc4)c(-c4ccc(-c5nc6ccccc6n5-c5ccccc5)cc4)sc23)cc1] | 731 |
| 1-1-11 | compound 1-1-11 | 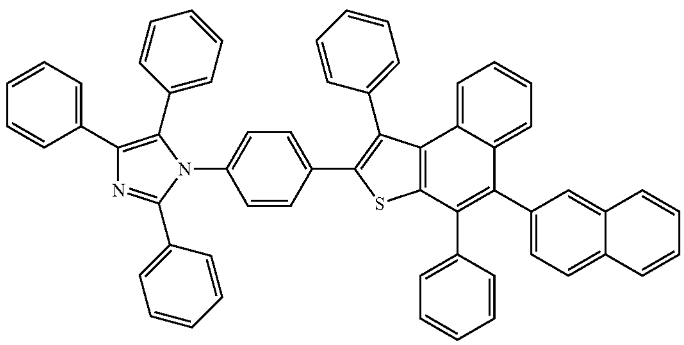 [SMILES: c1ccc(-c2nc(-c3ccccc3)n(-c3ccc(-c4sc5c(-c6ccccc6)c(-c6ccc7ccccc7c6)c6ccccc6c5c4-c4ccccc4)cc3)c2-c2ccccc2)cc1] | 833 |
| 1-1-12 | compound 1-1-12 | 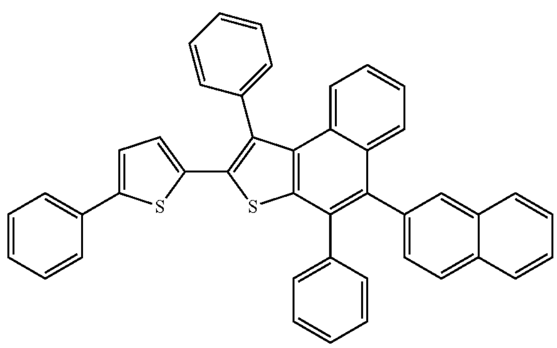 [SMILES: c1ccc(-c2ccc(-c3sc4c(-c5ccccc5)c(-c5ccc6ccccc6c5)c5ccccc5c4c3-c3ccccc3)s2)cc1] | 621 |
| 1-1-13 | compound 1-1-13 | 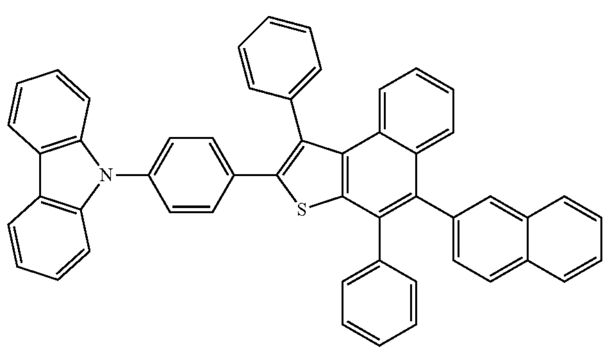 [SMILES: c1ccc(-c2c(-c3ccc4ccccc4c3)c3ccccc3c3c(-c4ccccc4)c(-c4ccc(-n5c6ccccc6c6ccccc65)cc4)sc23)cc1] | 704 |

TABLE 1-1-continued

| Prep. Ex. 1-1-No | Product 1-1-No | structure | MS [M + H]+ |
|---|---|---|---|
| 1-1-14 | compound 1-1-14 | 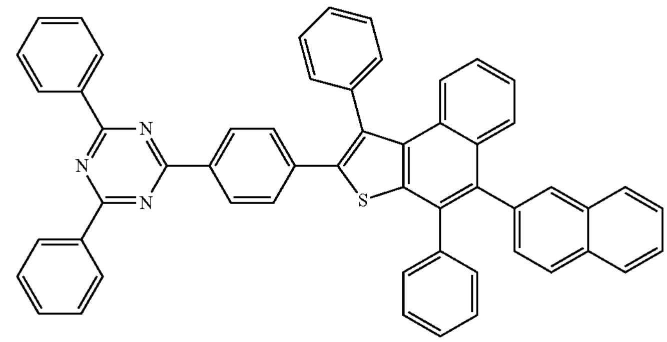 [SMILES: c1ccc(-c2nc(-c3ccccc3)nc(-c3ccc(-c4sc5c(-c6ccccc6)c(-c6ccc7ccccc7c6)c6ccccc6c5c4-c4ccccc4)cc3)n2)cc1] | 770 |

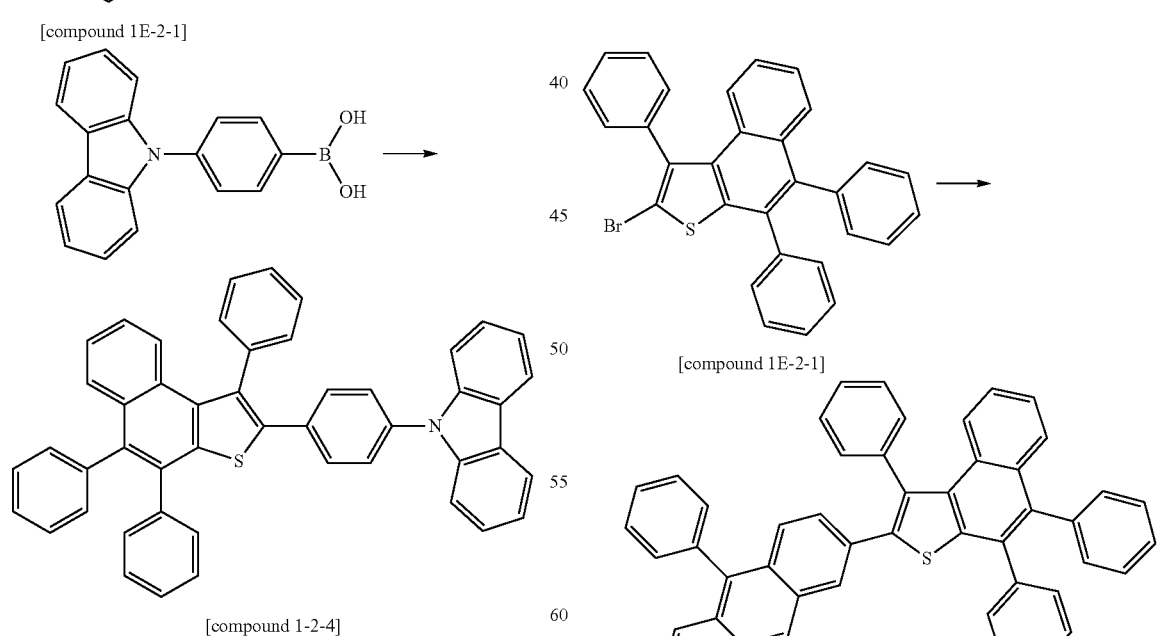

PREPARATION EXAMPLE 1-2-4

Preparation of the Compound 1-2-4

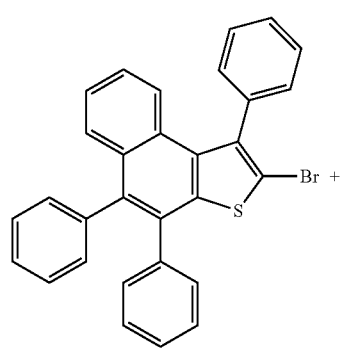

[4-(9H-carbazol-9-yl)phenyl boronic acid (1.4 g, 4.9 mmol), the compound E-2 (2.0 g, 4.1 mmol) that was prepared in Preparation Example 2, and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 1-2-4 (1.6 g, yield 58%).

In Preparation Examples 1-2-1 to 1-2-3, Preparation Examples 1-2-5 to 1-2-7, Preparation Examples 1-2-11, 1-2-13, 1-2-15 and Preparation Examples 1-2-16 to 1-2-20, they were prepared by using the same method as Preparation Example 1-2-8, except that the reactants having different substituent groups were used as the boronic acid or boron ester reactant.

PREPARATION EXAMPLE 1-2-8

Preparation of the Compound 1-2-8

133

2-[9,10-diphenyl-2-anthracenyl]-4,4,5,5-tetramethyl-1,3,2-dioxaborolane (2.2 g, 4.9 mmol) that was the reactant S-10, the compound 1E-1-2 (2.0 g, 4.1 mmol) that was prepared in Synthesis Example 1-9-1, and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 1-2-8 (2.2 g, yield 73%).

PREPARATION EXAMPLE 1-2-9

Preparation of the Compound 1-2-9

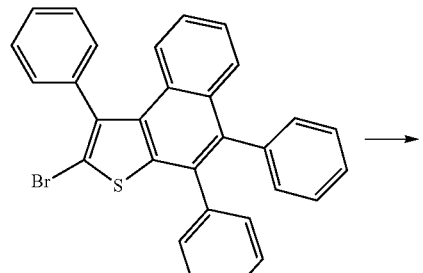

[compound 1E-2-1]

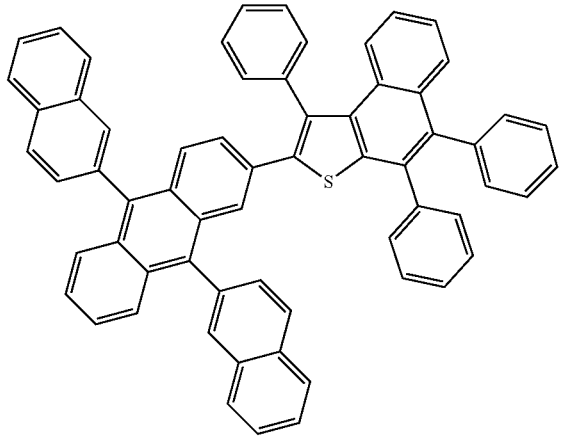

[compound 1-2-9]

2-[9,10-di-2-naphthalenyl-2-anthracenyl]-4,4,5,5-tetramethyl-1,3,2-dioxaborolane (2.7 g, 4.9 mmol) that was the reactant S-10, the compound 1E-2-1 (2.0 g, 4.1 mmol) that was prepared in Synthesis Example 1-1-9, and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 1-2-9 (2.5 g, yield 76%).

134

PREPARATION EXAMPLE 1-2-10

Preparation of the Compound 1-2-10

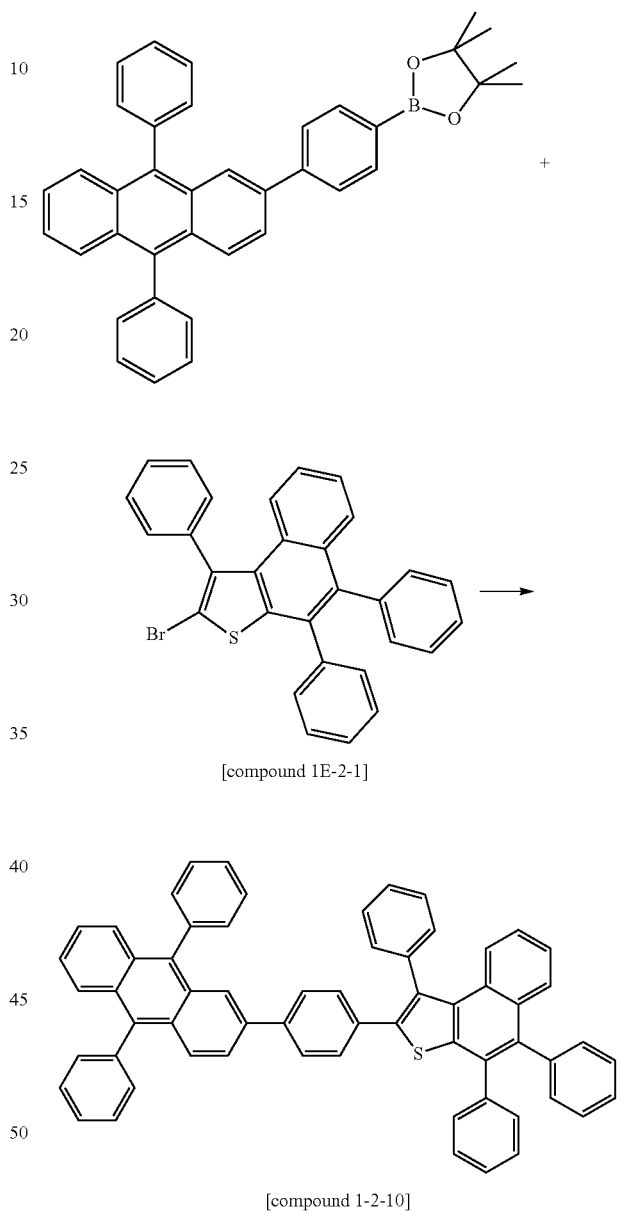

[compound 1E-2-1]

[compound 1-2-10]

2-[9,10-diphenyl-2-anthracenyl]-4,4,5,5-tetramethyl-1,3,2-dioxaborolane (2.6 g, 4.9 mmol) that was the reactant S-22, the compound 1E-2-1 (2.0 g, 4.1 mmol) that was prepared in Synthesis Example 1-9-1, and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 1-2-10 (2.5 g, yield 75%).

PREPARATION EXAMPLE 1-2-12

Preparation of the Compound 1-2-12

[compound 1E-2-1] →

[compound 1-2-12]

4-[9-(2-naphthyl-10-phenylene]-4,4,5,5-tetramethyl-1,3,2-dioxaborolane) (2.2 g, 4.9 mmol) that was the reactant S-6, the compound 1E-2-1 (2.0 g, 4.1 mmol) that was prepared in Synthesis Example 1-9-1, and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 1-2-12 (2.5 g, yield 77%).

PREPARATION EXAMPLE 1-2-14

Preparation of the Compound 1-2-14

[compound 1E-2-1] →

[compound 1-2-14]

The reactant S-15 (1.9 g, 4.9 mmol), the compound 1E-2-1 (2.0 g, 4.1 mmol) that was prepared in Synthesis Example 1-9-1, and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 1-2-14 (1.9 g, yield 67%).

TABLE 1-2

| Prep. Ex. 1-2-No | Product 1-2-No | structure | MS [M + H]+ |
|---|---|---|---|
| 1-2-1 | compound 1-2-1 | 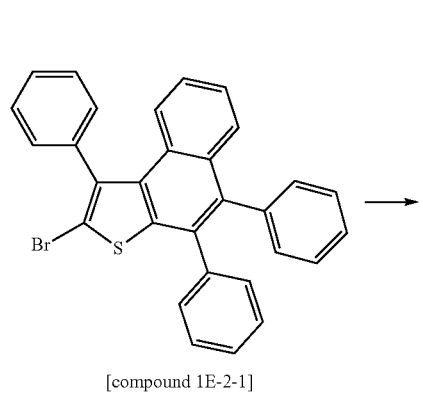 | 666 |

TABLE 1-2-continued

| Prep. Ex. 1-2-No | Product 1-2-No | structure | MS [M + H]+ |
|---|---|---|---|
| 1-2-2 | compound 1-2-2 | 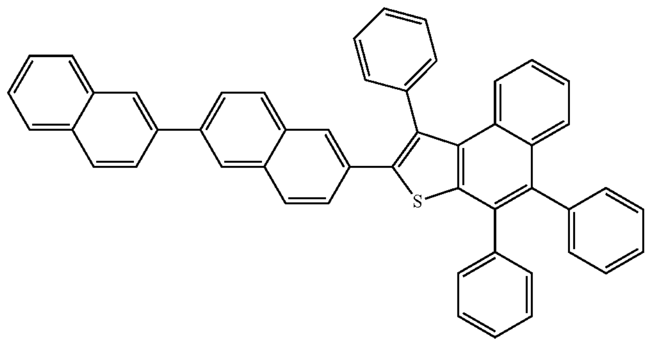 [SMILES: c1ccc(-c2c(-c3ccccc3)c3sc(-c4ccc5cc(-c6ccc7ccccc7c6)ccc5c4)c(-c4ccccc4)c3c3ccccc23)cc1] | 665 |
| 1-2-3 | compound 1-2-3 | 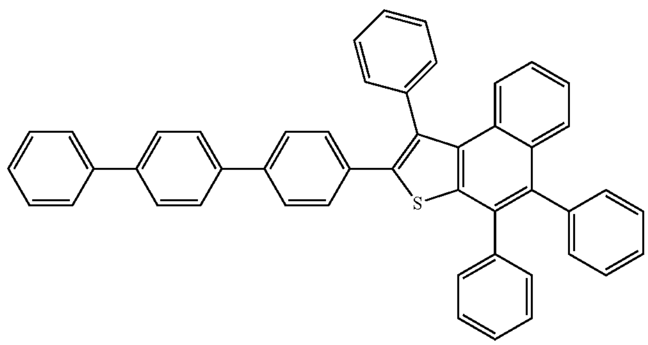 [SMILES: c1ccc(-c2ccc(-c3ccc(-c4sc5c(-c6ccccc6)c(-c6ccccc6)c6ccccc6c5c4-c4ccccc4)cc3)cc2)cc1] | 641 |
| 1-2-4 | compound 1-2-4 | 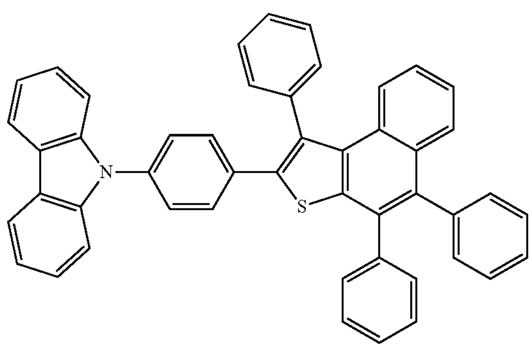 [SMILES: c1ccc(-c2c(-c3ccccc3)c3sc(-c4ccc(-n5c6ccccc6c6ccccc65)cc4)c(-c4ccccc4)c3c3ccccc23)cc1] | 654 |
| 1-2-5 | compound 1-2-5 | 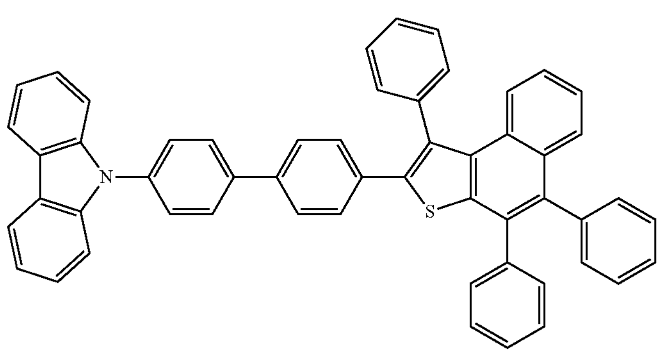 [SMILES: c1ccc(-c2c(-c3ccccc3)c3sc(-c4ccc(-c5ccc(-n6c7ccccc7c7ccccc76)cc5)cc4)c(-c4ccccc4)c3c3ccccc23)cc1] | 730 |

TABLE 1-2-continued

| Prep. Ex. 1-2-No | Product 1-2-No | structure | MS [M + H]+ |
|---|---|---|---|
| 1-2-6 | compound 1-2-6 | 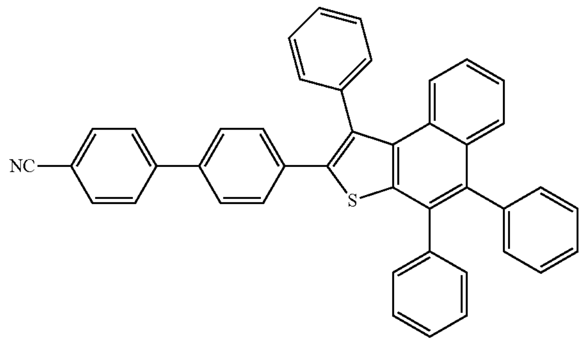 [SMILES: N#Cc1ccc(-c2ccc(-c3sc4c(-c5ccccc5)c(-c5ccccc5)c5ccccc5c4c3-c3ccccc3)cc2)cc1] | 590 |
| 1-2-7 | compound 1-2-7 | 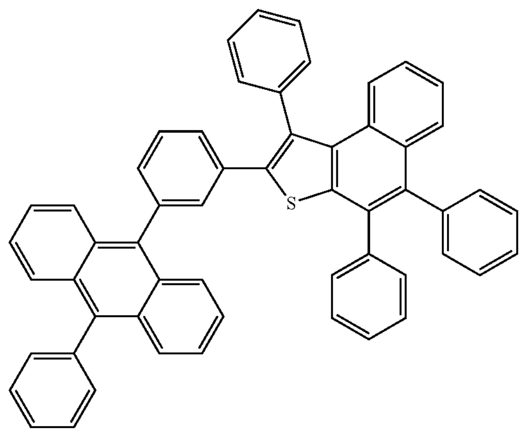 [SMILES: c1ccc(-c2c3ccccc3c(-c3cccc(-c4sc5c(-c6ccccc6)c(-c6ccccc6)c6ccccc6c5c4-c4ccccc4)c3)c3ccccc23)cc1] | 741 |
| 1-2-8 | compound 1-2-8 | 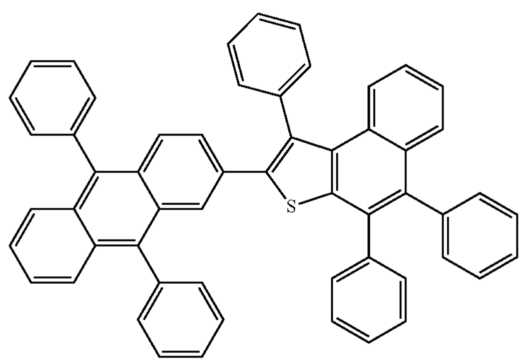 [SMILES: c1ccc(-c2c3ccccc3c(-c3ccccc3)c3cc(-c4sc5c(-c6ccccc6)c(-c6ccccc6)c6ccccc6c5c4-c4ccccc4)ccc23)cc1] | 741 |
| 1-2-9 | compound 1-2-9 | 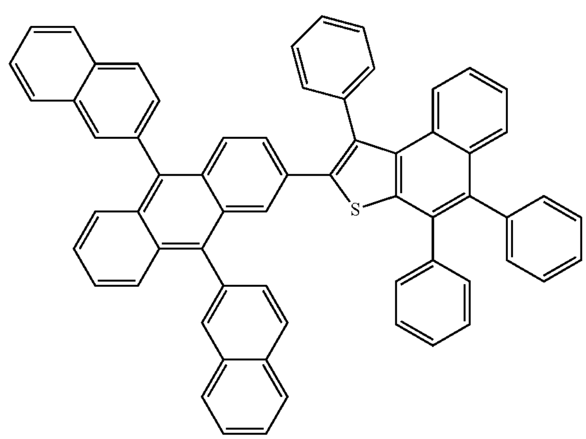 [SMILES: c1ccc(-c2c(-c3ccccc3)c3sc(-c4ccc5c(-c6ccc7ccccc7c6)c6ccccc6c(-c6ccc7ccccc7c6)c5c4)c(-c4ccccc4)c3c3ccccc23)cc1] | 841 |

TABLE 1-2-continued

| Prep. Ex. 1-2-No | Product 1-2-No | structure | MS [M + H]+ |
|---|---|---|---|
| 1-2-10 | compound 1-2-10 | 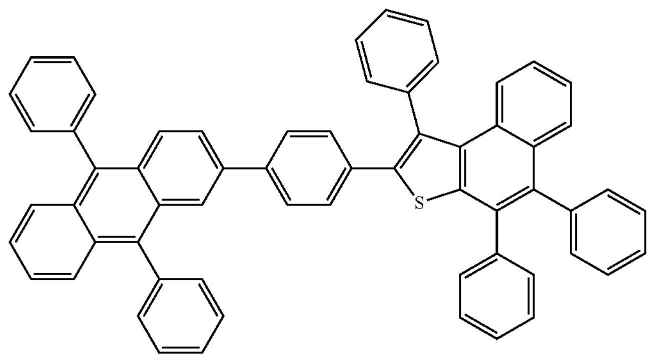 [SMILES: c1ccc(-c2c3ccccc3c(-c3ccccc3)c3cc(-c4ccc(-c5sc6c(-c7ccccc7)c(-c7ccccc7)c7ccccc7c6c5-c5ccccc5)cc4)ccc23)cc1] | 817 |
| 1-2-11 | compound 1-2-11 | 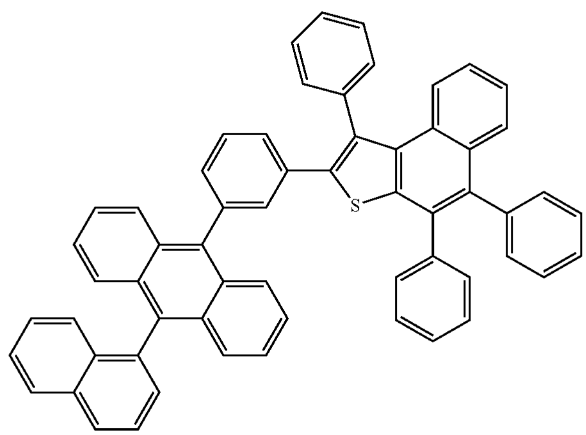 [SMILES: c1ccc(-c2c(-c3ccccc3)c3sc(-c4cccc(-c5c6ccccc6c(-c6cccc7ccccc67)c6ccccc56)c4)c(-c4ccccc4)c3c3ccccc23)cc1] | 791 |
| 1-2-12 | compound 1-2-12 | 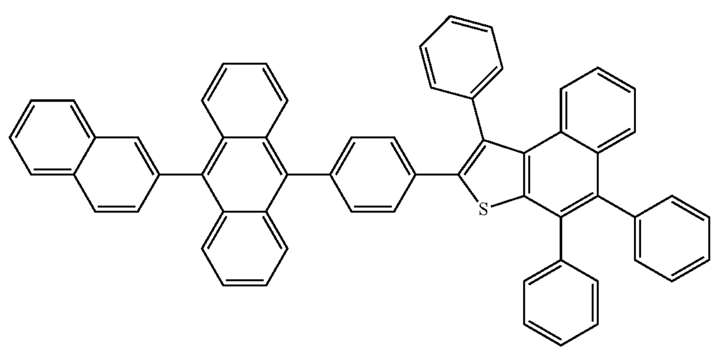 [SMILES: c1ccc(-c2c(-c3ccccc3)c3sc(-c4ccc(-c5c6ccccc6c(-c6ccc7ccccc7c6)c6ccccc56)cc4)c(-c4ccccc4)c3c3ccccc23)cc1] | 791 |
| 1-2-13 | compound 1-2-13 | 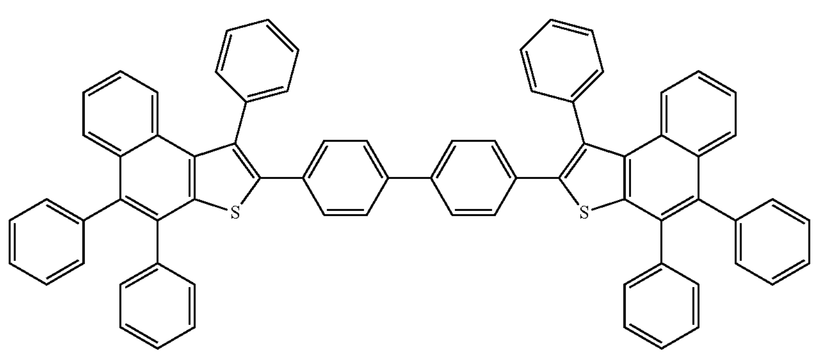 [SMILES: c1ccc(-c2c(-c3ccccc3)c3sc(-c4ccc(-c5ccc(-c6sc7c(-c8ccccc8)c(-c8ccccc8)c8ccccc8c7c6-c6ccccc6)cc5)cc4)c(-c4ccccc4)c3c3ccccc23)cc1] | 975 |

TABLE 1-2-continued

| Prep. Ex. 1-2-No | Product 1-2-No | structure | MS [M + H]+ |
|---|---|---|---|
| 1-2-14 | compound 1-2-14 | 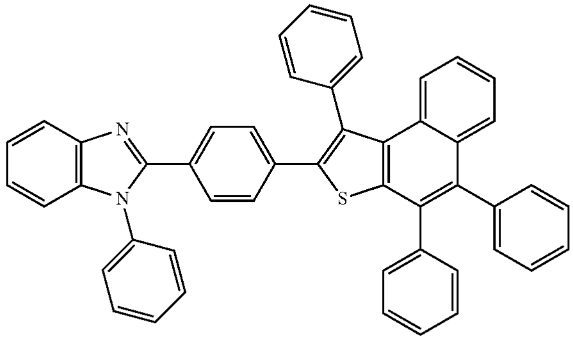 [SMILES: c1ccc(-c2c(-c3ccccc3)c3sc(-c4ccc(-c5nc6ccccc6n5-c5ccccc5)cc4)c(-c4ccccc4)c3c3ccccc23)cc1] | 681 |
| 1-2-15 | compound 1-2-15 | 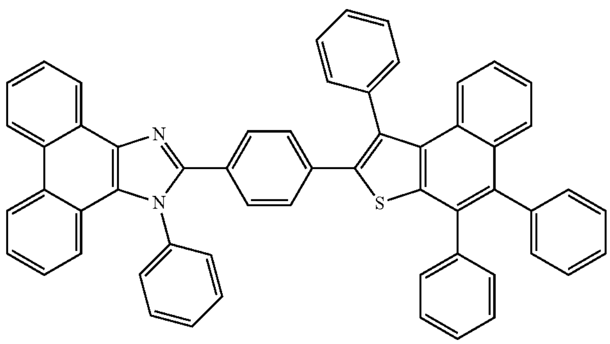 [SMILES: c1ccc(-c2c(-c3ccccc3)c3sc(-c4ccc(-c5nc6c7ccccc7c7ccccc7c6n5-c5ccccc5)cc4)c(-c4ccccc4)c3c3ccccc23)cc1] | 781 |
| 1-2-16 | compound 1-2-16 | 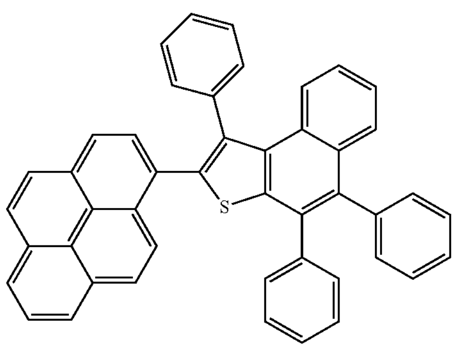 [SMILES: c1ccc(-c2c(-c3ccccc3)c3sc(-c4ccc5ccc6cccc7ccc4c5c67)c(-c4ccccc4)c3c3ccccc23)cc1] | 613 |
| 1-2-17 | compound 1-2-17 | 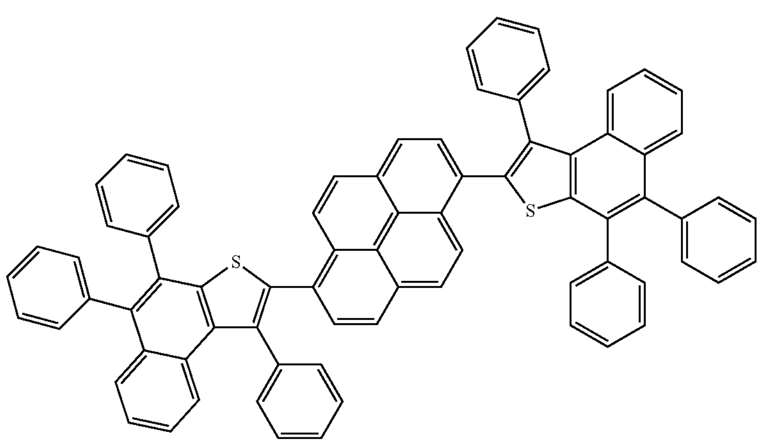 [SMILES: c1ccc(-c2c(-c3ccccc3)c3sc(-c4ccc5ccc6c(-c7sc8c(-c9ccccc9)c(-c9ccccc9)c9ccccc9c8c7-c7ccccc7)ccc7ccc4c5c76)c(-c4ccccc4)c3c3ccccc23)cc1] | 1023 |

TABLE 1-2-continued

| Prep. Ex. 1-2-No | Product 1-2-No | structure | MS [M + H]+ |
|---|---|---|---|
| 1-2-16 | compound 1-2-16 | 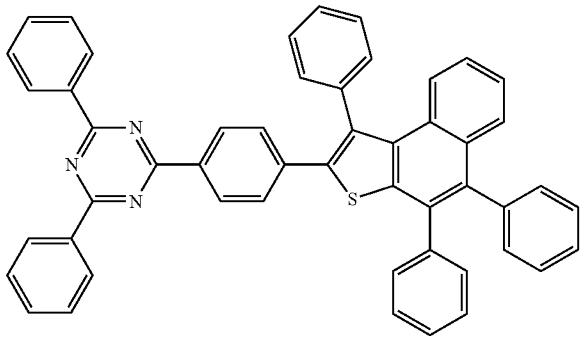 [SMILES: c1ccc(-c2nc(-c3ccccc3)nc(-c3ccc(-c4sc5c(-c6ccccc6)c(-c6ccccc6)c6ccccc6c5c4-c4ccccc4)cc3)n2)cc1] | 719 |
| 1-2-17 | compound 1-2-17 | 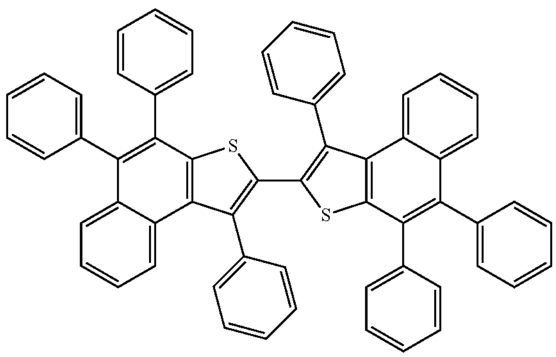 [SMILES: c1ccc(-c2c(-c3ccccc3)c3sc(-c4sc5c(-c6ccccc6)c(-c6ccccc6)c6ccccc6c5c4-c4ccccc4)c(-c4ccccc4)c3c3ccccc23)cc1] | 823 |
| 1-2-18 | compound 1-2-18 | 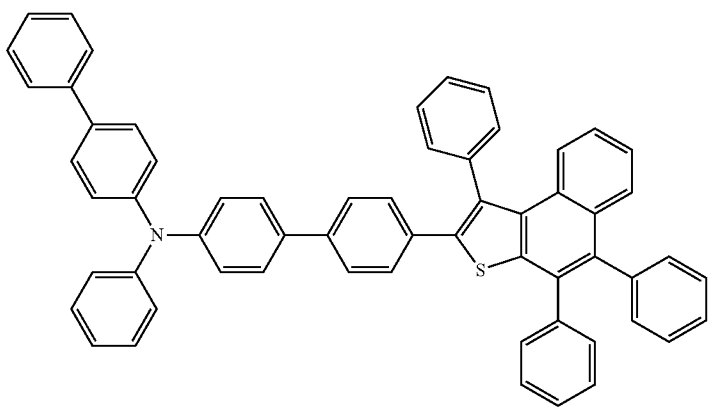 [SMILES: c1ccc(-c2ccc(N(c3ccccc3)c3ccc(-c4ccc(-c5sc6c(-c7ccccc7)c(-c7ccccc7)c7ccccc7c6c5-c5ccccc5)cc4)cc3)cc2)cc1] | 808 |
| 1-2-19 | compound 1-2-19 | 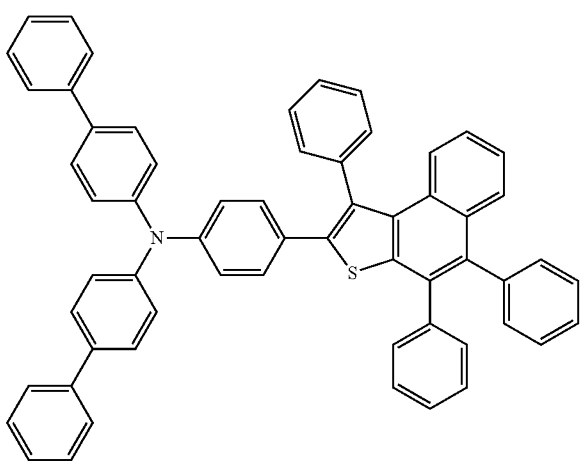 [SMILES: c1ccc(-c2ccc(N(c3ccc(-c4ccccc4)cc3)c3ccc(-c4sc5c(-c6ccccc6)c(-c6ccccc6)c6ccccc6c5c4-c4ccccc4)cc3)cc2)cc1] | 808 |

TABLE 1-2-continued

| Prep. Ex. 1-2-No | Product 1-2-No | structure | MS [M + H]+ |
|---|---|---|---|
| 1-2-20 | compound 1-2-20 | 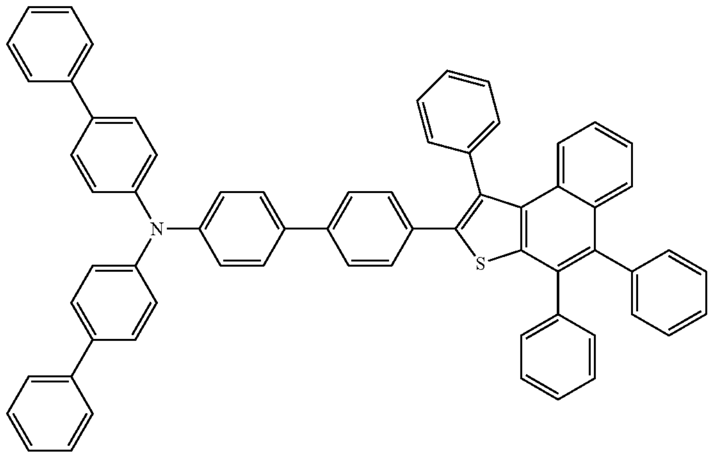 [SMILES: c1ccc(-c2ccc(N(c3ccc(-c4ccccc4)cc3)c3ccc(-c4ccc(-c5sc6c(-c7ccccc7)c(-c7ccccc7)c7ccccc7c6c5-c5ccccc5)cc4)cc3)cc2)cc1] | 884 |

PREPARATION EXAMPLE 1-3-1

Preparation of the Compound 1-3-1

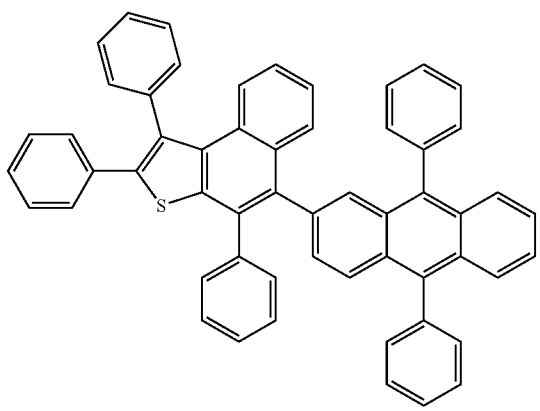 [SMILES: c1ccc(-c2sc3c(-c4ccccc4)c(-c4ccc5c(-c6ccccc6)c6ccccc6c(-c6ccccc6)c5c4)c4ccccc4c3c2-c2ccccc2)cc1]

[compound 1-3-1]

Phenyl boronic acid (2.5 g, 20.5 mmol), the compound 1E-3-4 (5.6 g, 9.3 mmol) that was prepared in Synthesis Example 1-10-4, and sodium carbonate (2.8 g, 20.5 mmol) were suspended in the mixture of tetrahydrofurane (100 mL) and water (50 mL). Tetrakis(triphenylphosphine)palladium (0.1 g, 0.2 mmol) was applied to the suspension solution. The mixture was refluxed and agitated for about 24 hours, and the refluxed mixture was cooled to room temperature. The prepared solid was purified with filtered THF/EtOH to prepare the compound 1-3-1 (3.2 g, yield 46%).

MS [M+H]$^+$=741

PREPARATION EXAMPLE 1-3-2

Preparation of the Compound 1-3-2

In Preparation Example 1-3-1, it was prepared by using the same method to prepare the compound 1-3-2, except that the compound of 1E-3-6 synthesized in Synthesis Example 1-10-6 was used.

PREPARATION EXAMPLE 1-3-3

Preparation of the Compound 1-3-3

In Preparation Example 1-3-1, it was prepared by using the same method to prepare the compound 1-3-3, except that the compound of 1E-3-7 synthesized in Synthesis Example 1-10-7 was used.

PREPARATION EXAMPLE 1-3-4

Preparation of the Compound 1-3-4

In Preparation Example 1-3-1, it was prepared by using the same method to prepare the compound 1-3-4, except that the compound of 1E-3-8 synthesized in Synthesis Example 1-10-8 was used.

TABLE 1-3
| Prep. Ex. 1-3-No | Product 1-3-No | structure | MS [M + H]+ |
|---|---|---|---|
| 1-3-1 | compound 1-3-1 | 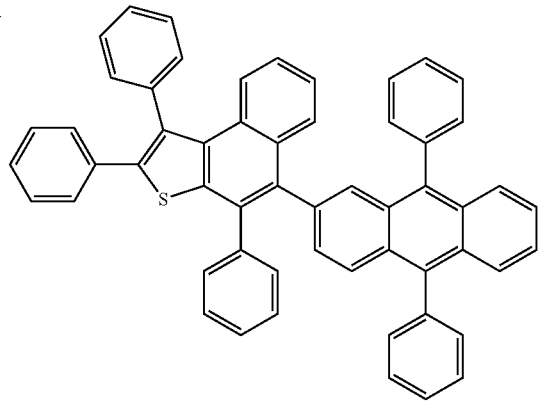 | 741 |
| 1-3-2 | compound 1-3-2 | 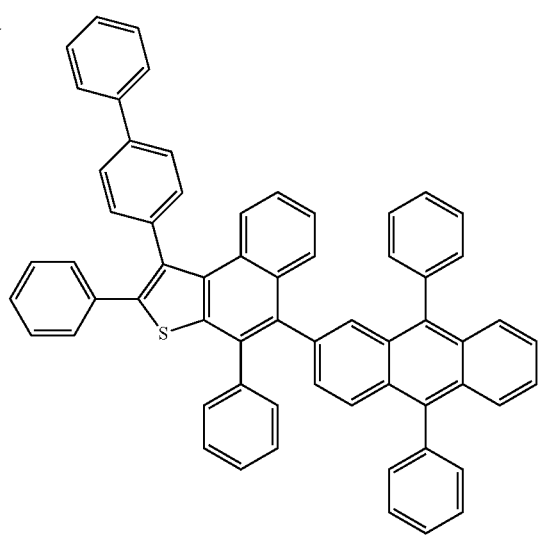 | 817 |
| 1-3-3 | compound 1-3-3 | 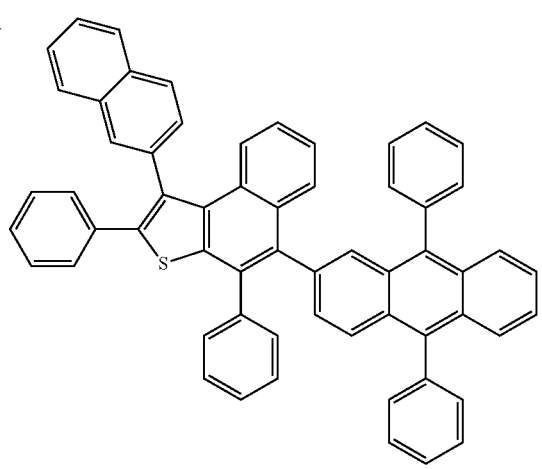 | 665 |

TABLE 1-3-continued

| Prep. Ex. 1-3-No | Product 1-3-No | structure | MS [M + H]+ |
|---|---|---|---|
| 1-3-4 | compound 1-3-4 | 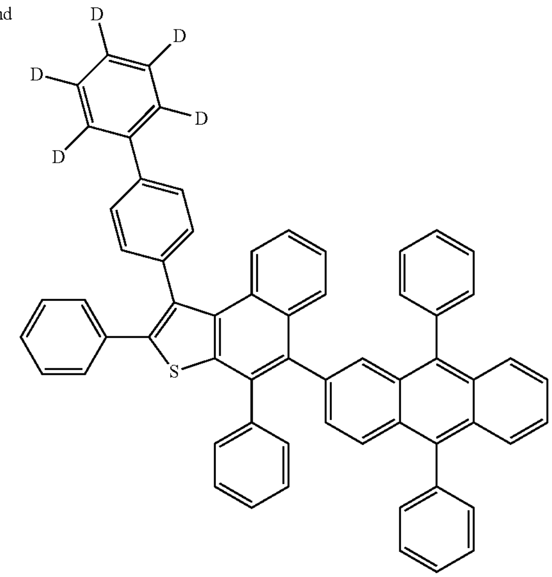 | 822 |

PREPARATION EXAMPLE 1-4-1

Preparation of the Compound 1-4-1

In Preparation Example 1-4-2, the compound 1-4-1 was prepared by using the same method, except that phenyl boronic acid was used instead of naphthyl boronic acid.

PREPARATION EXAMPLE 1-4-2

Preparation of the Compound 1-4-2

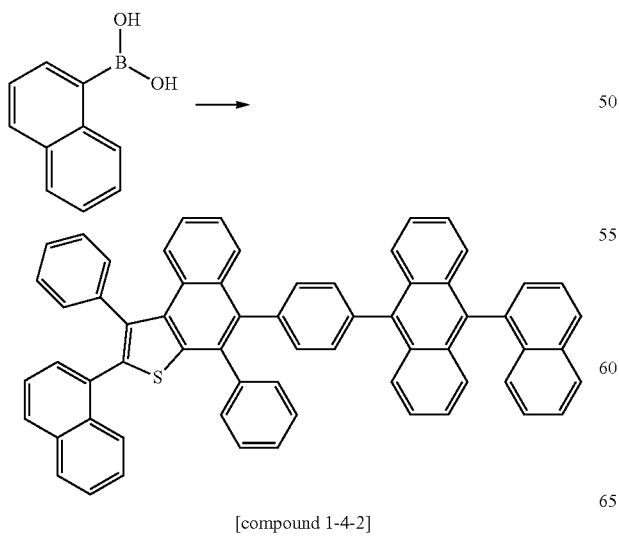

[compound 1-4-2]

Naphthyl boronic acid (3.5 g, 20.5 mmol), the compound 1E-3-2 (5.6 g, 9.3 mmol) that was prepared in Synthesis Example 1-10-2, and sodium carbonate (2.8 g, 20.5 mmol) were suspended in the mixture of tetrahydrofurane (100 mL) and water (50 mL). Tetrakis(triphenylphosphine)palladium (0.1 g, 0.2 mmol) was applied to the suspension solution. The mixture was refluxed and agitated for about 24 hours, and the refluxed mixture was cooled to room temperature. The prepared solid was purified with filtered THF/EtOH to prepare the compound 1-4-2 (3.2 g, yield 46%).

PREPARATION EXAMPLE 1-4-3

Preparation of the Compound 1-4-3

In Preparation Example 1-4-1, it was prepared by using the same method to prepare the compound 1-4-3, except that the compound of 1E-3-2 synthesized in Synthesis Example 1-10-2 was used.

TABLE 1-4

| Prep. Ex. 1-4-No | Product 1-4-No | structure | MS [M + H]+ |
|---|---|---|---|
| 1-4-1 | compound 1-4-1 | 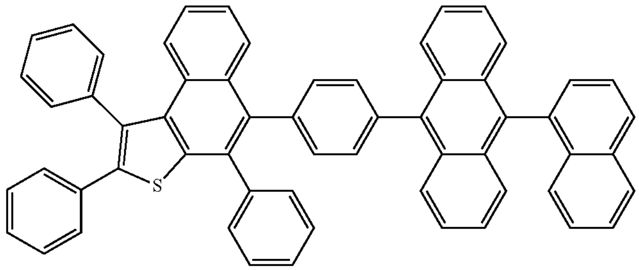 [SMILES: c1ccc(-c2sc3c(-c4ccccc4)c(-c4ccc(-c5c6ccccc6c(-c6cccc7ccccc67)c6ccccc56)cc4)c4ccccc4c3c2-c2ccccc2)cc1] | 791 |
| 1-4-2 | compound 1-4-2 | 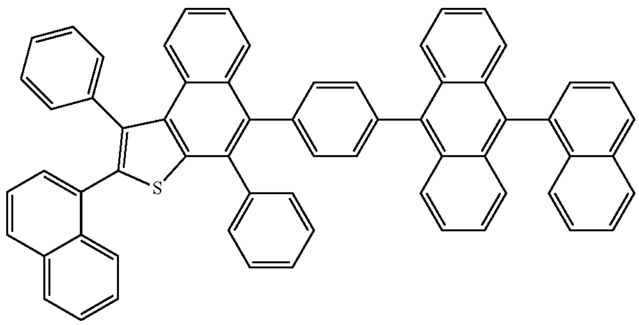 [SMILES: c1ccc(-c2c(-c3ccc(-c4c5ccccc5c(-c5cccc6ccccc56)c5ccccc45)cc3)c3ccccc3c3c(-c4ccccc4)c(-c4cccc5ccccc45)sc23)cc1] | 841 |
| 1-4-3 | compound 1-4-3 | 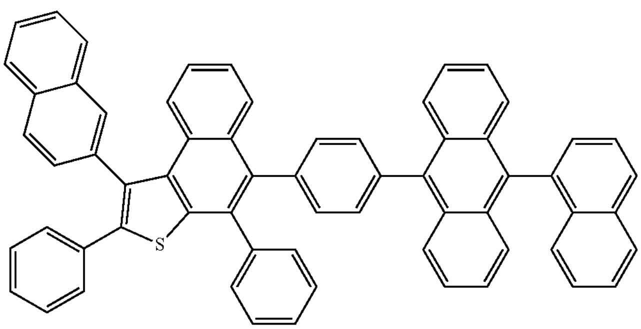 [SMILES: c1ccc(-c2sc3c(-c4ccccc4)c(-c4ccc(-c5c6ccccc6c(-c6cccc7ccccc67)c6ccccc56)cc4)c4ccccc4c3c2-c2ccc3ccccc3c2)cc1] | 841 |

PREPARATION EXAMPLE 1-5-1

Preparation of the Compound 1-5-1

Preparation of the Compound 1-12-1

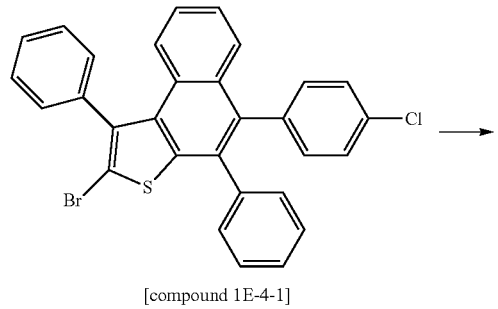

[compound 1E-4-1]

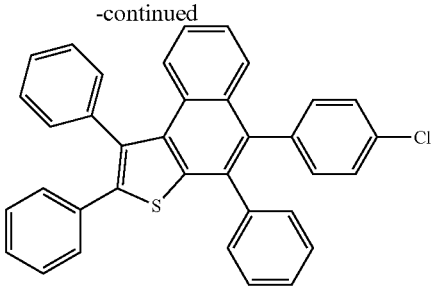

[compound 1-12-1]

In Preparation Example 1-4-2, it was prepared by using the same method to prepare the compound 1-12-1, except that phenyl boronic acid was used instead of naphthyl boronic acid and the compound 1E-4-1 was used instead of the compound 1E-3-2.

Preparation of the Compound 1-5-1

The compound 1-12-1 (20.2 g, 38.6 mmol), and the reactant S-28 (12.4 g, 38.6 mmol) were dissolved in 200 ml of xylene, 5.6 g of sodium-tertiary-botoxide (57.9 mmol), and Pd[P(t-Bu)$_3$]$_2$ (0.19 g, 0.386 mmol) were added thereto, and refluxed for 5 hours under the nitrogen atmosphere. Distilled water was put into the reaction solution, the termination of the reaction was carried out, and the organic material layer was extracted. After the column separation was carried out with normal-hexane/tetrahydrofurane=10/1 solvent, it was agitated in petroleum ether, and dried under vacuum to manufacture the compound 1-5-1 (22.5 g, yield 72%).

PREPARATION EXAMPLE 1-5-2

Preparation of the Compound 1-5-2

Preparation of the Compound 1-12-3

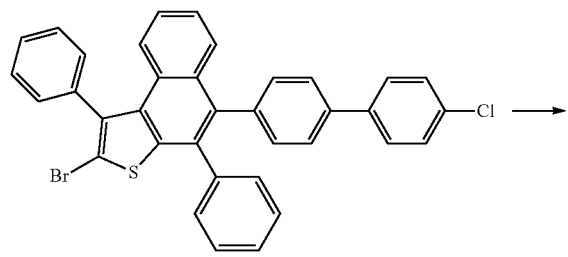

[compound 1E-4-3]

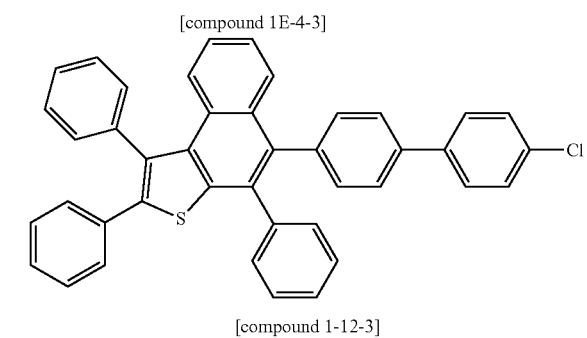

[compound 1-12-3]

In Preparation Example 1-4-2, it was prepared by using the same method to prepare the compound 1-12-3, except that phenyl boronic acid was used instead of naphthyl boronic acid and the compound 1E-4-3 was used instead of the compound 1E-3-2.

Preparation of the Compound 1-5-2

In Preparation Example 1-5-1, the compound 1-5-2 was prepared by using the same method, except that the compound 1-12-3 was used instead of the compound 1-12-1.

PREPARATION EXAMPLE 1-5-3

Preparation of the Compound 1-5-3

Preparation of the Compound 1-12-6

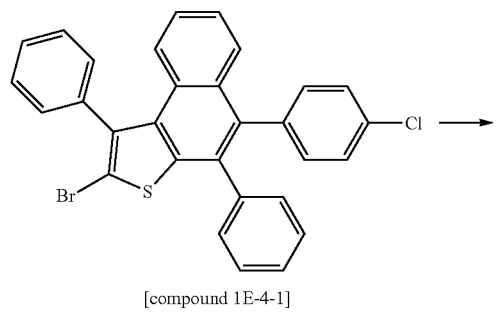

[compound 1E-4-1]

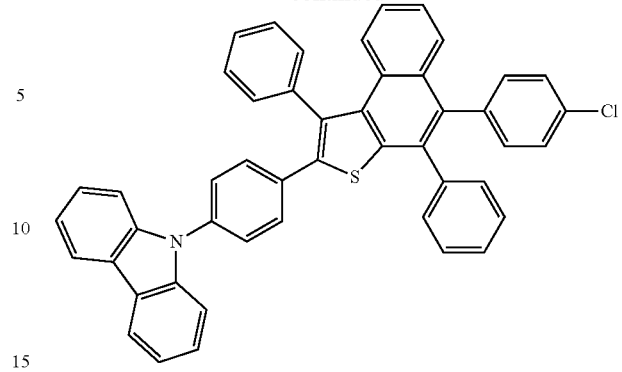

[compound 1-12-6]

In Preparation Example 1-4-2, it was prepared by using the same method to prepare the compound 1-12-6, except that the reactant S-18 was used instead of naphthyl boronic acid and the compound 1E-4-1 was used instead of the compound 1E-3-2.

Preparation of the Compound 1-5-3

In Preparation Example 1-5-1, the compound 1-5-3 was prepared by using the same method, except that the compound 1-12-6 was used instead of the compound 1-12-1 and the reactant S-30 was used instead of the reactant S-28.

PREPARATION EXAMPLE 1-5-4

Preparation of the Compound 1-5-4

Preparation of the Compound 1-12-2

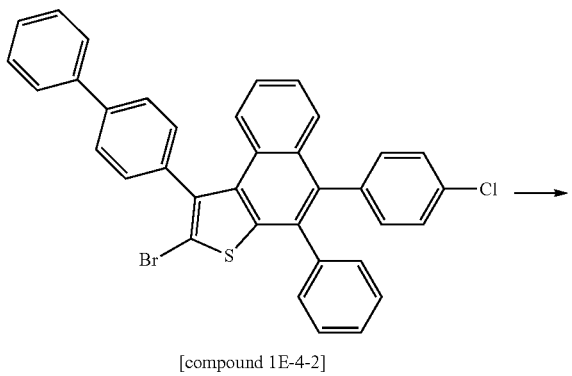

[compound 1E-4-2]

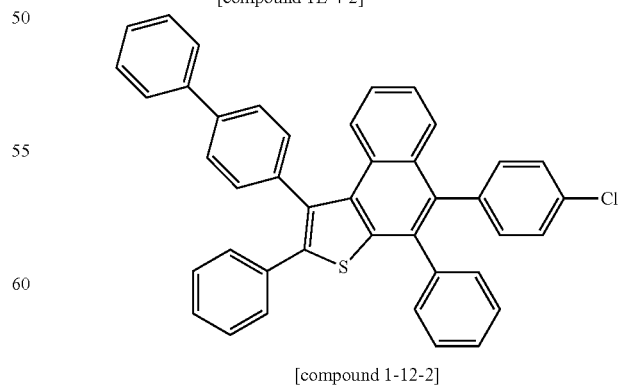

[compound 1-12-2]

In Preparation Example 1-4-2, it was prepared by using the same method to prepare the compound 1-12-2, except that phenyl boronic acid was used instead of naphthyl boronic acid and the compound 1E-4-2 was used instead of the compound 1E-3-2.

Preparation of the Compound 1-5-4

In Preparation Example 1-5-1, the compound 1-5-4 was prepared by using the same method, except that the compound 1-12-2 was used instead of the compound 1-12-1 and the reactant S-29 was used instead of the reactant S-28.

PREPARATION EXAMPLE 1-5-5

Preparation of the Compound 1-5-5

In Preparation Example 1-5-1, the compound 1-5-5 was prepared by using the same method, except that the reactant S-27 was used instead of the reactant S-28.

TABLE 1-5

| Prep. Ex. 1-5-No | Product 1-5-No | structure | MS [M + H]+ |
|---|---|---|---|
| 1-5-1 | compound 1-5-1 | 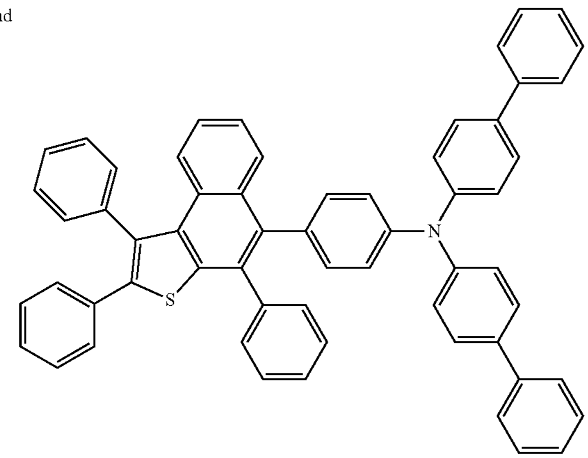 | 808 |
| 1-5-2 | compound 1-5-2 | 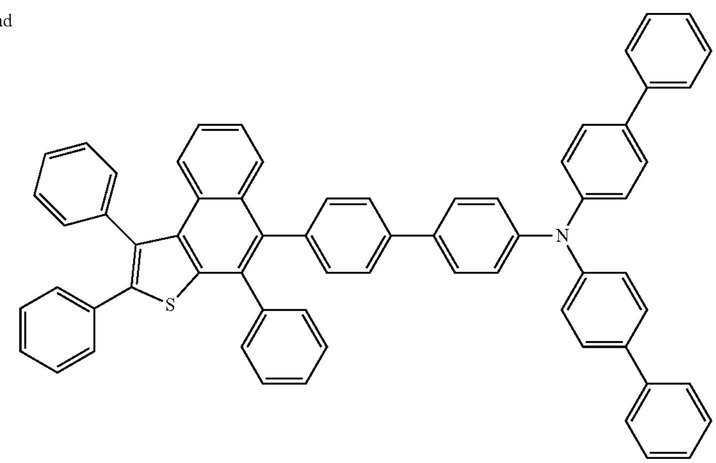 | 885 |
| 1-5-3 | compound 1-5-3 | 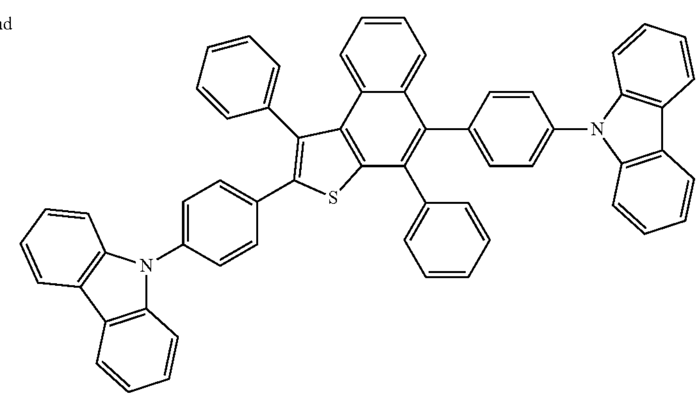 | 819 |

TABLE 1-5-continued

| Prep. Ex. 1-5-No | Product 1-5-No | structure | MS [M + H]+ |
|---|---|---|---|
| 1-5-4 | compound 1-5-4 | 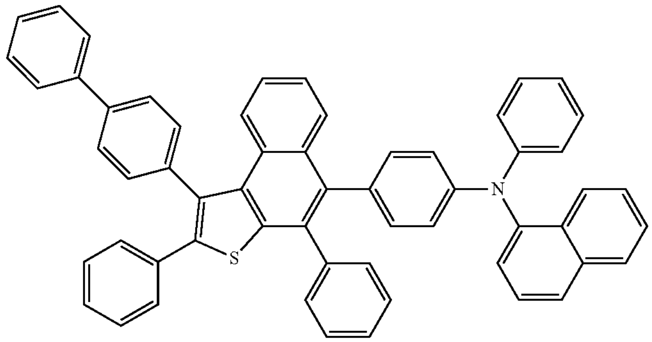 [SMILES: c1ccc(-c2ccc(-c3c(-c4ccccc4)sc4c(-c5ccccc5)c(-c5ccc(N(c6ccccc6)c6cccc7ccccc67)cc5)c5ccccc5c34)cc2)cc1] | 782 |
| 1-5-5 | compound 1-5-5 | 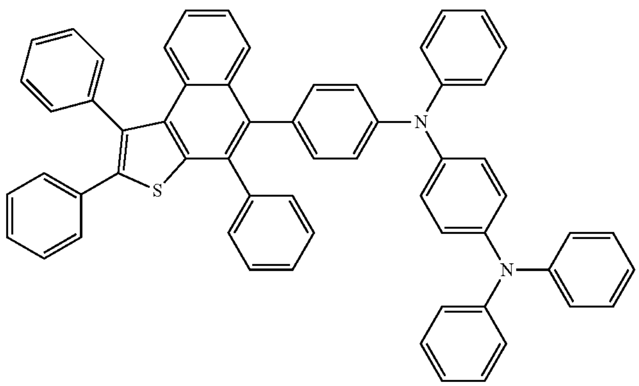 [SMILES: c1ccc(-c2sc3c(-c4ccccc4)c(-c4ccc(N(c5ccccc5)c5ccc(N(c6ccccc6)c6ccccc6)cc5)cc4)c4ccccc4c3c2-c2ccccc2)cc1] | 823 |

PREPARATION EXAMPLE 1-6-1

Preparation of the Compound 1-6-1

Preparation of the Compound 1-12-7

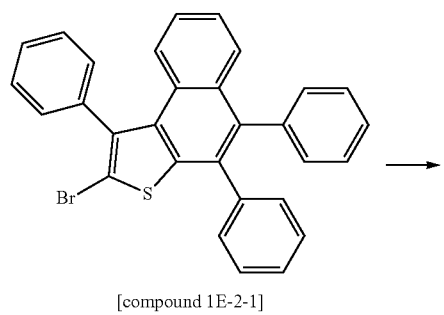

[compound 1E-2-1]

[compound 1-12-7]

In Preparation Example 1-4-2, it was prepared by using the same method to prepare the compound 1-12-7, except that the reactant S-14 was used instead of naphthyl boronic acid and the compound 1E-2-1 was used instead of the compound 1E-3-2.

Preparation of the Compound 1-6-1

In Preparation Example 1-5-1, the compound 1-6-1 was prepared by using the same method, except that the compound 1-12-7 was used instead of the compound 1-12-1 and the reactant S-30 was used instead of the reactant S-28.

PREPARATION EXAMPLE 1-6-2

Preparation of the Compound 1-6-2

Preparation of the Compound 1-12-8

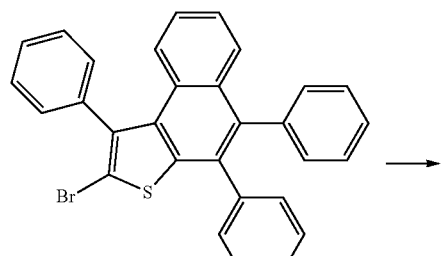

[compound 1E-2-1]

[compound 1-12-8]

In Preparation Example 1-4-2, it was prepared by using the same method to prepare the compound 1-12-8, except that the reactant S-13 was used instead of naphthyl boronic acid and the compound 1E-2-1 was used instead of the compound 1E-3-2.

Preparation of the Compound 1-6-2

In Preparation Example 1-5-1, the compound 1-6-2 was prepared by using the same method, except that the compound 1-12-8 was used instead of the compound 1-12-1 and the reactant S-30 was used instead of the reactant S-28.

PREPARATION EXAMPLE 1-6-3

Preparation of the Compound 1-6-3

In Preparation Example 1-5-1, the compound 1-6-3 was prepared by using the same method, except that the compound 1-12-7 was used instead of the compound 1-12-1.

TABLE 1-6

| Prep. Ex. 1-6-No | Product 1-6-No | structure | MS [M + H]+ |
|---|---|---|---|
| 1-6-1 | compound 1-6-1 | 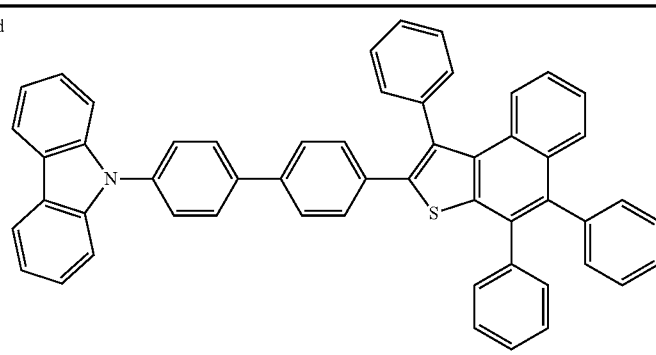 | 730 |
| 1-6-2 | compound 1-6-2 | 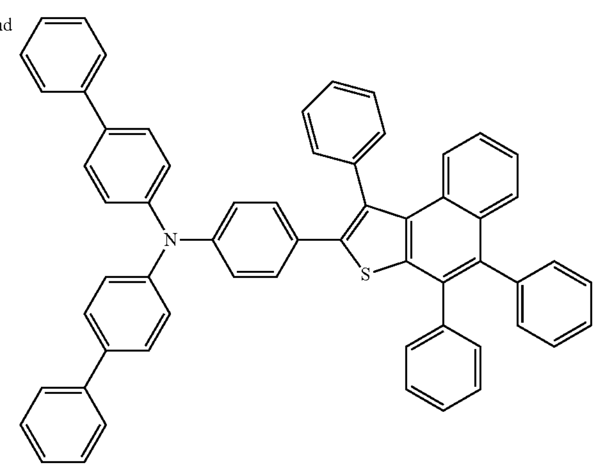 | 808 |

TABLE 1-6-continued

| Prep. Ex. 1-6-No | Product 1-6-No | structure | MS [M + H]+ |
|---|---|---|---|
| 1-6-3 | compound 1-6-3 | 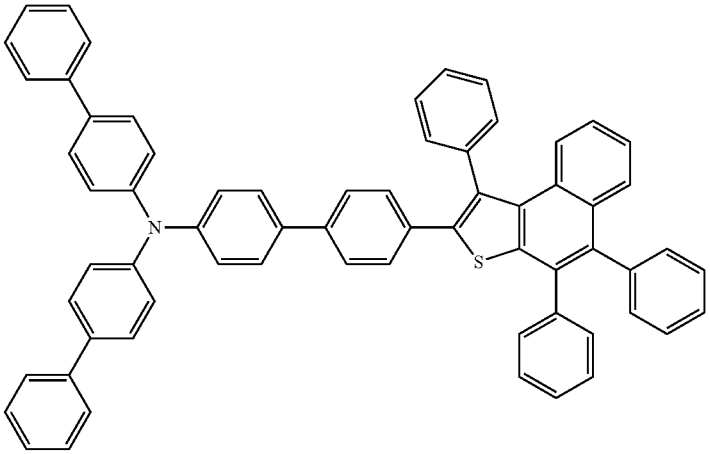 [SMILES: c1ccc(-c2ccc(N(c3ccc(-c4ccccc4)cc3)c3ccc(-c4ccc(-c5sc6c(-c7ccccc7)c(-c7ccccc7)c7ccccc7c6c5-c5ccccc5)cc4)cc3)cc2)cc1] | 884 |

PREPARATION EXAMPLE 1-7-1

Preparation of the Compound 1-7-1

In Preparation Example 1-4-2, it was prepared by using the same method to prepare the compound 1-7-1, except that phenyl boronic acid compound was used instead of naphthyl boronic acid and the compound 1E-3-3 was used instead of the compound 1E-3-2.

PREPARATION EXAMPLE 1-7-2

Preparation of the Compound 1-7-2

In Preparation Example 1-4-2, it was prepared by using the same method to prepare the compound 1-7-2, except that phenyl boronic acid compound was used instead of naphthyl boronic acid and the compound 1E-3-9 was used instead of the compound 1E-3-2.

PREPARATION EXAMPLE 1-7-3

Preparation of the Compound 1-7-3

In Preparation Example 1-4-2, it was prepared by using the same method to prepare the compound 1-7-3, except that phenyl boronic acid compound was used instead of naphthyl boronic acid and the compound 1E-3-5 was used instead of the compound 1E-3-2.

TABLE 1-7

| Prep. Ex. 1-7-No | Product 1-7-No | structure | MS [M + H]+ |
|---|---|---|---|
| 1-7-1 | compound 1-7-1 | 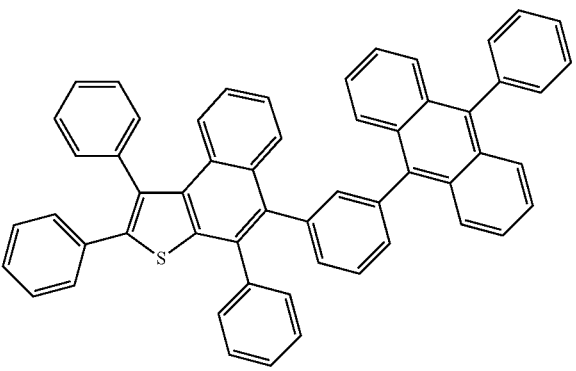 [SMILES: c1ccc(-c2sc3c(-c4ccccc4)c(-c4cccc(-c5c6ccccc6c(-c6ccccc6)c6ccccc56)c4)c4ccccc4c3c2-c2ccccc2)cc1] | 741 |

TABLE 1-7-continued

| Prep. Ex. 1-7-No | Product 1-7-No | structure | MS [M + H]+ |
|---|---|---|---|
| 1-7-2 | compound 1-7-2 | 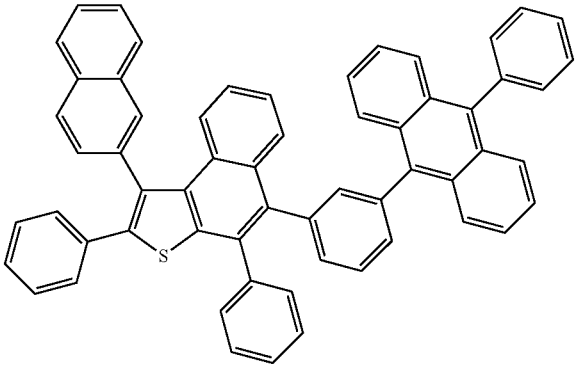 [SMILES: c1ccc(-c2sc3c(-c4ccccc4)c(-c4cccc(-c5c6ccccc6c(-c6ccccc6)c6ccccc56)c4)c4ccccc4c3c2-c2ccc3ccccc3c2)cc1] | 885 |
| 1-7-3 | compound 1-7-3 | 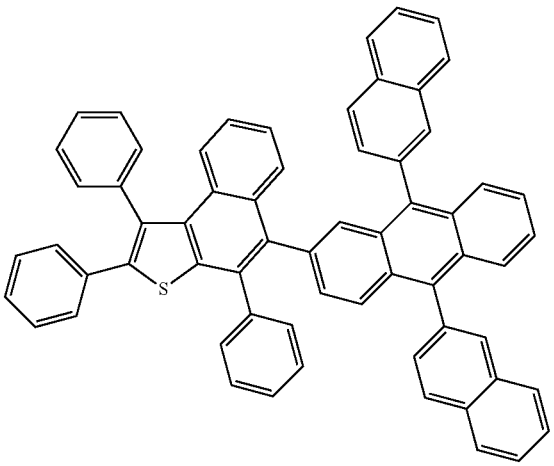 [SMILES: c1ccc(-c2sc3c(-c4ccccc4)c(-c4ccc5c(-c6ccc7ccccc7c6)c6ccccc6c(-c6ccc7ccccc7c6)c5c4)c4ccccc4c3c2-c2ccccc2)cc1] | 841 |

PREPARATION EXAMPLE 2-1-1

Preparation of the Compound 2-1-1

In Preparation Example 1-4-2, it was prepared by using the same method to prepare the compound 2-1-1, except that the reactant S-10 was used instead of naphthyl boronic acid and the compound 2E-1-1 was used instead of the compound 1E-3-2.

PREPARATION EXAMPLE 2-1-2

Preparation of the Compound 2-1-2

In Preparation Example 1-4-2, it was prepared by using the same method to prepare the compound 2-1-2, except that the reactant S-31 was used instead of naphthyl boronic acid and the compound 2E-1-2 was used instead of the compound 1E-3-2.

PREPARATION EXAMPLE 2-1-3

Preparation of the Compound 2-1-3

In Preparation Example 1-4-2, it was prepared by using the same method to prepare the compound 2-1-3, except that phenyl boronic acid compound was used instead of naphthyl boronic acid and the compound 2E-1-4 was used instead of the compound 1E-3-2.

PREPARATION EXAMPLE 2-1-4

Preparation of the Compound 2-1-4

In Preparation Example 1-4-2, it was prepared by using the same method to prepare the compound 2-1-4, except that phenyl boronic acid was used instead of naphthyl boronic acid and the compound 2E-1-6 was used instead of the compound 1E-3-2.

PREPARATION EXAMPLE 2-1-5

Preparation of the Compound 2-1-5

In Preparation Example 1-4-2, it was prepared by using the same method to prepare the compound 2-1-5, except that phenyl boronic acid was used instead of naphthyl boronic acid and the compound 2E-1-5 was used instead of the compound 1E-3-2.

PREPARATION EXAMPLE 2-1-6

Preparation of the Compound 2-1-6

In Preparation Example 1-4-2, it was prepared by using the same method to prepare the compound 2-1-6, except that the reactant S-33 was used instead of naphthyl boronic acid in an equivalent of 2.4 and the compound 2E-1-1 was used instead of the compound 1E-3-2.

TABLE 2-1

| Prep. Ex. 2-1-No | Product 2-1-No | structure | MS [M + H]+ |
|---|---|---|---|
| 2-1-1 | compound 2-1-1 | 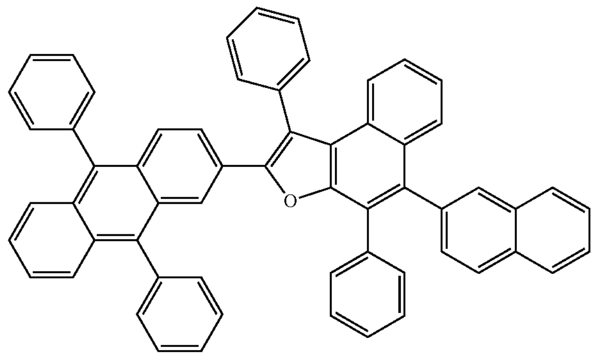 | 775 |
| 2-1-2 | compound 2-1-2 | 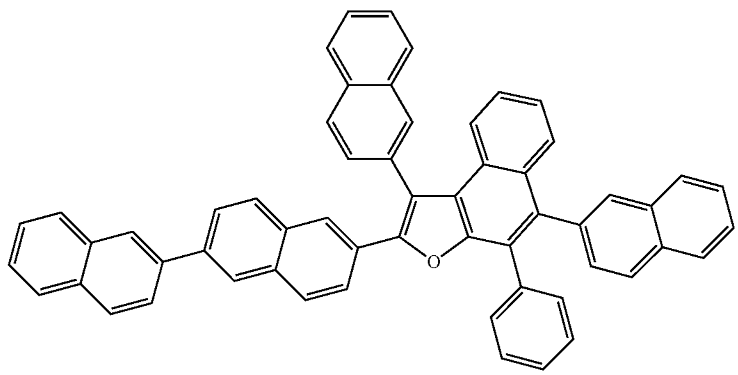 [SMILES: c1ccc(-c2c(-c3ccc4ccccc4c3)c3ccccc3c3c(-c4ccc5ccccc5c4)c(-c4ccc5cc(-c6ccc7ccccc7c6)ccc5c4)oc23)cc1] | 749 |
| 2-1-3 | compound 2-1-3 | 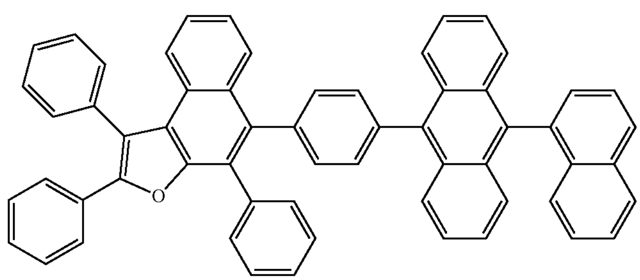 [SMILES: c1ccc(-c2oc3c(-c4ccccc4)c(-c4ccc(-c5c6ccccc6c(-c6cccc7ccccc67)c6ccccc56)cc4)c4ccccc4c3c2-c2ccccc2)cc1] | 775 |
| 2-1-4 | compound 2-1-4 | 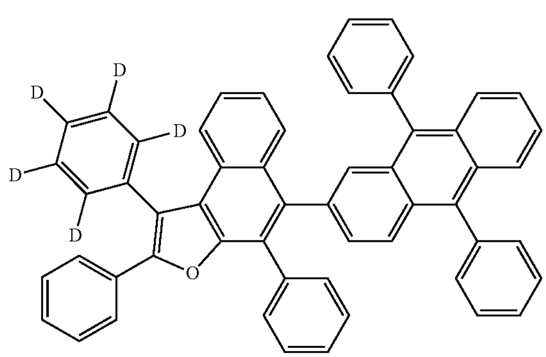 [SMILES: [2H]c1c([2H])c([2H])c(-c2c(-c3ccccc3)oc3c(-c4ccccc4)c(-c4ccc5c(-c6ccccc6)c6ccccc6c(-c6ccccc6)c5c4)c4ccccc4c23)c([2H])c1[2H]] | 730 |

TABLE 2-1-continued

| Prep. Ex. 2-1-No | Product 2-1-No | structure | MS [M + H]+ |
|---|---|---|---|
| 2-1-5 | compound 2-1-5 | 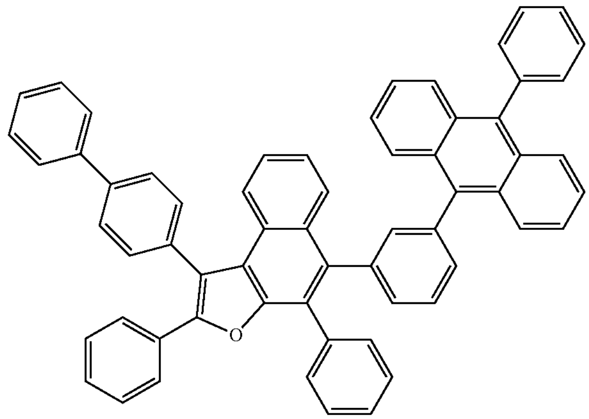 [SMILES: c1ccc(-c2ccc(-c3c(-c4ccccc4)oc4c(-c5ccccc5)c(-c5cccc(-c6c7ccccc7c(-c7ccccc7)c7ccccc67)c5)c5ccccc5c34)cc2)cc1] | 801 |
| 2-1-6 | 2-1-6 | 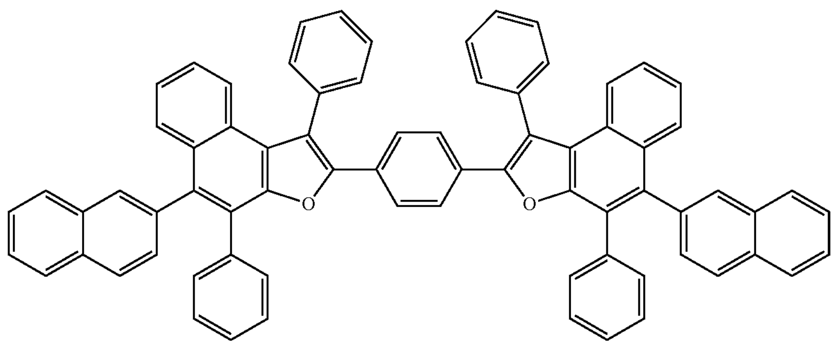 [SMILES: c1ccc(-c2c(-c3ccc4ccccc4c3)c3ccccc3c3c(-c4ccccc4)c(-c4ccc(-c5oc6c(-c7ccccc7)c(-c7ccc8ccccc8c7)c7ccccc7c6c5-c5ccccc5)cc4)oc23)cc1] | 967 |

PREPARATION EXAMPLE 3-1-2

Preparation of the Compound 3-1-2

[compound 3-1-2]

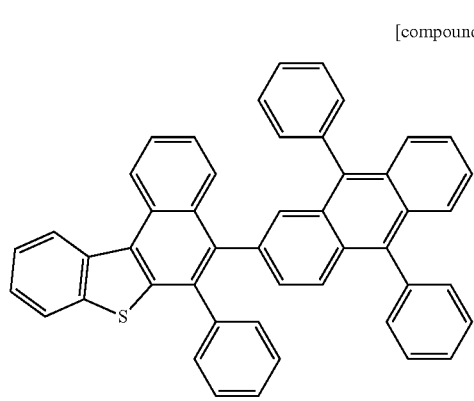

2-[9,10-diphenyl-2-anthracenyl]-4,4,5,5-tetramethyl-1,3,2-dioxaborolane (2.2 g, 4.9 mmol) that was the reactant S-10, the prepared compound A-3 (1.8 g, 4.1 mmol), and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 3-1-2 (2.1 g, yield 68%).

PREPARATION EXAMPLE 3-1-3

Preparation of the Compound 3-1-3

[compound 3-1-3]

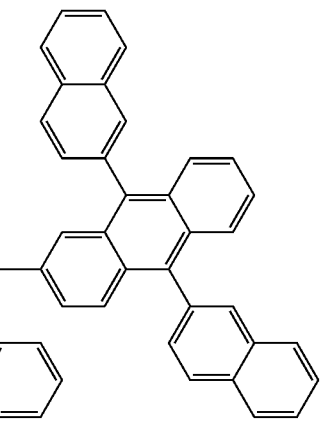

2-[9,10-di-2-naphthalenyl-2-anthracenyl]-4,4,5,5,-tetramethyl-1,3,2-dioxaborolane (2.7 g, 4.9 mmol) that was the reactant S-9, the prepared compound A-3 (1.8 g, 4.1 mmol), and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 3-1-3 (2.5 g, yield 82%).

PREPARATION EXAMPLE 3-1-13

Preparation of the Compound 3-1-13

[compound 3-1-13]

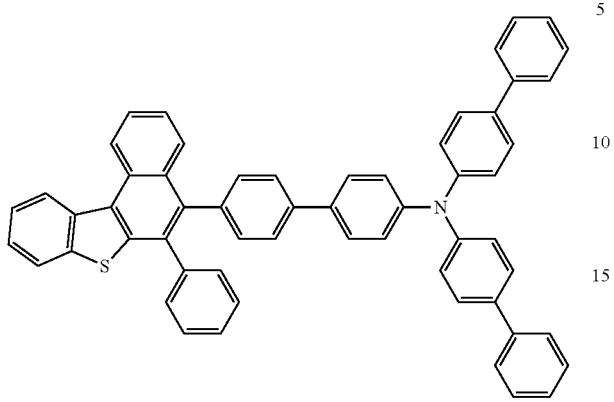

4'-(dibiphenylamino)(1,1'-biphenyl)-4-yl boronic acid (2.5 g, 4.9 mmol) that was the reactant S-23, the prepared compound A-3 (1.8 g, 4.1 mmol), and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 3-1-13 (1.8 g, yield 56%).

PREPARATION EXAMPLE 3-1-15

Preparation of the Compound 3-1-15

[compound 3-1-15]

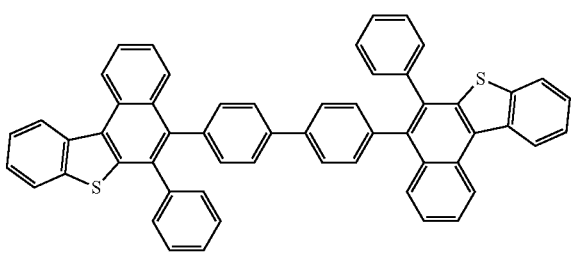

The reactant S-23 (1.9 g, 4.9 mmol), the prepared compound A-3 (1.8 g, 4.1 mmol), and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 3-1-15 (1.5 g, yield 47%).

PREPARATION EXAMPLE 3-1-16

Preparation of the Compound 3-1-16

[compound 3-1-16]

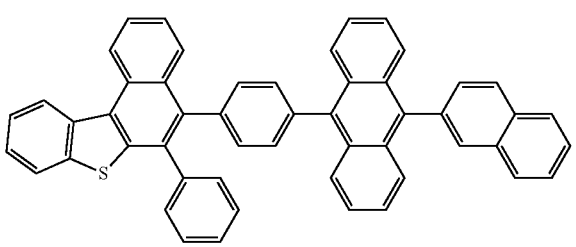

4-[9-(2-naphthyl-10-phenylene]-4,4,5,5-tetramethyl-1,3,2-dioxaborolane (2.2 g, 4.9 mmol) that was the reactant S-33, the prepared compound A-3 (1.8 g, 4.1 mmol), and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 3-1-16 (1.47 g, yield 52%).

PREPARATION EXAMPLE 3-1-1

Preparation of the Compound 3-1-1

In Preparation Example 3-1-16, the compound 3-1-1 was prepared by using the same method, except that the reactant S-10 was used instead of the reactant S-33.

PREPARATION EXAMPLE 3-1-4

Preparation of the Compound 3-1-4

In Preparation Example 3-1-16, the compound 3-1-4 was prepared by using the same method, except that the reactant S-5 was used instead of the reactant S-33.

PREPARATION EXAMPLE 3-1-5

Preparation of the Compound 3-1-5

In Preparation Example 3-1-16, the compound 3-1-5 was prepared by using the same method, except that the reactant S-8 was used instead of the reactant S-33.

PREPARATION EXAMPLE 3-1-6

Preparation of the Compound 3-1-6

In Preparation Example 3-1-16, it was prepared by using the same method to prepare the compound 3-1-6, except that the reactant S-7 was used instead of the reactant S-33.

PREPARATION EXAMPLE 3-1-7

Preparation of the Compound 3-1-7

In Preparation Example 3-1-16, it was prepared by using the same method to prepare the compound 3-1-7, except that the reactant S-31 was used instead of the reactant S-33.

PREPARATION EXAMPLE 3-1-8

Preparation of the Compound 3-1-8

In Preparation Example 3-1-16, it was prepared by using the same method to prepare the compound 3-1-8, except that the reactant S-38 was used instead of the reactant S-33.

PREPARATION EXAMPLE 3-1-9

Preparation of the Compound 3-1-9

In Preparation Example 3-1-16, it was prepared by using the same method to prepare the compound 3-1-9, except that the reactant S-39 was used instead of the reactant S-33.

PREPARATION EXAMPLE 3-1-10

Preparation of the Compound 3-1-10

In Preparation Example 3-1-16, it was prepared by using the same method to prepare the compound 3-1-10, except that the reactant S-36 was used instead of the reactant S-33.

PREPARATION EXAMPLE 3-1-11

Preparation of the Compound 3-1-11

In Preparation Example 3-1-16, it was prepared by using the same method to prepare the compound 3-1-11, except that the reactant S-35 was used instead of the reactant S-33.

PREPARATION EXAMPLE 3-1-12

Preparation of the Compound 3-1-12

In Preparation Example 3-1-16, it was prepared by using the same method to prepare the compound 3-1-12, except that the reactant S-34 was used instead of the reactant S-33.

TABLE 3-1

| Prep. Ex. 3-1-No | Product 3-1-No | structure | MS [M + H]+ |
|---|---|---|---|
| 3-1-1 | compound 3-1-1 | 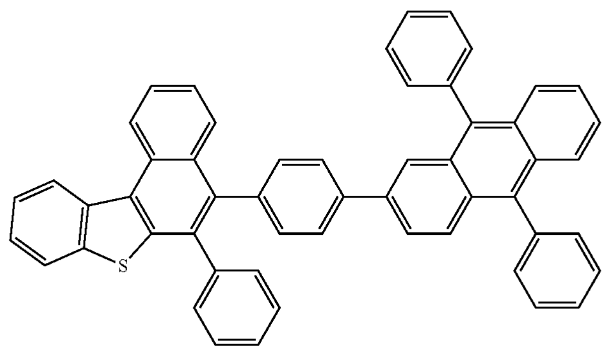 | 715 |
| 3-1-2 | compound 3-1-2 | 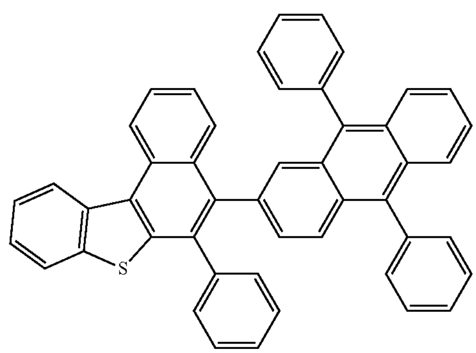 | 639 |
| 3-1-3 | compound 3-1-3 | 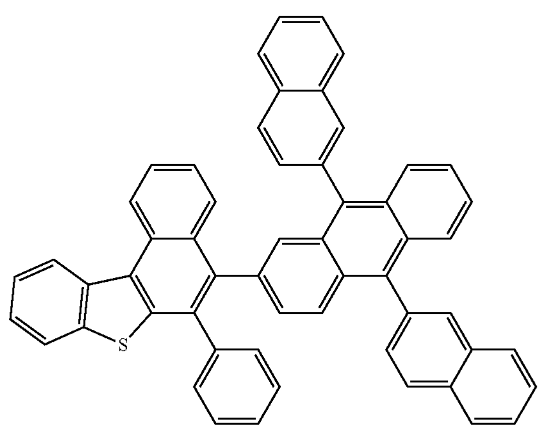 [SMILES: c1ccc(-c2c(-c3ccc4c(-c5ccc6ccccc6c5)c5ccccc5c(-c5ccc6ccccc6c5)c4c3)c3ccccc3c3c2sc2ccccc23)cc1] | 739 |

TABLE 3-1-continued

| Prep. Ex. 3-1-No | Product 3-1-No | structure | MS [M + H]+ |
|---|---|---|---|
| 3-1-4 | compound 3-1-4 | 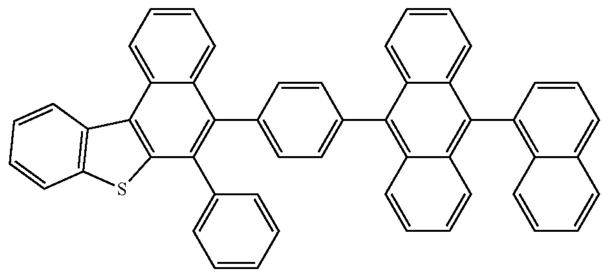 [SMILES: c1ccc(-c2c(-c3ccc(-c4c5ccccc5c(-c5cccc6ccccc56)c5ccccc45)cc3)c3ccccc3c3c2sc2ccccc23)cc1] | 689 |
| 3-1-5 | compound 3-1-5 | 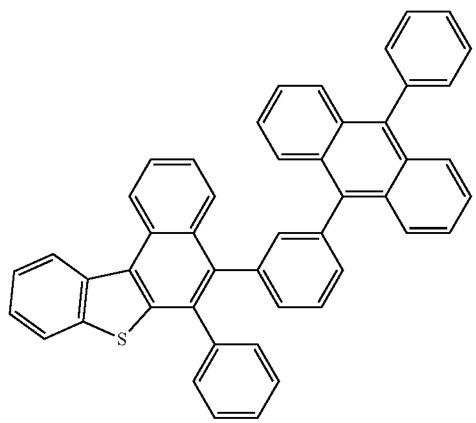 | 639 |
| 3-1-6 | compound 3-1-6 | 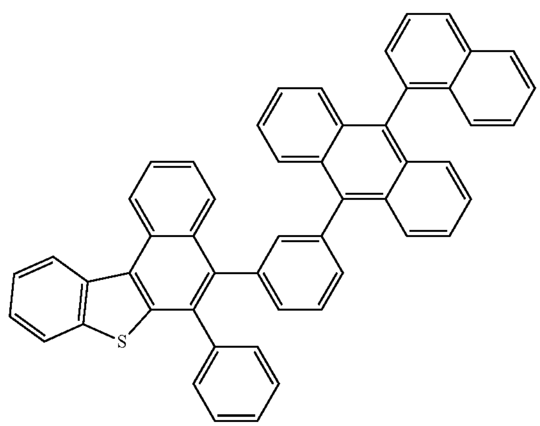 [SMILES: c1ccc(-c2c(-c3cccc(-c4c5ccccc5c(-c5cccc6ccccc56)c5ccccc45)c3)c3ccccc3c3c2sc2ccccc23)cc1] | 689 |
| 3-1-7 | compound 3-1-7 | 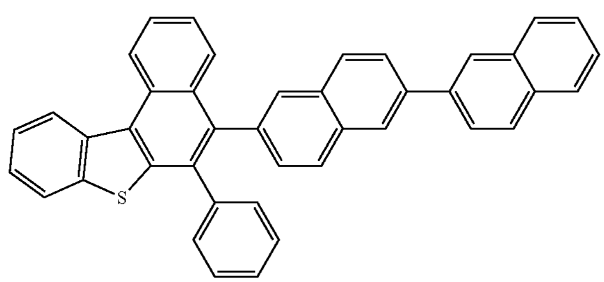 | 563 |

TABLE 3-1-continued

| Prep. Ex. 3-1-No | Product 3-1-No | structure | MS [M + H]+ |
|---|---|---|---|
| 3-1-8 | compound 3-1-8 | 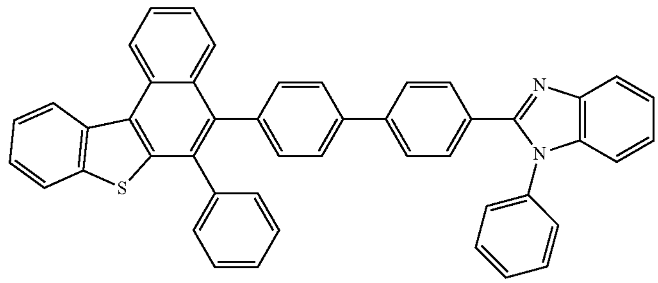 | 655 |
| 3-1-9 | compound 3-1-9 | 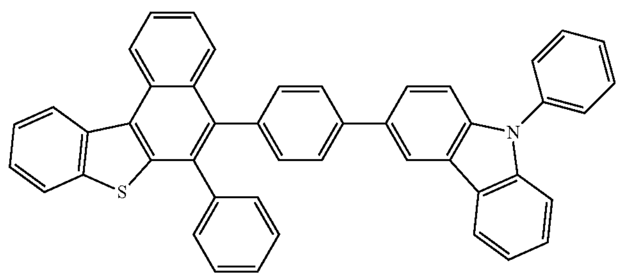 [SMILES: c1ccc(-c2c(-c3ccc(-c4ccc5c(c4)c4ccccc4n5-c4ccccc4)cc3)c3ccccc3c3c2sc2ccccc23)cc1] | 628 |
| 3-1-10 | compound 3-1-10 | 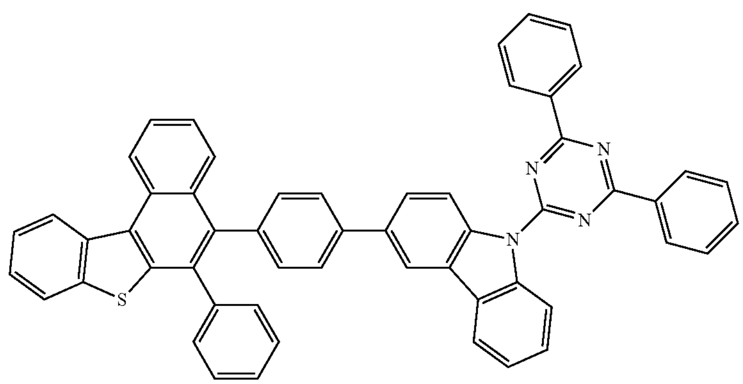 | 783 |
| 3-1-11 | compound 3-1-11 | 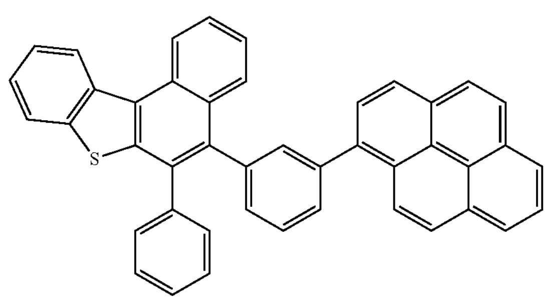 [SMILES: c1ccc(-c2c(-c3cccc(-c4ccc5ccc6cccc7ccc4c5c67)c3)c3ccccc3c3c2sc2ccccc23)cc1] | 587 |
| 3-1-12 | compound 3-1-12 | 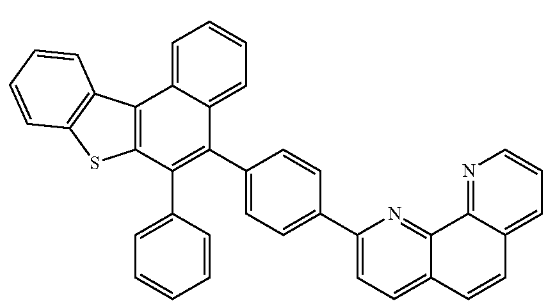 [SMILES: c1ccc(-c2c(-c3ccc(-c4ccc5ccc6cccnc6c5n4)cc3)c3ccccc3c3c2sc2ccccc23)cc1] | 565 |

TABLE 3-1-continued

| Prep. Ex. 3-1-No | Product 3-1-No | structure | MS [M + H]+ |
|---|---|---|---|
| 3-1-13 | compound 3-1-13 | 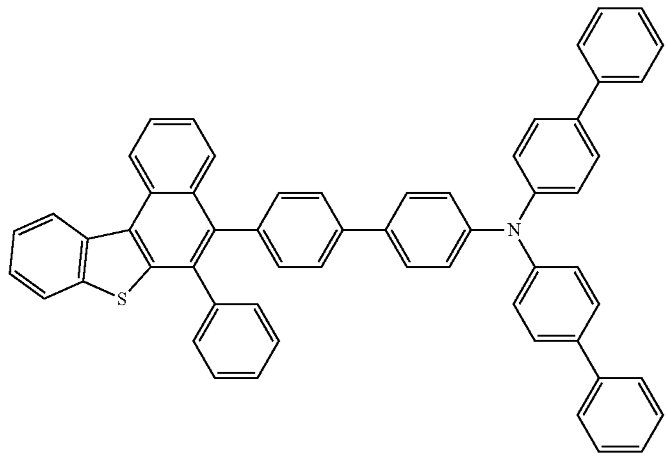 | 782 |
| 3-1-14 | compound 3-1-14 | 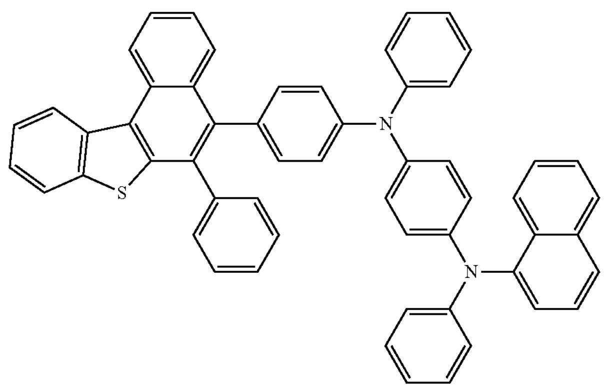 | 771 |
| 3-1-15 | compound 3-1-15 | 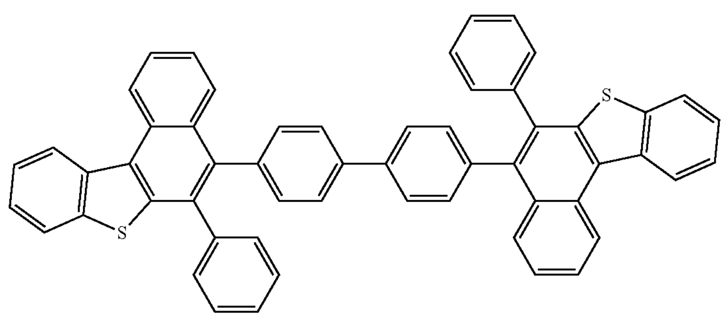 [SMILES: c1ccc(-c2c(-c3ccc(-c4ccc(-c5c(-c6ccccc6)c6sc7ccccc7c6c6ccccc56)cc4)cc3)c3ccccc3c3c2sc2ccccc23)cc1] | 771 |
| 3-1-16 | compound 3-1-16 | 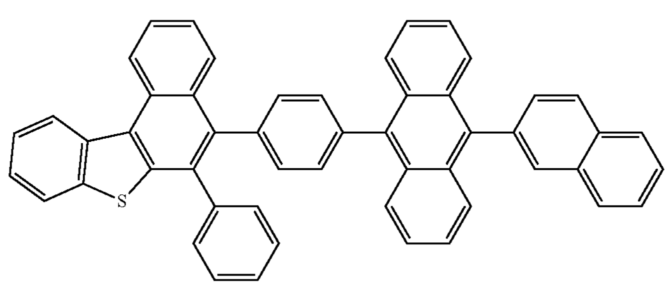 [SMILES: c1ccc(-c2c(-c3ccc(-c4c5ccccc5c(-c5ccc6ccccc6c5)c5ccccc45)cc3)c3ccccc3c3c2sc2ccccc23)cc1] | 689 |

TABLE 3-1-continued

| Prep. Ex. 3-1-No | Product 3-1-No | structure | MS [M + H]+ |
|---|---|---|---|
| 3-1-17 | compound 3-1-17 | 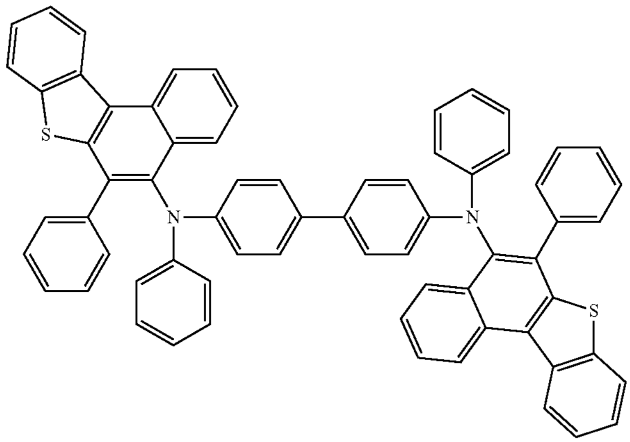 [SMILES: c1ccc(-c2c(N(c3ccccc3)c3ccc(-c4ccc(N(c5ccccc5)c5c(-c6ccccc6)c6sc7ccccc7c6c6ccccc56)cc4)cc3)c3ccccc3c3c2sc2ccccc23)cc1] | 953 |
| 3-1-18 | compound 3-1-18 | 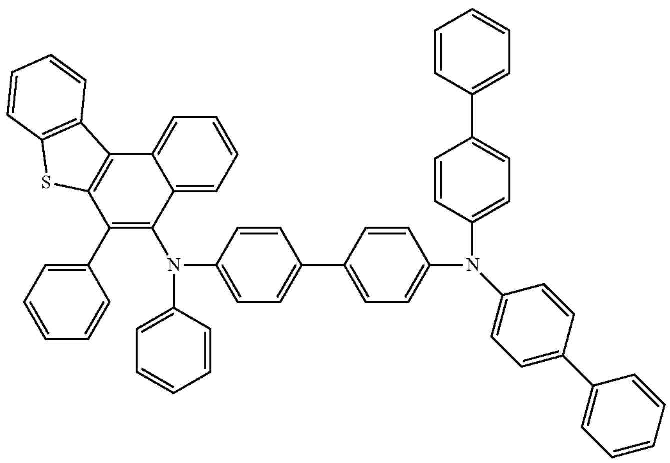 [SMILES: c1ccc(-c2ccc(N(c3ccc(-c4ccccc4)cc3)c3ccc(-c4ccc(N(c5ccccc5)c5c(-c6ccccc6)c6sc7ccccc7c6c6ccccc56)cc4)cc3)cc2)cc1] | 873 |
| 3-1-19 | compound 3-1-19 | 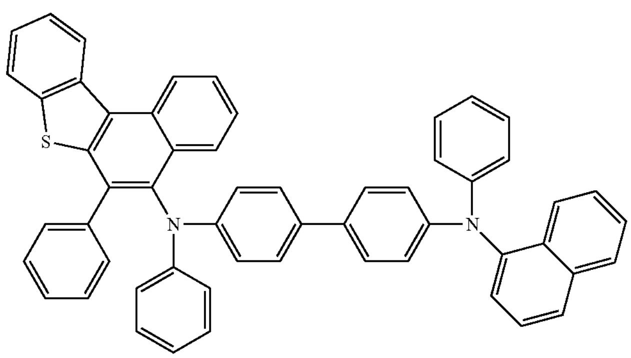 [SMILES: c1ccc(-c2c(N(c3ccccc3)c3ccc(-c4ccc(N(c5ccccc5)c5cccc6ccccc56)cc4)cc3)c3ccccc3c3c2sc2ccccc23)cc1] | 771 |
| 3-1-20 | compound 3-1-20 | 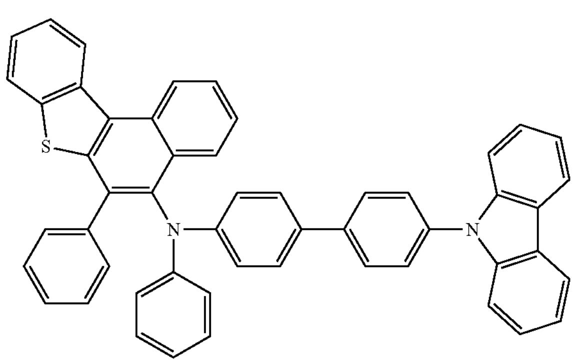 [SMILES: c1ccc(-c2c(N(c3ccccc3)c3ccc(-c4ccc(-n5c6ccccc6c6ccccc65)cc4)cc3)c3ccccc3c3c2sc2ccccc23)cc1] | 719 |

PREPARATION EXAMPLE 3-1-17

Preparation of the Compound 3-1-17

In Preparation Example 1-5-1, the compound 3-1-17 was prepared by using the same method, except that 2.4 equivalents of the compound A-3 and 4.8 equivalents of sodium-tertiary-botoxide were used instead of the compound 1-12-1 and the reactant S-41 was used instead of the reactant S-28.

PREPARATION EXAMPLE 3-1-18

Preparation of the Compound 3-1-18

In Preparation Example 1-5-1, the compound 3-1-18 was prepared by using the same method, except that the compound A-3 was used instead of the compound 1-12-1 and the reactant S-43 was used instead of the reactant S-28.

PREPARATION EXAMPLE 3-1-19

Preparation of the Compound 3-1-19

In Preparation Example 1-5-1, the compound 3-1-19 was prepared by using the same method, except that the compound A-3 was used instead of the compound 1-12-1 and the reactant S-44 was used instead of the reactant S-28.

PREPARATION EXAMPLE 3-1-20

Preparation of the Compound 3-1-20

In Preparation Example 1-5-1, the compound 3-1-20 was prepared by using the same method, except that the compound A-3 was used instead of the compound 1-12-1 and the reactant S-42 was used instead of the reactant S-28.

PREPARATION EXAMPLE 4-1-14

Preparation of the Compound 4-1-14

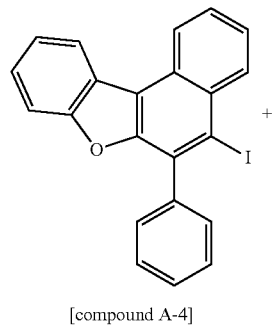

[compound A-4]

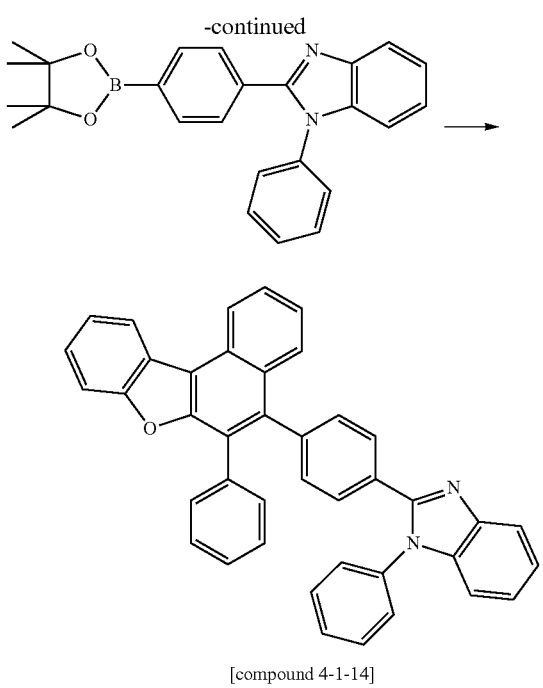

[compound 4-1-14]

The reactant S-15 (1.5 g, 4.9 mmol), the prepared compound A-4 (1.7 g, 4.1 mmol), and sodium carbonate (1.4 g, 10.0 mmol) were suspended in the mixture of tetrahydrofurane (100 mL) and water (50 mL). Tetrakis(triphenylphosphine)palladium (0.1 g, 0.1 mmol) was applied to the suspension solution. The mixture was refluxed and agitated for about 24 hours, and the refluxed mixture was cooled to room temperature. The prepared solid was purified with filtered THF/EtOH to prepare the compound 4-1-14 (2.3 g, yield 82%).

PREPARATION EXAMPLE 4-1-1 TO 4-1-12

Preparation of the Compounds 4-1-1 to 4-1-12

In Preparation Example 4-1-14, it was prepared by using the same method to prepare the compounds 4-1-1 to 4-1-12, except that the reactants S-22, S-10, S-9, S-5, S-8, S-7, S-31, S-38, S-36, S-34, and S-25 were used instead of the reactant S-15.

PREPARATION EXAMPLE 4-1-13

Preparation of the Compound 4-1-13

In Preparation Example 4-1-14, it was prepared by using the same method to prepare the compound 4-1-13, except that the reactant S-23 was used instead of the reactant S-15 in an equivalent of 2.4.

TABLE 4-1

| Prep. Ex. 4-1-No | Product 4-1-No | structure | MS [M + H]+ |
|---|---|---|---|
| 4-1-1 | compound 4-1-1 | 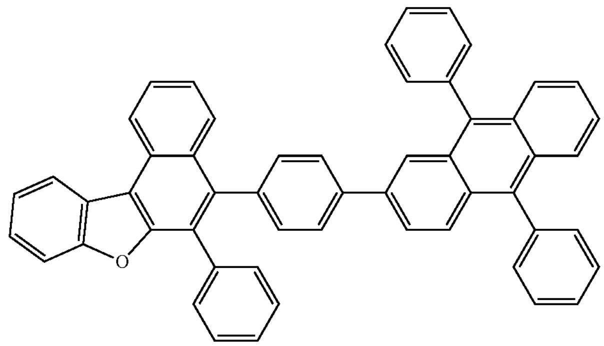 [SMILES: c1ccc(-c2c3ccccc3c(-c3ccccc3)c3cc(-c4ccc(-c5c(-c6ccccc6)c6oc7ccccc7c6c6ccccc56)cc4)ccc23)cc1] | 699 |
| 4-1-2 | compound 4-1-2 | 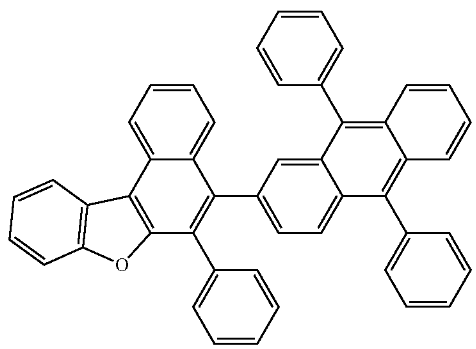 [SMILES: c1ccc(-c2c3ccccc3c(-c3ccccc3)c3cc(-c4c(-c5ccccc5)c5oc6ccccc6c5c5ccccc45)ccc23)cc1] | 623 |
| 4-1-3 | compound 4-1-3 | 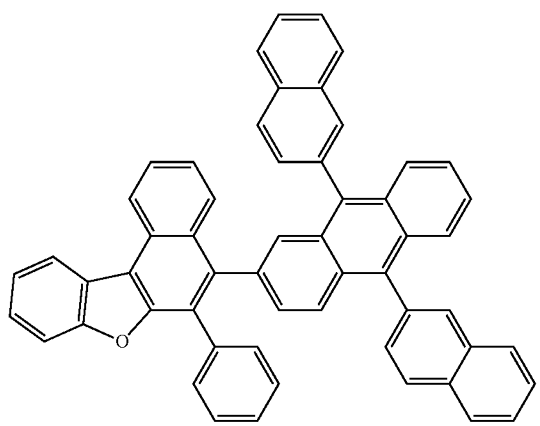 | 723 |
| 4-1-4 | compound 4-1-4 | 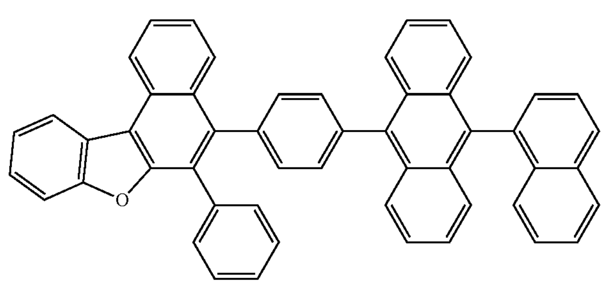 | 673 |

TABLE 4-1-continued

| Prep. Ex. 4-1-No | Product 4-1-No | structure | MS [M + H]+ |
|---|---|---|---|
| 4-1-5 | compound 4-1-5 | 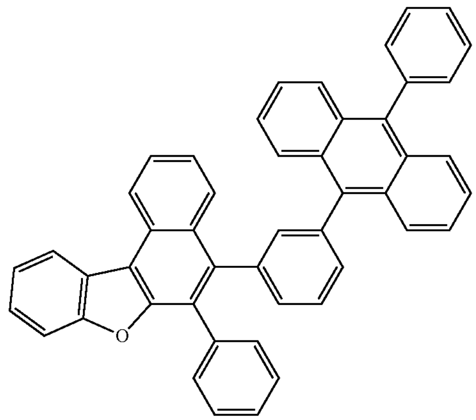 [SMILES: c1ccc(-c2c3ccccc3c(-c3cccc(-c4c(-c5ccccc5)c5oc6ccccc6c5c5ccccc45)c3)c3ccccc23)cc1] | 623 |
| 4-1-6 | compound 4-1-6 | 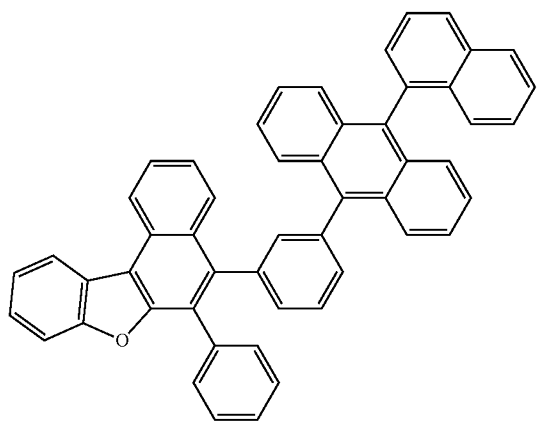 | 673 |
| 4-1-7 | compound 4-1-7 | 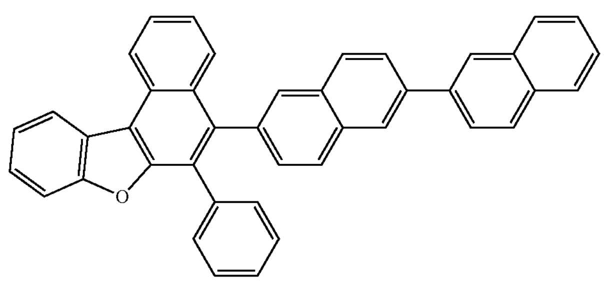 | 547 |
| 4-1-8 | compound 4-1-8 | 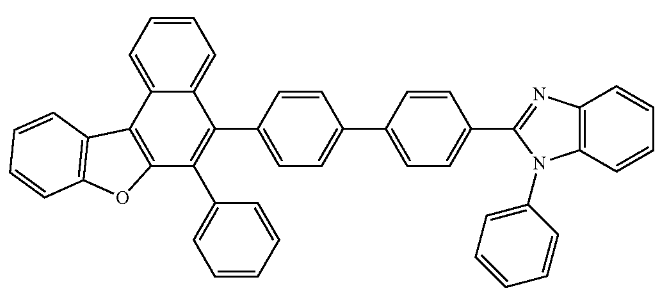 | 639 |

TABLE 4-1-continued

| Prep. Ex. 4-1-No | Product 4-1-No | structure | MS [M + H]+ |
|---|---|---|---|
| 4-1-9 | compound 4-1-9 | 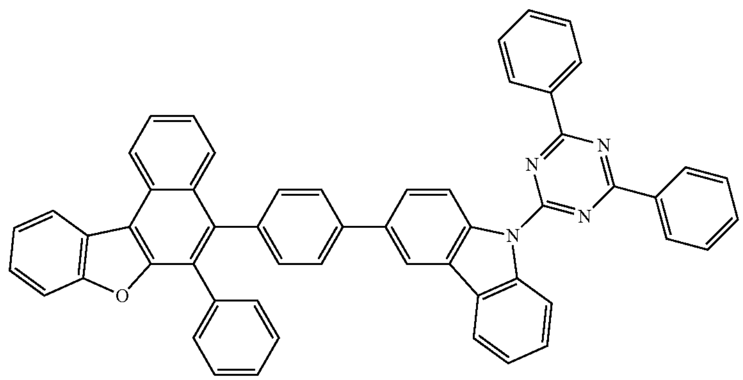 | 767 |
| 4-1-10 | compound 4-1-10 | 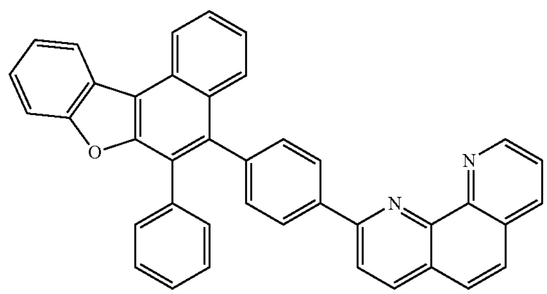 | 549 |
| 4-1-11 | compound 4-1-11 | 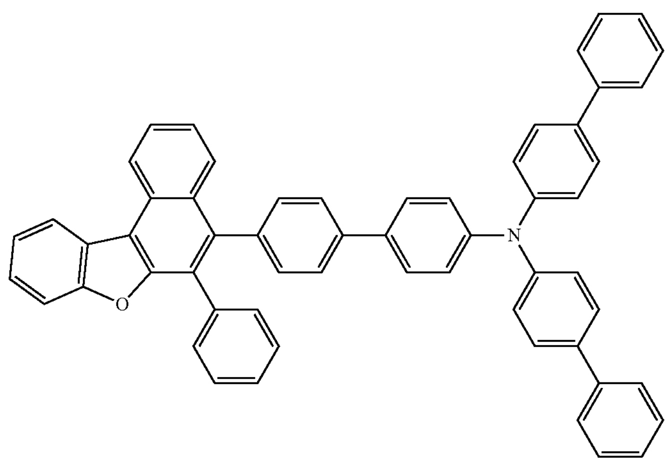 | 766 |
| 4-1-12 | compound 4-1-12 | 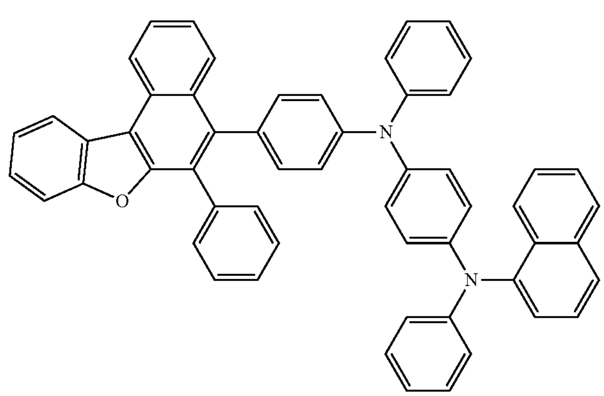 [SMILES: c1ccc(-c2c(-c3ccc(N(c4ccccc4)c4ccc(N(c5ccccc5)c5cccc6ccccc56)cc4)cc3)c3ccccc3c3c2oc2ccccc23)cc1] | 755 |

TABLE 4-1-continued

| Prep. Ex. 4-1-No | Product 4-1-No | structure | MS [M + H]+ |
|---|---|---|---|
| 4-1-13 | compound 4-1-13 | 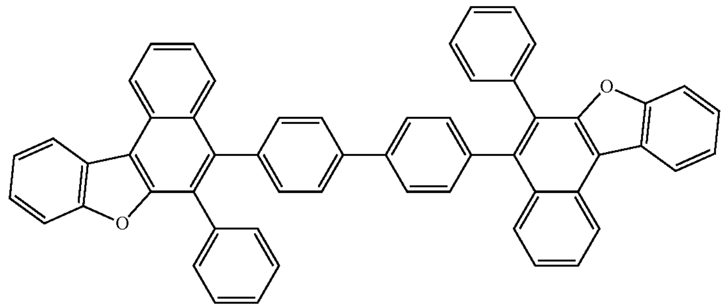 [SMILES: c1ccc(-c2c(-c3ccc(-c4ccc(-c5c(-c6ccccc6)c6oc7ccccc7c6c6ccccc56)cc4)cc3)c3ccccc3c3c2oc2ccccc23)cc1] | 739 |
| 4-1-14 | compound 4-1-14 | 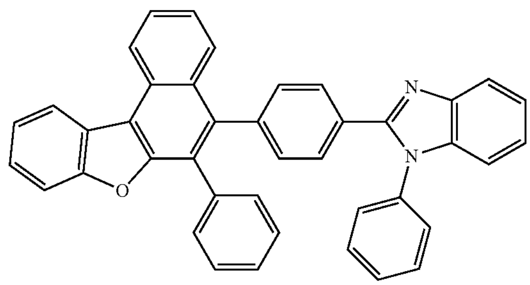 [SMILES: c1ccc(-c2c(-c3ccc(-c4nc5ccccc5n4-c4ccccc4)cc3)c3ccccc3c3c2oc2ccccc23)cc1] | 563 |

PREPARATION EXAMPLE 5-1-1

Preparation of the Compound 5-1-1

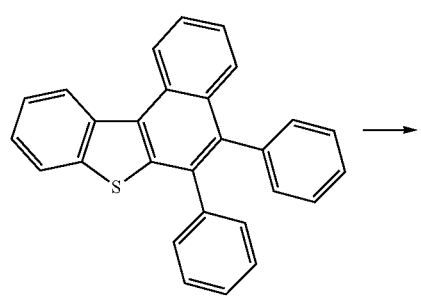

[compound A-3]

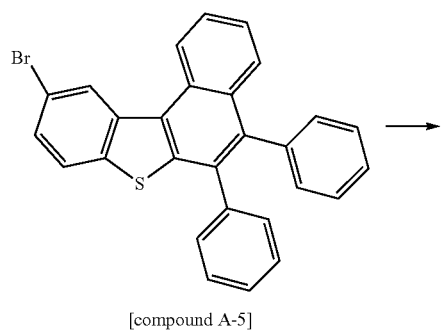

[compound A-5]

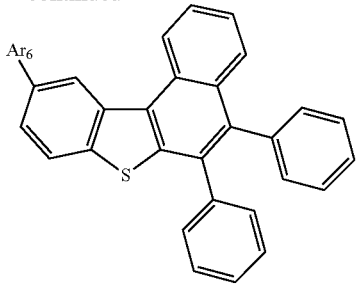

[compound 5-1-No]

Synthesis of the Compound A-5

In Preparation Example 3-1-16, it was prepared by using the same method to prepare the compound A-5, except that the phenyl boronic acid that was the reactant S-3 was used instead of the reactant S-33.

Synthesis of the Compound C-5-1

After the compound B-5-1 (4.6 g, 12.0 mmol) was dissolved in DMF 60 mL, NBS (2.2 g, 12.0 mmol) was applied thereto and agitated at normal temperature for 2 hours. After water 120 mL was applied thereto to precipitate the solid, it was filtered, washed with ethanol, and dried to prepare the compound C-5-1 (3.8 g, yield 68%).

MS $[M]^+$=465

Preparation of the Compound 5-1-1

In Preparation Example 3-1-16, the compound 5-1-1 was prepared by using the same method, except that the compound A-5 was used instead of the compound A-3 and the reactant S-26 was used instead of the reactant S-33.

PREPARATION EXAMPLE 5-1-2

Preparation of the Compound 5-1-2

In Preparation Example 3-1-16, the compound 5-1-2 was prepared by using the same method, except that the compound A-5 was used instead of the compound A-3 and the reactant S-16 was used instead of the reactant S-33.

PREPARATION EXAMPLE 5-1-3

Preparation of the Compound 5-1-3

In Preparation Example 3-1-16, the compound 5-1-3 was prepared by using the same method, except that the compound A-5 was used instead of the compound A-3 and the reactant S-40 was used instead of the reactant S-33.

TABLE 5-1

| Prep. Ex. 5-1-No | Product 5-1-No | structure | MS [M + H]+ |
|---|---|---|---|
| 5-1-1 | compound 5-1-1 | 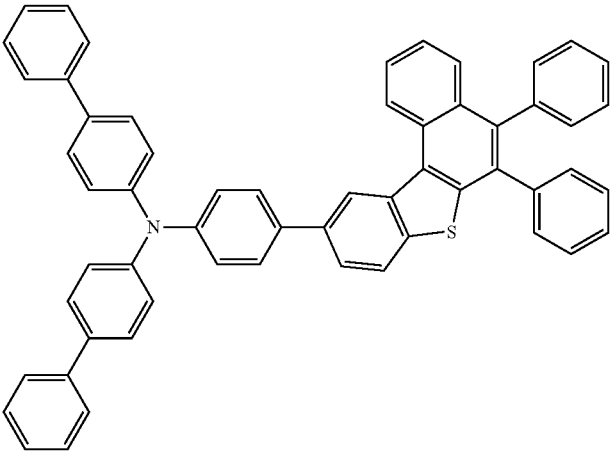 [SMILES: c1ccc(-c2ccc(N(c3ccc(-c4ccccc4)cc3)c3ccc(-c4ccc5sc6c(-c7ccccc7)c(-c7ccccc7)c7ccccc7c6c5c4)cc3)cc2)cc1] | 782 |
| 5-1-2 | compound 5-1-2 | 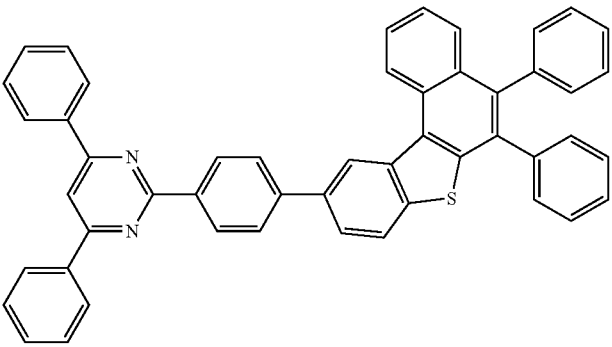 [SMILES: c1ccc(-c2cc(-c3ccccc3)nc(-c3ccc(-c4ccc5sc6c(-c7ccccc7)c(-c7ccccc7)c7ccccc7c6c5c4)cc3)n2)cc1] | 694 |
| 5-1-3 | compound 5-1-3 | 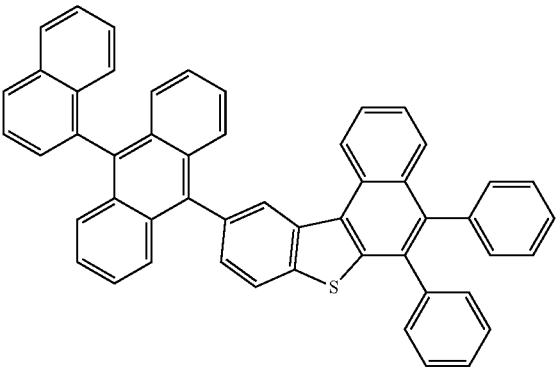 [SMILES: c1ccc(-c2c(-c3ccccc3)c3sc4ccc(-c5c6ccccc6c(-c6cccc7ccccc67)c6ccccc56)cc4c3c3ccccc23)cc1] | 689 |

EXPERIMENTAL EXAMPLE 1-1

A glass substrate on which a thin film of ITO (indium tin oxide) was coated to a thickness of 1500 Å was immersed in distilled water having a detergent dissolved therein to wash the substrate with ultrasonic waves. At this time, the detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was subsequently carried out by using solvents such as isopropyl alcohol, acetone and methanol, the resultant product was dried, and transported to the plasma washing machine. In addition, the substrate was washed by using the oxygen plasma for 5 min, and the substrate was transported to the vacuum deposition machine.

On the ITO transparent electrode thus prepared, hexanitrile hexaazatriphenylene was coated to thicknesses of 500 Å by thermal vacuum deposition to form a hole injecting layer. After NPB (400 Å) that was the material transporting the holes was deposited under the vacuum state thereon, the host H1 and the dopant D1 compound were deposited under the vacuum state in a thickness of 300 Å as a light emitting layer.

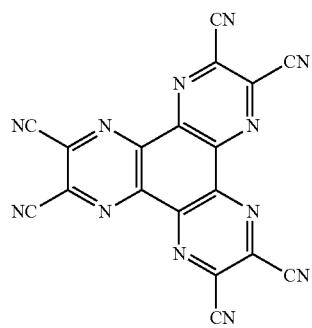

[hexanitrile hexaazatriphenylene]

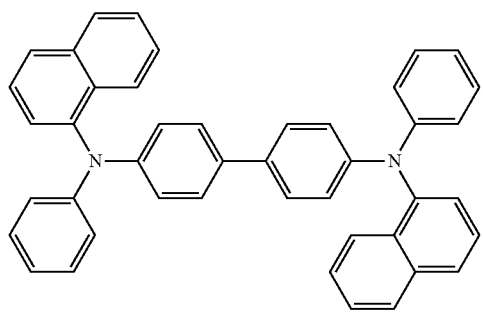

[NPB]

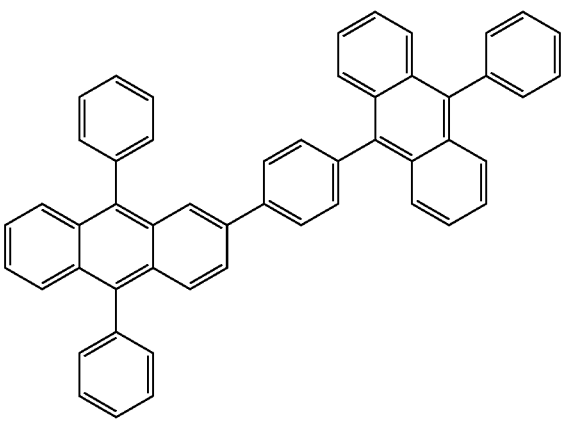

[H1]

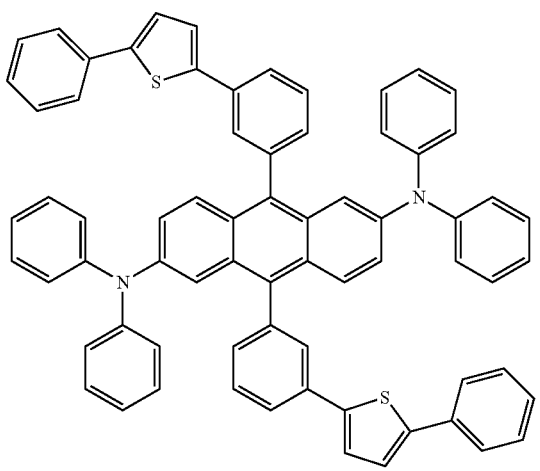

[D1]

[E1]

On the light emitting layer, the compound 1-1-10— prepared in Preparation Example 1-1-10 was deposited under the vacuum state in a thickness of 200 Å to form the electron injection and transport layer. On the electron injection and transport layer, lithium fluoride (LiF) in a thickness of 12 Å and aluminium in a thickness of 2000 Å were subsequently deposited to form a cathode.

In the above process, the deposition speed of the organic substance was maintained at 1 Å/sec, that of lithium fluoride was maintained at 0.2 Å/sec, and that of aluminium was maintained at 3 to 7 Å/sec.

EXPERIMENTAL 1-2 TO EXPERIMENTAL EXAMPLE 1-12

In Experimental Example 1-1, the same experiment was performed, except that on the light emitting layer, the compounds 1-1-11, 1-1-14, 1-2-1, 1-2-5, 1-2-11, 1-2-14, 3-1-8, 3-1-12, 4-1-8, 4-1-10, 4-1-14, and 5-1-2 were used instead of the compound 1-1-10 prepared in Preparation Example 1-1-10.

COMPARATIVE EXAMPLE 1

In Experimental Example 1-1, the same experiment was performed, except that on the light emitting layer, the compound Alq$_3$ was used instead of the compound 1-1-10.

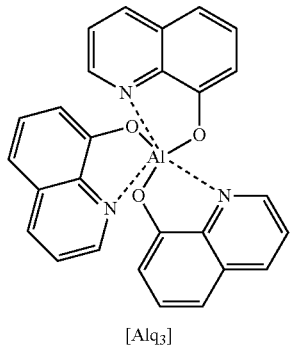

[Alq$_3$]

Like Experimental Examples 1-1 to 1-12 and Comparative Example 1, the test results of the organic light emitting device that was prepared by using each compound as the electron injection and transport layer material are described in Table 11.

TABLE 11

| Exp. Ex. 100 mA/cm$^2$ | compound | Voltage (V) | Cur. Eff. (cd/A) | Color Coordinate (x, y) |
|---|---|---|---|---|
| Com. Ex. 1 | Alq$_3$ | 10.91 | 10.96 | (0.323, 0.644) |
| Exp. Ex. 1-1 | 1-1-10 | 7.76 | 21.06 | (0.317, 0.649) |
| Exp. Ex. 1-2 | 1-1-11 | 7.05 | 24.22 | (0.323, 0.647) |
| Exp. Ex. 1-3 | 1-1-14 | 8.14 | 24.28 | (0.314, 0.650) |
| Exp. Ex. 1-4 | 1-2-1 | 6.91 | 23.27 | (0.310, 0.652) |
| Exp. Ex. 1-5 | 1-2-5 | 8.29 | 24.63 | (0.318, 0.653) |
| Exp. Ex. 1-6 | 1-2-11 | 8.91 | 18.44 | (0.317, 0.645) |
| Exp. Ex. 1-7 | 1-2-14 | 8.28 | 18.61 | (0.318, 0.652) |
| Exp. Ex. 1-8 | 3-1-8 | 7.31 | 21.12 | (0.318, 0.658) |
| Exp. Ex. 1-9 | 3-1-12 | 7.12 | 24.34 | (0.319, 0.657) |
| Exp. Ex. 1-10 | 4-1-8 | 8.19 | 24.65 | (0.318, 0.658) |
| Exp. Ex. 1-11 | 4-1-10 | 8.37 | 22.52 | (0.318, 0.653) |
| Exp. Ex. 1-11 | 4-1-14 | 8.31 | 22.91 | (0.317, 0.651) |
| Exp. Ex. 1-12 | 5-1-2 | 8.32 | 20.98 | (0.317, 0.653) |

As shown in the results of Table 11, properties are improved in terms of low voltage and efficiency in comparison with the results of the device of Comparative Example 1. In the compounds of Table 11, the substituent group having relatively excellent electron injection and transport properties is introduced. The properties of them are not lowered but improved by the basic structure of Formula 1. This is because the structure of Formula 1 has an appropriate LUMO so as to easily transport electrons to the light emitting layer by introducing the frame having the relatively large energy band gap or the substituent groups having the electron injection and transport properties.

EXPERIMENTAL EXAMPLE 2-1

A glass substrate on which a thin film of ITO (indium tin oxide) was coated to a thickness of 1500 Å was immersed in distilled water having a detergent dissolved therein to wash the substrate with ultrasonic waves. At this time, the detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was subsequently carried out by using solvents such as isopropyl alcohol, acetone and methanol, the resultant product was dried, and transported to the plasma washing machine. In addition, the substrate was washed by using the oxygen plasma for 5 min, and the substrate was transported to the vacuum deposition machine.

On the ITO transparent electrode thus prepared, hexanitrile hexaazatriphenylene was coated to thicknesses of 500 Å by thermal vacuum deposition to form a hole injecting layer. After NPB (400 Å) that was the material transporting the holes was deposited under the vacuum state thereon, the compound 1-1-7 that was prepared in Preparation Example 1-1-7 as the host H1 and the dopant D1 compound were deposited under the vacuum state in a thickness of 300 Å as a light emitting layer. On the light emitting layer, the electron injection and transport layer was formed by depositing E1 under the vacuum state in a thickness of 200 Å on the light emitting layer. On the electron transport layer, lithium fluoride (LiF) in a thickness of 12 Å and aluminium in a thickness of 2000 Å were subsequently deposited to form a cathode, thereby manufacturing the organic light emitting device.

In the above process, the deposition speed of the organic material was maintained at 0.4 to 0.7 Å/sec, the deposition speed of the lithium fluoride of the cathode was maintained at 0.3 Å/sec, the deposition speed of aluminium was maintained at 2 Å/sec, and the degree of vacuum in the deposition was maintained at 2×10$^{-7}$ to 5×10$^{-8}$ torr.

EXPERIMENTAL EXAMPLE 2-2 TO EXPERIMENTAL EXAMPLE 2-36

In Experimental Example 2-1, the organic light emitting device was experimented by using the same method, except that the compounds 1-1-6, 1-2-6, 1-2-7, 1-2-8, 1-2-9, 1-2-10, 1-2-12, 1-2-13, 1-3-1, 1-3-2, 1-3-3, 1-3-4, 1-4-1, 1-4-2, 1-4-3, 1-7-1, 1-7-3, 2-1-1, 2-1-3, 2-1-4, 2-1-5, 3-1-1, 3-1-2, 3-1-3, 3-1-4, 3-1-5, 3-1-6, 4-1-1, 4-1-2, 4-1-3, 4-1-4, 4-1-5, 4-1-6, 4-1-7, and 5-1-3 were used instead of the compound 1-1-7 on the hole transport layer, and the results thereof are described in Table 12.

TABLE 12

| Exp. Ex. 100 mA/cm$^2$ | Host Material | Dopant Material | Voltage (V) | Cur. Eff. (cd/A) | Color Coordinate (x, y) |
|---|---|---|---|---|---|
| Exp. Ex. 2-1 | 1-1-7 | D1 | 7.34 | 23.35 | (0.314, 0.652) |
| Exp. Ex. 2-2 | 1-1-6 | D1 | 7.61 | 21.62 | (0.314, 0.650) |

TABLE 12-continued

| Exp. Ex. 100 mA/cm² | Host Material | Dopant Material | Voltage (V) | Cur. Eff. (cd/A) | Color Coordinate (x, y) |
|---|---|---|---|---|---|
| Exp. Ex. 2-3 | 1-2-6 | D1 | 8.82 | 22.04 | (0.315, 0.648) |
| Exp. Ex. 2-4 | 1-2-7 | D1 | 8.09 | 21.63 | (0.317, 0.650) |
| Exp. Ex. 2-5 | 1-2-8 | D1 | 7.67 | 23.06 | (0.315, 0.651) |
| Exp. Ex. 2-6 | 1-2-9 | D1 | 8.67 | 20.23 | (0.315, 0.650) |
| Exp. Ex. 2-7 | 1-2-10 | D1 | 10.51 | 16.26 | (0.314, 0.650) |
| Exp. Ex. 2-8 | 1-2-12 | D1 | 10.06 | 20.46 | (0.317, 0.650) |
| Exp. Ex. 2-9 | 1-2-13 | D1 | 8.08 | 21.40 | (0.317, 0.647) |
| Exp. Ex. 2-10 | 1-3-1 | D1 | 8.05 | 26.10 | (0.315, 0.648) |
| Exp. Ex. 2-11 | 1-3-2 | D1 | 8.01 | 26.18 | (0.316, 0.648) |
| Exp. Ex. 2-12 | 1-3-3 | D1 | 7.62 | 20.26 | (0.314, 0.650) |
| Exp. Ex. 2-13 | 1-3-4 | D1 | 8.01 | 21.36 | (0.317, 0.650) |
| Exp. Ex. 2-14 | 1-4-1 | D1 | 7.65 | 23.63 | (0.315, 0.651) |
| Exp. Ex. 2-15 | 1-4-2 | D1 | 8.53 | 22.21 | (0.315, 0.650) |
| Exp. Ex. 2-16 | 1-4-3 | D1 | 8.10 | 20.05 | (0.314, 0.650) |
| Exp. Ex. 2-17 | 1-7-1 | D1 | 11.71 | 24.02 | (0.319, 0.649) |
| Exp. Ex. 2-18 | 1-7-3 | D1 | 10.32 | 21.46 | (0.317, 0.650) |
| Exp. Ex. 2-19 | 2-1-1 | D1 | 8.23 | 23.40 | (0.317, 0.647) |
| Exp. Ex. 2-20 | 2-1-3 | D1 | 8.91 | 22.02 | (0.319, 0.649) |
| Exp. Ex. 2-21 | 2-1-4 | D1 | 7.22 | 22.10 | (0.315, 0.648) |
| Exp. Ex. 2-22 | 2-1-5 | D1 | 7.67 | 20.06 | (0.315, 0.651) |
| Exp. Ex. 2-23 | 3-1-1 | D1 | 7.15 | 21.06 | (0.315, 0.651) |
| Exp. Ex. 2-24 | 3-1-2 | D1 | 8.47 | 21.23 | (0.315, 0.650) |
| Exp. Ex. 2-25 | 3-1-3 | D1 | 8.85 | 22.08 | (0.317, 0.648) |
| Exp. Ex. 2-26 | 3-1-4 | D1 | 7.66 | 20.57 | (0.315, 0.649) |
| Exp. Ex. 2-27 | 3-1-5 | D1 | 7.46 | 21.22 | (0.316, 0.652) |
| Exp. Ex. 2-28 | 3-1-6 | D1 | 7.98 | 19.98 | (0.314, 0.652) |
| Exp. Ex. 2-29 | 4-1-1 | D1 | 8.38 | 19.89 | (0.314, 0.650) |
| Exp. Ex. 2-30 | 4-1-2 | D1 | 8.32 | 21.89 | (0.315, 0.647) |
| Exp. Ex. 2-31 | 4-1-3 | D1 | 7.55 | 20.02 | (0.319, 0.649) |
| Exp. Ex. 2-32 | 4-1-4 | D1 | 7.97 | 23.07 | (0.318, 0.651) |
| Exp. Ex. 2-33 | 4-1-5 | D1 | 8.29 | 24.01 | (0.317, 0.649) |
| Exp. Ex. 2-34 | 4-1-6 | D1 | 8.43 | 20.78 | (0.317, 0.651) |
| Exp. Ex. 2-35 | 4-1-7 | D1 | 9.03 | 16.56 | (0.317, 0.650) |
| Exp. Ex. 2-36 | 5-1-3 | D1 | 8.81 | 23.80 | (0.317, 0.647) |

As shown in the results of Table 12, the compounds of Formula 1 may be used as the light emitting layer in conjunction with the dopant by introducing the aryl group such as anthracene.

EXPERIMENTAL EXAMPLE 3-1

A glass substrate (corning 7059 glass) on which a thin film of ITO (indium tin oxide) was coated to a thickness of 1000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol, and the resultant product was dried.

On the ITO transparent electrode thus prepared, hexanitrile hexaazatriphenylene was coated to thicknesses of 500 Å by thermal vacuum deposition to form a hole injecting layer. After the compound 1-5-1 (400 Å) prepared in Preparation Example 1-5-1, which was the material transporting the holes was deposited under the vacuum state thereon, the host H1 and the dopant D1 compound were deposited under the vacuum state in a thickness of 300 Å as a light emitting layer. Thereafter, the E1 compound (300 Å) was deposited by heating under the vacuum as the electron injection and the transport layer. On the electron transport layer, lithium fluoride (LiF) in a thickness of 12 Å and aluminium in a thickness of 2,000 Å were subsequently deposited to form a cathode, thereby manufacturing the organic light emitting device.

In the above process, the deposition speed of the organic substance was maintained at 1 Å/sec, that of lithium fluoride was maintained at 0.2 Å/sec, and that of aluminium was maintained at 3 to 7 Å/sec.

EXPERIMENTAL EXAMPLE 3-2
EXPERIMENTAL EXAMPLE 3-18

In Experimental Example 3-1, the organic light emitting device was experimented by using the same method, except that the compounds 11-5-2, 1-5-3, 1-5-4, 1-5-5, 1-6-1, 1-6-2, 1-6-3, 3-1-13, 3-1-14, 3-1-15, 4-1-11, 4-1-12, 5-1-1, 3-1-17, 3-1-18, 3-1-19, and 3-1-20 were used, and the results thereof are described in Table 13.

TABLE 13

| Exp. Ex. 100 mA/cm² | HTL Material | Voltage (V) | Cur. Eff. (cd/A) | Color Coordinate (x, y) |
|---|---|---|---|---|
| Com. Ex. 2 | NPB | 8.89 | 21.23 | (0.323, 0.644) |
| Exp. Ex. 3-1 | 1-5-1 | 7.17 | 22.05 | (0.316, 0.650) |
| Exp. Ex. 3-2 | 1-5-2 | 6.49 | 19.08 | (0.312, 0.650) |
| Exp. Ex. 3-3 | 1-5-3 | 7.28 | 20.53 | (0.315, 0.648) |
| Exp. Ex. 3-4 | 1-5-4 | 7.73 | 23.72 | (0.310, 0.647) |
| Exp. Ex. 3-5 | 1-5-5 | 6.88 | 21.11 | (0.312, 0.651) |
| Exp. Ex. 3-6 | 1-6-1 | 6.17 | 20.05 | (0.313, 0.650) |
| Exp. Ex. 3-7 | 1-6-2 | 7.28 | 21.53 | (0.315, 0.648) |
| Exp. Ex. 3-8 | 1-6-3 | 7.73 | 24.72 | (0.310, 0.650) |
| Exp. Ex. 3-9 | 3-1-13 | 6.89 | 21.67 | (0.313, 0.651) |
| Exp. Ex. 3-10 | 3-1-14 | 7.02 | 21.05 | (0.317, 0.650) |
| Exp. Ex. 3-11 | 3-1-15 | 9.07 | 18.88 | (0.315, 0.651) |
| Exp. Ex. 3-12 | 4-1-11 | 7.27 | 21.87 | (0.312, 0.650) |
| Exp. Ex. 3-13 | 4-1-12 | 7.98 | 22.43 | (0.314, 0.648) |
| Exp. Ex. 3-14 | 5-1-1 | 7.48 | 20.07 | (0.314, 0.650) |
| Exp. Ex. 3-15 | 3-1-17 | 8.21 | 21.10 | (0.316, 0.649) |
| Exp. Ex. 3-16 | 3-1-18 | 7.68 | 22.02 | (0.318, 0.648) |
| Exp. Ex. 3-17 | 3-1-19 | 7.74 | 20.19 | (0.317, 0.650) |
| Exp. Ex. 3-18 | 3-1-20 | 7.51 | 19.78 | (0.312, 0.648) |

As shown in the results of Table 13, in the compound of Formula 1, low voltage and efficiency increase may be obtained by using the compounds that were prepared by introducing the aryl group substituted by the arylamin group as the hole transport layer.

EXPERIMENTAL EXAMPLE 4-1

A glass substrate (corning 7059 glass) on which a thin film of ITO (indium tin oxide) was coated to a thickness of 1000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol, and the resultant product was dried.

On the ITO transparent electrode thus prepared, hexanitrile hexaazatriphenylene was coated to thicknesses of 500 Å by thermal vacuum deposition to form a hole injecting layer. NPB (400 Å) was deposited under the vacuum state as the material transporting the holes thereon. As the light emitting layer, the compound 3-1-10 prepared in Preparation Example 3-1-10 and the dopant D2 (doping concentration 14%) compound were deposited under the vacuum state in a thickness of 300 Å.

[H2]

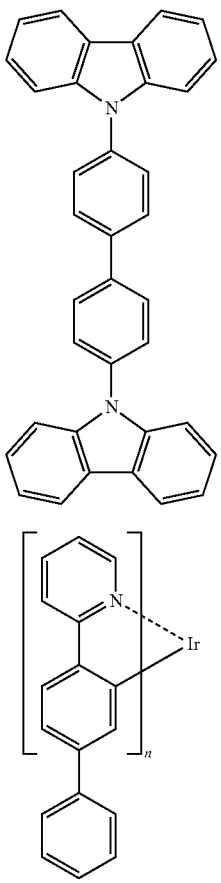

[D2]

Thereafter, the E1 compound (300 Å) was deposited by heating under the vacuum as the electron injection and the transport layer. On the electron transport layer, lithium fluoride (LiF) in a thickness of 12 Å and aluminium in a thickness of 2,000 Å were subsequently deposited to form a cathode, thereby manufacturing the organic light emitting device.

In the above process, the deposition speed of the organic substance was maintained at 1 Å/sec, that of lithium fluoride was maintained at 0.2 Å/sec, and that of aluminium was maintained at 3 to 7 Å/sec.

EXPERIMENTAL EXAMPLE 4-2 TO EXPERIMENTAL EXAMPLE 4-10

In Experimental Example 4-1, the compounds represented by Formulas 1-1-13, 1-1-14, 1-2-1, 1-2-4, 1-5-2, 1-5-3, 1-6-1, 3-1-9, and 4-1-9 were used instead of the compound 3-1-10, and the organic light emitting device was manufactured by using the compound E1, and the experimental results thereof are described in the following Table 14.

COMPARATIVE EXAMPLE 3

In Experimental Example 4-1, the same experiment was performed, except that the compound H2 was used instead of the compound 3-1-10.

TABLE 14

| Exp. Ex. 20 mA/cm$^2$ | EML (Host:D3) | Voltage (V) | Cur. Eff. (cd/A) | Color Coordinate (x, y) |
|---|---|---|---|---|
| Com. Ex. 3 | H2 | 6.74 | 16.28 | (0.371, 0.595) |
| Exp. Ex. 4-1 | 3-1-10 | 5.71 | 33.28 | (0.371, 0.595) |
| Exp. Ex. 4-2 | 1-1-13 | 5.24 | 31.28 | (0.371, 0.595) |
| Exp. Ex. 4-3 | 1-1-14 | 5.52 | 18.75 | (0.354, 0.611) |
| Exp. Ex. 4-4 | 1-2-1 | 5.74 | 28.28 | (0.371, 0.595) |
| Exp. Ex. 4-5 | 1-2-4 | 4.89 | 31.12 | (0.365, 0.601) |
| Exp. Ex. 4-6 | 1-5-2 | 4.31 | 32.07 | (0.362, 0.607) |
| Exp. Ex. 4-7 | 1-5-3 | 4.96 | 33.07 | (0.362, 0.607) |
| Exp. Ex. 4-8 | 1-6-1 | 4.57 | 33.96 | (0.380, 0.589) |
| Exp. Ex. 4-9 | 3-1-9 | 4.31 | 30.07 | (0.362, 0.607) |
| Exp. Ex. 4-10 | 4-1-9 | 6.23 | 22.77 | (0.367, 0.601) |

As shown in Table 14, the compound derivative that is represented by Formula according to the present invention can function as the light emitting material in the organic light emitting device and the organic electronic device, and the device according to the present invention shows excellent characteristics in views of efficiency, the driving voltage, and stability. In particular, in views of efficiency, the high light emitting characteristics are shown.

INDUSTRIAL APPLICABILITY

An organic light emitting device and an organic electronic device that were prepared by using a novel compound according to the present invention as an organic material layer may act as a hole injection, hole transport, electron injection and transport, or light emitting material, and show excellent properties in terms of efficiency, a driving voltage, and stability.

The invention claimed is:
1. A compound that is represented by the following Formula 1:

[Formula 1]

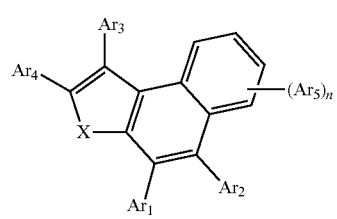

X is S or O, n is an integer in the range of 0 to 4, $Ar_1$, $Ar_2$, $Ar_3$, and $Ar_4$, may be the same as or different from each other, and each independently selected from the group consisting of heavy hydrogen atom; amino group; nitrile group; nitro group; amide group; $C_1$-$C_{30}$ alkoxy group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{60}$ heteroaryl group; $C_6$-$C_{30}$ aryloxy group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{60}$ heteroaryl group; $C_1$-$C_{30}$ alkylthioxy group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{60}$ heteroaryl group; $C_6$-$C_{30}$ arylthioxy group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{60}$ heteroaryl group; $C_1$-$C_{30}$ alkylaminyl group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{60}$ heteroaryl group; $C_6$-$C_{60}$ aralkylaminyl group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{60}$ heteroaryl group; $C_6$-$C_{60}$ arylaminyl group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ hetero-cycloalkyl group, $C_6$-$C_{60}$ aryl group and $C_3$-$C_{60}$ heteroaryl group; $C_6$-$C_{60}$ aryl group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_6$-$C_{30}$ aryloxy group, $C_1$-$C_{30}$ alkylthioxy group, $C_6$-$C_{30}$ arylthioxy group, $C_3$-$C_{30}$ cycloalkyl group, $C_2$-$C_{30}$ heterocycloalkyl group, substituted or unsubstituted $C_1$-$C_{30}$ alkylaminyl group, substituted or unsubstituted $C_1$-$C_{30}$ aralkylaminyl group, substituted or unsubstituted $C_6$-$C_{60}$ arylaminyl group, $C_6$-$C_{60}$ aryl group and $C_3$-$C_{60}$ heteroaryl group; $C_3$-$C_{60}$ heteroaryl group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_6$-$C_{30}$ aryloxy group, $C_1$-$C_{30}$ alkylthioxy group, $C_6$-$C_{30}$ arylthioxy group, $C_3$-$C_{30}$ cycloalkyl group, $C_2$-$C_{30}$ heterocycloalkyl group, substituted or unsubstituted $C_1$-$C_{30}$ alkylaminyl group, substituted or unsubstituted $C_1$-$C_{30}$ aralkylaminyl group, substituted or unsubstituted $C_6$-$C_{60}$ arylaminyl group, $C_6$-$C_{60}$ aryl group and $C_3$-$C_{60}$ heteroaryl group; boron group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{60}$ heteroaryl group; silyl group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{60}$ heteroaryl group; and ester group that is unsubstituted or substituted by one or more groups that are selected from the group consisting of heavy hydrogen atom, halogen group, hydroxy group, formyl group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{60}$ heteroaryl group, or may form an aliphatic, aromatic, aliphatic hetero or aromatic hetero condensated ring or a spiro bond in conjunction with an adjacent group, $Ar_5$ represents hydrogen atom, and the $C_6$-$C_{60}$ aryl group is selected from the group consisting of phenyl group, biphenyl group, terphenyl group, fluorenyl group, naphthyl group, anthracenyl group, and phenanthryl group.

2. The compound as set forth in claim 1, wherein the compound that is represented by Formula 1 is represented by the following Formula 2 or 3:

[Formula 2]

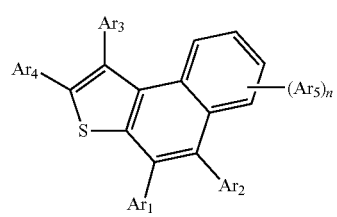

[Formula 3]

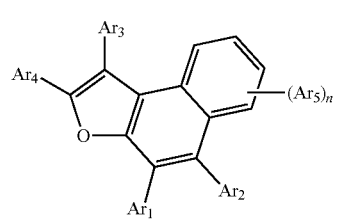

wherein, $Ar_1$ to $Ar_5$ and n are the same as those defined in Formula 1.

3. The compound as set forth in claim 1, wherein the compound that is represented by Formula 1 is represented by the following Formula 4:

[Formula 4]

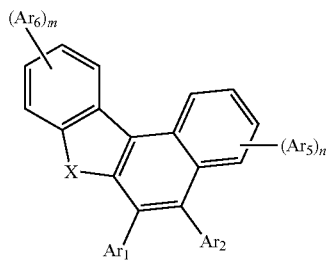

wherein X is S or O, m and n are each independently 0 to 4, $Ar_1, Ar_2, Ar_5, Ar_6$ and n are the same as definition of $Ar_1$ to $Ar_5$ of Formula 1.

4. The compound as set forth in claim 1, wherein in Formula 1, $Ar_2$ to $Ar_5$ may be the same as or different from each other, and each independently $C_6$-$C_{60}$ arylaminyl group that is unsubstituted or substituted by one or more groups that are selected from the group consisting of heavy hydrogen atom, halogen group, amino group, nitrile group, nitro group, $C_1$-$C_{30}$ alkyl group, $C_2$-$C_{30}$ alkenyl group, $C_1$-$C_{30}$ alkoxy group, $C_3$-$C_{30}$ cycloalkyl group, $C_2$-$C_{30}$ heterocycloalkyl group, $C_6$-$C_{60}$ aryl group and $C_3$-$C_{30}$ heteroaryl group, and the $C_6$-$C_{60}$ aryl group is selected from the group consisting of phenyl group, biphenyl group, terphenyl group, fluorenyl group, naphthyl group, anthracenyl group, and phenanthryl group.

5. The compound as set forth in claim 1, wherein in Formula 1, $Ar_2$ to $Ar_5$ may be the same as or different from each other, and each independently $C_6$-$C_{60}$ aryl group that is unsubstituted or substituted by one or more groups that are selected from the group consisting of heavy hydrogen atom, halogen group, amino group, nitrile group, nitro group, $C_1$-$C_{30}$ alkyl group, $C_2$-$C_{30}$ alkenyl group, $C_1$-$C_{30}$ alkoxy group, $C_6$-$C_{30}$ aryloxy group, $C_1$-$C_{30}$ alkylthioxy group, $C_6$-$C_{30}$ arylthioxy group, $C_3$-$C_{30}$ cycloalkyl group, $C_2$-$C_{30}$ heterocycloalkyl group, substituted or unsubstituted $C_1$-$C_{30}$ alkylaminyl group, substituted or unsubstituted $C_1$-$C_{30}$ aralkylaminyl group, substituted or unsubstituted $C_6$-$C_{60}$ arylaminyl group, $C_6$-$C_{60}$ aryl group and $C_3$-$C_{60}$ heteroaryl group, and the $C_6$-$C_{60}$ aryl group is selected from the group consisting of phenyl group, biphenyl group, terphenyl group, fluorenyl group, naphthyl group, anthracenyl group, and phenanthryl group.

6. The compound as set forth in claim 1, wherein in Formula 1, $Ar_2$ to $Ar_5$ may be the same as or different from each other, and each independently $C_3$-$C_{60}$ heteroaryl group that is unsubstituted or substituted by one or more groups that are selected from the group consisting of heavy hydrogen atom, halogen group, amino group, nitrile group, nitro group, $C_1$-$C_{30}$ alkyl group, $C_2$-$C_{30}$ alkenyl group, $C_1$-$C_{30}$ alkoxy group, $C_6$-$C_{30}$ aryloxy group, $C_1$-$C_{30}$ alkylthioxy group, $C_6$-$C_{30}$ arylthioxy group, $C_3$-$C_{30}$ cycloalkyl group, $C_2$-$C_{30}$ heterocycloalkyl group, substituted or unsubstituted $C_1$-$C_{30}$ alkylaminyl group, substituted or unsubstituted $C_1$-$C_{30}$ aralkylaminyl group, substituted or unsubstituted $C_6$-$C_{60}$ arylaminyl group, $C_6$-$C_{60}$ aryl group and $C_3$-$C_{60}$ heteroaryl group, and the $C_6$-$C_{60}$ aryl group is selected from the group consisting of phenyl group, biphenyl group, terphenyl group, fluorenyl group, naphthyl group, anthracenyl group, and phenanthryl group.

7. The compound as set forth in claim 1, wherein in Formula 1, the fluorenyl group is represented by the following Structural Formulas:

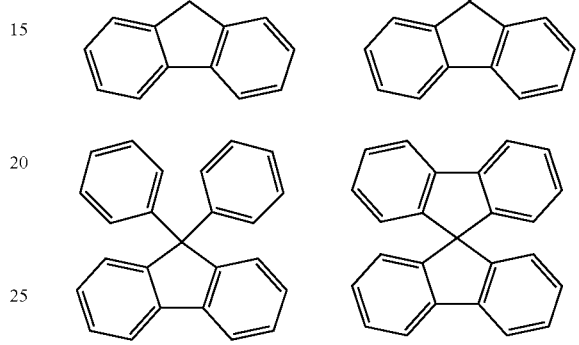

8. The compound as set forth in claim 1, wherein in Formula 1, the $C_6$-$C_{60}$ heteroaryl is selected from the following Structural Formulas or condensated ring group thereof:

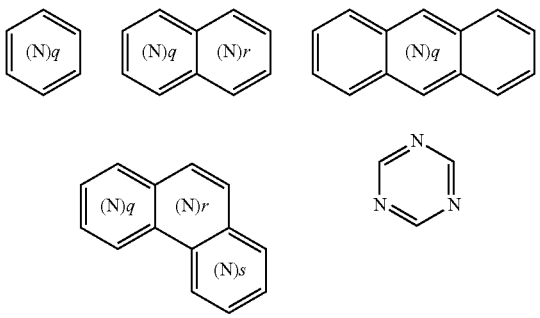

wherein (N)q, (N)r, to (N)s mean that at least one nitrogen atoms exist instead of a carbon atom in a benzene ring, and in (N)q, (N)r and (N)s, q, r and s are each an integer of 1 or 2

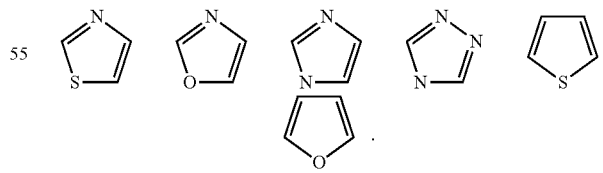

9. The compound as set forth in claim 1, wherein $Ar_1$ is a phenyl group.

10. The compound as set forth in claim 1, wherein the compound that is represented by Formula 1 is selected from the compounds that are represented by the compounds described in the following Table:

TABLE 1-1
| Product 1-1-No | structure |
|---|---|
| compound 1-1-1 | 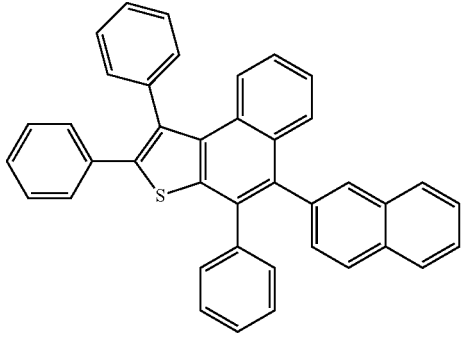 [SMILES: c1ccc(-c2sc3c(-c4ccccc4)c(-c4ccc5ccccc5c4)c4ccccc4c3c2-c2ccccc2)cc1] |
| compound 1-1-2 | 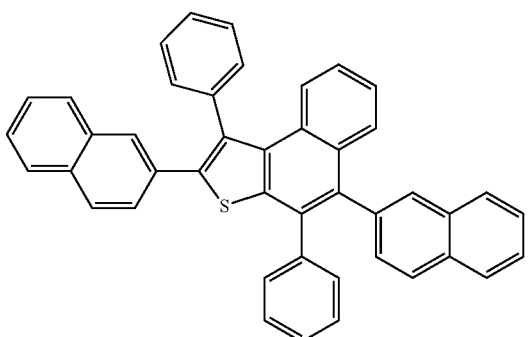 |
| compound 1-1-3 | 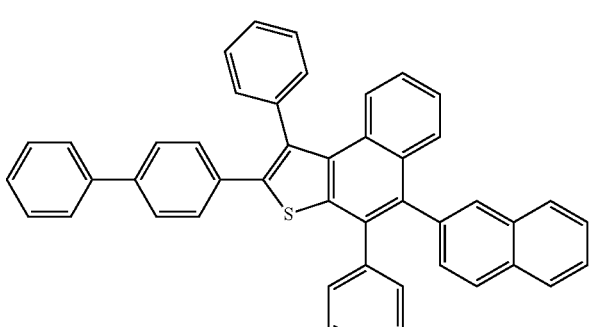 |
| compound 1-1-4 | 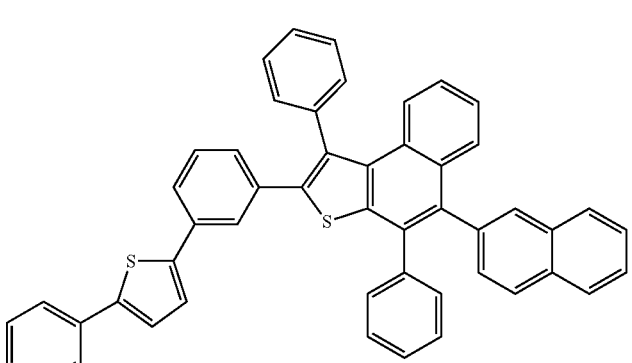 |

TABLE 1-1-continued
| Product 1-1-No | structure |
|---|---|
| compound 1-1-5 | 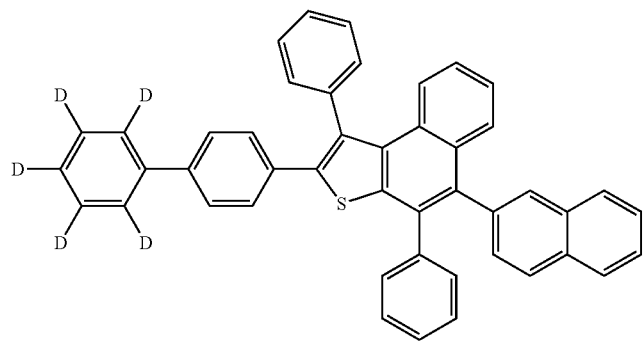 [SMILES: [2H]c1c([2H])c([2H])c(-c2ccc(-c3sc4c(-c5ccccc5)c(-c5ccc6ccccc6c5)c5ccccc5c4c3-c3ccccc3)cc2)c([2H])c1[2H]] |
| compound 1-1-6 | 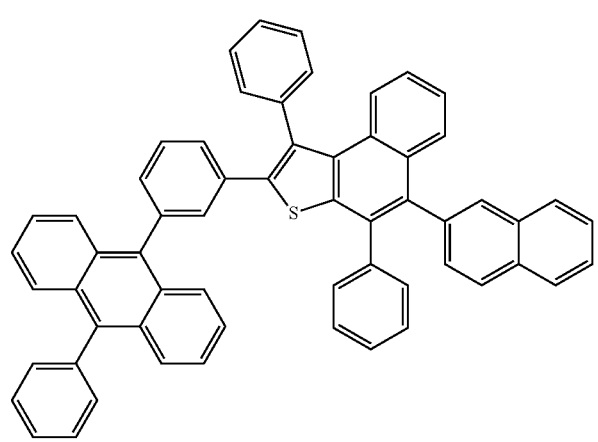 [SMILES: c1ccc(-c2c3ccccc3c(-c3cccc(-c4sc5c(-c6ccccc6)c(-c6ccc7ccccc7c6)c6ccccc6c5c4-c4ccccc4)c3)c3ccccc23)cc1] |
| compound 1-1-7 | 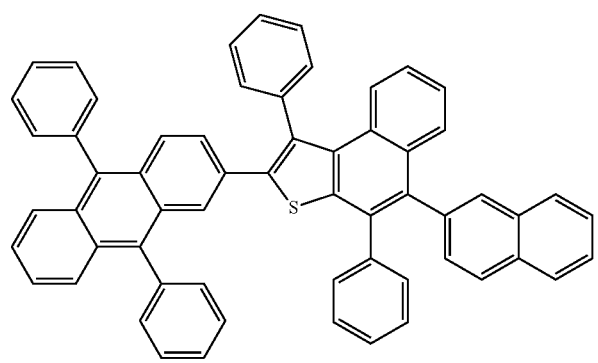 |
| compound 1-1-8 | 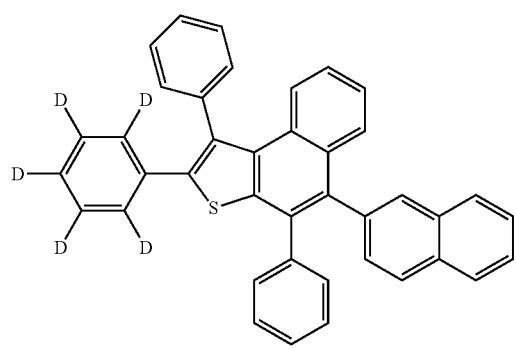 [SMILES: [2H]c1c([2H])c([2H])c(-c2sc3c(-c4ccccc4)c(-c4ccc5ccccc5c4)c4ccccc4c3c2-c2ccccc2)c([2H])c1[2H]] |

TABLE 1-1-continued
| Product 1-1-No | structure |
|---|---|
| compound 1-1-9 | 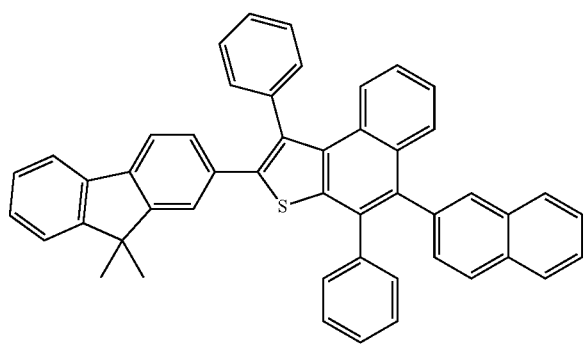 [SMILES: CC1(C)c2ccccc2-c2ccc(-c3sc4c(-c5ccccc5)c(-c5ccc6ccccc6c5)c5ccccc5c4c3-c3ccccc3)cc21] |
| compound 1-1-10 | 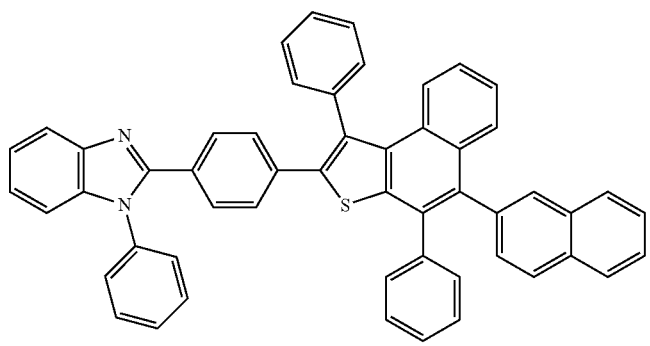 [SMILES: c1ccc(-c2c(-c3ccc4ccccc4c3)c3ccccc3c3c(-c4ccccc4)c(-c4ccc(-c5nc6ccccc6n5-c5ccccc5)cc4)sc23)cc1] |
| compound 1-1-11 | 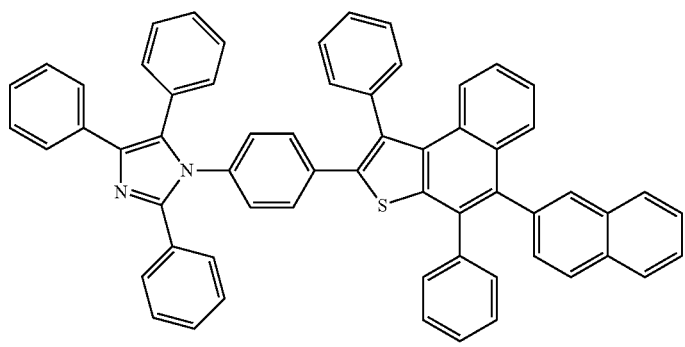 [SMILES: c1ccc(-c2nc(-c3ccccc3)n(-c3ccc(-c4sc5c(-c6ccccc6)c(-c6ccc7ccccc7c6)c6ccccc6c5c4-c4ccccc4)cc3)c2-c2ccccc2)cc1] |
| compound 1-1-12 | 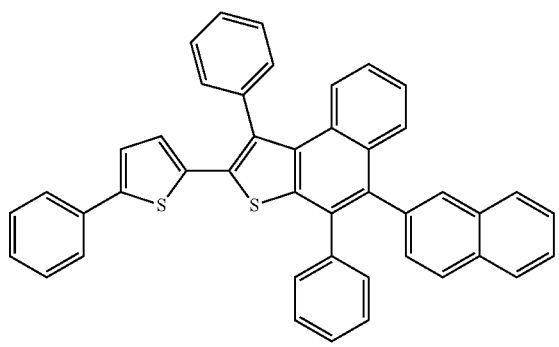 [SMILES: c1ccc(-c2ccc(-c3sc4c(-c5ccccc5)c(-c5ccc6ccccc6c5)c5ccccc5c4c3-c3ccccc3)s2)cc1] |

TABLE 1-1-continued

| Product 1-1-No | structure |
|---|---|
| compound 1-1-13 | 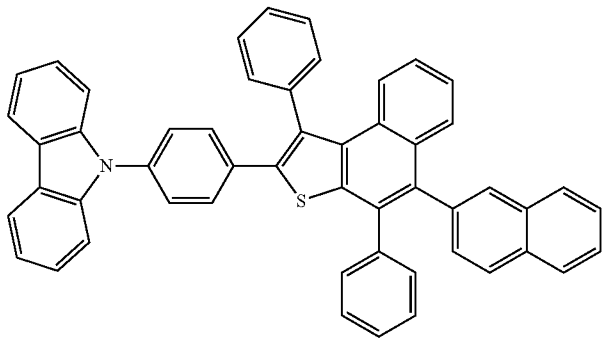 [SMILES: c1ccc(-c2c(-c3ccc4ccccc4c3)c3ccccc3c3c(-c4ccccc4)c(-c4ccc(-n5c6ccccc6c6ccccc65)cc4)sc23)cc1] |
| compound 1-1-14 | 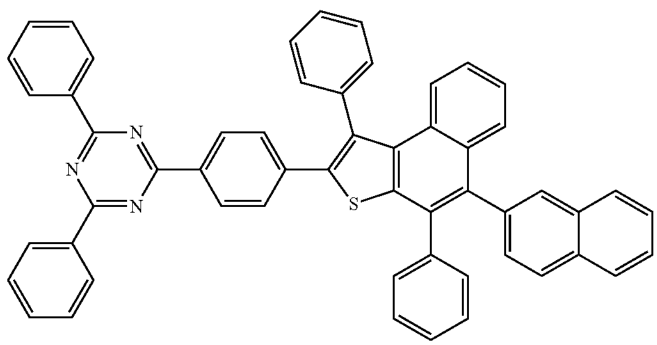 [SMILES: c1ccc(-c2nc(-c3ccccc3)nc(-c3ccc(-c4sc5c(-c6ccccc6)c(-c6ccc7ccccc7c6)c6ccccc6c5c4-c4ccccc4)cc3)n2)cc1] |

TABLE 1-2

| Product 1-2-No | structure |
|---|---|
| compound 1-2-1 | 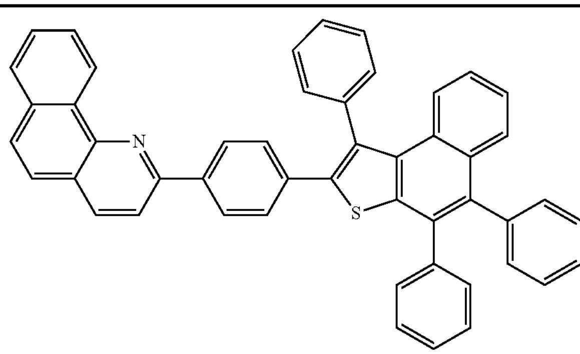 |
| compound 1-2-2 | 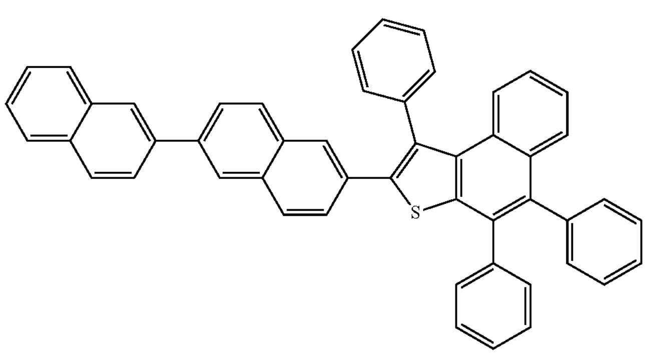 [SMILES: c1ccc(-c2c(-c3ccccc3)c3sc(-c4ccc5cc(-c6ccc7ccccc7c6)ccc5c4)c(-c4ccccc4)c3c3ccccc23)cc1] |

TABLE 1-2-continued

| Product 1-2-No | structure |
|---|---|
| compound 1-2-3 | 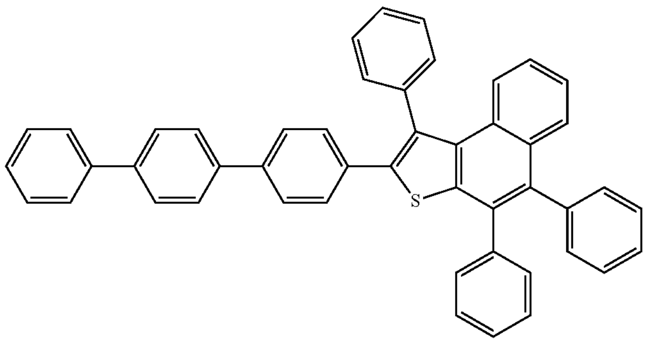 [SMILES: c1ccc(-c2ccc(-c3ccc(-c4sc5c(-c6ccccc6)c(-c6ccccc6)c6ccccc6c5c4-c4ccccc4)cc3)cc2)cc1] |
| compound 1-2-4 | 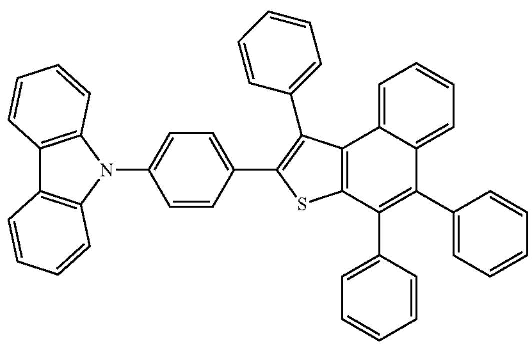 [SMILES: c1ccc(-c2c(-c3ccccc3)c3sc(-c4ccc(-n5c6ccccc6c6ccccc65)cc4)c(-c4ccccc4)c3c3ccccc23)cc1] |
| compound 1-2-5 | 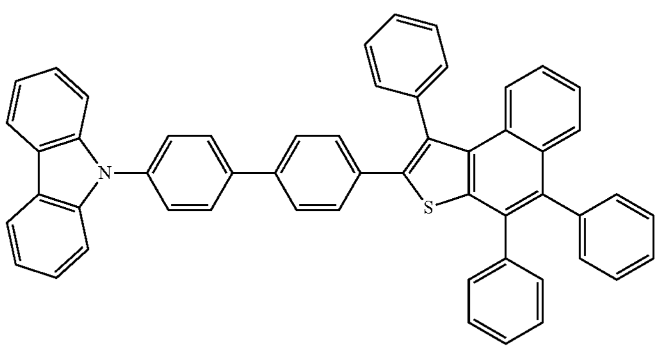 [SMILES: c1ccc(-c2c(-c3ccccc3)c3sc(-c4ccc(-c5ccc(-n6c7ccccc7c7ccccc76)cc5)cc4)c(-c4ccccc4)c3c3ccccc23)cc1] |
| compound 1-2-6 | 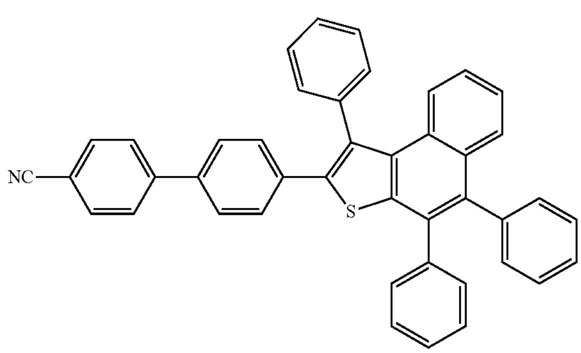 [SMILES: N#Cc1ccc(-c2ccc(-c3sc4c(-c5ccccc5)c(-c5ccccc5)c5ccccc5c4c3-c3ccccc3)cc2)cc1] |

TABLE 1-2-continued

| Product 1-2-No | structure |
| --- | --- |
| compound 1-2-7 | 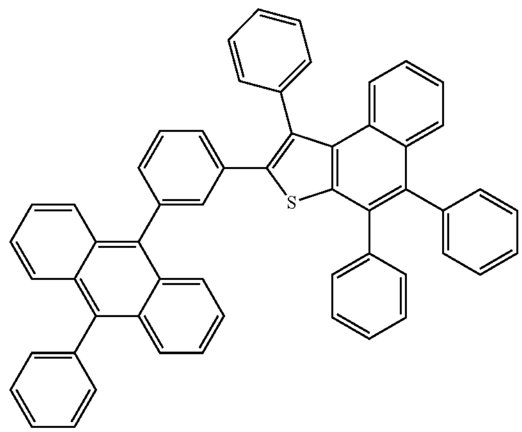 [SMILES: c1ccc(-c2c3ccccc3c(-c3cccc(-c4sc5c(-c6ccccc6)c(-c6ccccc6)c6ccccc6c5c4-c4ccccc4)c3)c3ccccc23)cc1] |
| compound 1-2-8 | 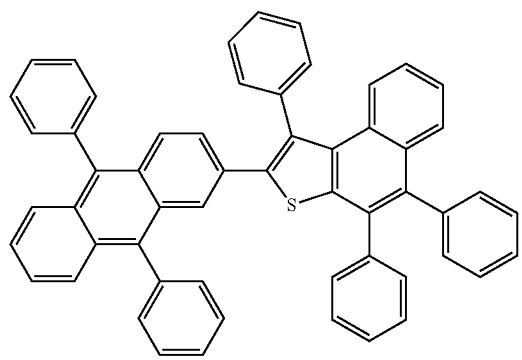 [SMILES: c1ccc(-c2c3ccccc3c(-c3ccccc3)c3cc(-c4sc5c(-c6ccccc6)c(-c6ccccc6)c6ccccc6c5c4-c4ccccc4)ccc23)cc1] |
| compound 1-2-9 | 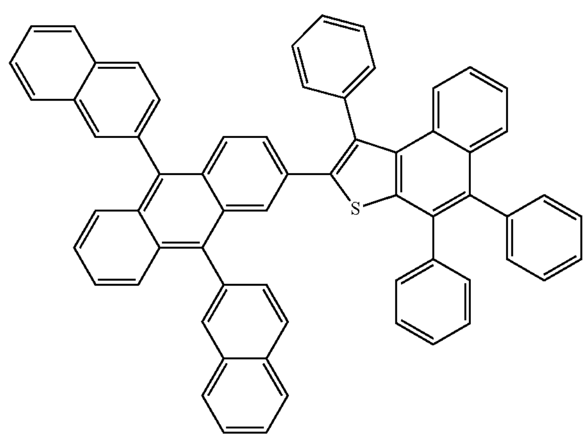 [SMILES: c1ccc(-c2c(-c3ccccc3)c3sc(-c4ccc5c(-c6ccc7ccccc7c6)c6ccccc6c(-c6ccc7ccccc7c6)c5c4)c(-c4ccccc4)c3c3ccccc23)cc1] |
| compound 1-2-10 | 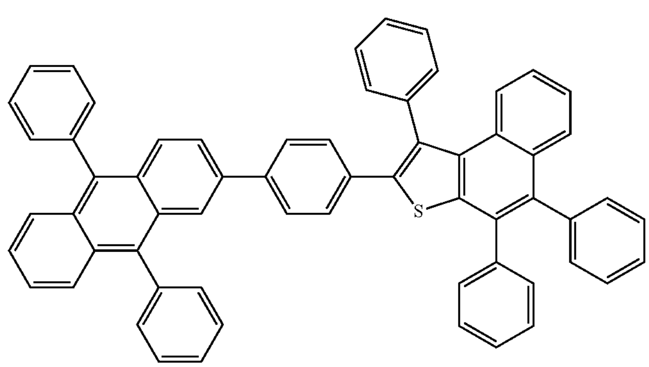 [SMILES: c1ccc(-c2c3ccccc3c(-c3ccccc3)c3cc(-c4ccc(-c5sc6c(-c7ccccc7)c(-c7ccccc7)c7ccccc7c6c5-c5ccccc5)cc4)ccc23)cc1] |

TABLE 1-2-continued
| Product 1-2-No | structure |
|---|---|
| compound 1-2-11 | 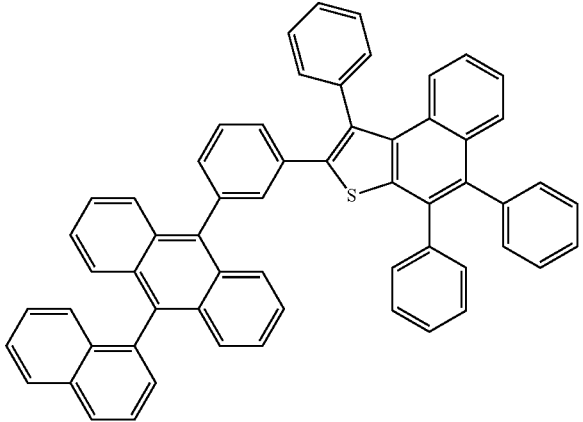 [SMILES: c1ccc(-c2c(-c3ccccc3)c3sc(-c4cccc(-c5c6ccccc6c(-c6cccc7ccccc67)c6ccccc56)c4)c(-c4ccccc4)c3c3ccccc23)cc1] |
| compound 1-2-12 | 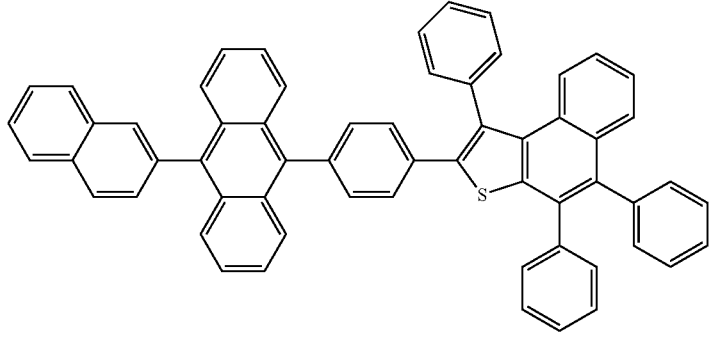 [SMILES: c1ccc(-c2c(-c3ccccc3)c3sc(-c4ccc(-c5c6ccccc6c(-c6ccc7ccccc7c6)c6ccccc56)cc4)c(-c4ccccc4)c3c3ccccc23)cc1] |
| compound 1-2-13 | 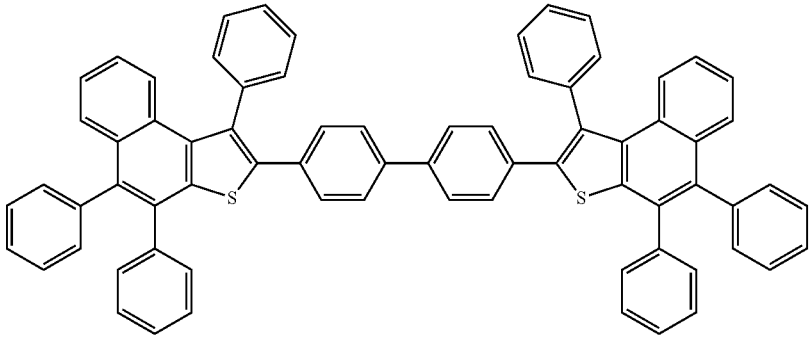 [SMILES: c1ccc(-c2c(-c3ccccc3)c3sc(-c4ccc(-c5ccc(-c6sc7c(-c8ccccc8)c(-c8ccccc8)c8ccccc8c7c6-c6ccccc6)cc5)cc4)c(-c4ccccc4)c3c3ccccc23)cc1] |
| compound 1-2-14 | 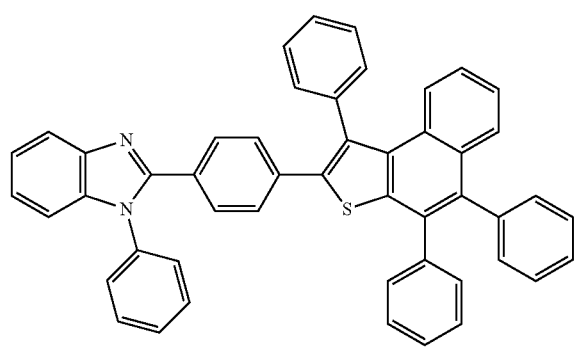 [SMILES: c1ccc(-c2c(-c3ccccc3)c3sc(-c4ccc(-c5nc6ccccc6n5-c5ccccc5)cc4)c(-c4ccccc4)c3c3ccccc23)cc1] |

TABLE 1-2-continued

| Product 1-2-No | structure |
|---|---|
| compound 1-2-15 | 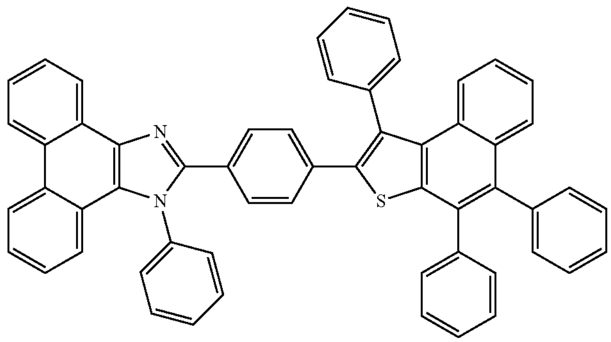 [SMILES: c1ccc(-c2c(-c3ccccc3)c3sc(-c4ccc(-c5nc6c7ccccc7c7ccccc7c6n5-c5ccccc5)cc4)c(-c4ccccc4)c3c3ccccc23)cc1] |
| compound 1-2-16 | 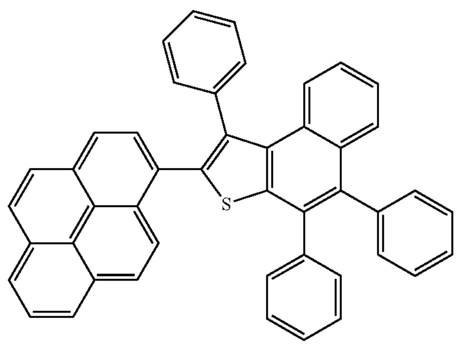 [SMILES: c1ccc(-c2c(-c3ccccc3)c3sc(-c4ccc5ccc6cccc7ccc4c5c67)c(-c4ccccc4)c3c3ccccc23)cc1] |
| compound 1-2-17 | 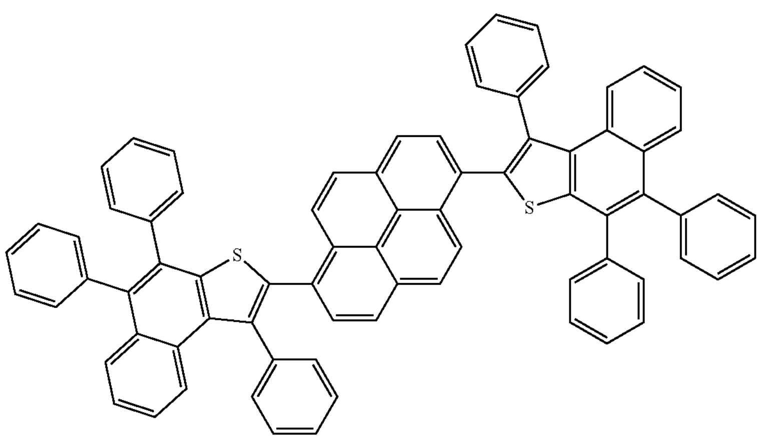 [SMILES: c1ccc(-c2c(-c3ccccc3)c3sc(-c4ccc5ccc6c(-c7sc8c(-c9ccccc9)c(-c9ccccc9)c9ccccc9c8c7-c7ccccc7)ccc7ccc4c5c76)c(-c4ccccc4)c3c3ccccc23)cc1] |
| compound 1-2-18 | 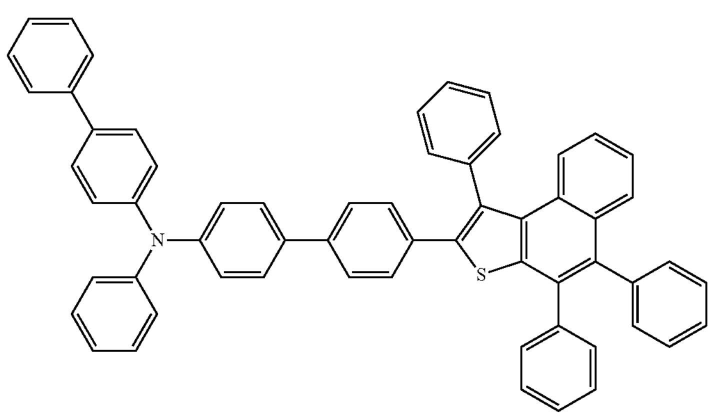 [SMILES: c1ccc(-c2ccc(N(c3ccccc3)c3ccc(-c4ccc(-c5sc6c(-c7ccccc7)c(-c7ccccc7)c7ccccc7c6c5-c5ccccc5)cc4)cc3)cc2)cc1] |

TABLE 1-2-continued

| Product 1-2-No | structure |
|---|---|
| compound 1-2-19 | 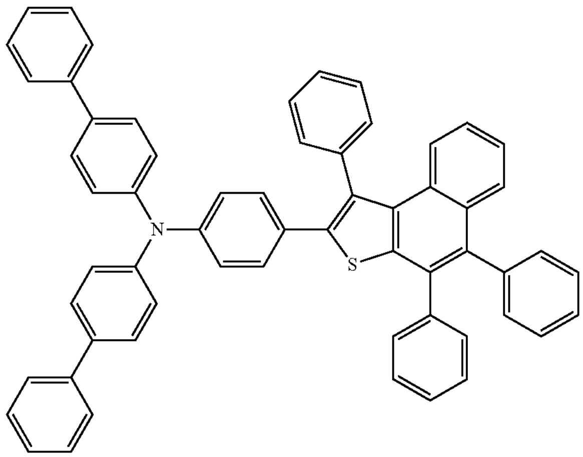 [SMILES: c1ccc(-c2ccc(N(c3ccc(-c4ccccc4)cc3)c3ccc(-c4sc5c(-c6ccccc6)c(-c6ccccc6)c6ccccc6c5c4-c4ccccc4)cc3)cc2)cc1] |
| compound 1-2-20 | 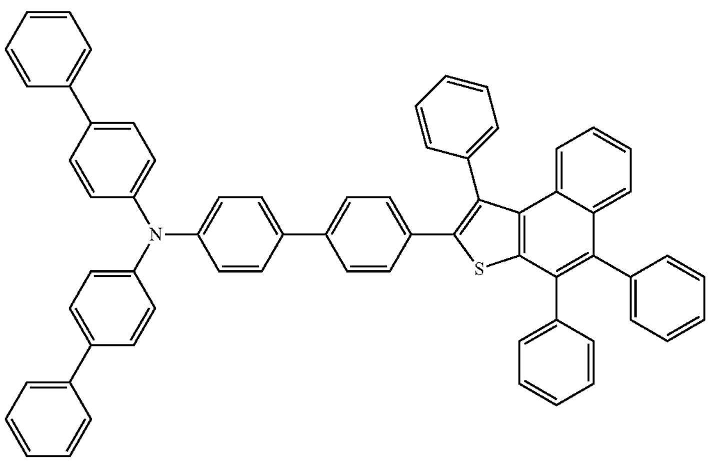 [SMILES: c1ccc(-c2ccc(N(c3ccc(-c4ccccc4)cc3)c3ccc(-c4ccc(-c5sc6c(-c7ccccc7)c(-c7ccccc7)c7ccccc7c6c5-c5ccccc5)cc4)cc3)cc2)cc1] |

TABLE 1-3

| Product 1-3-No | structure |
|---|---|
| compound 1-3-1 | 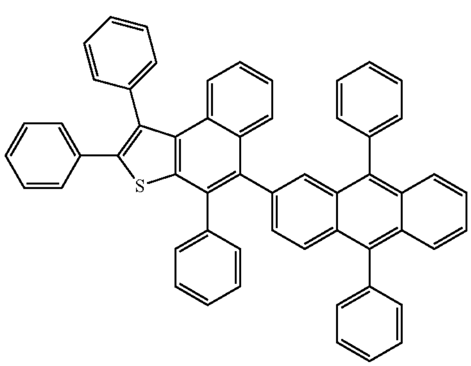 [SMILES: c1ccc(-c2sc3c(-c4ccccc4)c(-c4ccc5c(-c6ccccc6)c6ccccc6c(-c6ccccc6)c5c4)c4ccccc4c3c2-c2ccccc2)cc1] |

TABLE 1-3-continued

| Product 1-3-No | structure |
|---|---|
| compound 1-3-2 | 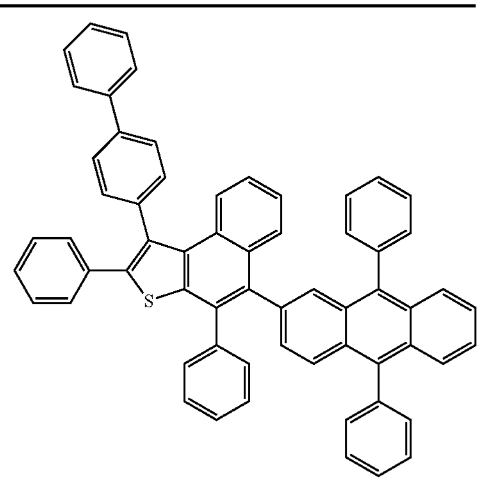 |

TABLE 1-3-continued
| Product 1-3-No | structure |
|---|---|
| compound 1-3-3 | 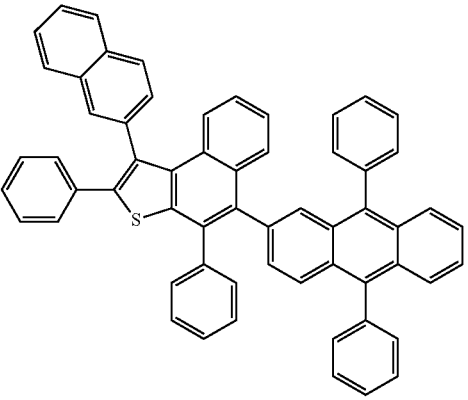 [SMILES: c1ccc(-c2sc3c(-c4ccccc4)c(-c4ccc5c(-c6ccccc6)c6ccccc6c(-c6ccccc6)c5c4)c4ccccc4c3c2-c2ccc3ccccc3c2)cc1] |
| compound 1-3-4 | 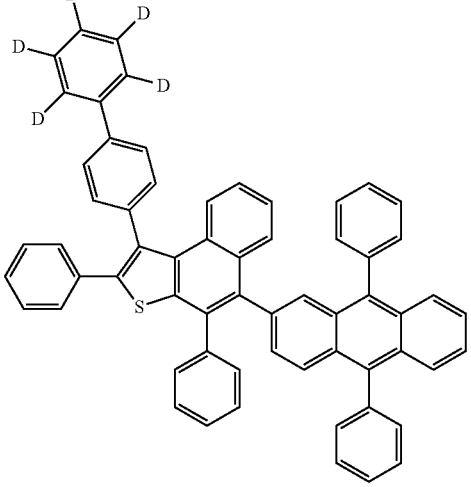 |
TABLE 1-4
| Product 1-4-No | structure |
|---|---|
| compound 1-4-1 | 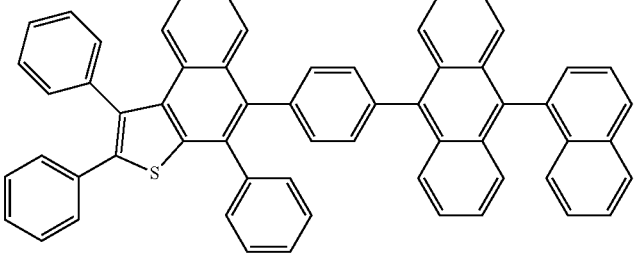 |
| compound 1-4-2 | 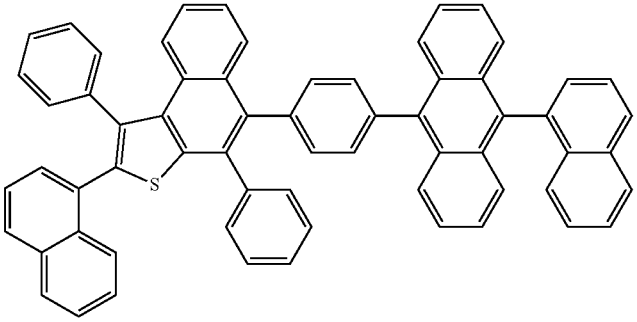 [SMILES: c1ccc(-c2c(-c3ccc(-c4c5ccccc5c(-c5cccc6ccccc56)c5ccccc45)cc3)c3ccccc3c3c(-c4ccccc4)c(-c4cccc5ccccc45)sc23)cc1] |
| compound 1-4-3 | 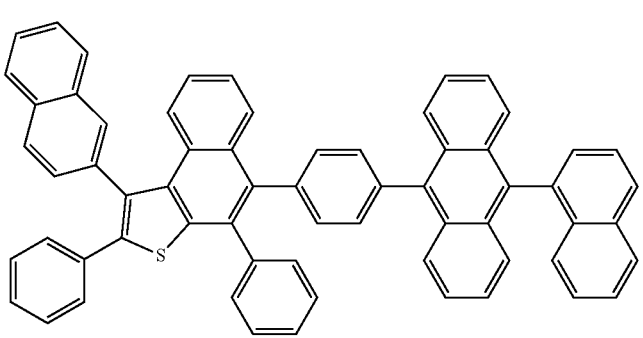 [SMILES: c1ccc(-c2sc3c(-c4ccccc4)c(-c4ccc(-c5c6ccccc6c(-c6cccc7ccccc67)c6ccccc56)cc4)c4ccccc4c3c2-c2ccc3ccccc3c2)cc1] |

TABLE 1-5

| Product 1-5-No | structure |
|---|---|
| compound 1-5-1 | 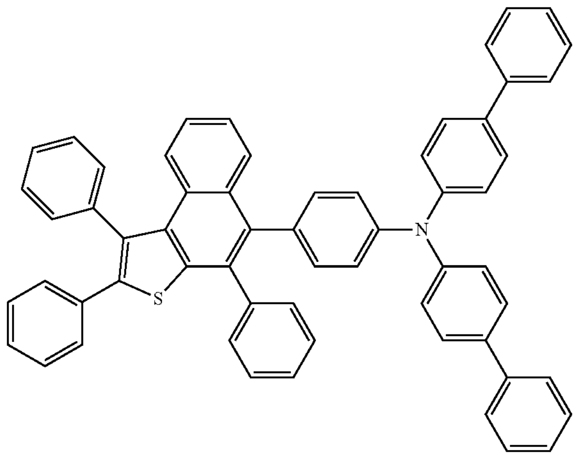 [SMILES: c1ccc(-c2ccc(N(c3ccc(-c4ccccc4)cc3)c3ccc(-c4c(-c5ccccc5)c5sc(-c6ccccc6)c(-c6ccccc6)c5c5ccccc45)cc3)cc2)cc1] |
| compound 1-5-2 | 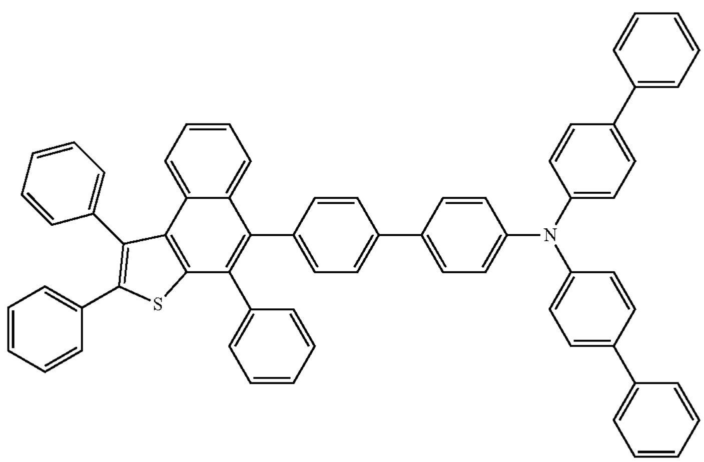 [SMILES: c1ccc(-c2ccc(N(c3ccc(-c4ccccc4)cc3)c3ccc(-c4ccc(-c5c(-c6ccccc6)c6sc(-c7ccccc7)c(-c7ccccc7)c6c6ccccc56)cc4)cc3)cc2)cc1] |
| compound 1-5-3 | 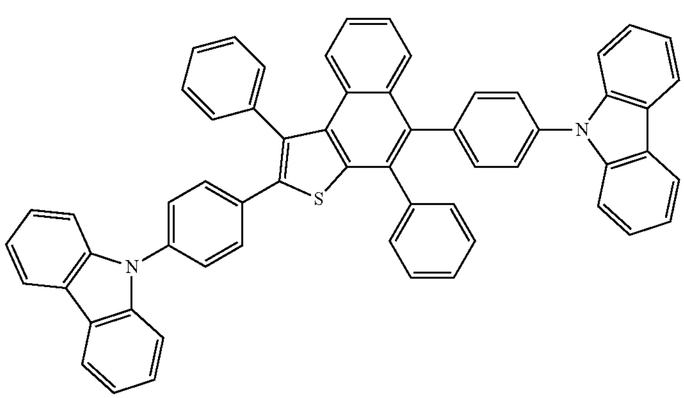 [SMILES: c1ccc(-c2c(-c3ccc(-n4c5ccccc5c5ccccc54)cc3)c3ccccc3c3c(-c4ccccc4)c(-c4ccc(-n5c6ccccc6c6ccccc65)cc4)sc23)cc1] |

TABLE 1-5-continued

| Product 1-5-No | structure |
|---|---|
| compound 1-5-4 | 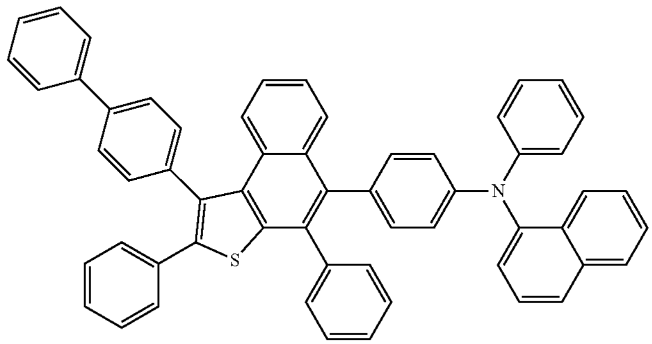 [SMILES: c1ccc(-c2ccc(-c3c(-c4ccccc4)sc4c(-c5ccccc5)c(-c5ccc(N(c6ccccc6)c6cccc7ccccc67)cc5)c5ccccc5c34)cc2)cc1] |
| compound 1-5-5 | 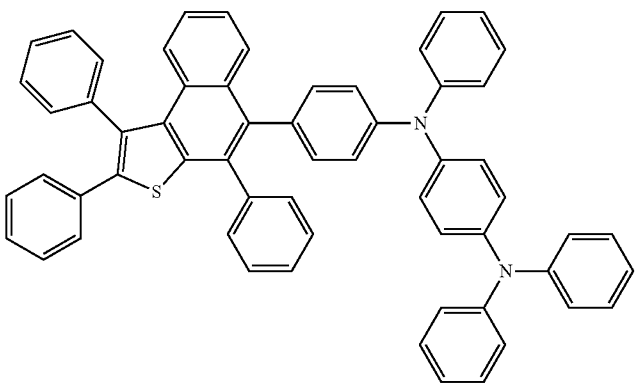 [SMILES: c1ccc(-c2sc3c(-c4ccccc4)c(-c4ccc(N(c5ccccc5)c5ccc(N(c6ccccc6)c6ccccc6)cc5)cc4)c4ccccc4c3c2-c2ccccc2)cc1] |

TABLE 1-6

| Product 1-6-No | structure |
|---|---|
| compound 1-6-1 | 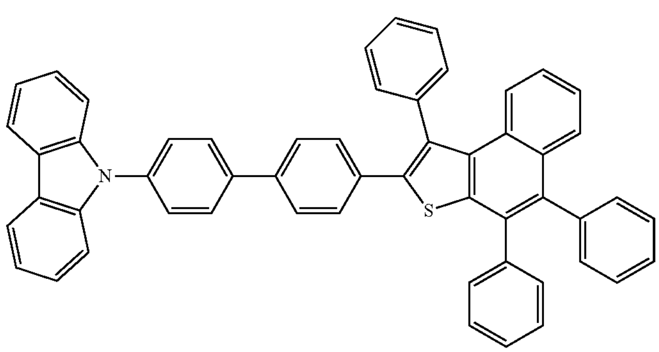 [SMILES: c1ccc(-c2c(-c3ccccc3)c3sc(-c4ccc(-c5ccc(-n6c7ccccc7c7ccccc76)cc5)cc4)c(-c4ccccc4)c3c3ccccc23)cc1] |

TABLE 1-6-continued

| Product 1-6-No | structure |
|---|---|
| compound 1-6-2 | 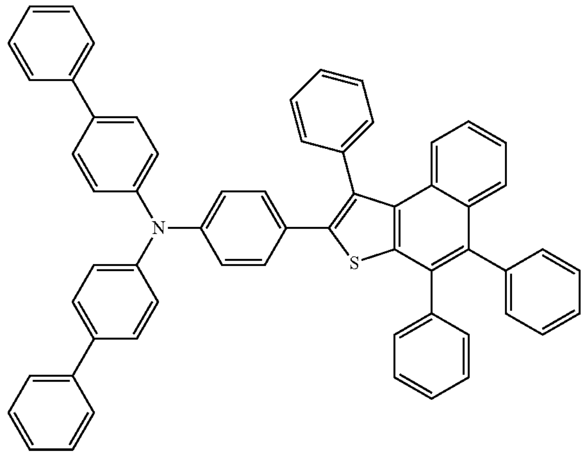 [SMILES: c1ccc(-c2ccc(N(c3ccc(-c4ccccc4)cc3)c3ccc(-c4sc5c(-c6ccccc6)c(-c6ccccc6)c6ccccc6c5c4-c4ccccc4)cc3)cc2)cc1] |
| compound 1-6-3 | 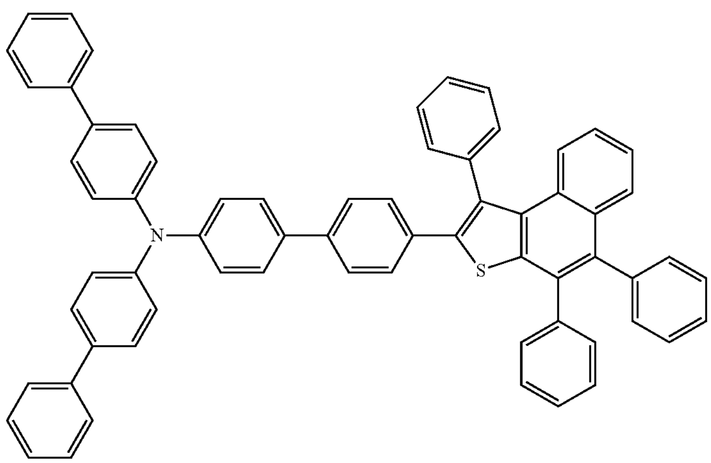 [SMILES: c1ccc(-c2ccc(N(c3ccc(-c4ccccc4)cc3)c3ccc(-c4ccc(-c5sc6c(-c7ccccc7)c(-c7ccccc7)c7ccccc7c6c5-c5ccccc5)cc4)cc3)cc2)cc1] |

TABLE 1-7

| Product 1-7-No | structure |
|---|---|
| compound 1-7-1 | 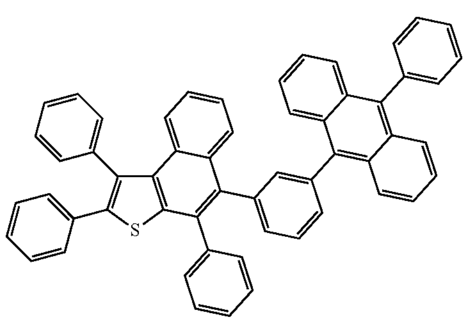 [SMILES: c1ccc(-c2sc3c(-c4ccccc4)c(-c4cccc(-c5c6ccccc6c(-c6ccccc6)c6ccccc56)c4)c4ccccc4c3c2-c2ccccc2)cc1] |

TABLE 1-7-continued

| Product 1-7-No | structure |
|---|---|
| compound 1-7-2 | 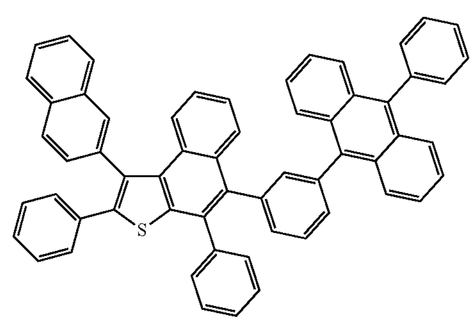 [SMILES: c1ccc(-c2sc3c(-c4ccccc4)c(-c4cccc(-c5c6ccccc6c(-c6ccccc6)c6ccccc56)c4)c4ccccc4c3c2-c2ccc3ccccc3c2)cc1] |

TABLE 1-7-continued
| Product 1-7-No | structure |
|---|---|
| compound 1-7-3 | 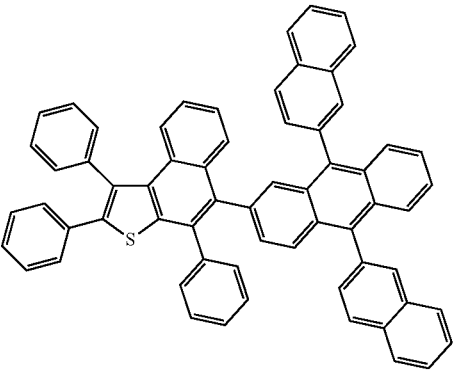 [SMILES: c1ccc(-c2sc3c(-c4ccccc4)c(-c4ccc5c(-c6ccc7ccccc7c6)c6ccccc6c(-c6ccc7ccccc7c6)c5c4)c4ccccc4c3c2-c2ccccc2)cc1] |
TABLE 2-1
| Product 2-1-No | structure |
|---|---|
| compound 2-1-1 | 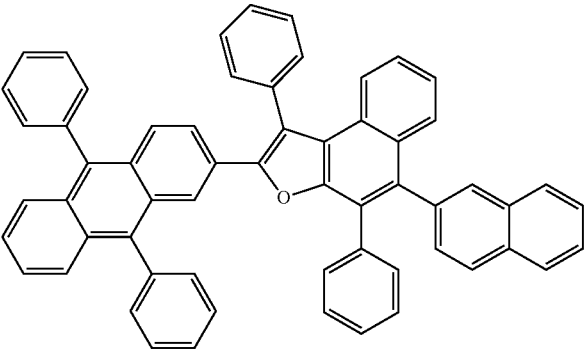 [SMILES: c1ccc(-c2c3ccccc3c(-c3ccccc3)c3cc(-c4oc5c(-c6ccccc6)c(-c6ccc7ccccc7c6)c6ccccc6c5c4-c4ccccc4)ccc23)cc1] |
| compound 2-1-2 | 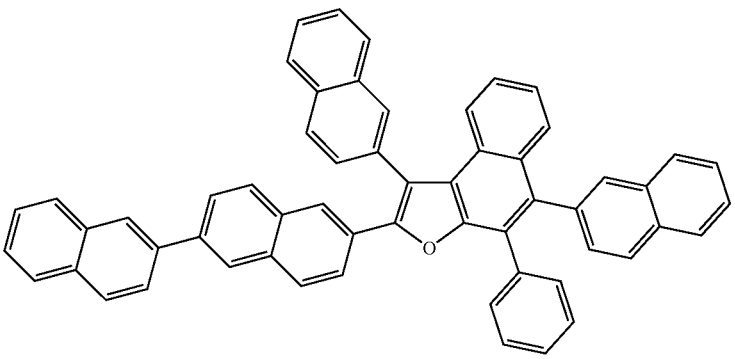 [SMILES: c1ccc(-c2c(-c3ccc4ccccc4c3)c3ccccc3c3c(-c4ccc5ccccc5c4)c(-c4ccc5cc(-c6ccc7ccccc7c6)ccc5c4)oc23)cc1] |
| compound 2-1-3 | 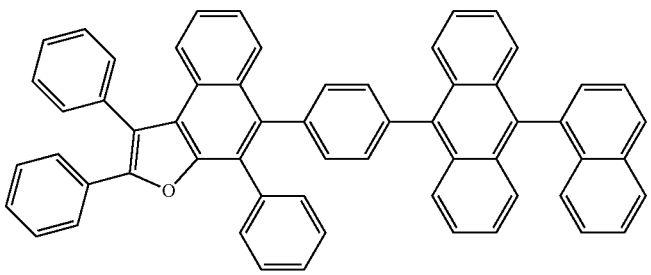 [SMILES: c1ccc(-c2oc3c(-c4ccccc4)c(-c4ccc(-c5c6ccccc6c(-c6cccc7ccccc67)c6ccccc56)cc4)c4ccccc4c3c2-c2ccccc2)cc1] |

TABLE 2-1-continued

| Product 2-1-No | structure |
|---|---|
| compound 2-1-4 | 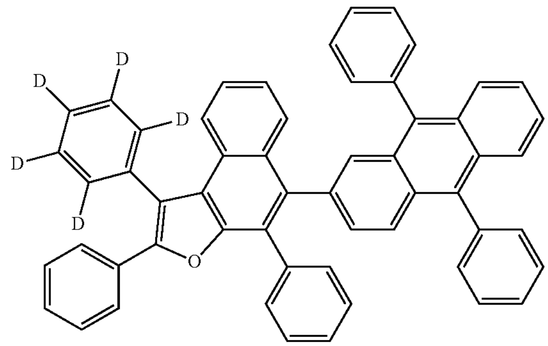 [SMILES: [2H]c1c([2H])c([2H])c(-c2c(-c3ccccc3)oc3c(-c4ccccc4)c(-c4ccc5c(-c6ccccc6)c6ccccc6c(-c6ccccc6)c5c4)c4ccccc4c23)c([2H])c1[2H]] |
| compound 2-1-5 | 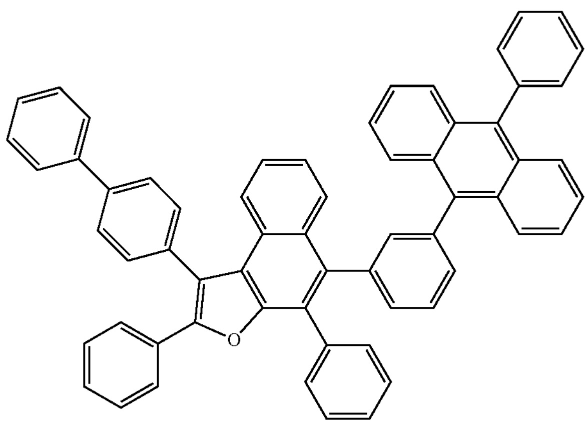 [SMILES: c1ccc(-c2ccc(-c3c(-c4ccccc4)oc4c(-c5ccccc5)c(-c5cccc(-c6c7ccccc7c(-c7ccccc7)c7ccccc67)c5)c5ccccc5c34)cc2)cc1] |
| compound 2-1-6 | 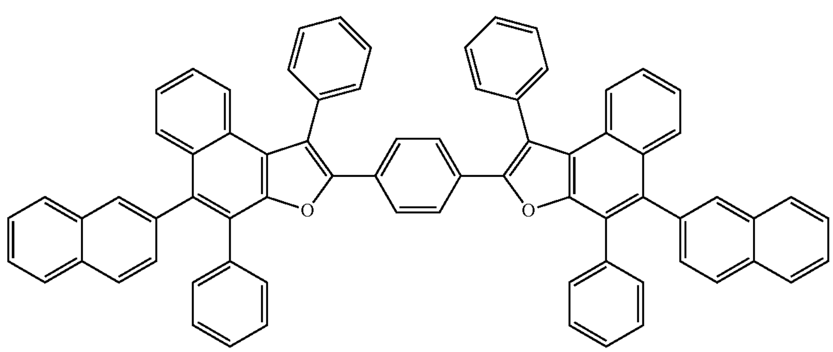 [SMILES: c1ccc(-c2c(-c3ccc4ccccc4c3)c3ccccc3c3c(-c4ccccc4)c(-c4ccc(-c5oc6c(-c7ccccc7)c(-c7ccc8ccccc8c7)c7ccccc7c6c5-c5ccccc5)cc4)oc23)cc1] |

TABLE 3-1

| Product 3-1-No | structure |
|---|---|
| compound 3-1-1 | 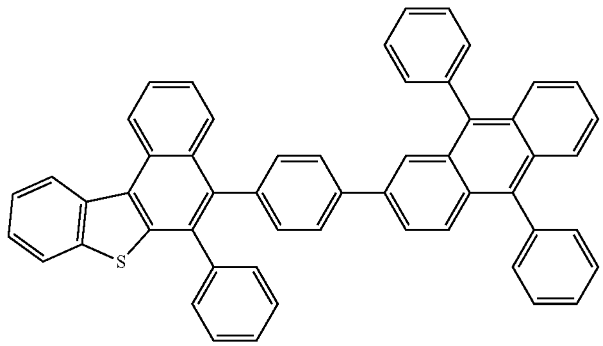 |
| compound 3-1-2 | 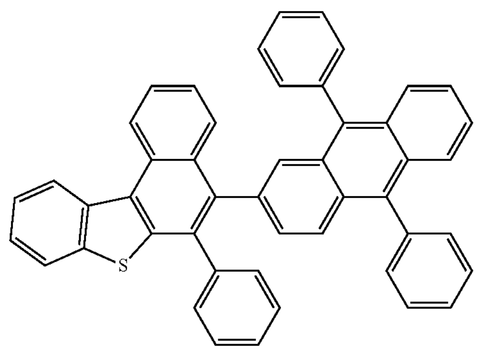 |
| compound 3-1-3 | 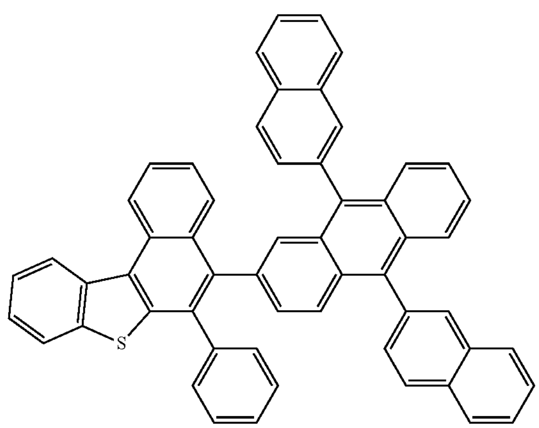 |
| compound 3-1-4 | 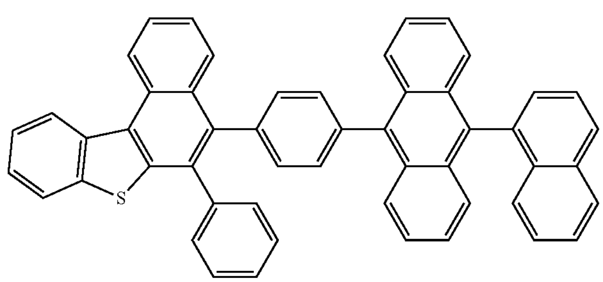 |

TABLE 3-1-continued

| Product 3-1-No | structure |
|---|---|
| compound 3-1-5 | 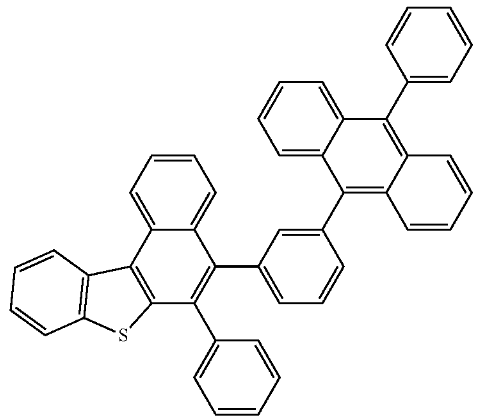 |
| compound 3-1-6 | 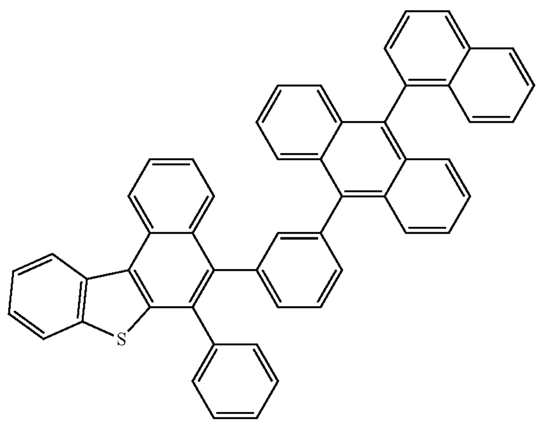 |
| compound 3-1-7 | 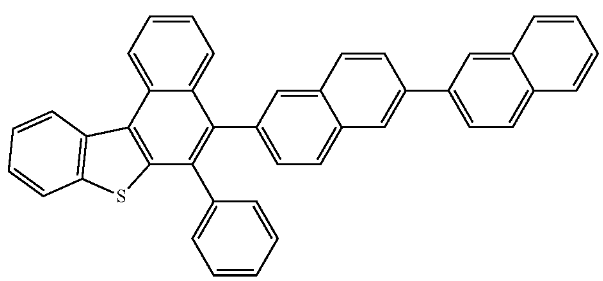 [SMILES: c1ccc(-c2c(-c3ccc4cc(-c5ccc6ccccc6c5)ccc4c3)c3ccccc3c3c2sc2ccccc23)cc1] |
| compound 3-1-8 | 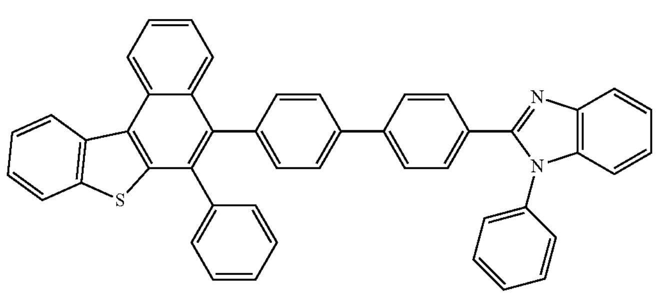 |

TABLE 3-1-continued

| Product 3-1-No | structure |
|---|---|
| compound 3-1-9 | 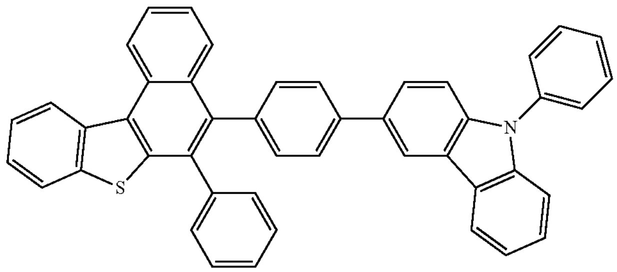 [SMILES: c1ccc(-c2c(-c3ccc(-c4ccc5c(c4)c4ccccc4n5-c4ccccc4)cc3)c3ccccc3c3c2sc2ccccc23)cc1] |
| compound 3-1-10 | 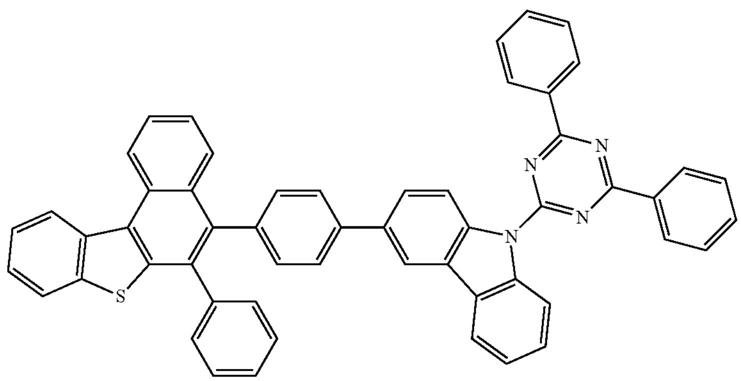 |
| compound 3-1-11 | 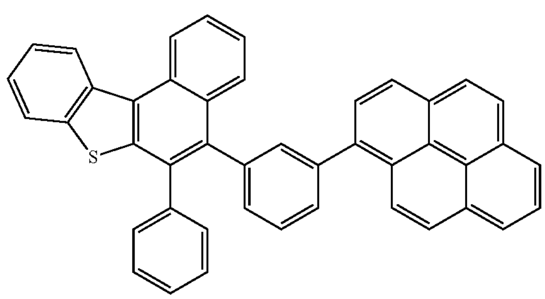 [SMILES: c1ccc(-c2c(-c3cccc(-c4ccc5ccc6cccc7ccc4c5c67)c3)c3ccccc3c3c2sc2ccccc23)cc1] |
| compound 3-1-12 | 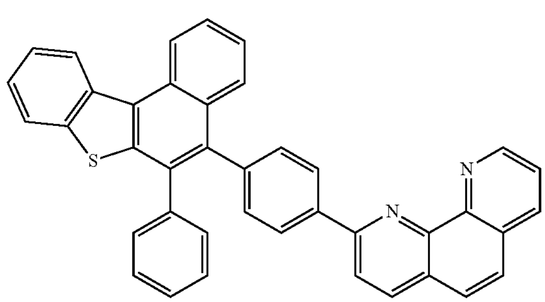 |

TABLE 3-1-continued

| Product 3-1-No | structure |
|---|---|
| compound 3-1-13 | 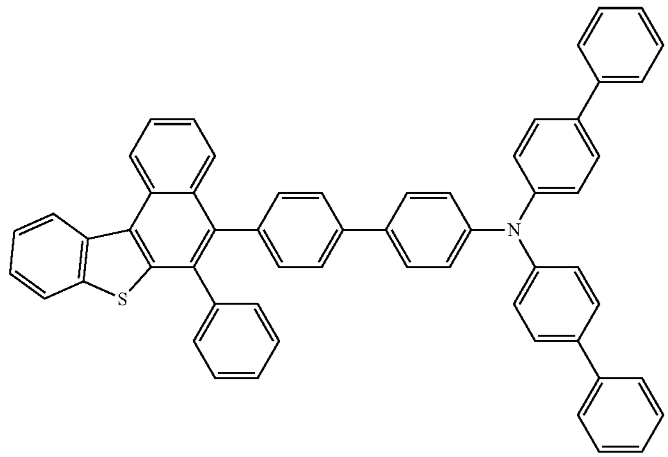 |
| compound 3-1-14 | 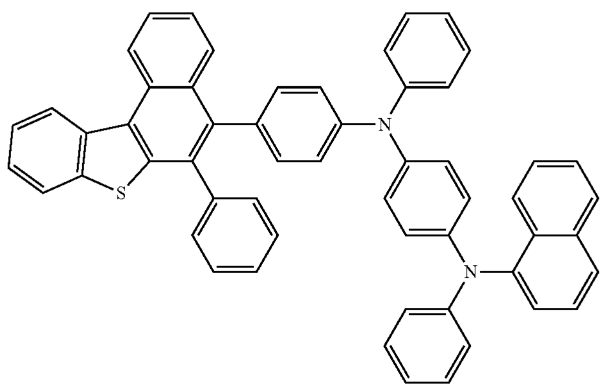 |
| compound 3-1-15 | 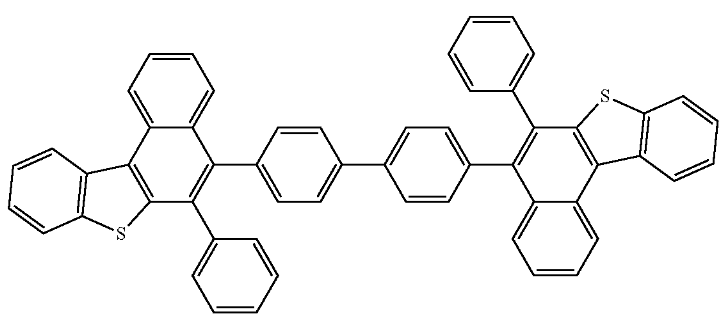 [SMILES: c1ccc(-c2c(-c3ccc(-c4ccc(-c5c(-c6ccccc6)c6sc7ccccc7c6c6ccccc56)cc4)cc3)c3ccccc3c3c2sc2ccccc23)cc1] |
| compound 3-1-16 | 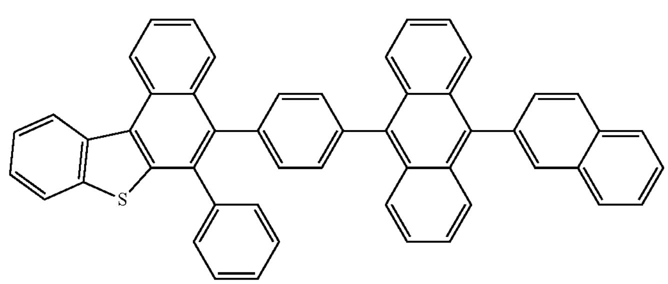 [SMILES: c1ccc(-c2c(-c3ccc(-c4c5ccccc5c(-c5ccc6ccccc6c5)c5ccccc45)cc3)c3ccccc3c3c2sc2ccccc23)cc1] |

TABLE 3-1-continued
| Product 3-1-No | structure |
|---|---|
| compound 3-1-17 | 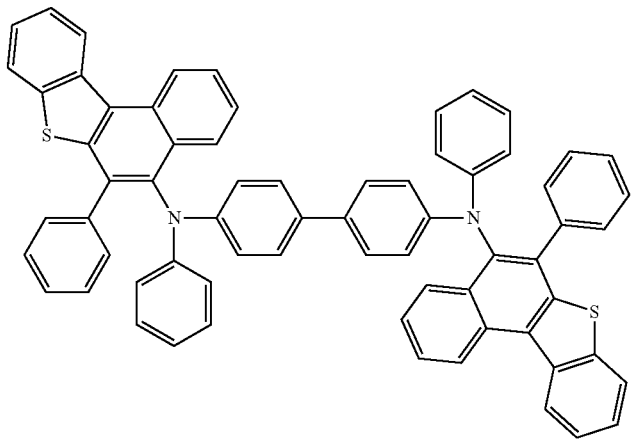 [SMILES: c1ccc(-c2c(N(c3ccccc3)c3ccc(-c4ccc(N(c5ccccc5)c5c(-c6ccccc6)c6sc7ccccc7c6c6ccccc56)cc4)cc3)c3ccccc3c3c2sc2ccccc23)cc1] |
| compound 3-1-18 | 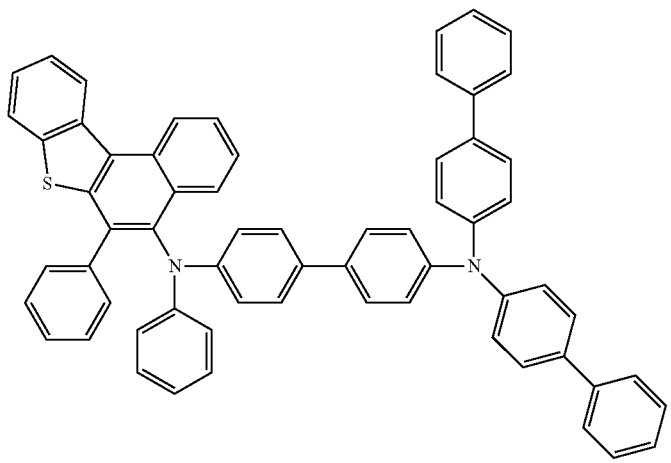 [SMILES: c1ccc(-c2ccc(N(c3ccc(-c4ccccc4)cc3)c3ccc(-c4ccc(N(c5ccccc5)c5c(-c6ccccc6)c6sc7ccccc7c6c6ccccc56)cc4)cc3)cc2)cc1] |
| compound 3-1-19 | 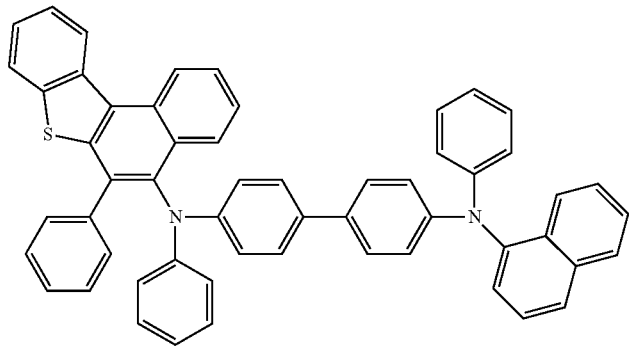 [SMILES: c1ccc(-c2c(N(c3ccccc3)c3ccc(-c4ccc(N(c5ccccc5)c5cccc6ccccc56)cc4)cc3)c3ccccc3c3c2sc2ccccc23)cc1] |

TABLE 3-1-continued
| Product 3-1-No | structure |
|---|---|
| compound 3-1-20 | 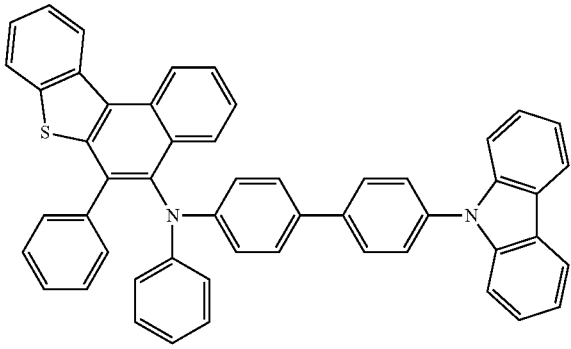 [SMILES: c1ccc(-c2c(N(c3ccccc3)c3ccc(-c4ccc(-n5c6ccccc6c6ccccc65)cc4)cc3)c3ccccc3c3c2sc2ccccc23)cc1] |
TABLE 4-1
| Product 4-1-No | structure |
|---|---|
| compound 4-1-1 | 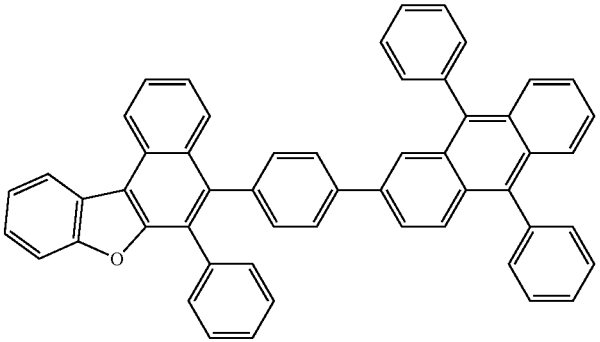 [SMILES: c1ccc(-c2c3ccccc3c(-c3ccccc3)c3cc(-c4ccc(-c5c(-c6ccccc6)c6oc7ccccc7c6c6ccccc56)cc4)ccc23)cc1] |
| compound 4-1-2 | 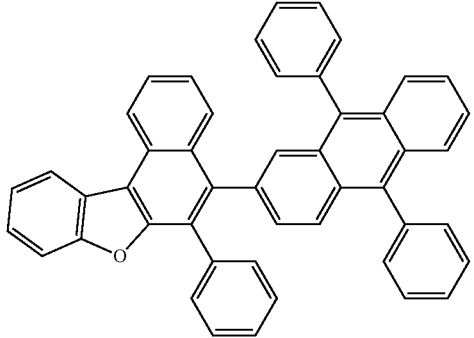 |

TABLE 4-1-continued
| Product 4-1-No | structure |
|---|---|
| compound 4-1-3 | 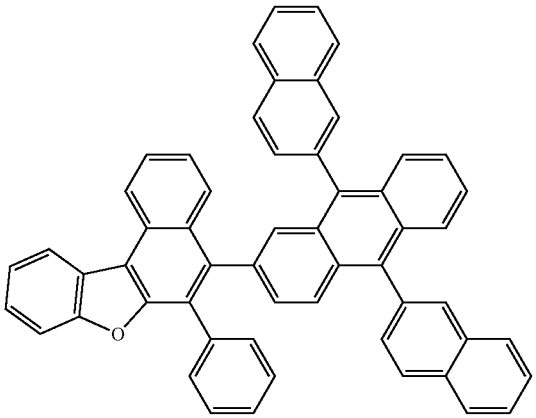 |
| compound 4-1-4 | 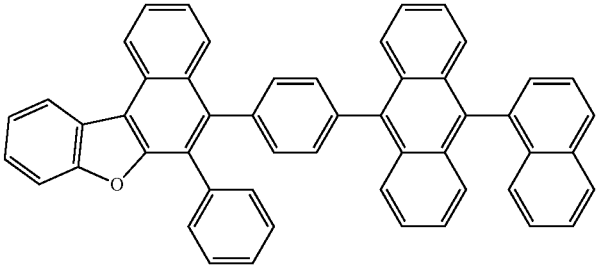 [SMILES: c1ccc(-c2c(-c3ccc(-c4c5ccccc5c(-c5cccc6ccccc56)c5ccccc45)cc3)c3ccccc3c3c2oc2ccccc23)cc1] |
| compound 4-1-5 | 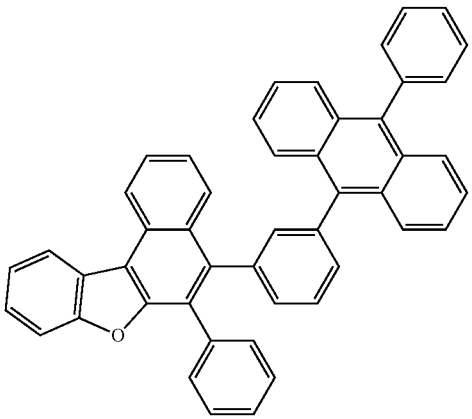 [SMILES: c1ccc(-c2c3ccccc3c(-c3cccc(-c4c(-c5ccccc5)c5oc6ccccc6c5c5ccccc45)c3)c3ccccc23)cc1] |
| compound 4-1-6 | 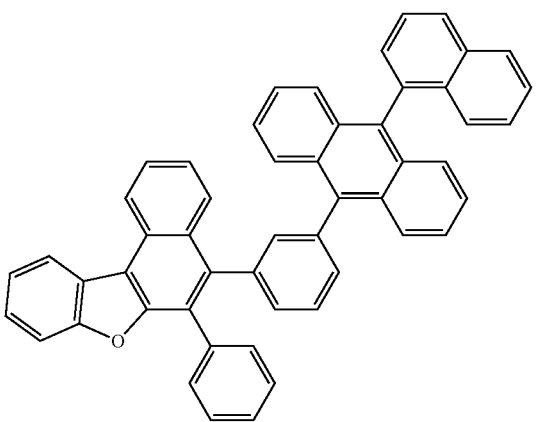 |

TABLE 4-1-continued
| Product 4-1-No | structure |
|---|---|
| compound 4-1-7 | 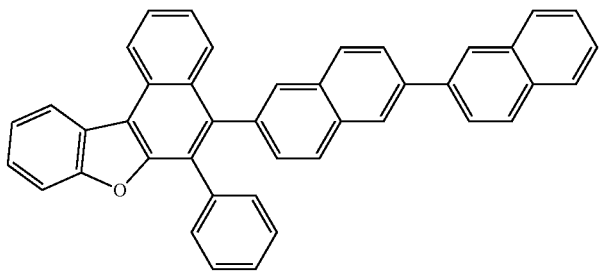 [SMILES: c1ccc(-c2c(-c3ccc4cc(-c5ccc6ccccc6c5)ccc4c3)c3ccccc3c3c2oc2ccccc23)cc1] |
| compound 4-1-8 | 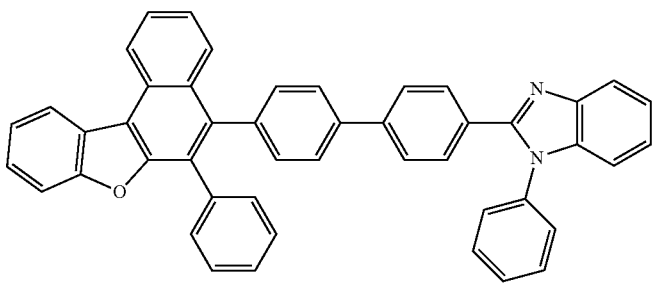 |
| compound 4-1-9 | 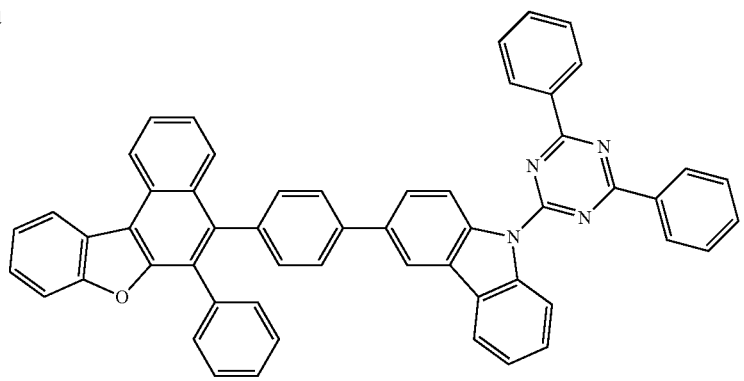 |
| compound 4-1-10 | 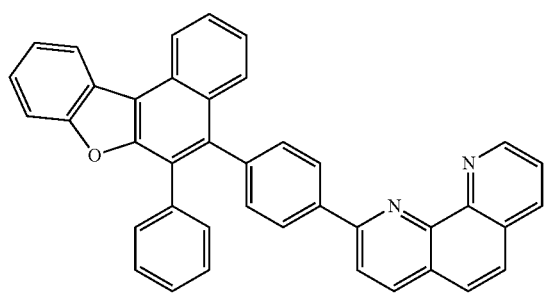 [SMILES: c1ccc(-c2c(-c3ccc(-c4ccc5ccc6cccnc6c5n4)cc3)c3ccccc3c3c2oc2ccccc23)cc1] |

TABLE 4-1-continued
| Product 4-1-No | structure |
|---|---|
| compound 4-1-11 | 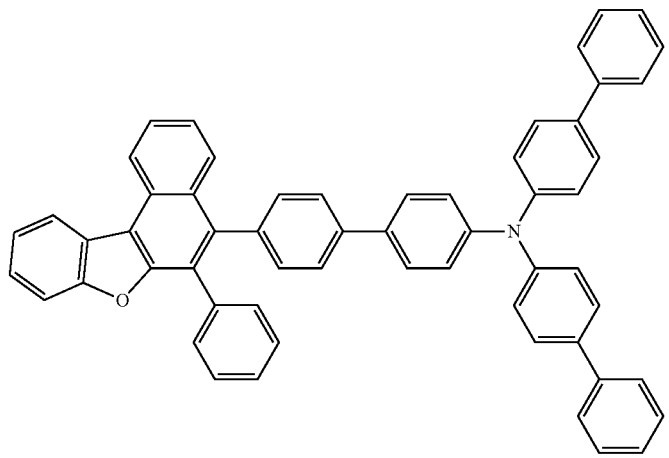 |
| compound 4-1-12 | 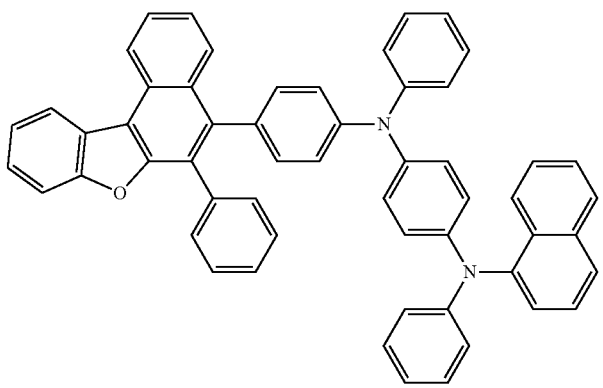 [SMILES: c1ccc(-c2c(-c3ccc(N(c4ccccc4)c4ccc(N(c5ccccc5)c5cccc6ccccc56)cc4)cc3)c3ccccc3c3c2oc2ccccc23)cc1] |
| compound 4-1-13 | 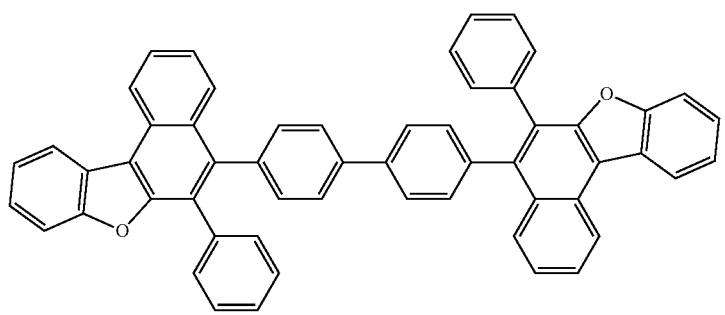 |
| compound 4-1-14 | 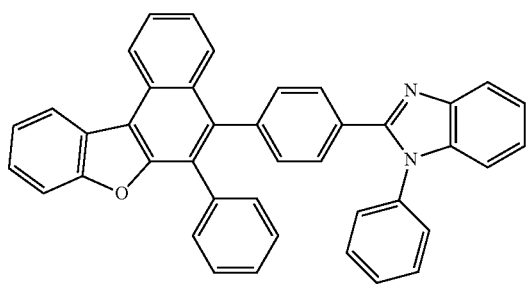 [SMILES: c1ccc(-c2c(-c3ccc(-c4nc5ccccc5n4-c4ccccc4)cc3)c3ccccc3c3c2oc2ccccc23)cc1] |

TABLE 5-1

| Product 5-1-No | structure |
|---|---|
| compound 5-1-1 | 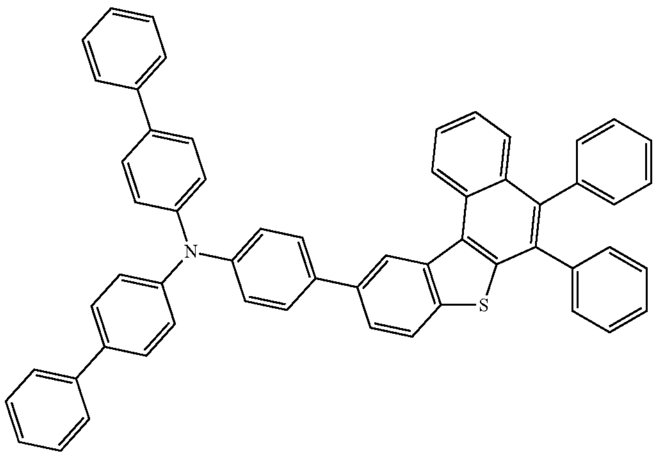 [SMILES: c1ccc(-c2ccc(N(c3ccc(-c4ccccc4)cc3)c3ccc(-c4ccc5sc6c(-c7ccccc7)c(-c7ccccc7)c7ccccc7c6c5c4)cc3)cc2)cc1] |
| compound 5-1-2 | 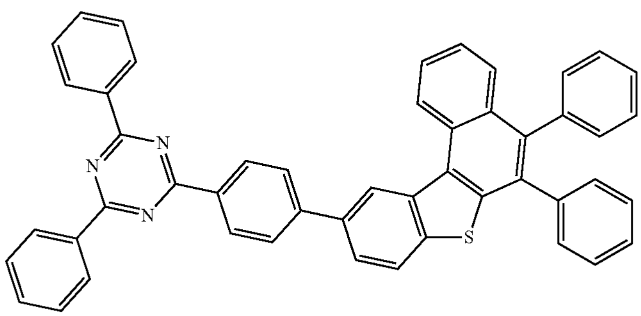 [SMILES: c1ccc(-c2nc(-c3ccccc3)nc(-c3ccc(-c4ccc5sc6c(-c7ccccc7)c(-c7ccccc7)c7ccccc7c6c5c4)cc3)n2)cc1] |
| compound 5-1-3 | 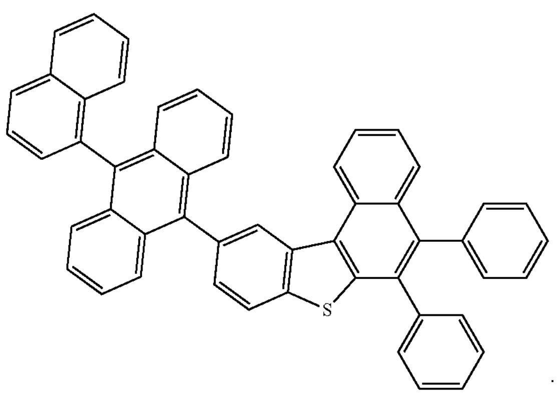 [SMILES: c1ccc(-c2c(-c3ccccc3)c3sc4ccc(-c5c6ccccc6c(-c6cccc7ccccc67)c6ccccc56)cc4c3c3ccccc23)cc1] |

11. An organic electronic device which includes a first electrode, a second electrode, and one or more organic material layers that are disposed between the first electrode and the second electrode, wherein one or more layers of the organic material layers include the compound according to claim 1.

12. The organic electronic device as set forth in claim 11, wherein the organic material layer includes a hole injection layer or a hole transport layer, and the hole injection layer or hole transport layer includes the compound of Formula 1.

13. The organic electronic device as set forth in claim 12, wherein the hole injection layer or hole transport layer further includes a dopant material.

14. The organic electronic device as set forth in claim 11, wherein the organic material layer includes a light emitting layer, and the light emitting layer includes the compound of Formula 1.

15. The organic electronic device as set forth in claim 14, wherein the light emitting layer that includes the compound of Formula 1 further includes a fluorescent dopant material or phosphorescent dopant material.

16. The organic electronic device as set forth in claim 11, wherein the organic material layer includes an electron injection layer or an electron transport layer, and the electron injection layer or electron transport layer includes the compound of Formula 1.

17. The organic electronic device as set forth in claim 16, wherein the electron injection layer or electron transport layer further includes a dopant material.

18. The organic electronic device as set forth in claim 11, wherein the organic electronic device is selected from the group consisting of an organic light emitting device, an organic solar cell, an organic photoconductor (OPC) drum and an organic transistor.

19. An organic device which includes a first electrode, a second electrode, and one or more organic material layers that are disposed between the first electrode and the second electrode, wherein one or more layers of the organic material layers include the compound according to claim 3.

20. An organic device which includes a first electrode, a second electrode, and one or more organic material layers that are disposed between the first electrode and the second electrode, wherein one or more layers of the organic material layers include the compound according to claim 10.

\* \* \* \* \*